US012187804B2

(12) United States Patent
Eckelman et al.

(10) Patent No.: US 12,187,804 B2
(45) Date of Patent: Jan. 7, 2025

(54) MULTIVALENT AND MULTISPECIFIC 41BB-BINDING PROTEINS

(71) Applicant: Inhibrx Biosciences, Inc., La Jolla, CA (US)

(72) Inventors: Brendan P. Eckelman, Encinitas, CA (US); John C. Timmer, San Diego, CA (US); Chelsie Macedo, La Jolla, CA (US); Kyle S. Jones, San Marcos, CA (US); Abrahim Hussain, La Jolla, CA (US); Amir S. Razai, La Jolla, CA (US); Bryan Becklund, San Diego, CA (US); Rajay Pandit, La Jolla, CA (US); Mike Kaplan, La Jolla, CA (US); Lucas Rascon, La Jolla, CA (US); Quinn Deveraux, La Jolla, CA (US)

(73) Assignee: Inhibrx Biosciences, Inc., La Jolla, CA (US)

( * ) Notice: Subject to any disclaimer, the term of this patent is extended or adjusted under 35 U.S.C. 154(b) by 0 days.

(21) Appl. No.: 18/067,484

(22) Filed: Dec. 16, 2022

(65) Prior Publication Data

US 2023/0416387 A1 Dec. 28, 2023

Related U.S. Application Data

(62) Division of application No. 16/601,825, filed on Oct. 15, 2019, now Pat. No. 11,566,078, which is a division of application No. 15/404,016, filed on Jan. 11, 2017, now Pat. No. 10,501,551.

(60) Provisional application No. 62/277,028, filed on Jan. 11, 2016.

(51) Int. Cl.
*C07K 16/28* (2006.01)

(52) U.S. Cl.
CPC ...... *C07K 16/2878* (2013.01); *C07K 16/2827* (2013.01); *C07K 2317/24* (2013.01); *C07K 2317/31* (2013.01); *C07K 2317/33* (2013.01); *C07K 2317/35* (2013.01); *C07K 2317/52* (2013.01); *C07K 2317/569* (2013.01); *C07K 2317/75* (2013.01); *C07K 2317/76* (2013.01); *C07K 2317/92* (2013.01); *C07K 2319/00* (2013.01)

(58) Field of Classification Search
None
See application file for complete search history.

(56) References Cited

U.S. PATENT DOCUMENTS

| | | |
|---|---|---|
| 2004/0038307 A1 | 2/2004 | Lee et al. |
| 2005/0032174 A1 | 2/2005 | Peters et al. |
| 2008/0108070 A1 | 5/2008 | Xu et al. |
| 2011/0262348 A1 | 10/2011 | Movahedi et al. |
| 2012/0039906 A1 | 2/2012 | Olive |
| 2012/0237498 A1 | 9/2012 | Ahrens et al. |
| 2012/0269859 A1 | 10/2012 | Minato et al. |
| 2014/0079701 A1 | 3/2014 | Miller et al. |
| 2014/0242077 A1 | 8/2014 | Choi et al. |
| 2015/0190506 A1 | 7/2015 | Cheung et al. |
| 2015/0266958 A1 | 9/2015 | Hermans et al. |
| 2015/0355184 A1 | 12/2015 | Pierce et al. |
| 2017/0290913 A1 | 10/2017 | Cheung et al. |

FOREIGN PATENT DOCUMENTS

| | | |
|---|---|---|
| JP | 2009504191 A | 2/2009 |
| JP | 2013539364 A | 10/2013 |
| RU | 2013110576 A | 10/2014 |
| WO | 2007024715 A2 | 3/2007 |
| WO | 2010007376 A2 | 1/2010 |
| WO | 2010077634 A1 | 7/2010 |
| WO | 2012027570 A2 | 3/2012 |
| WO | 2012032433 A1 | 3/2012 |
| WO | 2014022758 A1 | 2/2014 |
| WO | 2014028776 A1 | 2/2014 |
| WO | 2014100079 A1 | 6/2014 |
| WO | 2014209804 A1 | 12/2014 |
| WO | 2015095412 A1 | 6/2015 |
| WO | 2016149201 A2 | 9/2016 |
| WO | 2018115003 A2 | 6/2018 |

OTHER PUBLICATIONS

Bartkowiak et al., "4-1BB agonists: Multi-potent potentiators of tumor immunity," Frontiers in Oncology, vol. 5, No. 117, pp. 1-16 (2015).
Borisov et al., "Tumor microenvironment as a target of malignant gliomas treatment" Malignant Tumours; vol. 4:14-23 (2015).
Cardoso et al., "Single-Domain Antibodies Targeting Neuraminidase Protect against an H5N1 Influenza Virus Challenge," Journal of Virology; vol. 88, No. 15; pp. 8278-8296 (2014).
Chang et. al., "The Development of Bispecific Hexavalent Antibodies as a Novel Class of Dock-and-LockTM (DNLTM) Complexes," Antibodies., vol. 2, No. 2; pp. 353-370 (2013).
Chen et al., "Combination of 4-1BB Agonist and PD-1 Antagonist Promotes Antitumor Effector/Memory CD8 T Cells in a Poorly Immunogenic Tumor Model," Cancer Immunology research. vol. 3, No. 2; pp. 149-160 (2014).
Chen et al., "Fusion protein linkers: property, design and functionality," Advanced drug delivery reviews, vol. 65, No. 10, p. 1357-1365 (2013).
Colman et al., "Effects of amino acid sequence changes on antibody-antigen interactions, Research in Immunology," vol. 145, No. 1, p. 33-36 (1994).
Cuesta et al., "Multivalent antibodies: when design surpasses evolution," Cell Press Trends in Biotechnology (28), pp. 355-362 (2010).
Dondelinger et al., "Understanding the Significance and Implications of Antibody Numbering and Antigen-Binding Surface/Residue Definition." Frontiers in Immunology, vol. 9, pp. 1-15 (2018).

(Continued)

Primary Examiner — Amy E Juedes
(74) Attorney, Agent, or Firm — McNeill PLLC

(57) ABSTRACT

This invention relates generally to molecules that specifically engage 41BB, a member of the TNF receptor superfamily (TNFRSF). More specifically, this invention relates to multivalent and multispecific molecules that bind at least 41BB.

12 Claims, 28 Drawing Sheets

Specification includes a Sequence Listing.

(56) References Cited

OTHER PUBLICATIONS

Extended European Search Report dated Aug. 19, 2019 for International Application No. PCT/US2017/013040; 7 pages.
Fisicaro et al., "Combined Blockade of Programmed Death-1 and Activation of CD137 Increase Responses of Human Liver T Cells Against HBV, But Not HCV," Gastroenterology, vol. 143, No. 6, pp. 1576-1585 (2012).
Gilboa et al., "Use of Oligonucleotide Aptamer Ligands to Modulate the Function of Immune Receptors," Clin. Cancer Res. vol. 19, No. 5, pp. 1054-1062 (2013).
He et al., "Remarkably similar CTLA-4 binding properties of therapeutic ipilimumab and tremelimumab antibodies," Oncotarget, vol. 8: 67129-67139 (2017).
Holt et al., "Domain antibodies: proteins for therapy," Trends in Biotechnology, vol. 21: 484-490 (2003).
Huang et al., Human B Cells Accumulate immunoglobulin V Gene Somatic Mutations in a Cell Contact-Dependent Manner in Cultures Supported by Activated T cells But Not in Cultures Supported by CD40 Ligand. Clinical and Experimental Immunology. vol. 116, No. 3; pp. 441-448 (1999).
Iezzi et al., "Promise of Modular Targeting in Cancer Imaging and Treatment," Frontiers in Immunology, vol. 9: 1-11, 11 pages (2018).
Inman et al., "Utomilumab/Pembrolizumab Combo Shows responses in Different Solid Tumors", XP002793239, Retrieved from the Internet: URL:https://www.targetedonc.com/conference/asco-immune-2016/utomiluma/pembrolizumab; 2 pages (2016).
International Search Report and Written Opinion for International Application PCT/US17/13040 dated Jul. 20, 2017; 8 pages.
Kontermann et al., "Bispecific antibodies", Drug Discovery Today, vol. 7, No. 20, p. 838-847 (2015).
Linch et al., "OX40 agonists and combination immunotherapy: putting the pedal to the metal," Frontiers in Oncology, vol. 5, pp. 34:1-14 (2015).
Locksley et al., "The TNF and TNF receptor superfamilies: integrating mammalian biology," Cell, vol. 104, No. 4, p. 487-501 (2001).
Lu et al. "Structure of FcγRI in Complex with Fc Reveals the Importance of Glycan Recognition for High-Affinity IgG Binding," Proceedings to the National Academy of Sciences of USA. vol. 112, No. 3; pp. 833-838; p. 834, col. 2, paragraph 3; Genbank supplement pp. 1-2; DOI: 10.1073/pnas.1418812112 (2015).
Maeda et al., "Engineering of functional chimeric protein G-Vargula Luciferase," Analytical biochemistry, vol. 249, No. 2, p. 147-152 (1997).
Nelson et al., "The "Trojan Horse" Approach to Tumor Immunotherapy: Targeting the Tumor Microenvironment," J. Immunol. Res., N.789069, pp. 1-14 (2014).

Pakula et al., "Genetic analysis of protein stability and function," Annual Review of Genetics, V. 23, pp. 289-310 (1989).
Pardon et al., "A general protocol for the generation of Nanobodies for structural biology," Nature Protocols (9)(3), pp. 674-693 (2014).
Raaphorst et al. Restricted Utilization of Germ-line VH3 genes and Short Diverse Third Complementarity-Determining Regions (CDR3) in Human Fetal B Lymphocyte Immunoglobulin Heavy Chain Rearrangements. European Journal of Immunology. vol. 22, No. 1; pp. 247-251; (1992).
Rahbarizadeh et al., "Nanobody; an Old Concept and New Vehicle for Immunotargeting," Immunological Investigations, Informa Healthcare USA, Inc. vol. 40, No. 3, pp. 299-338, (2011).
Rahbarizadeh et al., "Nanobody, New Agent for Combating Against Breast Cancer Cells", Breast Cancer—Current and Alternative Therapeutic Modalities, pp. 347-370 (2011).
Rossi et al., "The Dock-and-Lock Method Combines Recombinant Engineering with Site-Specific Covalent Conjugation to Generate Multifunctional Structures," American Chemical Society. p. 309-323 (2011).
Safdari et al., "Antibody humanization methods—a review and update," Biotechnology and Genetic Engineering Reviews, vol. 29, No. 2, p. 175-186 (2013).
Sanmamed et al., "Nivolumab and Urelumab Enhance Antitumor Activity of Human T Lymphocytes Engrafted in Rag2−/−IL2Rγnull Immunodeficient Mice", Cancer Research, (75)(17), pp. 3466-3478 (2015).
Scott et al., "Antibody therapy of cancer," Nat Rev. vol. 12: 278-287 (2012).
Search Report issued in corresponding Singaporean Application No. 11201805532X, dated Aug. 30, 3019, 5 pages.
Shen et al., "Single variable domain-IgG fusion: a novel recombinant approach to Fc domain-containing bispecific antibodies," Journal of Biological Chemistry, vol. 281, No. 16, pp. 10706-10714 (2006).
Teplyakov et al., "Antibody modeling assessment II Structures and models," Proteins: Structure, Function, and Bioinformatics, vol. 82, No. 8, p. 1563-1582 (2014).
Torres M. et al., "The immunoglobulin constant region contributes to affinity and specificity," Trends in immunology, vol. 29, No. 2, p. 91-97, pp. 93-94 (2008).
Tran et al., Production of Anti-cancer Immunotoxins in Algae: Ribosome Inactivating Proteins as Fusion Partners. Biotechnology and Bioengineering, vol. 110, No. 11; pp. 1-32 (2013).
Williams et al., "The Human Neonatal B Cell Response to Respiratory Syncytial Virus uses a Biased Antibody Variable Gene Repertoire that Lacks Somatic Mutations" Molecular Immunology. vol. 47, No. 2-3; pp. 1-21; p. 5 (2009).
Zhang et al., "Structural basis of a novel PD-L1 nanobody for immune checkpoint blockade," Cell Disco. vol. 3: 1-12, (2017).

No 41BB signaling

PDL1-dependent 41BB signaling

- ■ PDL1-CHO: 28A10-RH3 (PDL1 x 41BB)
- ▲ PDL1-CHO: 28A10-4E01 (PDL1 x 41BB)
- □ NT-CHO: 28A10-RH3 (PDL1 x 41BB)
- △ NT-CHO: 28A10-4E01 (PDL1 x 41BB)

MULTIVALENT AND MULTISPECIFIC 41BB-BINDING PROTEINS

RELATED APPLICATIONS

This application is a divisional of U.S. patent application Ser. No. 16/601,825, filed Oct. 15, 2019, which is a divisional of U.S. patent application Ser. No. 15/404,016, filed Jan. 11, 2017, which claims the benefit of U.S. Provisional Application No. 62/277,028, filed Jan. 11, 2016; the contents of each of which are incorporated herein by reference in their entirety.

SEQUENCE LISTING

The present application contains a Sequence Listing which has been submitted electronically in XML format and is hereby incorporated by reference in its entirety. Said XML copy, created on Dec. 14, 2022, is named "2022-12-14_01202-0005-02US.xml" and is 617,844 bytes in size. The information in the electronic format of the sequence listing is incorporated herein by reference in its entirety.

FIELD OF THE INVENTION

This invention relates generally to molecules that specifically engage 41BB, a member of the TNF receptor superfamily (TNFRSF). More specifically, this invention relates to multivalent and/or multispecific molecules that bind at least 41BB.

BACKGROUND OF THE INVENTION

The tumor necrosis factor receptor superfamily consists of several structurally related cell surface receptors. Activation by multimeric ligands is a common feature of many of these receptors. Many members of the TNFRSF have therapeutic utility in numerous pathologies, if activated properly. Agonism of this receptor family often requires higher order clustering, and conventional bivalent antibodies are not ideal for this purpose. Therefore, there exists a therapeutic need for more potent agonist molecules of the TNFRSF.

SUMMARY OF THE INVENTION

The disclosure provides multivalent and multispecific TNF receptor superfamily (TNFRSF) binding fusion polypeptides that bind at least 41BB (also known as tumor necrosis factor receptor superfamily, member 4 (TNFRSF9) and/or CD137)). The use of the term "41BB" is intended to cover any variation thereof, such as, by way of non-limiting example, 41-BB and/or 4-1BB, and all variations are used herein interchangeably. These molecules that bind at least 41BB are referred to herein as "41BB-targeting molecules" or "41BB-targeting fusions" or "41BB-targeting proteins" or "41BB-targeting fusion polypeptides" or "41BB-targeting fusion proteins." In some embodiments, the 41BB-targeting molecule is a multivalent molecule, for example, a multivalent 41BB-targeting fusion protein. In some embodiments, the 41BB-targeting molecule is a multispecific molecule, for example, a multispecific 41BB-targeting fusion protein. In some embodiments, the 41BB-targeting molecule is a multivalent and multispecific molecule, for example, a multivalent and multispecific 41BB-targeting fusion protein. As used herein, the term "fusion protein" or "fusion polypeptide" or "41BB-targeting fusion protein" or "41BB-targeting fusion polypeptide," unless otherwise specifically denoted, refers to any fusion protein embodiment of the disclosure, including, but not limited to, multivalent fusion proteins, multispecific fusion proteins, or multivalent and multispecific fusion proteins.

The disclosure also provides multivalent and multispecific fusion polypeptides that bind at least programmed death ligand 1 (PDL1), also known as PD-L1, CD274, B7 homolog 1 and/or B7-H1. The use of the term "PDL1" is intended to cover any variation thereof, such as, by way of non-limiting example, PD-L1 and/or PDL-1, all variations are used herein interchangeably. These molecules that bind at least PDL1 are referred to herein as "PDL1-targeting molecules" or "PDL1-targeting fusions" or "PDL1-targeting proteins" or "PDL1-targeting fusion polypeptides" or "PDL1-targeting fusion proteins." In some embodiments, the PDL1-targeting molecule is a multivalent molecule, for example, a multivalent PDL1-targeting fusion protein. In some embodiments, the PDL1-targeting molecule is a multispecific molecule, for example, a multispecific PDL1-targeting fusion protein. In some embodiments, the PDL1-targeting molecule is a multivalent and multispecific molecule, for example, a multivalent and multispecific PDL1-targeting fusion protein. As used herein, the term "fusion protein" or "fusion polypeptide" or "PDL1-targeting fusion protein" or "PDL1-targeting fusion polypeptide," unless otherwise specifically denoted, refers to any fusion protein embodiment of the disclosure, including, but not limited to, multivalent fusion proteins, multispecific fusion proteins, or multivalent and multispecific fusion proteins.

The disclosure also provides multivalent and multispecific fusion polypeptides that bind at least PDL1 and 41BB. These molecules that bind at least PDL1 are referred to herein as "PDL1×41BB-targeting molecules" or "PDL1×41BB-targeting fusions" or "PDL1×41BB-targeting proteins" or "PDL1×41BB-targeting fusion polypeptides" or "PDL1×41BB-targeting fusion proteins." In some embodiments, the PDL1×41BB-targeting molecule is a multivalent molecule, for example, a multivalent PDL1×41BB-targeting fusion protein. In some embodiments, the PDL1×41BB-targeting molecule is a multispecific molecule, for example, a multispecific PDL1×41BB-targeting fusion protein. In some embodiments, the PDL1×41BB-targeting molecule is a multivalent and multispecific molecule, for example, a multivalent and multispecific PDL1-targeting fusion protein. As used herein, the term "fusion protein" or "fusion polypeptide" or "PDL1×41BB-targeting fusion protein" or "PDL1×41BB-targeting fusion polypeptide," unless otherwise specifically denoted, refers to any fusion protein embodiment of the disclosure, including, but not limited to, multivalent fusion proteins, multispecific fusion proteins, or multivalent and multispecific fusion proteins.

In some embodiments, the multivalent and/or multispecific fusion protein binds at least 41BB. Conventional antibodies targeting members of the TNF receptor superfamily (TNFRSF) have been shown to require exogenous crosslinking to achieve sufficient agonist activity, as evidenced by the necessity for Fc-gamma Receptor (FcγRs) for the activity of antibodies to DR4, DR5, GITR and OX40 (Ichikawa et al 2001 al Nat. Med. 7, 954-960, Li et al 2008 Drug Dev. Res. 69, 69-82; Pukac et al 2005 Br. J. Cancer 92, 1430-1441; Yanda et al 2008 Ann. Oncol. 19, 1060-1067; Yang et al 2007 Cancer Lett. 251:146-157; Bulliard et al 2013 JEM 210(9): 1685; Bulliard et al 2014 Immunol and Cell Biol 92: 475-480). In addition to crosslinking via FcγRs other exogenous agents including addition of the oligomeric ligand or antibody binding entities (e.g. protein A and secondary antibodies) have been demonstrated to enhance anti-TN- FRSF antibody clustering and downstream signaling. For example, the addition of the DR5 ligand TRAIL enhanced the apoptosis inducing ability of an anti-DR5 antibody (Graves et al 2014 Cancer Cell 26: 177-189). These findings suggest the need for clustering of TNFRSFs beyond a dimer.

The present disclosure provides multivalent TNFRSF binding fusion proteins, which comprise 2 or more TNFRSF binding domains (TBDs) where at least one TBD binds 41BB. In some embodiments, the fusion proteins of the present disclosure have utility in treating neoplasms.

In some embodiments, the fusion protein contains two or more different TBDs, where each TBD binds 41BB. In some embodiments, the fusion protein contains multiple copies of a TBD that binds 41BB. For example, in some embodiments, the fusion protein contains at least two copies of a TBD that binds 41BB. In some embodiments, the fusion protein contains at least three copies of a TBD that binds 41BB. In some embodiments, the fusion protein contains at least four copies of a TBD that binds 41BB. In some embodiments, the fusion protein contains at least five copies of a TBD that binds 41BB. In some embodiments, the fusion protein contains at least six copies of a TBD that binds 41BB. In some embodiments, the fusion protein contains six or more copies of a TBD that binds 41BB.

In other embodiments, the fusion proteins of the present disclosure bind 41BB and a second TNFRSF member for example GITR, OX40, CD27, TNFR2 and/or CD40. In these embodiments, the fusion proteins of the present disclosure modulate immune cells leading to enhanced tumor destruction. In other embodiments, the fusion proteins of the present disclosure have utility in treating inflammatory conditions. In these embodiments, the fusion proteins of the present disclosure modulate immune cells leading to dampening of the inflammatory insult. For example, specifically agonizing TNFR2 can enhance Treg proliferation leading to immune suppression.

The fusion proteins of the present disclosure are capable of enhanced clustering of TNFRSF members compared to non-cross-linked bivalent antibodies. The enhanced clustered of TNFRSF members mediated by the fusion proteins of the present disclosure induce enhanced TNFRSF-dependent signaling compared to non-cross-linked bivalent antibodies. In most embodiments, the fusion protein will incorporate more than 2 TBDs, for example, three, four, five, or six.

In some embodiments, the fusion proteins are multispecific containing a TBD and a binding domain directed toward a second antigen. In these, embodiments, the binding to the second antigen is capable of providing the additional crosslinking function and TNFRSF activation can be achieved with only one or two TBDs. In these embodiments, the TNFRSF signaling is enhanced and focused by the presence of the second antigen. These multispecific TBD containing fusion proteins are useful means to achieve conditional signaling of a given TNFRSF member.

In these embodiments, binding to the TNFRSF member by the TBD induces minimal signaling unless the second antigen is co-engaged. For example, the multispecific fusion proteins of the present disclosure are capable binding 41BB and PD-L1 and 41BB-dependent signaling is greatly enhanced when the fusion protein is bound to a PD-L1 expressing cell. In another example, the multispecific fusion proteins of the present disclosure are capable binding 41BB and Folate Receptor Alpha (FRα) and 41BB-dependent signaling is greatly enhanced when the fusion protein is bound to a FRα expressing cell.

The present disclosure provides isolated polypeptides that specifically bind 41BB. In some embodiments, the isolated polypeptide is derived from antibodies or antibody fragments including scFv, Fabs, single domain antibodies (sdAb), $V_{NAR}$, or VHHs. In some embodiments, the isolated polypeptide is human or humanized sdAb. The sdAb fragments can be derived from VHH, $V_{NAR}$, engineered VH or VK domains. VHHs can be generated from camelid heavy chain only antibodies. $V_{NARS}$ can be generated from cartilaginous fish heavy chain only antibodies. Various methods have been implemented to generate monomeric sdAbs from conventionally heterodimeric VH and VK domains, including interface engineering and selection of specific germline families. In other embodiments, the isolated polypeptides are derived from non-antibody scaffold proteins for example but not limited to designed ankyrin repeat proteins (darpins), avimers, anticalin/lipocalins, centyrins and fynomers.

In some embodiments, the isolated polypeptide includes an amino acid sequence selected from the group consisting of SEQ ID NO: 16, 20, 23, 25, 29, 33, 39, 33-41, 43, 45-47, 49, 51, 53, 54, 56, 58-60, 62, 65, 66, 68, 70, 72, 74, 76, 78, and 80-83. In some embodiments, the isolated polypeptide includes an amino acid sequence selected from the group consisting of SEQ ID NO: 33, 39, 33-41, 43, 45-47, 49, 51, 53, 54, 56, 58-60, 62, 65, 66, 68, 70, 72, 74, 76, 78, and 80-83.

In some embodiments, the isolated polypeptide includes an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 16, 20, 23, 25, 29, 33, 39, 33-41, 43, 45-47, 49, 51, 53, 54, 56, 58-60, 62, 65, 66, 68, 70, 72, 74, 76, 78, and 80-83. In some embodiments, the isolated polypeptide includes an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 33, 39, 33-41, 43, 45-47, 49, 51, 53, 54, 56, 58-60, 62, 65, 66, 68, 70, 72, 74, 76, 78, and 80-83.

In some embodiments, the isolated polypeptide comprises a complementarity determining region 1 (CDR1) comprising an amino acid sequence selected from the group consisting of SEQ ID NO: 17, 21, 26, 30, 50, 65, and 69; a complementarity determining region 2 (CDR2) comprising an amino acid sequence selected from the group consisting of SEQ ID NO: 18, 27, 31, 42, 44, 48, 52, 61, 63, 71, 73, 75, 77, and 79; and a complementarity determining region 3 (CDR3) comprising an amino acid sequence selected from the group consisting of SEQ ID NO: 19, 22, 24, 28, 32, 55, and 57.

The present disclosure provides multivalent fusion proteins, which comprise two or more binding domains (BDs) where at least one BD binds PDL1. In some embodiments, the fusion proteins of the present disclosure have utility in treating neoplasms.

In some embodiments, the fusion protein contains two or more different BDs, where each BD binds PDL1. In some embodiments, the fusion protein contains multiple copies of a BD that binds PDL1. For example, in some embodiments, the fusion protein contains at least two copies of a BD that binds PDL1. In some embodiments, the fusion protein contains at least three copies of a BD that binds PDL1. In some embodiments, the fusion protein contains at least four copies of a BD that binds PDL1. In some embodiments, the fusion protein contains at least five copies of a BD that binds PDL1. In some embodiments, the fusion protein contains at least six copies of a BD that binds PDL1. In some embodiments, the fusion protein contains six or more copies of a BD that binds PDL1.

The present disclosure provides isolated polypeptides that specifically bind 41BB. In some embodiments, the isolated polypeptide is derived from antibodies or antibody fragments including scFv, Fabs, single domain antibodies (sdAb), $V_{NAR}$, or VHHs. In some embodiments, the isolated polypeptide is human or humanized sdAb. The sdAb fragments can be derived from VI-1H, $V_{NAR}$, engineered VH or VK domains. VHHs can be generated from camelid heavy chain only antibodies. $V_{NARS}$ can be generated from cartilaginous fish heavy chain only antibodies. Various methods have been implemented to generate monomeric sdAbs from conventionally heterodimeric VH and VK domains, including interface engineering and selection of specific germline families. In other embodiments, the isolated polypeptides are derived from non-antibody scaffold proteins for example but not limited to designed ankyrin repeat proteins (darpins), avimers, anticalin/lipocalins, centyrins and fynomers.

In some embodiments, the isolated polypeptide includes an amino acid sequence selected from the group consisting of SEQ ID NO: 100, 104, 108, 112, 114, 116, and 119-124. In some embodiments, the isolated polypeptide includes an amino acid sequence selected from the group consisting of SEQ ID NO: 119-124.

In some embodiments, the isolated polypeptide includes an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 100, 104, 108, 112, 114, 116, and 119-124. In some embodiments, the isolated polypeptide includes an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 119-124.

In some embodiments, the isolated polypeptide comprises a complementarity determining region 1 (CDR1) comprising an amino acid sequence selected from the group consisting of SEQ ID NO: 101, 105, and 109; a complementarity determining region 2 (CDR2) comprising an amino acid sequence selected from the group consisting of SEQ ID NO: 102, 106, 110, and 117; and a complementarity determining region 3 (CDR3) comprising an amino acid sequence selected from the group consisting of SEQ ID NO: 103, 107, 111, 113, 115, and 118.

In some embodiments, the present disclosure provides isolated polypeptides that specifically bind at least 41BB and PDL1. In some embodiments, each binding domain (BD) in the isolated polypeptide is derived from antibodies or antibody fragments including scFv, Fabs, single domain antibodies (sdAb), $V_{NAR}$, or VHHs. In some embodiments, each BD is human or humanized sdAb. The sdAb fragments can be derived from VHH, $V_{NAR}$, engineered VH or VK domains. VHHs can be generated from camelid heavy chain only antibodies. $V_{NARS}$ can be generated from cartilaginous fish heavy chain only antibodies. Various methods have been implemented to generate monomeric sdAbs from conventionally heterodimeric VH and VK domains, including interface engineering and selection of specific germline families. In other embodiments, the isolated polypeptides are derived from non-antibody scaffold proteins for example but not limited to designed ankyrin repeat proteins (darpins), avimers, anticalin/lipocalins, centyrins and fynomers.

In some embodiments, the isolated polypeptide includes a first amino acid sequence that binds 4B11 selected from the group consisting of SEQ ID NO: 16, 20, 23, 25, 29, 33, 39, 33-41, 43, 45-47, 49, 51, 53, 54, 56, 58-60, 62, 65, 66, 68, 70, 72, 74, 76, 78, and 80-83, and a second amino acid sequence that binds PDL1 selected from the group consisting of SEQ ID NO: 100, 104, 108, 112, 114, 116, and 119-124.

In some embodiments, the isolated polypeptide includes a first amino acid sequence that binds 4B11 selected from the group consisting of SEQ ID NO: 33, 39, 33-41, 43, 49, 51, 53, 54, 56, 58-60, 62, 65, 66, 68, 70, 72, 74, 76, 78, and 80-83, and a second amino acid sequence that binds PDL1 selected from the group consisting of SEQ ID NO: 119-124.

In some embodiments, the isolated polypeptide includes a first amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence that binds 4B11 selected from the group consisting of SEQ ID NO: 16, 20, 23, 25, 29, 33, 39, 33-41, 43, 45-47, 49, 51, 53, 54, 56, 58-60, 62, 65, 66, 68, 70, 72, 74, 76, 78, and 80-83, and a second amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence that binds PDL1 selected from the group consisting of SEQ ID NO: 100, 104, 108, 112, 114, 116, and 119-124.

In some embodiments, the isolated polypeptide includes a first amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence that binds 4B11 selected from the group consisting of SEQ ID NO: 33, 39, 33-41, 43, 45-47, 49, 51, 53, 54, 56, 58-60, 62, 66, 68, 70, 72, 74, 76, 78, and 80-83, and a second amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence that binds PDL1 selected from the group consisting of SEQ ID NO: 119-124.

In some embodiments, the isolated polypeptide includes (i) a first amino acid sequence that binds 4B11 and comprises a complementarity determining region 1 (CDR1) comprising an amino acid sequence selected from the group consisting of SEQ ID NO: 17, 21, 26, 30, 50, 65, and 69; a complementarity determining region 2 (CDR2) comprising an amino acid sequence selected from the group consisting of SEQ ID NO: 18, 27, 31, 42, 44, 48, 52, 61, 63, 71, 73, 75, 77, and 79; and a complementarity determining region 3 (CDR3) comprising an amino acid sequence selected from the group consisting of SEQ ID NO: 19, 22, 24, 28, 32, 55, and 57; and (ii) a second amino acid sequence that binds PDL1 and comprises a CDR1 comprising an amino acid sequence selected from the group consisting of SEQ ID NO: 101, 105, and 109; a CDR2 comprising an amino acid sequence selected from the group consisting of SEQ ID NO: 102, 106, 110, and 117; and a CDR3 comprising an amino acid sequence selected from the group consisting of SEQ ID NO: 103, 107, 111, 113, 115, and 118.

In some embodiments, the binding domains (BDs) of the present disclosure, e.g., the 41BB-binding domains and/or the PDL1-binding domains, are derived from antibodies or antibody fragments including scFv, Fabs, single domain antibodies (sdAb), $V_{NAR}$, or VHHs. In some embodiments, the BDs are human or humanized sdAb. The sdAb fragments, can be derived from VHH, $V_{NAR}$, engineered VH or VK domains. VHHs can be generated from camelid heavy chain only antibodies. $V_{NARS}$ can be generated from cartilaginous fish heavy chain only antibodies. Various methods have been implemented to generate monomeric sdAbs from conventionally heterodimeric VH and VK domains, including interface engineering and selection of specific germline families. In other embodiments, the BDs are derived from non-antibody scaffold proteins for example but not limited to designed ankyrin repeat proteins (darpins), avimer, anticalin/lipocalins, centyrins and fynomers.

Generally, the fusion proteins of the present disclosure consist of at least two or more BDs operably linked via a linker polypeptide. The utilization of sdAb fragments as the specific BD within the fusion the present disclosure has the benefit of avoiding the heavy chain: light chain mis-pairing problem common to many bi/multispecific antibody approaches. In addition, the fusion proteins of the present disclosure avoid the use of long linkers necessitated by many bispecific antibodies.

In some embodiments, all of the BDs of the fusion protein are TBDs that recognize the same epitope on the given TNFRSF member. For example, the fusion proteins of present disclosure may incorporate 2, 3, 4, 5, or 6 TBDs with identical specificity to 41BB. In other embodiments, the fusion protein incorporates TBDs that recognize distinct epitopes on the given TNFRSF member. For example, the fusion proteins of present disclosure may incorporate 2, 3, 4, 5, or 6 TBDs with distinct recognition specificities toward various epitopes on 41BB. In these embodiments, the fusion proteins of the present disclosure contain multiple TBDs that target distinct regions of the particular TNFRSF member. In some embodiments, the TBDs may recognize different epitopes on the same TNFRSF member or recognize epitopes on distinct TNFRSF members. For example, the present disclosure provides multispecific fusion proteins incorporating TBDs that bind GITR and 41BB or OX40 and 41BB, or CD27 and 41BB.

In some embodiments, the multispecific fusion protein is a bispecific molecule that targets 41BB and PDL1. In some embodiments, the bispecific fusion protein includes a 41BB-targeting binding domain selected from the group consisting of SEQ ID NO: 16, 20, 23, 29, 33, 39, 33-41, 43, 45-47, 49, 51, 53, 54, 56, 58-60, 62, 65, 66, 68, 70, 72, 74, 76, 78, and operably linked to a second binding domain (BD2) that binds PDL1. In some embodiments, the BD2 comprises an amino acid sequence that specifically binds PDL1. In some embodiments, the BD2 comprises a PDL1-targeting domain selected from the group consisting of SEQ ID NO: 100, 104, 108, 112, 114, 116, and 119-124. some embodiments, the BD2 comprises a PDL1-targeting domain selected from the group consisting of SEQ ID NO: 119-124. In some embodiments, the BD2 comprises an amino acid sequence that specifically binds PDL1 and is selected from the group consisting of SEQ ID NO: 126-408.

In some embodiments, the multispecific fusion protein is a bispecific molecule that targets 41BB and PDL1. In some embodiments, the bispecific fusion protein includes a 41BB-targeting binding domain selected from the group consisting of SEQ ID NO: 33-41, 43, 49, 51, 53, 54, 56, 58-60, 62, 65, 66, 68, 70, 72, 74, 76, 78, and 80-83, operably linked to a second binding domain (BD2) that binds PDL1. In some embodiments, the BD2 comprises an amino acid sequence that specifically binds PDL1. In some embodiments, the BD2 comprises a PDL1-targeting domain selected from the group consisting of SEQ ID NO: 100, 104, 108, 112, 114, 116, and 119-124. In some embodiments, the BD2 comprises a PDL1-targeting domain selected from the group consisting of SEQ ID NO: 119-124. In some embodiments, the BD2 comprises an amino acid sequence that specifically binds PDL1 and is selected from the group consisting of SEQ ID NO: 126-408.

In some embodiments, the multispecific fusion protein is a bispecific molecule that targets 41BB and PDL1. In some embodiments, the bispecific fusion protein includes a PDL1-targeting binding domain selected from the group consisting of SEQ ID NO: 100, 104, 108, 112, 114, 116, and 119-124, operably linked to a second TBD (TBD2) that binds 41BB. In some embodiments, the TBD2 comprises an amino acid sequence that specifically binds 41BB. In some embodiments, the TBD2 comprises a 41BB-targeting domain selected from the group consisting of SEQ ID NO: 16, 20, 23, 25, 29, 33, 39, 33-41, 43, 45-47, 49, 51, 53, 54, 56, 58-60, 62, 65, 66, 68, 70, 72, 74, 76, 78, and 80-83. In some embodiments, the TBD2 comprises an amino acid sequence that specifically binds 41BB and is selected from the group consisting of SEQ ID NO: 84-99.

In some embodiments, the multispecific fusion protein is a bispecific molecule that targets 41BB and PDL1. In some embodiments, the bispecific fusion protein includes a PDL1-targeting binding domain selected from the group consisting of SEQ ID NO: 119-124, operably linked to a second TBD (TBD2) that binds 41BB. In some embodiments, the TBD2 comprises an amino acid sequence that specifically binds 41BB. In some embodiments, the TBD2 comprises a 41BB-targeting domain selected from the group consisting of SEQ ID NO: 33, 39, 33-41, 43, 45-47, 49, 51, 53, 54, 56, 58-60, 62, 65, 66, 68, 70, 72, 74, 76, 78, and 80-83. In some embodiments, the TBD2 comprises an amino acid sequence that specifically binds 41BB and is selected from the group consisting of SEQ ID NO: 84-99.

In some embodiments, the multispecific fusion protein is a bispecific molecule that targets 41BB and PDL1 and comprises an amino acid sequence that is selected from the group consisting of SEQ ID NO: 448-456.

In some embodiments, the multispecific fusion protein is a bispecific molecule that targets 41BB and PDL1 and comprises an amino acid sequence that is at least 50%, 60%, 65%, 70%, 75%, 80%, 85%, 90%, 91%, 92%, 93%, 94%, 95%, 96%, 97%, 98%, or 99% identical to an amino acid sequence selected from the group consisting of SEQ ID NO: 448-456.

In some embodiments, all of the BDs of the fusion protein recognize the same epitope on PDL1. For example, the fusion proteins of present disclosure may incorporate 2, 3, 4, or 6 BDs with identical specificity to PDL1. In other embodiments, the fusion protein incorporates BDs that recognize distinct epitopes on PDL1. For example, the fusion proteins of present disclosure may incorporate 2, 3, 4, 5, or 6 BDs with distinct recognition specificities toward various epitopes on PDL1. In these embodiments, the fusion proteins of the present disclosure contain multiple BDs that target distinct regions of the PDL1. In some embodiments, the BDs may recognize different epitopes on PDL1.

In some embodiments, the fusion protein of the present disclosure is composed of a single polypeptide. In other embodiments, the fusion protein of the present disclosure is composed of more than one polypeptide. For example, wherein a heterodimerization domain is incorporated into the fusion protein so as the construct an asymmetric fusion protein. For example, if an immunoglobulin Fc region is incorporated into the fusion protein the CH3 domain can be used as a homodimerization domain, or the CH3 dimer interface region can be mutated so as to enable heterodimerization.

In some embodiments, the fusion protein contains the BDs opposite ends. For example, the BDs are located on both the amino-terminal (N-terminal) portion of the fusion protein and the carboxy-terminal (C-terminal) portion of the fusion protein. In other embodiments, all the TBDs reside on the same end of the fusion protein. For example, BDs reside on either the amino- or carboxy-terminal portions of the fusion protein.

In some embodiments, the linker polypeptide contains an immunoglobulin Fc region. In some embodiments, the immunoglobulin Fc region is an IgG isotype selected from the group consisting of IgG1 subclass, IgG2 subclass, IgG3 subclass, and IgG4 subclass.

In some embodiments, the immunoglobulin Fc region or immunologically active fragment thereof is an IgG isotype. For example, the immunoglobulin Fc region of the fusion protein is of human IgG1 subclass, having an amino acid sequence:

```
                                          (SEQ ID NO: 1)
PAPELLGGPS    VFLFPPKPKD   TLMISRTPEV   TCVVVDVSHE

DPEVKFNWYV    DGVEVHNAKT   KPREEQYNST   YRVVSVLTVL

HQDWLNGKEY    KCKVSNKALP   APIEKTISKA   KGQPREPQVY

TLPPSRDELT    KNQVSLTCLV   KGFYPSDIAV   EWESNGQPEN

NYKTTPPVLD    SDGSFFLYSK   LTVDKSRWQQ   GNVFSCSVMH

EALHNHYTQK    SLSLSPGK
```

In some embodiments, the immunoglobulin Fc region or immunologically active fragment thereof comprises a human IgG1 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 1.

In some embodiments, the human IgG1 Fc region is modified at amino acid Asn297 (Boxed in SEQ ID NOs: 1-4, Kabat Numbering) to prevent to glycosylation of the fusion protein, e.g., Asn297Ala (N297A) or Asn297Asp (N297D). In some embodiments, the Fc region of the fusion protein is modified at amino acid Leu235 (Bold in SEQ ID NO: 1, Kabat Numbering) to alter Fc receptor interactions, e.g., Leu235Glu (L235E) or Leu235Ala (L235A). In some embodiments, the Fc region of the fusion protein is modified at amino acid Leu234 (Bold in SEQ ID NO: 1, Kabat Numbering) to alter Fc receptor interactions, e.g., Leu234Ala (L234A). In some embodiments, the Fc region of the fusion protein is modified at amino acid Leu234 (Boxed, Kabat Numbering) to alter Fc receptor interactions, e.g., Leu235Glu (L235E). In some embodiments, the Fc region of the fusion protein is altered at both amino acid 234 and 235, e.g., Leu234Ala and Leu235Ala (L234A/L235A) or Leu234Val and Leu235Ala (L234V/L235A). In some embodiments, the Fc region of the fusion protein is lacking an amino acid at one or more of the following positions to reduce Fc receptor binding: Glu233 (E233, Bold in SEQ ID NO: 1), Leu234 (L234), or Leu235 (L235). In some embodiments, the Fc region of the fusion protein is altered at Gly235 to reduce Fc receptor binding. For example, wherein Gly235 is deleted from the fusion protein. In some embodiments, the human IgG1 Fc region is modified at amino acid Gly236 (Boxed in SEQ ID NO: 1) to enhance the interaction with CD32A, e.g., Gly236Ala (G236A). In some embodiments, the human IgG1 Fc region lacks Lys447 (EU index of Kabat et al 1991 Sequences of Proteins of Immunological Interest).

In some embodiments, the Fc region of the fusion protein is altered at one or more of the following positions to reduce Fc receptor binding: Leu 234 (L234), Leu235 (L235), Asp265 (D265), Asp270 (D270), Ser298 (S298), Asn297 (N297), Asn325 (N325) or Ala327 (A327). For example, Leu 234Ala (L234A), Leu235Ala (L235A), Asp265Asn (D265N), Asp270Asn (D270N), Ser298Asn (S298N), Asn297Ala (N297A), Asn325Glu (N325E) or Ala327Ser (A327S). In preferred embodiments, modifications within the Fc region reduce binding to Fc-receptor-gamma receptors while have minimal impact on binding to the neonatal Fc receptor (FcRn).

In some embodiments, the Fc region of the fusion protein is lacking an amino acid at one or more of the following positions to reduce Fc receptor binding: Glu233 (E233), Leu234 (L234), or Leu235 (L235). In these embodiments, Fc deletion of these three amino acids reduces the complement protein C1q binding. These modified Fc region polypeptides are referred to herein as "Fc deletion" polypeptides.

```
                                          (SEQ ID NO: 2)
PAPGGPSVFL   FPPKPKDTLM   ISRTPEVTCV   VVDVSHEDPE

VKFNWYVDGV   EVHNAKTKPR   EEQYNSTYRV   VSVLTVLHQD

WLNGKEYKCK   VSNKALPAPI   EKTISKAKGQ   PREPQVYTLP

PSRDELTKNQ   VSLTCLVKGF   YPSDIAVEWE   SNGQPENNYK

TTPPVLDSDG   SFFLYSKLTV   DKSRWQQGNV   FSCSVMHEAL

HNHYTQKSLS   LSPGK
```

In some embodiments, the immunoglobulin Fc region or immunologically active fragment thereof comprises a human IgG1 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 2.

In some embodiments, the immunoglobulin Fc region or immunologically active fragment of the fusion protein is of human IgG2 subclass, having an amino acid sequence:

```
                                          (SEQ ID NO: 3)
PAPPVAGPSV   FLFPPKPKDT   LMISRTPEVT   CVVVDVSHED

PEVQFNWYVD   GVEVHNAKTK   PREEQFNSTF   RVVSVLTVVH

QDWLNGKEYK   CKVSNKGLPA   PIEKTISKTK   GQPREPQVYT

LPPSREEMTK   NQVSLTCLVK   GFYPSDISVE   WESNGQPENN

YKTTPPMLDS   DGSFFLYSKL   TVDKSRWQQG   NVFSCSVMHE

ALHNHYTQKS   LSLSPGK
```

In some embodiments, the fusion or immunologically active fragment thereof comprises a human IgG2 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 3.

In some embodiments, the human IgG2 Fc region is modified at amino acid Asn297 (Boxed in SEQ ID NOs: 1, 3, 4, and 5), to prevent to glycosylation of the antibody, e.g., Asn297Ala (N297A). In some embodiments, the human IgG2 Fc region lacks Lys447, which corresponds to residue 217 of SEQ ID NO: 3 (EU index of Kabat et al 1991 Sequences of Proteins of Immunological Interest).

In some embodiments, the immunoglobulin Fc region or immunologically active fragment of the fusion protein is of human IgG3 subclass, having an amino acid sequence:

(SEQ ID NO: 4)

```
PAPELLGGPS    VFLFPPKPKD    TLMISRTPEV    TCVVVDVSHE
DPEVQFKWYV    DGVEVHNAKT    KPREEQYNST    FRVVSVLTVL
HQDWLNGKEY    KCKVSNKALP    APIEKTISKT    KGQPREPQVY
TLPPSREEMT    KNQVSLTCLV    KGFYPSDIAV    EWESSGQPEN
NYNTTPPMLD    SDGSFFLYSK    LTVDKSRWQQ    GNIFSCSVMH
EALHNRFTQK    SLSLSPGK
```

In some embodiments, the antibody or immunologically active fragment thereof comprises a human IgG3 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 4.

In some embodiments, the human IgG3 Fc region is modified at amino acid Asn297 (Boxed in SEQ ID NOs: 1-4, Kabat Numbering) to prevent to glycosylation of the antibody, e.g., Asn297Ala (N297A). In some embodiments, the human IgG3 Fc region is modified at amino acid 435 to extend the half-life, e.g., Arg435His (R435H, Boxed in SEQ ID NO: 3). In some embodiments, the human IgG3 Fc region lacks Lys447, which corresponds to residue 218 of SEQ ID NO: 4 (EU index of Kabat et al 1991 Sequences of Proteins of Immunological Interest).

In some embodiments, the immunoglobulin Fc region or immunologically active fragment of the fusion protein is of human IgG4 subclass, having an amino acid sequence:

(SEQ ID NO: 5)

```
PAPEFLGGPS    VFLFPPKPKD    TLMISRTPEV    TCVVVDVSQE
DPEVQFNWYV    DGVEVHNAKT    KPREEQFNST    YRVVSVLTVL
HQDWLNGKEY    KCKVSNKGLP    SSIEKTISKA    KGQPREPQVY
TLPPSQEEMT    KNQVSLTCLV    KGFYPSDIAV    EWESNGQPEN
NYKTTPPVLD    SDGSFFLYSR    LTVDKSRWQE    GNVFSCSVMH
EALHNHYTQK    SLSLSLGK
```

In some embodiments, the antibody or immunologically active fragment thereof comprises a human IgG4 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 5.

In other embodiments, the human IgG4 Fc region is modified at amino acid 235 to alter Fc receptor interactions, e.g., Leu235Glu (L235E). In some embodiments, the human IgG4 Fc region is modified at amino acid Asn297 (Boxed in SEQ ID NOs: 1-4, Kabat Numbering) to prevent to glycosylation of the antibody, e.g., Asn297Ala (N297A). In some embodiments, the human IgG4 Fc region lacks Lys447, which corresponds to residue 218 of SEQ ID NO: 5 (EU index of Kabat et al 1991 Sequences of Proteins of Immunological Interest).

In some embodiments, the immunoglobulin Fc region or immunologically active fragment of the fusion protein is of human IgG4 isotype, having an amino acid sequence:

(SEQ ID NO: 6)

```
PAPELLGGPS    VFLFPPKPKD    TLMISRTPEV    TCVVVDVSQE
DPEVQFNWYV    DGVEVHNAKT    KPREEQFNST    YRVVSVLTVL
HQDWLNGKEY    KCKVSNKGLP    SSIEKTISKA    KGQPREPQVY
TLPPSQEEMT    KNQVSLTCLV    KGFYPSDIAV    EWESNGQPEN
NYKTTPPVLD    SDGSFFLYSR    LTVDKSRWQE    GNVFSCSVMH
EALHNHYTQK    SLSLSLGK
```

In some embodiments, the antibody or immunologically active fragment thereof comprises a human IgG4 polypeptide sequence that is at least 50%, 60%, 65%, 70%, 75%, 80%, 85%, 90%, 91%, 92%, 93%, 94%, 95%, 96%, 97%, 98%, or 99% identical to the amino acid sequence of SEQ ID NO: 6.

In some embodiments, the human IgG Fc region is modified to enhance FcRn binding. Examples of Fc mutations that enhance binding to FcRn are Met252Tyr, Ser254Thr, Thr256Glu (M252Y, S254T, T256E, respectively) (Kabat numbering, Dall'Acqua et al 2006, J. Biol Chem Vol. 281(33) 23514-23524), Met428Leu and Asn434Ser (M428L, N434S) (Zalevsky et al 2010 Nature Biotech, Vol. 28(2) 157-159), or Met252Ile, Thr256Asp, Met428Leu (M252I, T256D, M428L, respectively), (EU index of Kabat et al 1991 Sequences of Proteins of Immunological Interest). Met252 corresponds to residue 23 in SEQ ID NOs: 1, 4, and 5 and residue 22 in SEQ ID NO: 3. Ser254 corresponds to corresponds to residue 25 in SEQ ID NOs: 1, 4, and 5 and residue 24 in SEQ ID NO: 3. Thr256 corresponds to residue 27 in SEQ ID NOs: 1, 4, and 5 and residue 26 in SEQ ID NO: 3. Met428 corresponds to residue 199 in SEQ ID NOs: 1, 4, and 5 and residue 198 in SEQ ID NO: 3. Asn434 corresponds to residue 205 in SEQ ID NOs: 1, 4, and 5 and residue 204 in SEQ ID NO: 3. In some embodiments where the fusion protein of the disclosure includes an Fc polypeptide, the Fc polypeptide is mutated or modified. In these embodiments, the mutated or modified Fc polypeptide includes the following mutations: Met252Tyr and Met428Leu (M252Y, M428L) using the Kabat numbering system.

In some embodiments, the human IgG Fc region is modified to alter antibody-dependent cellular cytotoxicity (ADCC) and/or complement-dependent cytotoxicity (CDC), e.g., the amino acid modifications described in Natsume et al., 2008 Cancer Res, 68(10): 3863-72; Idusogie et al., 2001 J Immunol, 166(4): 2571-5; Moore et al., 2010 mAbs, 2(2): 181-189; Lazar et al., 2006 PNAS, 103(11): 4005-4010, Shields et al., 2001 JBC, 276(9): 6591-6604; Stavenhagen et al., 2007 Cancer Res, 67(18): 8882-8890; Stavenhagen et al., 2008 Advan. Enzyme Regul., 48: 152-164; Alegre et al, 1992 J Immunol, 148: 3461-3468; Reviewed in Kaneko and Niwa, 2011 Biodrugs, 25(1):1-11. Examples of mutations that enhance ADCC include modification at Ser239 and Ile332, for example Ser239Asp and Ile332Glu (S239D, I332E). Examples of mutations that enhance CDC include modifications at Lys326, which corresponds to residue 97 of SEQ ID NOs: 1, 4, and 5 and residue 96 of SEQ ID NO: 2, and Glu333, which corresponds to residue 104 of SEQ ID NOs: 1, 4, and 5 and residue 103 of SEQ ID NO: 3. In some embodiments the Fc region is modified at one or both of these positions, for example Lys326Ala and/or Glu333Ala (K326A and E333A).

In some embodiments, the human IgG Fc region is modified to induce heterodimerization. For example, having an amino acid modification within the CH3 domain at Thr366, which when replaced with a more bulky amino acid, e.g., Trp (T366W), is able to preferentially pair with a second CH3 domain having amino acid modifications to less bulky amino acids at positions Thr366, which corresponds to residue 137 of SEQ ID NOs: 1, 4, and 5 and residue 136 of SEQ ID NO: 3, Leu368, which corresponds to residue 139 of SEQ ID NOs: 1, 4, and 5 and residue 138 of SEQ ID NO: 2, and Tyr407, which corresponds to residue 178 of SEQ ID NOs: 1, 4, and 5 and residue 177 of SEQ ID NO: 3, e.g., Ser, Ala and Val, respectively (T366S/L368A/Y407V). Heterodimerization via CH3 modifications can be further stabilized by the introduction of a disulfide bond, for example by changing Ser354, which corresponds to residue 125 of SEQ ID NOs: 1, 4, and 5 and residue 124 of SEQ ID NO: 3, to Cys (S354C) and Tyr349, which corresponds to residue 120 of SEQ ID NOs: 1, 4, and 5 and residue 119 of SEQ ID NO: 3, to Cys (Y349C) on opposite CH3 domains (Reviewed in Carter, 2001 Journal of Immunological Methods, 248: 7-15). In some of these embodiments, the Fc region may be modified at the protein-A binding site on one member of the heterodimer so as to prevent protein-A binding and thereby enable more efficient purification of the heterodimeric fusion protein. An exemplary modification within this binding site is Ile253, which corresponds to residue 24 of SEQ ID NOs: 1, 4, and 5 and residue 23 of SEQ ID NO: 3, for example Ile253Arg (I253R). For example, the I253R modification may be combined with either the T366S/L368A/Y407V modifications or with the T366W modifications. The T366S/L368A/Y407V modified Fc is capable of forming homodimers as there is no steric occlusion of the dimerization interface as there is in the case of the T336W modified Fc. Therefore, in some embodiments, the I253R modification is combined with the T366S/L368A/Y407V modified Fc to disallow purification any homodimeric Fc that may have formed.

In some embodiments, the human IgG Fc region is modified to prevent dimerization. In these embodiments, the fusion proteins of the present disclosure are monomeric. For example, modification at residue Thr366 to a charged residue, e.g. Thr366Lys, Thr366Arg, Thr366Asp, or Thr366Glu (T366K, T366R, T366D, or T366E, respectively), prevents CH3-CH3 dimerization.

In some embodiments, the Fc region of the fusion protein is altered at one or more of the following positions to reduce Fc receptor binding: Leu 234 (L234), Leu235 (L235), Asp265 (D265), Asp270 (D270), Ser298 (S298), Asn297 (N297), Asn325 (N325) or Ala327 (A327). For example, Leu 234Ala (L234A), Leu235Ala (L235A), Asp265Asn (D265N), Asp270Asn (D270N), Ser298Asn (S298N), Asn297Ala (N297A), Asn325Glu (N325E) or Ala327Ser (A327S). In preferred embodiments, modifications within the Fc region reduce binding to Fc-receptor-gamma receptors while have minimal impact on binding to the neonatal Fc receptor (FcRn).

In some embodiments, the fusion protein contains a polypeptide derived from an immunoglobulin hinge region. The hinge region can be selected from any of the human IgG subclasses. For example, the fusion protein may contain a modified IgG1 hinge having the sequence of EPKSSDKTHTCPPC (SEQ ID NO: 7), where in the Cys220 that forms a disulfide with the C-terminal cysteine of the light chain is mutated to serine, e.g., Cys220Ser (C220S). In other embodiments, the fusion protein contains a truncated hinge having a sequence DKTHTCPPC (SEQ ID NO: 8).

In some embodiments, the fusion protein has a modified hinge from IgG4, which is modified to prevent or reduce strand exchange, e.g., Ser228Pro (S228P), having the sequence ESKYGPPCPPC (SEQ ID NO: 9). In some embodiments, the fusion protein contains one or more linker polypeptides. In other embodiments, the fusion protein contains linker and hinge polypeptides.

In some embodiments, the fusion proteins of the present disclosure lack or have reduced Fucose attached to the N-linked glycan-chain at N297. There are numerous ways to prevent fucosylation, including but not limited to production in a FUT8 deficient cell line; addition inhibitors to the mammalian cell culture media, for example Castanospermine, 2-deoxy-fucose, 2-flurofucose; the use of production cell lines with naturally reduced fucosylation pathways and metabolic engineering of the production cell line.

In some embodiments, the single domain antibody, VHH, or humanized single domain antibody, or human single domain antibody is engineered to eliminate recognition by pre-existing antibodies found in humans. In some embodiments, single domain antibodies of the present disclosure are modified by mutation of position Leu11, for example Leu11Glu (L11E) or Leu11Lys (L11K). In other embodiments, single domain antibodies of the present disclosure are modified by changes in carboxy-terminal region, for example the terminal sequence consists of GQGTLVTVKPGG (SEQ ID NO: 14) or GQGTLVTVEPGG (SEQ ID NO: 15) or modification thereof. In some embodiments, the single domain antibodies of the present disclosure are modified by mutation of position 11 and by changes in carboxy-terminal region.

In some embodiments, the BDs of the fusion proteins of the present disclosure are operably linked via amino acid linkers. In some embodiments, these linkers are composed predominately of the amino acids Glycine and Serine, denoted as GS-linkers herein. The GS-linkers of the fusion proteins of the present disclosure can be of various lengths, for example 5, 6, 7, 8, 9, 10, 11, 12, 13, 14, 15, 16, 17, 18, 19, 20 amino acids in length.

In some embodiments, the GS-linker comprises an amino acid sequence selected from the group consisting of GGSGGS, i.e., $(GGS)_2$ (SEQ ID NO: 10); GGSGGSGGS, i.e., $(GGS)_3$ (SEQ ID NO: 11); GGSGGSGGSGGS, i.e., $(GGS)_4$ (SEQ ID NO: 12); and GGSGGSGGSGGSGGS, i.e., $(GGS)_5$ (SEQ ID NO: 13).

In some embodiments, the multivalent binding fusion protein is tetravalent. In some embodiments, the tetravalent fusion protein has the following structure: BD-Linker-BD-Linker-Hinge-Fc. In some embodiments, the tetravalent fusion protein has the following structure: BD-Linker-Hinge-Fc-Linker-BD.

In some embodiments, the BD of the tetravalent fusion protein is a single domain antibody or VHH. In some embodiments, each BD of the tetravalent fusion protein is a single domain antibody or VHH. In some embodiments, the tetravalent fusion protein has the following structure: VHH-Linker-VHH-Linker-Hinge-Fc, where the VHH is a humanized or fully human VHH sequence. In some embodiments, the tetravalent fusion protein has the following structure: VHH-Linker-Hinge-Fc-Linker-VHH, where the VHH is a humanized or fully human VHH sequence.

In some embodiments, the multivalent TNFRSF binding fusion protein is tetravalent. In some embodiments, the tetravalent TNFRSF binding fusion protein has the following structure: TBD-Linker-TBD-Linker-Hinge-Fc. In some embodiments, the tetravalent TNFRSF binding fusion protein has the following structure: TBD-Linker-Hinge-Fc-Linker-TBD.

In some embodiments, the TBD of the tetravalent TNFRSF binding fusion protein is a single domain antibody or VHH. In some embodiments, each TBD of the multivalent TNFRSF binding fusion protein is single domain antibody or VHH. In some embodiments, the tetravalent TNFRSF binding fusion protein has the following structure: VHH-Linker-VHH-Linker-Hinge-Fc, where the VHH is a humanized or fully human VHH sequence. In some embodiments, the tetravalent TNFRSF binding fusion protein has the following structure: VHH-Linker-Hinge-Fc-Linker-VHH, where the VHH is a humanized or fully human VHH sequence.

In some embodiments, the GS-linker comprises an amino acid sequence selected from the group consisting of GGSGGS, i.e., $(GGS)_2$ (SEQ ID NO: 10); GGSGGSGGS, i.e., $(GGS)_3$ (SEQ ID NO: 11); GGSGGSGGSGGS, i.e., $(GGS)_4$ (SEQ ID NO: 12); and GGSGGSGGSGGSGGS, i.e., $(GGS)_5$ (SEQ ID NO: 13).

In some embodiments, the multivalent fusion protein is hexavalent. In some embodiments, the hexavalent fusion protein has the following structure: BD-Linker-TBD-Linker-BD-Linker-Hinge-Fc. In some embodiments, the hexavalent fusion protein has the following structure: BD-Linker-BD-Linker-Hinge-Fc-Linker-BD, or BD-Linker-Hinge-Fc-Linker-BD-Linker-BD.

In some embodiments, the BD of the hexavalent fusion protein is a single domain antibody or VHH. In some embodiments, each BD of the hexavalent fusion protein is a single domain antibody or VHH. In some embodiments, the hexavalent fusion protein has the following structure: VHH-Linker-VHH-Linker-VHH-Linker-Hinge-Fc, where the VHH is a humanized or fully human VHH sequence. In some embodiments, the hexavalent fusion protein has the following structure: VHH-Linker-VHH-Linker-Hinge-Fc-Linker-VHH, or VHH-Linker-Hinge-Fc-Linker-VHH-Linker-VHH where the VHH is a humanized or fully human VHH sequence.

In some embodiments, the multivalent TNFRSF binding fusion protein is hexavalent. In some embodiments, the hexavalent TNFRSF binding fusion protein has the following structure: TBD-Linker-TBD-Linker-TBD-Linker-Hinge-Fc. In some embodiments, the hexavalent TNFRSF binding fusion protein has the following structure: TBD-Linker-TBD-Linker-Hinge-Fc-Linker-TBD, or TBD-Linker-Hinge-Fc-Linker-TBD-Linker-TBD.

In some embodiments, the TBD of the hexavalent TNFRSF binding fusion protein is a single domain antibody or VHH. In some embodiments, each TBD of the hexavalent TNFRSF binding fusion protein is a single domain antibody or VHH. In some embodiments, the hexavalent TNFRSF binding fusion protein has the following structure: VHH-Linker-VHH-Linker-VHH-Linker-Hinge-Fc, where the VHH is a humanized or fully human VHH sequence. In some embodiments, the hexavalent TNFRSF binding fusion protein has the following structure: VHH-Linker-VHH-Linker-Hinge-Fc-Linker-VHH, or VHH-Linker-Hinge-Fc-Linker-VHH-Linker-VHH where the VHH is a humanized or fully human VHH sequence.

In some embodiments, the multivalent fusion protein lacks an Fc region. In some of these embodiments, the fusion protein is tetravalent and has the following structure BD-Linker-BD-Linker-BD-Linker-BD-Linker. In some of these embodiments, the fusion protein is pentavalent and has the following structure BD-Linker-BD-Linker-BD-Linker-BD-Linker-BD. In some of these embodiments, the fusion protein is hexavalent and has the following structure BD-Linker-BD-Linker-BD-Linker-BD-Linker-BD-Linker-BD.

In some embodiments, the multivalent TNFRSF binding fusion protein lacks an Fc region. In some of these embodiments, the TNFRSF binding fusion protein is tetravalent and has the following structure TBD-Linker-TBD-Linker-TBD-Linker-TBD-Linker. In some of these embodiments, the TNFRSF binding fusion protein is pentavalent and has the following structure TBD-Linker-TBD-Linker-TBD-Linker-TBD-Linker-TBD. In some of these embodiments, the TNFRSF binding fusion protein is hexavalent and has the following structure TBD-Linker-TBD-Linker-TBD-Linker-TBD-Linker-TBD-Linker-TBD.

In some embodiments, the BD of a multivalent fusion protein is a single domain antibody or VHH. In some embodiments, the multivalent fusion protein lacks an Fc region. In some of these embodiments, the fusion protein is tetravalent and has the following structure VHH-Linker-VHH-Linker-VHH-Linker-VHH-Linker. In some of these embodiments, the fusion protein is pentavalent and has the following structure VHH-Linker-VHH-Linker-VHH-Linker-VHH-Linker-VHH. In some of these embodiments, the fusion protein is hexavalent and has the following structure VHH-Linker-VHH-Linker-VHH-Linker-VHH-Linker-VHH-Linker-VHH. In any of these embodiments, the VHH is a humanized or fully human VHH sequence.

In some embodiments, the TBD of the a multivalent TNFRSF binding fusion protein is a single domain antibody or VHH. In some embodiments, the multivalent TNFRSF binding fusion protein lacks an Fc region. In some of these embodiments, the TNFRSF binding fusion protein is tetravalent and has the following structure VHH-Linker-VHH-Linker-VHH-Linker-VHH-Linker. In some of these embodiments, the TNFRSF binding fusion protein is pentavalent and has the following structure VHH-Linker-VHH-Linker-VHH-Linker-VHH-Linker-VHH. In some of these embodiments, the TNFRSF binding fusion protein is hexavalent and has the following structure VHH-Linker-VHH-Linker-VHH-Linker-VHH-Linker-VHH-Linker-VHH. In any of these embodiments, the VHH is a humanized or fully human VHH sequence.

In some embodiments, the GS-linker comprises an amino acid sequence selected from the group consisting of GGSGGS, i.e., $(GGS)_2$ (SEQ ID NO: 10); GGSGGSGGS, i.e., $(GGS)_3$ (SEQ ID NO: 11); GGSGGSGGSGGS, i.e., $(GGS)_4$ (SEQ ID NO: 12); and GGSGGSGGSGGSGGS, i.e., $(GGS)_5$ (SEQ ID NO: 13).

In some embodiments, the fusion proteins are multispecific containing a TBD and a binding domain directed toward a second antigen. In these embodiments, the second antigen binding domain can be positioned at numerous positions within the molecule relative to the TBD. In some embodiments, the second antigen binding domain is located N-terminal TBD. In other embodiments, the second antigen binding domain is located to C-terminal to the TBD. In other embodiments, the second antigen binding domain is located on a distinct polypeptide that associates with a first polypeptide containing the TBD.

In some embodiments, the fusion proteins are multispecific containing an anti-41BB binding domain and a binding domain directed toward a second antigen. In these embodiments, the second antigen binding domain can be positioned at numerous positions within the molecule relative to the an anti-41BB binding domain. In some embodiments, the second antigen binding domain is located N-terminal an anti-41BB binding domain. In other embodiments, the second antigen binding domain is located to C-terminal to the an anti-41BB binding domain. In other embodiments, the second antigen binding domain is located on a distinct polypeptide that associates with a first polypeptide containing the an anti-41BB binding domain.

In some embodiments, the fusion proteins are multispecific containing an anti-PDL1 binding domain and a binding domain directed toward a second antigen. In these embodiments, the second antigen binding domain can be positioned at numerous positions within the molecule relative to the an anti-PDL1 binding domain. In some embodiments, the second antigen binding domain is located N-terminal an anti-PDL1 binding domain. In other embodiments, the second antigen binding domain is located to C-terminal to the an anti-PDL1 binding domain. In other embodiments, the second antigen binding domain is located on a distinct polypeptide that associates with a first polypeptide containing the an anti-PDL1 binding domain.

In some embodiments, the TBD within the multispecific TNFRSF binding fusion protein is a single domain antibody or VHH. In some embodiments, the TBD within the multispecific TNFRSF binding fusion protein is a composed of antibody variable heavy (VH) chain and variable light (VL) chain region. In some embodiments, the VH and VL of the TBD are formatted as a single chain variable fragment (scFv) connected via a linker region. In some embodiments, the VH and VL of the TBD are formatted as a FAB fragment that associates via a constant heavy 1 (CH1) domain and a constant light chain (CL) domain. In some embodiments, non-antibody heterodimerization domains are utilized to enable the proper association of the VH and VL of the TBD. In some embodiments, the TBD within the multispecific TNFRSF binding fusion protein is derived from non-antibody scaffold proteins for example but not limited to designed ankyrin repeat proteins (darpins), avimer, anticalin/lipocalins, centyrins and fynomers.

In some embodiments, the TBD within the multispecific TNFRSF binding fusion protein is a single domain antibody or VHH that binds 41BB. In some embodiments, the anti-41BB binding domain within the multispecific TNFRSF binding fusion protein is a composed of antibody variable heavy (VH) chain and variable light (VL) chain region. In some embodiments, the VH and VL of the anti-41BB binding domain are formatted as a single chain variable fragment (scFv) connected via a linker region. In some embodiments, the VH and VL of the anti-41BB binding domain are formatted as a Fab fragment that associates via a constant heavy 1 (CH1) domain and a constant light chain (CL) domain. In some embodiments, non-antibody heterodimerization domains are utilized to enable the proper association of the VH and VL of the anti-41BB binding domain. In some embodiments, the anti-41BB binding domain within the multispecific TNFRSF binding fusion protein is derived from non-antibody scaffold proteins for example but not limited to designed ankyrin repeat proteins (darpins), avimer, anticalin/lipocalins, centyrins and fynomers.

In some embodiments, the binding domain within the multispecific fusion protein is a single domain antibody or VHH that binds PDL1. In some embodiments, the anti-PDL1 binding domain within the multispecific TNFRSF binding fusion protein is a composed of antibody variable heavy (VH) chain and variable light (VL) chain region. In some embodiments, the VH and VL of the anti-PDL1 binding domain are formatted as a single chain variable fragment (scFv) connected via a linker region. In some embodiments, the VH and VL of the anti-PDL1 binding domain are formatted as a Fab fragment that associates via a constant heavy 1 (CH1) domain and a constant light chain (CL) domain. In some embodiments, non-antibody heterodimerization domains are utilized to enable the proper association of the VH and VL of the anti-PDL1 binding domain. In some embodiments, the anti-PDL1 binding domain within the multispecific fusion protein is derived from non-antibody scaffold proteins for example but not limited to designed ankyrin repeat proteins (darpins), avimer, anticalin/lipocalins, centyrins and fynomers.

In some embodiments, the anti-41BB binding domain of the multispecific TNFRSF binding fusion protein is a bispecific antibody or antigen-binding fragment thereof.

In some embodiments, the anti-PDL1 binding domain of the multispecific fusion protein is a bispecific antibody or antigen-binding fragment thereof.

In any of these embodiments, the bispecific antibody or antigen-fragment thereof can be any suitable bispecific format known in the art, including, by way of non-limiting example, formats based on antibody fragments such as, e.g., X-Link Fab, cross-linked Fab fragments; tascFv/BiTE, tandem-scFv/Bispecific T cell Engager; db, diabody; taDb, tandem diabody; formats based on Fc-fusions such as, e.g., db-Fc, diabody-Fc fusion; taDb-Fc fusion, tandem diabody-Fc fusion; taDb-CH3, tandem diabody-CH3 fusion; (scFv) 4-Fc, tetra scFv-Fc fusion; DVD-Ig, dual variable domain immunoglobulin; IgG formats such as, e.g., knob-hole and SEED, strand exchange engineered domain; CrossMab, knob-hole combined with heavy and light chain domain exchange; bsAb, quadroma derived bispecific antibody; sdAb, single domain based antibody; and kappa-lambda bodies such as those described in PCT Publication No. WO 2012/023053.

In any of the above embodiments, at least one TBD comprises an amino acid sequence selected from the group consisting of SEQ ID NO: 16, 20, 23, 25, 29, 33, 39, 33-41, 43, 45-47, 49, 51, 53, 54, 56, 58-60, 62, 65, 66, 68, 70, 72, 74, 76, 78, and 80-83.

In any of the above embodiments, at least one TBD comprises an amino acid sequence selected from the group consisting of SEQ ID NO: 33, 39, 33-41, 43, 45-47, 49, 51, 53, 54, 56, 58-60, 62, 65, 66, 68, 70, 72, 74, 76, 78, and 80-83.

In any of the above embodiments, at least one TBD comprises a complementarity determining region 1 (CDR1) comprising an amino acid sequence selected from the group consisting of SEQ ID NO: 17, 21, 26, 30, 50, 65, and 69; a complementarity determining region 2 (CDR2) comprising an amino acid sequence selected from the group consisting of SEQ ID NO: 18, 27, 31, 42, 44, 48, 52, 61, 63, 71, 73, 75, 77, and 79; and a complementarity determining region 3 (CDR3) comprising an amino acid sequence selected from the group consisting of SEQ ID NO: 19, 22, 24, 28, 32, 55, and 57.

In any of the above embodiments, at least one BD comprises an amino acid sequence selected from the group consisting of SEQ ID NO: 100, 104, 108, 112, 114, 116, and 119-124.

In any of the above embodiments, at least one BD comprises an amino acid sequence selected from the group consisting of SEQ ID NO: 119-124.

In any of the above embodiments, at least one BD comprises a CDR1 comprising an amino acid sequence selected from the group consisting of SEQ ID NO: 101, 105, and 109; a CDR2 comprising an amino acid sequence selected from the group consisting of SEQ ID NO: 102, 106, 110, and 117; and a CDR3 comprising an amino acid sequence selected from the group consisting of SEQ ID NO: 103, 107, 111, 113, 115, and 118.

In any of the above embodiments, at least one TBD comprises an amino acid sequence selected from the group consisting of SEQ ID NO: 16, 20, 23, 25, 29, 33, 39, 33-41, 43, 45-47, 49, 51, 53, 54, 56, 58-60, 62, 65, 66, 68, 70, 72, 74, 76, 78, and 80-83, and at least one BD comprises an amino acid sequence selected from the group consisting of SEQ ID NO: 100, 104, 108, 112, 114, 116, and 119-124.

In any of the above embodiments, at least one TBD comprises an amino acid sequence selected from the group consisting of SEQ ID NO: 33, 39, 33-41, 43, 45-47, 49, 51, 53, 54, 56, 58-60, 62, 65, 66, 68, 70, 72, 74, 76, 78, and 80-83, and at least one BD comprises an amino acid sequence selected from the group consisting of SEQ ID NO: 119-124.

In any of the above embodiments, at least one TBD comprises a complementarity determining region 1 (CDR1) comprising an amino acid sequence selected from the group consisting of SEQ ID NO: 17, 21, 26, 30, 50, 65, and 69; a complementarity determining region 2 (CDR2) comprising an amino acid sequence selected from the group consisting of SEQ ID NO: 18, 27, 31, 42, 44, 48, 52, 61, 63, 71, 73, 75, 77, and 79; and a complementarity determining region 3 (CDR3) comprising an amino acid sequence selected from the group consisting of SEQ ID NO: 19, 22, 24, 28, 32, 55, and 57, and at least one BD comprises a CDR1 comprising an amino acid sequence selected from the group consisting of SEQ ID NO: 101, 105, and 109; a CDR2 comprising an amino acid sequence selected from the group consisting of SEQ ID NO: 102, 106, 110, and 117; and a CDR3 comprising an amino acid sequence selected from the group consisting of SEQ ID NO: 103, 107, 111, 113, 115, and 118.

BRIEF DESCRIPTION OF THE DRAWINGS

FIGS. 8A and 8B are conceptual schematics, wherein the bispecific fusion proteins have minimal 41BB agonistic properties (FIG. 8A) unless bound by a PD-L1 expressing cell (FIG. 8B). FIG. 8C is a graph demonstrating the ability of a PDL1-positive cell (here PDL1 transfected CHO cells) to mediate 41BB signaling and the inability of PDL1-negative cell (here untransfected CHO cells) to mediate 41BB signaling. 41BB signaling was monitored using a NF-kB reporter 293 cell line expressing 41BB.

FIG. 9E is a graph demonstrating that the humanized variants hzRH3v5-1 and hzRH3v9 do not block binding of 41BBL to cell surface 41BB. Herein a recombinant fusion protein 41BBL-mFc, containing a mouse Fc region was used and bound 41BBL was detected using an anti-mouse IgG-Fc specific secondary antibody.

FIG. 11D is a graph demonstrating that the humanized variants hz4E01v16, hz4E01v18, hz4E01v21, hz4E01v22 and hz4E01v23 block binding of 41BBL to cell surface 41BB. In these studies, a recombinant fusion protein 41BBL-mFc, containing a mouse Fc region was used and bound 41BBL was detected using an anti-mouse IgG-Fc specific secondary antibody.

FIG. 14C is a graph that demonstrates that the bispecific fusion protein containing hzRh3v5-1 does not block 41BBL binding to cell surface 41BB. Herein a recombinant fusion protein of 41BBL and mouse Fc region was used and bound 41BBL was detected using an anti-mouse IgG-Fc specific secondary antibody.

Figure 15A:
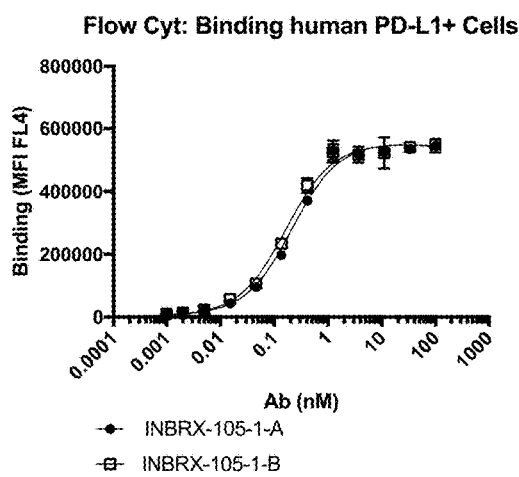
FIGS. 15A, 15B, 15C, and 15D are a series of graphs demonstrating the equivalent binding (FIG. 15A and FIG.
Figure 15B:
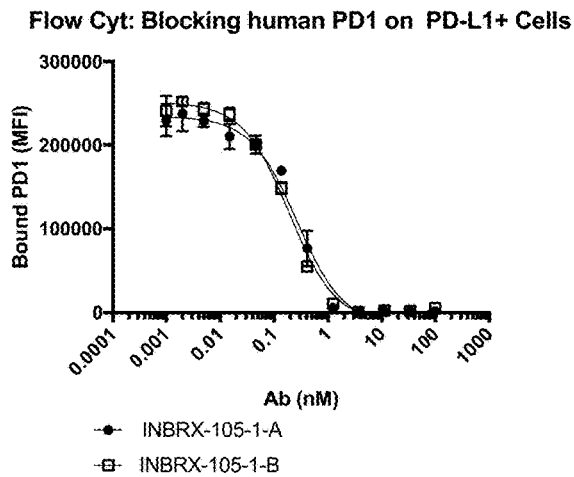
Figure 15C:
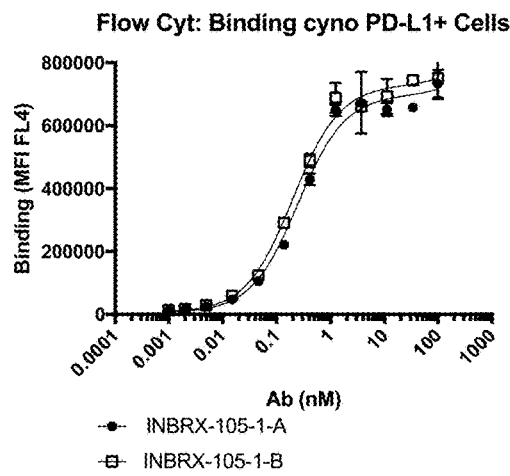
Figure 15D:
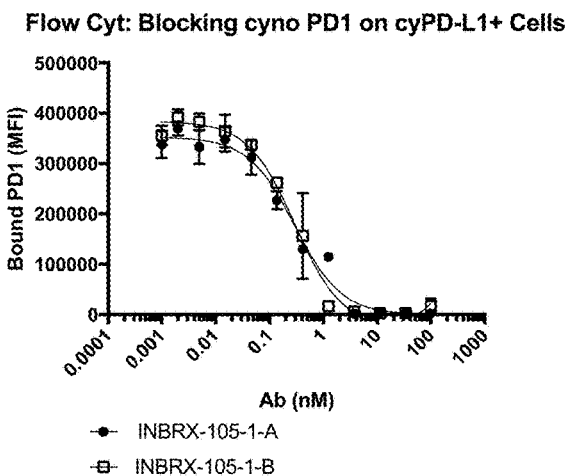

15C). and PD1 blocking (FIG. 15B and Figure by the two distinct formats of a bispecific fusion protein targeting PDL1 and 41BB referred to herein as INBRX-105-1-A and INBRX-105-1-B. Binding was assessed by flow cytometry on human (FIG. 15A) or cynomolgus monkey (FIG. 15C) PDL1 expressing 293freestyle cells. Blocking was assessed by flow cytometry using on human (FIG. 15B) or cynomolgus monkey (FIG. 15D) PDL1 expressing 293freestyle cells with either recombinant human (FIG. 15B) or cynomolgus monkey (FIG. 15D) PD1-mFc fusion protein. Bound PD1 was detected using an anti-mouse IgG-Fc specific secondary antibody.

Figure 16:
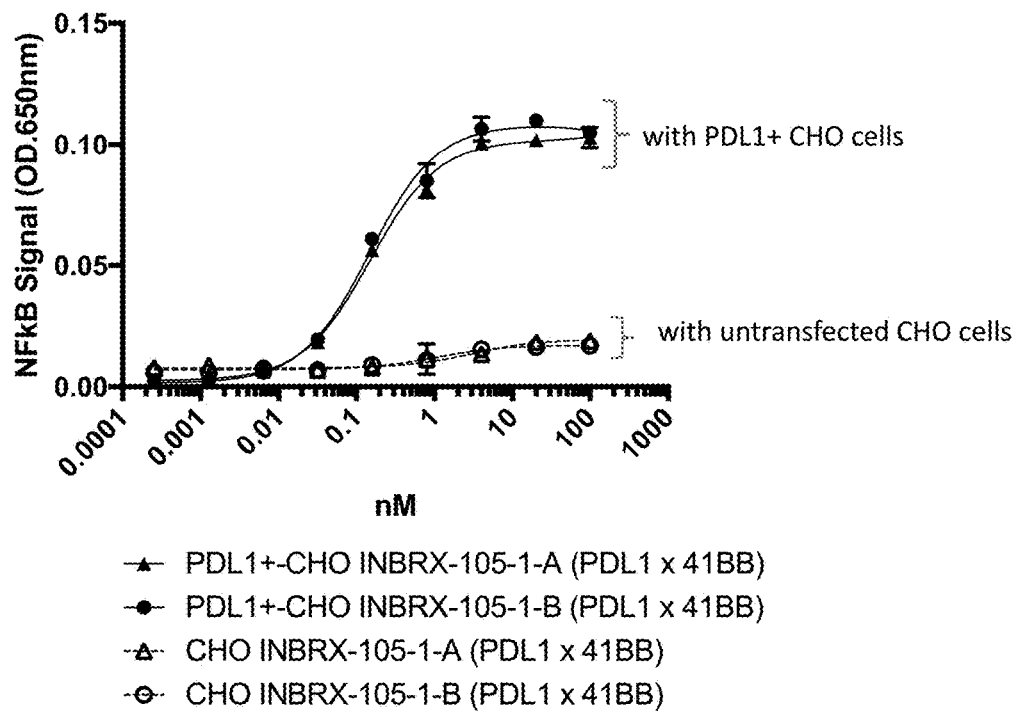

FIG. 16 is a graph demonstrating the ability of humanized versions of a PDL1×41BB bispecific fusion protein (INBRX-105-1) to induce PDL1-dependent 41BB agonism. A 41BB-expressing HEK293 NF-kB reporter cell line was used to assess 41BB signaling and a PDL1-expressing CHO cell line was used as the source of PDL1.

Figure 17A:
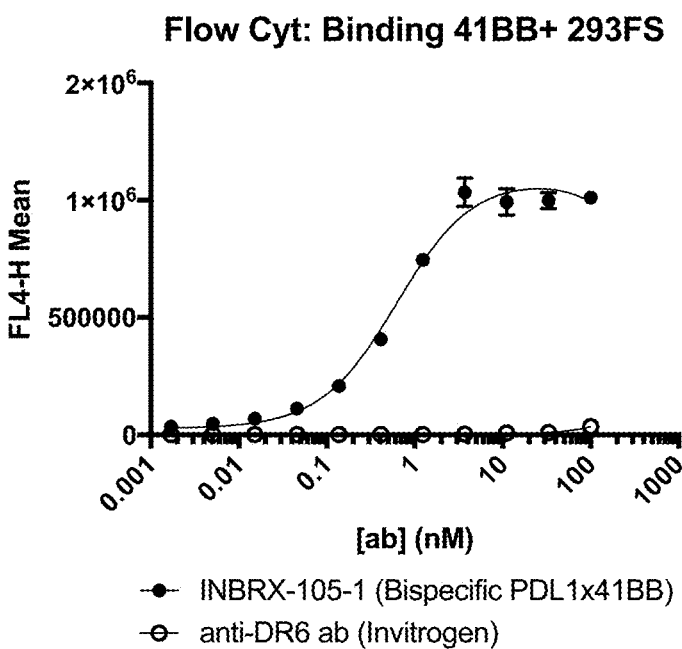
Figure 17B:
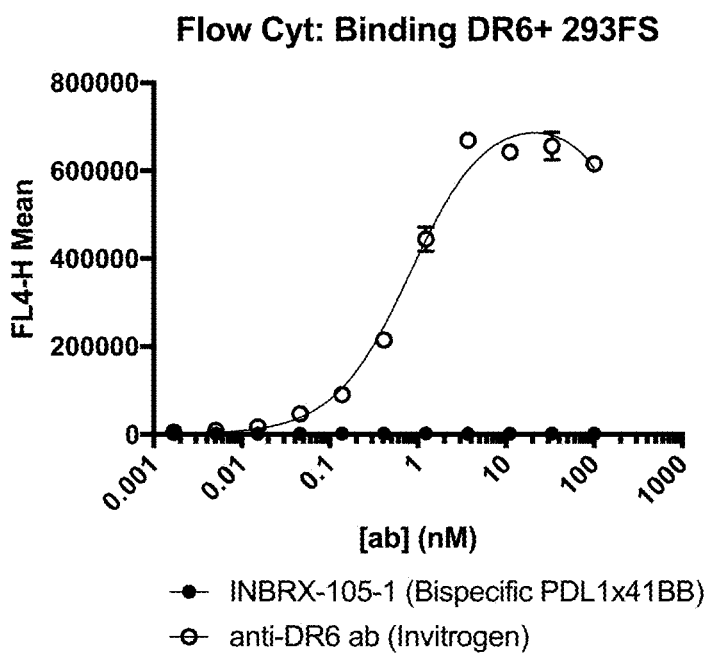

FIGS. 17A and 17B are a pair of graphs demonstrating the 41BB-specific binding by the 41BB-binding portion of a PDL1×41BB bispecific fusion protein (INBRX-105-1) of the present disclosure. Binding was assessed on 41BB (FIG. 17A) or the closest homolog, TNFRSF21/DR6 (FIG. 17B), expressing 293freestyle cells by flow cytometry. An anti-DR6 antibody (Invitrogen) was used to as positive control for DR6 expression.

Figure 18A:
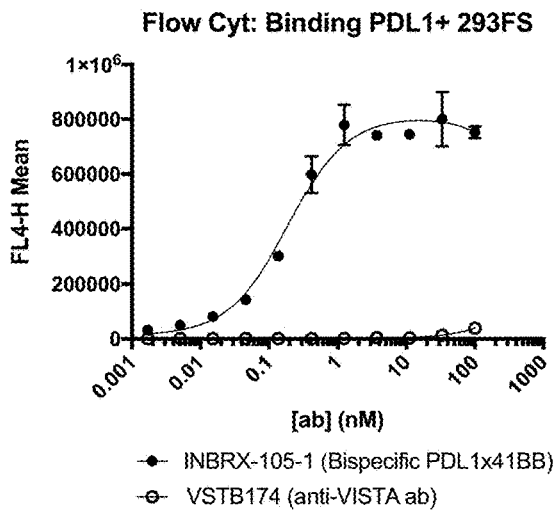
Figure 18B:
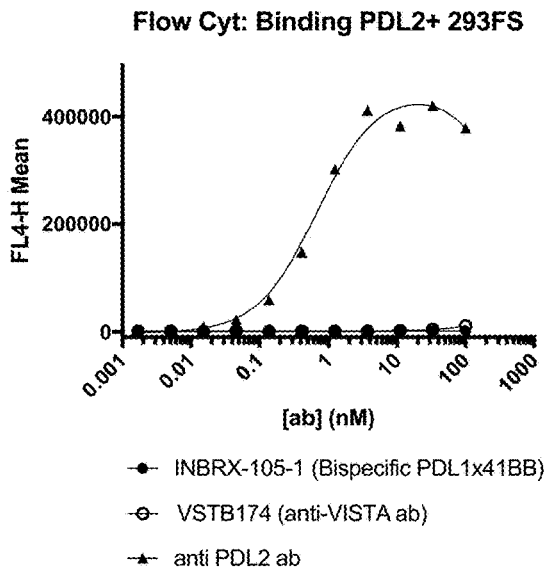
Figure 18C:
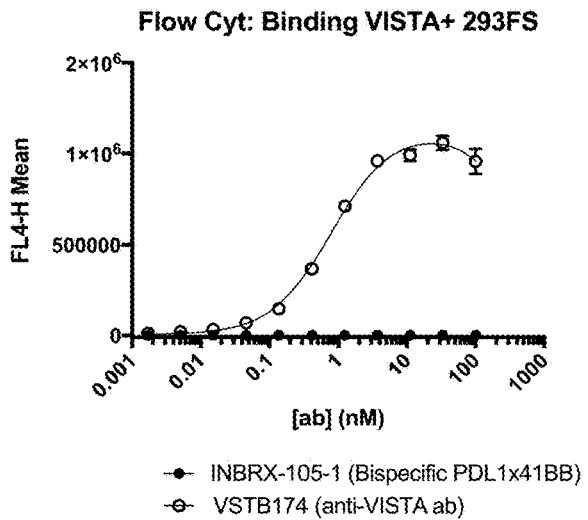

FIGS. 18A, 18B, and 18C are a series of graphs demonstrating the PDL1-specific binding by the PDL1-binding portion of a PDL1×41BB bispecific fusion protein (INBRX-105-1) of the present disclosure. Binding was assessed on PDL1 (FIG. 18A), and its closest homologs PDL2 (FIG. 18B) or VISTA/PDL3 (FIG. 18C), expressing 293freestyle cells by flow cytometry. Anti-PDL2 and anti-VISTA antibodies were used to as positive controls for PDL2 and PDL3 expression respectively.

Figure 19A:
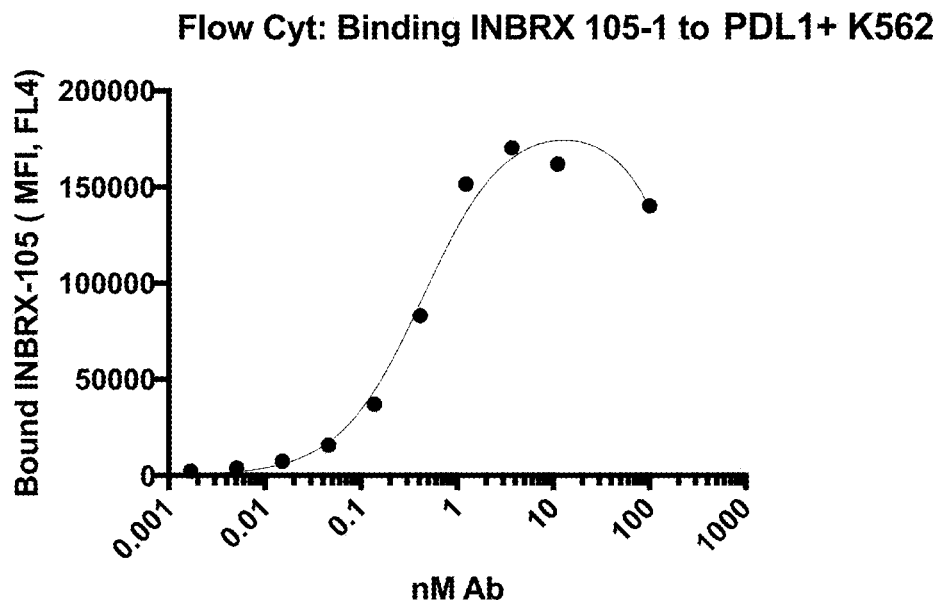
Figure 19B:
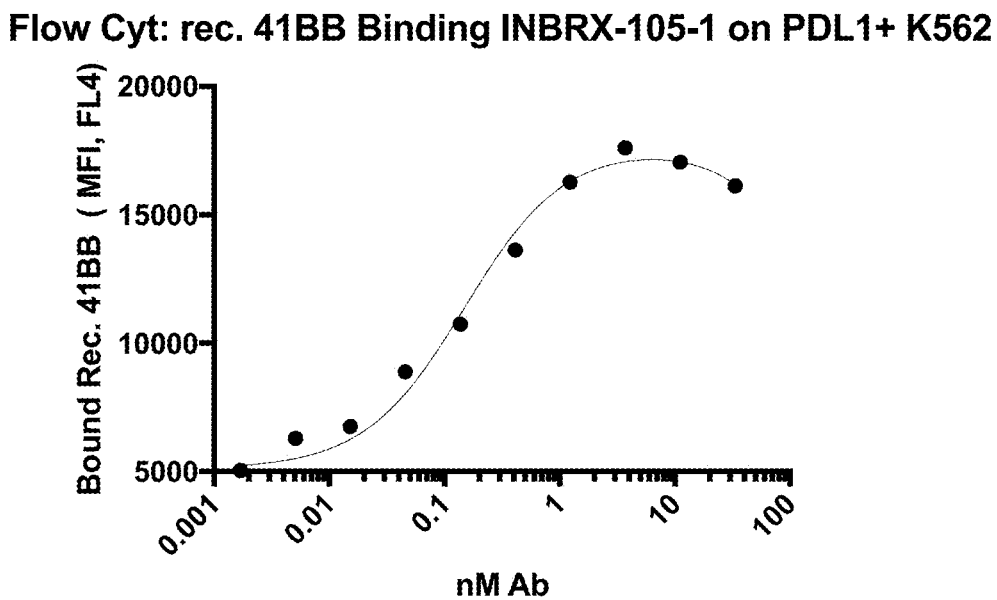

FIGS. 19A and 19B are a pair of graphs demonstrating the ability of a PDL1×41BB bispecific fusion protein to simultaneously bind PDL1 and 41BB. Bound 41BB was detected using an anti-mouse IgG-Fc specific secondary antibody. FIG. 19A. is a graph showing the binding of INBRX-105-1 to the PDL1 expressing K562 cells. FIG. 19B is a graph showing the binding of recombinant 41BB to INBRX-105-1 on the PDL1 expressing cells.

Figure 20:
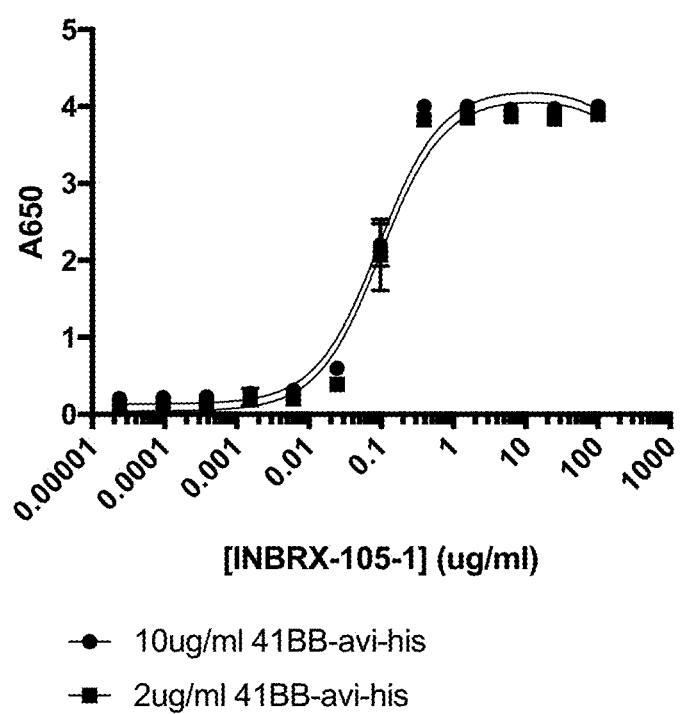

FIG. 20 is a graph demonstrating the ability of a PDL1× 41BB bispecific fusion protein to simultaneously bind recombinant PDL1 and recombinant 41BB in an ELISA. Bound recombinant 41BB was detected via streptavidin-HRP.

Figure 21A:
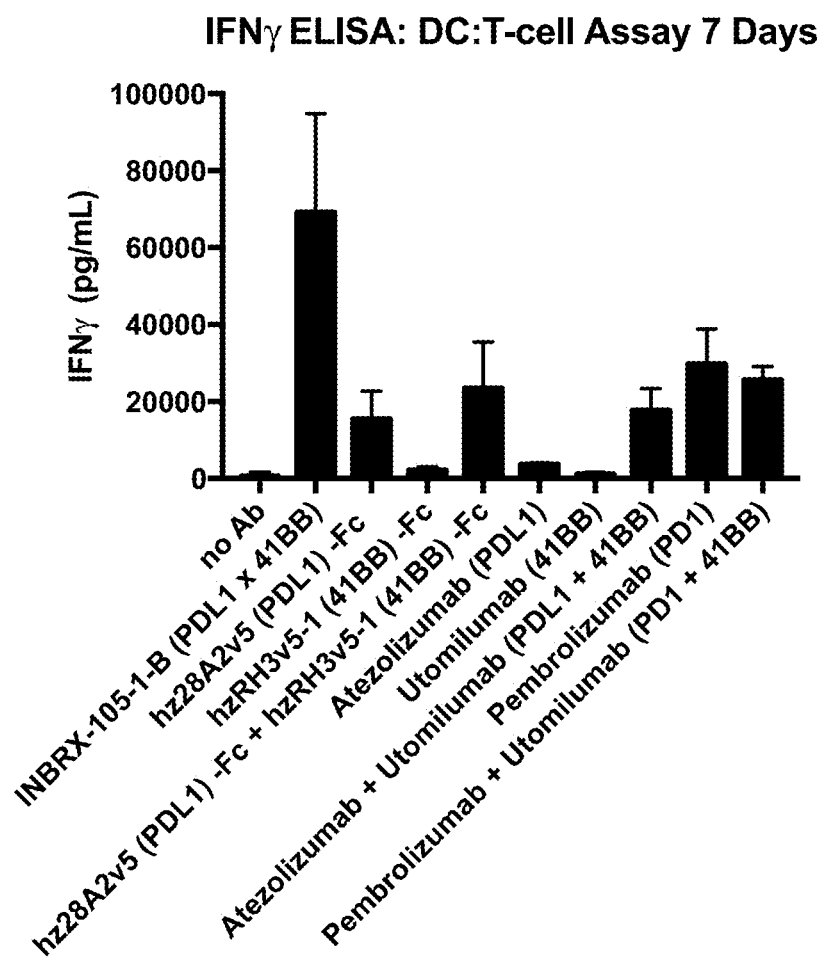
Figure 21B:
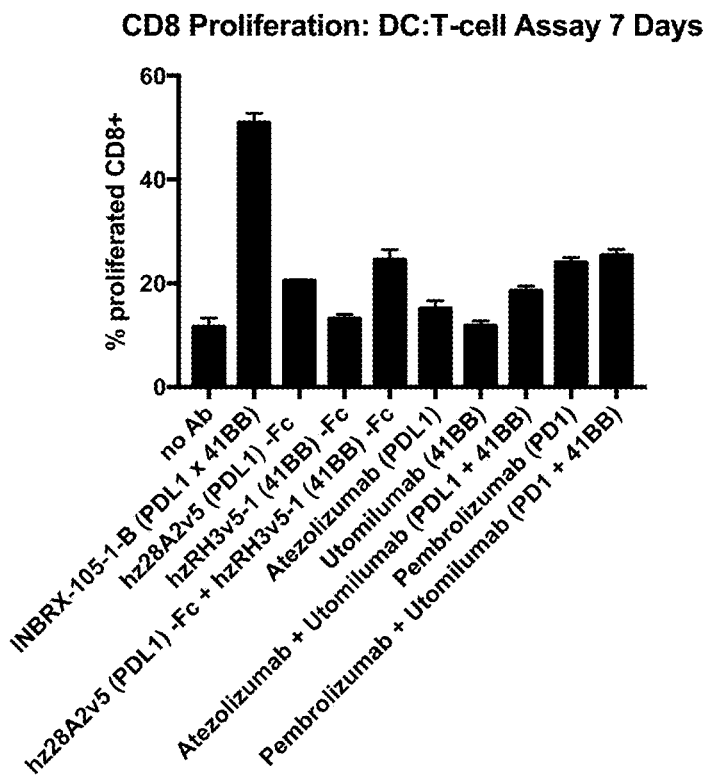
Figure 21C:
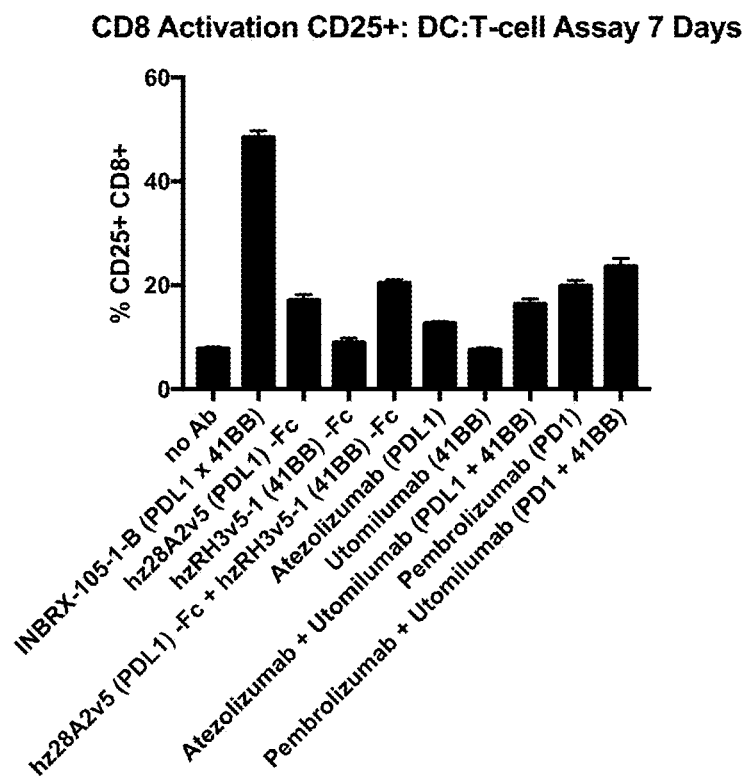

FIGS. 21A, 21B, and 21C are a series of graphs demonstrating the effect of a PDL1×41BB bispecific fusion protein (INBRX-105-1) of the present disclosure on T-cell activation and proliferation. INFγ production in the cell supernatant was monitored using an ELISA and normalized to the standard curve. T-cell proliferation was monitored by flow cytometry using CTV labeling of T-cells. T-cell activation was assessed by the presence of the activation marker CD25 monitored by flow cytometry. Antibodies were used at 10 nM.

Figure 22A:
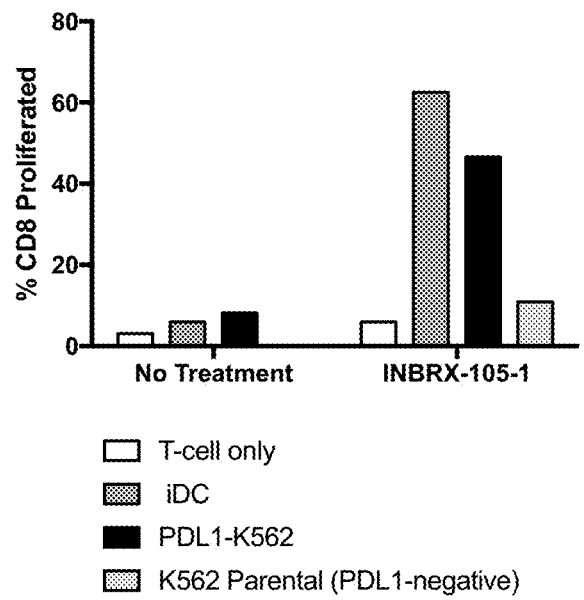
Figure 22B:
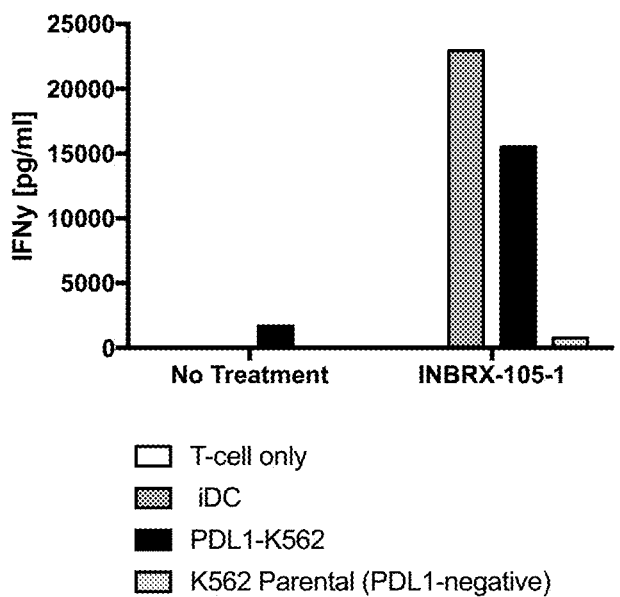

FIGS. 22A and 22B are a pair of graphs demonstrating PDL1-dependent 41BB agonism mediated by a PDL1× 41BB bispecific fusion protein (INBRX-105-1) of the present disclosure. CD8$^+$ T-cell proliferation (FIG. 22A) was monitored using CTV labeling and INFγ production (FIG. 22B) in the cell supernatant was monitored using an ELISA and normalized to the standard curve.

Figure 23:
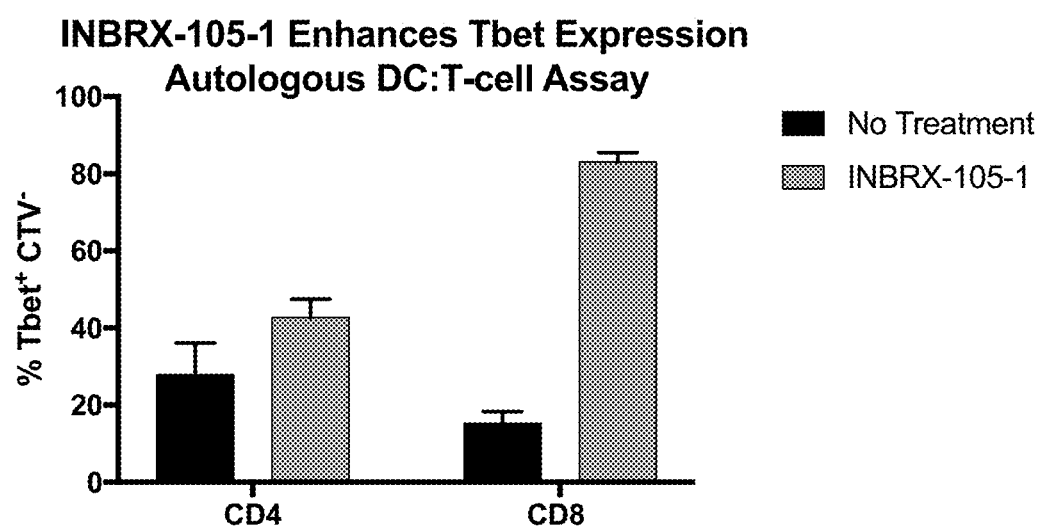

FIG. 23 is a graph demonstrating the capacity of a PDL1×41BB bispecific fusion protein (INBRX-105-1) of the present disclosure to enhance the Th1 lineage defining transcription factor, T-bet, expression in T-cell populations. T-bet expression was assessed on CD4$^+$ and CD8$^+$ T-cell population by flow cytometry via intracellular staining following fixation and permeabilization.

Figure 24A:
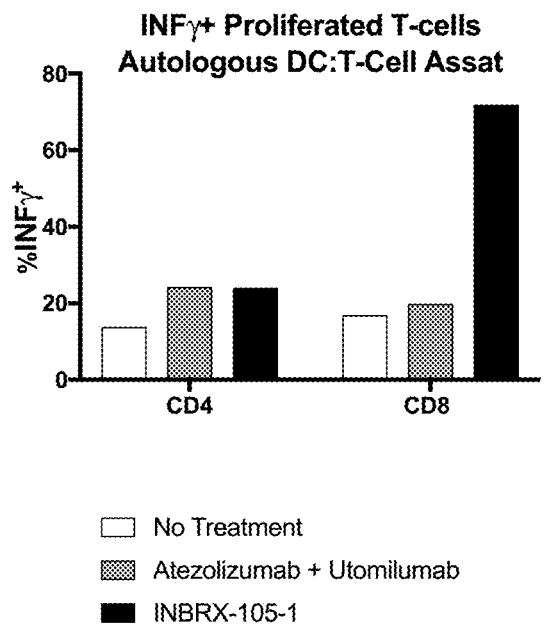
Figure 24B:
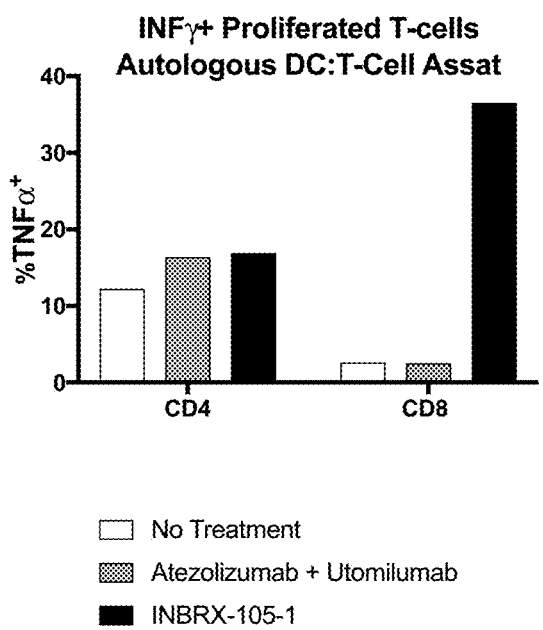

FIGS. 24A and 24B are a pair graphs contrasting the capacity of a PDL1×41BB bispecific fusion protein (INBRX-105-1) of the present disclosure and the combination of monospecific antibodies Atezolizumab (anti-PDL1) and Utomilumab (anti-41BB) to induce INFγ (FIG. 24A) or TNFα (FIG. 24B) production from CD4$^+$ or CD8$^+$ T-cells. Cytokine expression was assessed on CD4$^+$ and CD8$^+$ T-cell population by flow cytometry via intracellular staining following fixation and permeabilization.

Figure 25A:
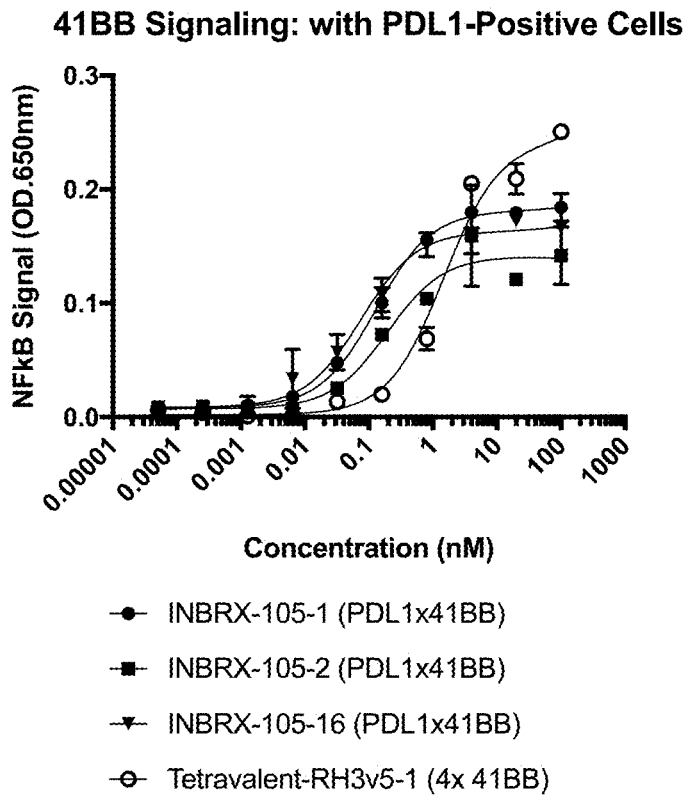
Figure 25B:
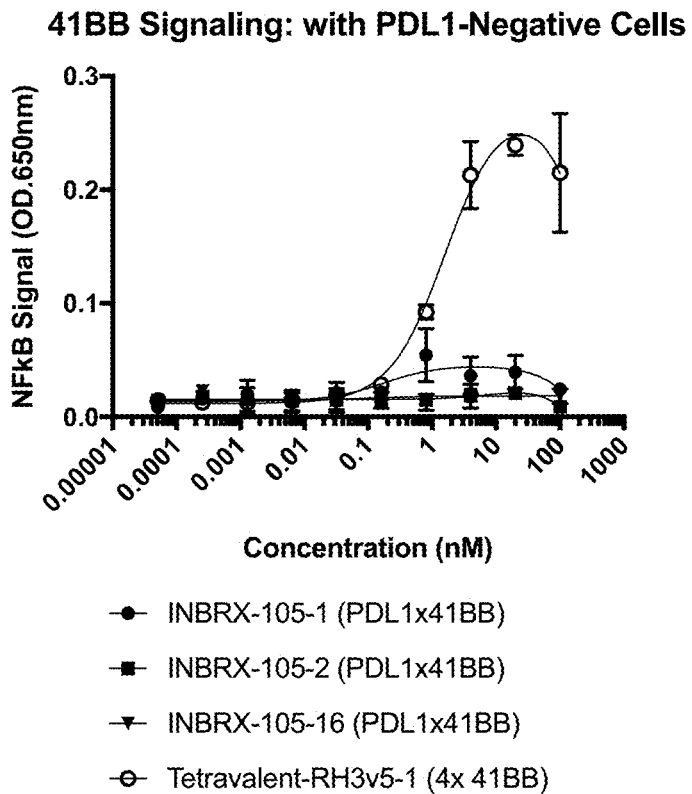

FIGS. 25A and 25B are a pair of graphs demonstrating the agonistic capacity of a tetravalent 41BB-binding fusion protein and PDL1×41BB bispecific fusion proteins of the present disclosure in the presence of an additional PDL1 positive (FIG. 25A) or negative (FIG. 25B) cell line. Herein a 41BB-expressing HEK293 NF-kB reporter cell was used and co-incubated with either the PDL1-negative K562 cell line (FIG. 25B) or a stably transfected, PDL1-expressing K562 cell line (FIG. 25A).

DETAILED DESCRIPTION OF THE INVENTION

All patents and publications mentioned in this specification are herein incorporated by reference to the same extent as if each independent patent and publication was specifically and individually indicated to be incorporated by reference.

Definitions

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular. Generally, nomenclatures utilized in connection with, and techniques of, cell and tissue culture, molecular biology, and protein and oligo- or polynucleotide chemistry and hybridization described herein are those well-known and commonly used in the art. Standard techniques are used for recombinant DNA, oligonucleotide synthesis, and tissue culture and transformation (e.g., electroporation, lipofection). Enzymatic reactions and purification techniques are performed according to manufacturer's specifications or as commonly accomplished in the art or as described herein. The foregoing techniques and procedures are generally performed according to conventional methods well known in the art and as described in various general and more specific references that are cited and discussed throughout the present specification. See e.g., Sambrook et al. Molecular Cloning: A Laboratory Manual (2d ed., Cold Spring Harbor Laboratory Press, Cold Spring Harbor, N.Y. (1989)). The nomenclatures utilized in connection with, and the laboratory procedures and techniques of, analytical chemistry, synthetic organic chemistry, and medicinal and pharmaceutical chemistry described herein are those well-known and commonly used in the art. Standard techniques are used for chemical syntheses, chemical analyses, pharmaceutical preparation, formulation, and delivery, and treatment of patients.

As utilized in accordance with the present disclosure, the following terms, unless otherwise indicated, shall be understood to have the following meanings:

As used herein, the terms "dual-targeting fusion protein" and "antibody" can be synonyms. As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically bind" or "immunoreacts with" "or directed against" is meant that the antibody reacts with one or more antigenic determinants of the desired antigen and does not react with other polypeptides or binds at much lower affinity ($K_d > 10^{-6}$). Antibodies include, but are not limited to, polyclonal, monoclonal, chimeric, dAb (domain antibody), single chain, Fab, Fab' and $F(ab')_2$ fragments, Fv, scFvs, a Fab expression library, and single domain antibody (sdAb) fragments, for example $V_H H$, $V_{NAR}$, engineered $V_H$ or $V_K$.

The basic antibody structural unit is known to comprise a tetramer. Each tetramer is composed of two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. In general, antibody molecules obtained from humans relate to any of the classes IgG, IgM, IgA, IgE and IgD, which differ from one another by the nature of the heavy chain present in the molecule. Certain classes have subclasses (also known as isotypes) as well, such as $IgG_1$, $IgG_2$, and others. Furthermore, in humans, the light chain may be a kappa chain or a lambda chain.

The term "monoclonal antibody" (MAb) or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

The term "antigen-binding site" or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three-dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs." The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196:901-917 (1987), Chothia et al. Nature 342:878-883 (1989).

The single domain antibody (sdAb) fragments portions of the fusion proteins of the present disclosure are referred to interchangeably herein as targeting polypeptides herein.

As used herein, the term "epitope" includes any protein determinant capable of specific binding to/by an immunoglobulin or fragment thereof, or a T-cell receptor. The term "epitope" includes any protein determinant capable of specific binding to/by an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is ≤1 mM, for example, ≤1 µM; e.g., ≤100 nM, for example, ≤10 nM and for example, ≤1 nM.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($k_{on}$) and the "off rate constant" ($k_{off}$) can be determined by calculation of the concentrations and the actual rates of association and dissociation. (See Nature 361:186-87 (1993)). The ratio of $k_{off}/k_{on}$ enables the cancellation of all parameters not related to affinity, and is equal to the dissociation constant $K_d$. (See, generally, Davies et al. (1990) Annual Rev Biochem 59:439-473). An antibody of the present disclosure is said to specifically bind to an antigen, when the equilibrium binding constant ($K_d$) is ≤1 µM, for example, ≤100 nM, for example, ≤10 nM, and for example, ≤100 µM to about 1 µM, as measured by assays such as radioligand binding assays, surface plasmon resonance (SPR), flow cytometry binding assay, or similar assays known to those skilled in the art.

The term "isolated polynucleotide" as used herein shall mean a polynucleotide of genomic, cDNA, or synthetic origin or some combination thereof, which by virtue of its origin the "isolated polynucleotide" (1) is not associated with all or a portion of a polynucleotide in which the "isolated polynucleotide" is found in nature, (2) is operably linked to a polynucleotide which it is not linked to in nature, or (3) does not occur in nature as part of a larger sequence.

The term "isolated protein" referred to herein means a protein of cDNA, recombinant RNA, or synthetic origin or some combination thereof, which by virtue of its origin, or source of derivation, the "isolated protein" (1) is not associated with proteins found in nature, (2) is free of other proteins from the same source, e.g., free of marine proteins, (3) is expressed by a cell from a different species, or (4) does not occur in nature.

The term "polypeptide" is used herein as a generic term to refer to native protein, fragments, or analogs of a polypeptide sequence. Hence, native protein fragments, and analogs are species of the polypeptide genus.

The term "naturally-occurring" as used herein as applied to an object refers to the fact that an object can be found in nature. For example, a polypeptide or polynucleotide sequence that is present in an organism (including viruses) that can be isolated from a source in nature and which has not been intentionally modified by man in the laboratory or otherwise is naturally-occurring.

The term "operably linked" as used herein refers to positions of components so described are in a relationship permitting them to function in their intended manner. A control sequence "operably linked" to a coding sequence is ligated in such a way that expression of the coding sequence is achieved under conditions compatible with the control sequences.

The term "control sequence" as used herein refers to polynucleotide sequences which are necessary to effect the expression and processing of coding sequences to which they are ligated. The nature of such control sequences differs depending upon the host organism in prokaryotes, such control sequences generally include promoter, ribosomal binding site, and transcription termination sequence in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences. The term "polynucleotide," as referred to herein, refers to a polymeric boron of nucleotides of at least 10 bases in length, either ribonucleotides or deoxynucleotides or a modified form of either type of nucleotide. The term includes single and double stranded forms of DNA.

The term "oligonucleotide" referred to herein includes naturally occurring, and modified nucleotides linked together by naturally occurring, and non-naturally occurring oligonucleotide linkages. Oligonucleotides are a polynucleotide subset generally comprising a length of 200 bases or fewer. In some embodiments, oligonucleotides are 10 to 60 bases in length and for example, 12, 13, 14, 15, 16, 17, 18, 19, or 20 to 40 bases in length. Oligonucleotides are usually single stranded, e.g., for probes, although oligonucleotides may be double stranded, e.g., for use in the construction of a gene mutant. Oligonucleotides of the disclosure are either sense or antisense oligonucleotides.

The term "naturally occurring nucleotides" referred to herein includes deoxyribonucleotides and ribonucleotides. The term "modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselerloate, phosphorodiselenoate, phosphoroanilothioate, phoshoraniladate, phosphoronmidate, and the like. See e.g., LaPlanche et al. Nucl. Acids Res. 14:9081 (1986); Stec et al. J. Am. Chem. Soc. 106:6077 (1984), Stein et al. Nucl. Acids Res. 16:3209 (1988), Zon et al. Anti Cancer Drug Design 6:539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90:543 (1990). An oligonucleotide can include a label for detection, if desired.

The term "selectively hybridize" referred to herein means to detectably and specifically bind. Polynucleotides, oligonucleotides and fragments thereof in accordance with the disclosure selectively hybridize to nucleic acid strands under hybridization and wash conditions that minimize appreciable amounts of detectable binding to nonspecific nucleic acids. High stringency conditions can be used to achieve selective hybridization conditions as known in the art and discussed herein. Generally, the nucleic acid sequence homology between the polynucleotides, oligonucleotides, and fragments of the disclosure and a nucleic acid sequence of interest will be at least 80%, and more typically with increasing homologies of at least 85%, 90%, 95%, 99%, and 100%. Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching gap lengths of or less are preferred with 2 or less being more preferred. Alternatively, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program. The term "corresponds to" is used herein to mean that a polynucleotide sequence is homologous (i.e., is identical, not strictly evolutionarily related) to all or a portion of a reference polynucleotide sequence, or that a polypeptide sequence is identical to a reference polypeptide sequence. In contradistinction, the term "complementary to" is used herein to mean that the complementary sequence is homologous to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i.e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman Adv. Appl. Math. 2:482 (1981), by the homology alignment algorithm of Needleman and Wunsch J. Mol. Biol. 48:443 (1970), by the search for similarity method of Pearson and Lipman Proc. Natl. Acad. Sci. (U.S.A.) 85:2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i.e., resulting in the highest percentage of homology over the comparison window) generated by the various methods is selected.

The term "sequence identity" means that two polynucleotide or amino acid sequences are identical (i.e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e.g., A, T, C, G, U or I) or residue occurs in both sequences to yield the number of matched positions, dividing the number of matched positions by the total number of positions in the comparison window (i.e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that has at least 85 percent sequence identity, preferably at least 90 to 95 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As used herein, the twenty conventional amino acids and their abbreviations follow conventional usage. See Immunology—A Synthesis (2nd Edition, E. S. Golub and D. R. Gren, Eds., Sinauer Associates, Sunderland7 Mass. (1991)). Stereoisomers (e.g., D-amino acids) of the twenty conventional amino acids, unnatural amino acids such as α-α-disubstituted amino acids, N-alkyl amino acids, lactic acid, and other unconventional amino acids may also be suitable components for polypeptides of the present disclosure. Examples of unconventional amino acids include: 4 hydroxyproline, γ-carboxyglutamate, ε-N,N,N-trimethyllysine, ε-N-acetyllysine, 0-phosphoserine, N-acetylserine, N-formylmethionine, 3-methylhistidine, 5-hydroxylysine, τ-N-methylarginine, and other similar amino acids and imino acids (e.g., 4-hydroxyproline). In the polypeptide notation used herein, the left-hand direction is the amino terminal direction and the right-hand direction is the carboxy-terminal direction, in accordance with standard usage and convention.

Similarly, unless specified otherwise, the left-hand end of single-stranded polynucleotide sequences is the 5' the left-hand direction of double-stranded polynucleotide sequences is referred to as the 5' direction. The direction of 5' to 3' addition of nascent RNA transcripts is referred to as the transcription direction sequence regions on the DNA strand having the same sequence as the RNA and which are 5' to the 5' end of the RNA transcript are referred to as "upstream sequences", sequence regions on the DNA strand having the same sequence as the RNA and which are 3' to the 3' end of the RNA transcript are referred to as "downstream sequences".

As applied to polypeptides, the term "substantial identity" means that two peptide sequences, when optimally aligned, such as by the programs GAP or BESTFIT using default gap weights, share at least 80 percent sequence identity, for example, at least 90 percent sequence identity, for example, at least 95 percent sequence identity, and for example, at least 99 percent sequence identity.

In some embodiments, residue positions which are not identical differ by conservative amino acid substitutions.

Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Suitable conservative amino acids substitution groups are: valine-leucine-isoleucine, phenylalanine-tyrosine, lysine-arginine, alanine valine, glutamic-aspartic, and asparagine-glutamine.

As discussed herein, minor variations in the amino acid sequences of antibodies or immunoglobulin molecules are contemplated as being encompassed by the present disclosure, providing that the variations in the amino acid sequence maintain at least 75%, for example, at least 80%, 90%, 95%, and for example, 99%. In particular, conservative amino acid replacements are contemplated. Conservative replacements are those that take place within a family of amino acids that are related in their side chains. Genetically encoded amino acids are generally divided into families: (1) acidic amino acids are aspartate, glutamate; (2) basic amino acids are lysine, arginine, histidine; (3) non-polar amino acids are alanine, valine, leucine, isoleucine, proline, phenylalanine, methionine, tryptophan, and (4) uncharged polar amino acids are glycine, asparagine, glutamine, cysteine, serine, threonine, tyrosine. The hydrophilic amino acids include arginine, asparagine, aspartate, glutamine, glutamate, histidine, lysine, serine, and threonine. The hydrophobic amino acids include alanine, cysteine, isoleucine, leucine, methionine, phenylalanine, proline, tryptophan, tyrosine and valine. Other families of amino acids include (i) serine and threonine, which are the aliphatic-hydroxy family; (ii) asparagine and glutamine, which are the amide containing family; (iii) alanine, valine, leucine and isoleucine, which are the aliphatic family; and (iv) phenylalanine, tryptophan, and tyrosine, which are the aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein. Fragments or analogs of antibodies or immunoglobulin molecules can be readily prepared by those of ordinary skill in the art. Suitable amino- and carboxy-termini of fragments or analogs occur near boundaries of functional domains. Structural and functional domains can be identified by comparison of the nucleotide and/or amino acid sequence data to public or proprietary sequence databases. In some embodiments, computerized comparison methods are used to identify sequence motifs or predicted protein conformation domains that occur in other proteins of known structure and/or function. Methods to identify protein sequences that fold into a known three-dimensional structure are known. Bowie et al. Science 253:164 (1991). Thus, the foregoing examples demonstrate that those of skill in the art can recognize sequence motifs and structural conformations that may be used to define structural and functional domains in accordance with the disclosure.

Suitable amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (for example, conservative amino acid substitutions) may be made in the naturally-occurring sequence (for example, in the portion of the polypeptide outside the domain(s) forming intermolecular contacts. A conservative amino acid substitution should not substantially change the structural characteristics of the parent sequence (e.g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, New York (1991)); and Thornton et al. Nature 354:105 (1991).

The term "polypeptide fragment" as used herein refers to a polypeptide that has an amino terminal and/or carboxy-terminal deletion, but where the remaining amino acid sequence is identical to the corresponding positions in the naturally-occurring sequence deduced, for example, from a full length cDNA sequence. Fragments typically are at least 5, 6, 8 or 10 amino acids long, for example, at least 14 amino acids long, for example, at least 20 amino acids long, usually at least 50 amino acids long, and for example, at least 70 amino acids long. The term "analog" as used herein refers to polypeptides which are comprised of a segment of at least 25 amino acids that has substantial identity to a portion of a deduced amino acid sequence and which has specific binding to CD47, under suitable binding conditions. Typically, polypeptide analogs comprise a conservative amino acid substitution (or addition or deletion) with respect to the naturally-occurring sequence. Analogs typically are at least 20 amino acids long, for example, at least 50 amino acids long or longer, and can often be as long as a full-length naturally-occurring polypeptide.

Peptide analogs are commonly used in the pharmaceutical industry as non-peptide drugs with properties analogous to those of the template peptide. These types of non-peptide compound are termed "peptide mimetics" or "peptidomimetics". Fauchere, J. Adv. Drug Res. 15:29 (1986), Veber and Freidinger TINS p.392 (1985); and Evans et al. J. Med. Chem. 30:1229 (1987). Such compounds are often developed with the aid of computerized molecular modeling. Peptide mimetics that are structurally similar to therapeutically useful peptides may be used to produce an equivalent therapeutic or prophylactic effect. Generally, peptidomimetics are structurally similar to a paradigm polypeptide (i.e., a polypeptide that has a biochemical property or pharmacological activity), such as human antibody, but have one or more peptide linkages optionally replaced by a linkage selected from the group consisting of: —$CH_2NH$—, —$CH_2S$—, —$CH_2$—$CH_2$—, —CH=CH—(cis and trans), —$COCH_2$—, $CH(OH)CH_2$—, and —$CH_2SO$—, by methods well known in the art. Systematic substitution of one or more amino acids of a consensus sequence with a D-amino acid of the same type (e.g., D-lysine in place of L-lysine) may be used to generate more stable peptides. In addition, constrained peptides comprising a consensus sequence or a substantially identical consensus sequence variation may be generated by methods known in the art (Rizo and Gierasch Ann. Rev. Biochem. 61:387 (1992)); for example, by adding internal cysteine residues capable of forming intramolecular disulfide bridges which cyclize the peptide.

The term "agent" is used herein to denote a chemical compound, a mixture of chemical compounds, a biological macromolecule, and/or an extract made from biological materials.

As used herein, the terms "label" or "labeled" refers to incorporation of a detectable marker, e.g., by incorporation of a radiolabeled amino acid or attachment to a polypeptide of biotinyl moieties that can be detected by marked avidin (e.g., streptavidin containing a fluorescent marker or enzymatic activity that can be detected by optical or calorimetric methods). In certain situations, the label or marker can also be therapeutic. Various methods of labeling polypeptides and glycoproteins are known in the art and may be used. Examples of labels for polypeptides include, but are not limited to, the following: radioisotopes or radionuclides (e.g., $^3H$, $^{14}C$, $^{15}N$, $^{35}S$, $^{90}Y$, $^{99}Tc$, $^{111}In$, $^{125}I$, $^{131}I$), fluorescent labels (e.g., FITC, rhodamine, lanthanide phosphors), enzymatic labels (e.g., horseradish peroxidase, β-galactosidase, luciferase, alkaline phosphatase), chemiluminescent, biotinyl groups, predetermined polypeptide epitopes recognized by a secondary reporter (e.g., leucine zipper pair sequences, binding sites for secondary antibodies, metal binding domains, epitope tags). In some embodiments, labels are attached by spacer arms of various lengths to reduce potential steric hindrance. The term "pharmaceutical agent or drug" as used herein refers to a chemical compound or composition capable of inducing a desired therapeutic effect when properly administered to a patient.

The term "antineoplastic agent" is used herein to refer to agents that have the functional property of inhibiting a development or progression of a neoplasm in a human, particularly a malignant (cancerous) lesion, such as a carcinoma, sarcoma, lymphoma, or leukemia. Inhibition of metastasis is frequently a property of antineoplastic agents.

As used herein, the terms "treat," treating," "treatment," and the like refer to reducing and/or ameliorating a disorder and/or symptoms associated therewith. By "alleviate" and/or "alleviating" is meant decrease, suppress, attenuate, diminish, arrest, and/or stabilize the development or progression of a disease such as, for example, a cancer. It will be appreciated that, although not precluded, treating a disorder or condition does not require that the disorder, condition or symptoms associated therewith be completely eliminated.

Other chemistry terms herein are used according to conventional usage in the art, as exemplified by The McGraw-Hill Dictionary of Chemical Terms (Parker, S., Ed., McGraw-Hill, San Francisco (1985)).

As used herein, "substantially pure" means an object species is the predominant species present (i.e., on a molar basis it is more abundant than any other individual species in the composition), and a substantially purified fraction is a composition wherein the object species comprises at least about 50 percent (on a molar basis) of all macromolecular species present.

Generally, a substantially pure composition will comprise more than about 80 percent of all macromolecular species present in the composition, for example, more than about 85%, 90%, 95%, and 99%. In some embodiments, the object species is purified to essential homogeneity (contaminant species cannot be detected in the composition by conventional detection methods) wherein the composition consists essentially of a single macromolecular species.

In this disclosure, "comprises," "comprising," "containing," "having," and the like can have the meaning ascribed to them in U.S. Patent law and can mean "includes," "including," and the like; the terms "consisting essentially of" or "consists essentially" likewise have the meaning ascribed in U.S. Patent law and these terms are open-ended, allowing for the presence of more than that which is recited so long as basic or novel characteristics of that which is recited are not changed by the presence of more than that which is recited, but excludes prior art embodiments.

By "effective amount" is meant the amount required to ameliorate the symptoms of a disease relative to an untreated patient. The effective amount of active compound(s) used to practice the present disclosure for therapeutic treatment of a disease varies depending upon the manner of administration, the age, body weight, and general health of the subject. Ultimately, the attending physician or veterinarian will decide the appropriate amount and dosage regimen. Such amount is referred to as an "effective" amount.

By "subject" is meant a mammal, including, but not limited to, a human or non-human mammal, such as a bovine, equine, canine, rodent, ovine, primate, camelid, or feline.

The term "administering," as used herein, refers to any mode of transferring, delivering, introducing, or transporting a therapeutic agent to a subject in need of treatment with such an agent. Such modes include, but are not limited to, oral, topical, intravenous, intraperitoneal, intramuscular, intradermal, intranasal, and subcutaneous administration.

By "fragment" is meant a portion of a polypeptide or nucleic acid molecule. This portion contains, for example, at least 10%, 20%, 30%, 40%, 50%, 60%, 70%, 80%, or 90% of the entire length of the reference nucleic acid molecule or polypeptide. A fragment may contain 10, 20, 30, 40, 50, 60, 70, 80, 90, or 100, 200, 300, 400, 500, 600, 700, 800, 900, or 1000 nucleotides or amino acids.

Ranges provided herein are understood to be shorthand for all of the values within the range. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50.

Unless specifically stated or obvious from context, as used herein, the terms "a," "an," and "the" are understood to be singular or plural. Unless specifically stated or obvious from context, as used herein, the term "or" is understood to be inclusive.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from the context, all numerical values provided herein are modified by the term "about."

41BB (CD137, TNFRSF9) Targeting

41BB is a member of the TNF receptor superfamily that is predominately expressed on activated T-cells and NK cells and serves as a co-stimulatory molecule. Agonizing 41BB enhances T cell proliferation and survival, cytolytic activity and cytokine secretion (e.g., IL-2, TNFα and INFγ). In mice, 41BB engagement has been shown to enhance anti-tumor immunity. (Croft, 2009, Nat Rev Immunol 9:271-285; Lynch, 2008, Immunol Rev. 22: 277-286). Importantly, tumor infiltrating cytotoxic T-cells (CTLs), have been shown to be express 41BB and it is these 41BB positive CTLs that have the highest anti-tumor cytotoxic activity (Ye et al Clin Cancer Res; 20(1): 44-55). The ligand for 41BB, 41BBL, naturally forms a homotrimer any thereby suggests that signaling is mediated by higher order clustering of 41BB. This is activation mechanism is shared with many members of the TNFRSF. Interest in exploiting 41BB signaling for anti-tumor immunotherapy has prompted the development of therapeutic 41BB antibodies. However, the capacity of bivalent 41BB antibodies to induce signaling is weak in absence of an exogenous clustering event. This can be achieved to some degree through the interaction with Fcγ-receptors (FcγRs), yet this can also lead to depletion of the 41BB-expressing cell through effector mechanisms (e.g. ADCC and ADCP). Furthermore, competition with the high concentration of IgG in serum attenuates efficient FcγR interactions. Therefore, current bivalent antibodies targeting 41BB are either ineffective agonists or have the liability of depleting the vary cells wherein 41BB signaling is desired. It has previously been shown that the therapeutic 41BB antibody, PF-05082566 is only capable of mediated 41BB signaling with cross-linked with anti-human secondary antibody (Fisher et al Cancer Immunol Immunother (2012) 61:1721-1733). Therefore, there exists a need for optimized 41BB agonist capable of mediating signaling in the absence of an exogenous crosslinking agent or FcγR interaction. The fusion proteins of the present disclosure are capable of mediating potent 41BB signaling 1) without any additional interactions when formatted as a multivalent fusion protein or 2) conditionally when engaged with at least a second antigen interaction when formatted as a multispecific fusion protein. The fusion proteins of the present disclosure are capable of standalone (multivalent) or conditional (multispecific) co-stimulatory activity on T-cell and NK cells.

Exemplary amino acid sequences of 41BB binding single domain antibodies are shown below:

4H04:
(SEQ ID NO: 16)
QVQLQESGGGLVQAGDSLRLSCAAS GWAFDNYG MAWFRQAPGKEREFIGR LAWNGGST DYADSV

KGRFTISRDNPKNTLYLQMNNLKPEDTAVYYC ARQRSYSGYGIRTPQTYDY WGQGTQVT (SEQ ID NO: 17)
CDR1: GWAFDNYG (SEQ ID NO: 18)
CDR2: LAWNGGST (SEQ ID NO: 19)
CDR3: ARQRSYSGYGIRTPQTYDY

4E1:
(SEQ ID NO: 20)
QVQLQQSGGGLVQAGDSLRLSCAAS GWAFGNYG MAWFRRAPGKEREFIGR LAWNGGST DYVDSV

KGRFTISRDNPKNTLYLQMNNLKPDDTAVYYC ARQRSYSRYDIRTPQTYDY WGQGTQVT (SEQ ID NO: 21)
CDR1: GWAFGNYG (SEQ ID NO: 18)
CDR2: LAWNGGST (SEQ ID NO: 22)
CDR3: ARQRSYSRYDIRTPQTYDY

4F5:
(SEQ ID NO: 23)
QVQLVQSGGGLVQPGGSLRLSCAAS GWAFDNYG MAWFRQAPGKEREFIGR LAWNGGST DYADSV

KGRFTISRDNPKNTLYLQMNSLKPEDTAVYYC ARQRSYSRYGIRAPQTYDY WGQGTQVT (SEQ ID NO: 17)
CDR1: GWAFDNYG (SEQ ID NO: 18)
CDR2: LAWNGGST (SEQ ID NO: 24)
CDR3: ARQRSYSRYGIRAPQTYDY

RH3:
(SEQ ID NO: 25)
QVQLQESGGGLVQPGGSLRLSCAVS GFSFSINA MGWYRQAPGKRREFLAA IDSGRNT VYAVSVK

GRFTISRDNAKNTVYLQMNSLKPEDTAIYYC GLLKGNRVVSPSVAY WGQGTQVT (SEQ ID NO: 26)
CDR1: GFSFSINA (SEQ ID NO: 27)
CDR2: IDSGRNT (SEQ ID NO: 28)
CDR3: GLLKGNRVVSPSVAY

D1:
(SEQ ID NO: 29)
EVQPVQSGGGLVQAGESLRLSCAAS ATIFSNNA MGWYRQAPGKQRELVAT ITTGGFT NYRDSVK

GRFDISRDNAKNTVYLQMNNLKPEDTAVYYC NVVLRYSRDYSYTTVKEY WGQGTQV (SEQ ID NO: 30)
CDR1: ATIFSNNA (SEQ ID NO: 31)
CDR2: ITTGGFT (SEQ ID NO: 32)
CDR3: NVVLRYSRDYSYTTVKEY

1G3:
(SEQ ID NO: 432)
QVQLVQSGGGLVQPGGSLRLSCAASGFTFSSYAMSWVRQAPGKGLEWVSAIPAGDGSTKYADSV

KGRFTISRDNAKNTVYLQMDSLKPEDTAVYFCAKSRGWSTVDDMDYWGKGTQV (SEQ ID NO: 433)
CDR1: GFTFSSYA (SEQ ID NO: 434)
CDR2: IPAGDGST (SEQ ID NO: 435)
CDR3: AKSRGWSTVDDMDY

1H4:
(SEQ ID NO: 436)
QVQLVQSGGGLVQPGGSLRLSCVVSGFTFRSYAMSWVRQAPGKGLEWVSTINSGESSTKYADSV

KGRFTISRDDAKNTLYLQMSDLKPEDTAVYFCAKHRGWSTVDDINYWGKGTQV (SEQ ID NO: 437)
CDR1: GFTFRSYA (SEQ ID NO: 438)
CDR2: INSGESST (SEQ ID NO: 439)
CDR3: AKHRGWSTVDDINY

1H1:
(SEQ ID NO: 440)
QVQLVQSGGGLVQPGGSLRLSCAASGFTFDDHAMSWVRQAPGKGLEWVSAISWNGHYTYYAESM

KGRFAISRDNAKNTLYLQMNSLKSEDTAVYYCVKGWRGSYTRDRPFASWGQGTQV (SEQ ID NO: 441)
CDR1: GFTFDDHA (SEQ ID NO: 442)
CDR2: ISWNGHYT (SEQ ID NO: 443)
CDR3: VKGWRGSYTRDRPFAS

1H8:
(SEQ ID NO: 444)
EVQLVQSGGGLVQPGGSLRLSCAASGFTFSSYYMSWVRQAPGKGLEWVSTISTNTGGGSTYYAY

ADSVKGRFTISRDNAKNTLYLEMNSLKPEDTAQYYCVRTRWEGVYDYWGLGTQV (SEQ ID NO: 445)
CDR1: GFTFSSYY (SEQ ID NO: 446)
CDR2: ISTNTGGGST (SEQ ID NO: 447)
CDR3: VRTRWEGVYDY

Hz4E1-v1:
(SEQ ID NO: 33)
EVQLLESGGGEVQPGGSLRLSCAASGWAFGNYGMAWFRQAPGKGLEWVARLAWNGGSTDYAESV

KGRFTISRDNAKNTLYLQMSSLRAEDTAVYYCARQRSYSRYDIRTPQTYDYWGQGTLVTVKP (SEQ ID NO: 21)
CDR1: GWAFGNYG (SEQ ID NO: 18)
CDR2: LAWNGGST (SEQ ID NO: 22)
CDR3: ARQRSYSRYDIRTPQTYDY

```
Hz4E1-v3:
                                                         (SEQ ID NO: 34)
EVQLLESGGGEVQPGGSLRLSCAAS GWAFGNYG MAWFRQAPGKGREFVAR LAWNGGST DYAESV

KGRFTISRDNAKNTLYLQMSSLRAEDTAVYYC ARQRSYSRYDIRTPQTYDY WGQGTLVTVKP (SEQ ID NO: 21)
CDR1: GWAFGNYG (SEQ ID NO: 18)
CDR2: LAWNGGST (SEQ ID NO: 22)
CDR3: ARQRSYSRYDIRTPQTYDY hz4E01v7-1:
                                                         (SEQ ID NO: 35)
EVQLLESGGGEVQPGGSLRLSCAAS GWAFGNYG MAWFRQAPGKEREFVSR LAWNGGST DYVAES

VKGRFTISRDNAKNTLYLQMSSLRAEDTAVYYC ARQRSYSRYDIRTPQTYDY WGQGTLVTVK (SEQ ID NO: 21)
CDR1: GWAFGNYG (SEQ ID NO: 18)
CDR2: LAWNGGST (SEQ ID NO: 22)
CDR3: ARQRSYSRYDIRTPQTYDY hz4E01v8:
                                                         (SEQ ID NO: 36)
EVQLLESGGGEVQPGGSLRLSCAAS GWAFGNYG MAWFRQAPGKEREFIGR LAWNGGST DYVESV

KGRFTISRDNPKNTLYLQMSSLRAEDTAVYYC ARQRSYSRYDIRTPQTYDY WGQGTLVTVKP (SEQ ID NO: 21)
CDR1: GWAFGNYG (SEQ ID NO: 18)
CDR2: LAWNGGST (SEQ ID NO: 22)
CDR3: ARQRSYSRYDIRTPQTYDY hz4E01v9:
                                                         (SEQ ID NO: 37)
EVQLLESGGGEVQPGGSLRLSCAAS GWAFGNYG MAWFRQAPGKEREFVSR LAWNGGST DYVESV

KGRFTISRDNAKNTLYLQMSSLRAEDTAVYYC ARQRSYSRYDIRTPQTYDY WGQGTLVTVKP (SEQ ID NO: 21)
CDR1: GWAFGNYG (SEQ ID NO: 18)
CDR2: LAWNGGST (SEQ ID NO: 22)
CDR3: ARQRSYSRYDIRTPQTYDY hz4E01v10:
                                                         (SEQ ID NO: 38)
EVQLLESGGGEVQPGGSLRLSCAAS GWAFGNYG MAWFRQAPGKEREFVSR LAWNGGST DYVESV

KGRFTISRDNPKNTLYLQMSSLRAEDTAVYYC ARQRSYSRYDIRTPQTYDY WGQGTLVTVKP (SEQ ID NO: 21)
CDR1: GWAFGNYG (SEQ ID NO: 18)
CDR2: LAWNGGST (SEQ ID NO: 22)
CDR3: ARQRSYSRYDIRTPQTYDY
```

-continued hz4E01v11:
(SEQ ID NO: 39)
EVQLLESGGGEVQPGGSLRLSCAASGWAFGNYGMAWFRQAPGKEREFIGRLAWNGGSTDYVESV

KGRFTISRDNAKNTLYLQMSSLRAEDTAVYYCARQRSYSRYDIRTPQTYDYWGQGTLVTVKP (SEQ ID NO: 21)
CDR1: GWAFGNYG (SEQ ID NO: 18)
CDR2: LAWNGGST (SEQ ID NO: 22)
CDR3: ARQRSYSRYDIRTPQTYDY hz4E01v12:
(SEQ ID NO: 40)
EVQLLESGGGEVQPGGSLRLSCAASGWAFGNYGMAWFRQAPGKEREFIGRLAWNGGSTDYVESV

KGRFTISRDNPKNTLYLQMSSLRAEDTAVYYCARQRSYSRYDIRTPQTYDYWGQGTLVTVKP (SEQ ID NO: 21)
CDR1: GWAFGNYG (SEQ ID NO: 18)
CDR2: LAWNGGST (SEQ ID NO: 22)
CDR3: ARQRSYSRYDIRTPQTYDY hz4E01v13:
(SEQ ID NO: 41)
EVQLLESGGGEVQPGGSLRLSCAASGWAFGNYGMAWFRQAPGKEREFIGRLAWQGGSTDYVESV

KGRFTISRDNPKNTLYLQMSSLRAEDTAVYYCARQRSYSRYDIRTPQTYDYWGQGTLVTVKP (SEQ ID NO: 21)
CDR1: GWAFGNYG (SEQ ID NO: 42)
CDR2: LAWQGGST (SEQ ID NO: 22)
CDR3: ARQRSYSRYDIRTPQTYDY hz4E01v14:
(SEQ ID NO: 43)
EVQLLESGGGEVQPGGSLRLSCAASGWAFGNYGMAWFRQAPGKEREFIGRLAWNAGSTDYVESV

KGRFTISRDNPKNTLYLQMSSLRAEDTAVYYCARQRSYSRYDIRTPQTYDYWGQGTLVTVKP (SEQ ID NO: 21)
CDR1: GWAFGNYG (SEQ ID NO: 44)
CDR2: LAWNAGST (SEQ ID NO: 22)
CDR3: ARQRSYSRYDIRTPQTYDY hz4E01v16:
(SEQ ID NO: 45)
EVQLLESGGGEVQPGGSLRLSCAASGWAFGNYGMAWFRQAPGKEREFVSRLAWQGGSTDYVESV

KGRFTISRDNAKNTLYLQMSSLRAEDTAVYYCARQRSYSRYDIRTPQTYDYWGQGTLVTVKP (SEQ ID NO: 21)
CDR1: GWAFGNYG (SEQ ID NO: 42)
CDR2: LAWQGGST (SEQ ID NO: 22)
CDR3: ARQRSYSRYDIRTPQTYDY hz4E01v17:

(SEQ ID NO: 46)
EVQLLESGGGEVQPGGSLRLSCAAS`GWAFGNYG`MAWFRQAPGKEREFVSR`LAWNAGST`DYVESV
KGRFTISRDNAKNTLYLQMSSLRAEDTAVYYC`ARQRSYSRYDIRTPQTYDY`WGQGTLVTVKP (SEQ ID NO: 21)
CDR1: GWAFGNYG (SEQ ID NO: 44)
CDR2: LAWNAGST (SEQ ID NO: 22)
CDR3: ARQRSYSRYDIRTPQTYDY hz4E01v18:

(SEQ ID NO: 47)
EVQLLESGGGEVQPGGSLRLSCAAS`GWAFGNYG`MAWFRQAPGKEREFVSR`LAWGGGST`DYVESV
KGRFTISRDNAKNTLYLQMSSLRAEDTAVYYC`ARQRSYSRYDIRTPQTYDY`WGQGTLVTVKP (SEQ ID NO: 21)
CDR1: GWAFGNYG (SEQ ID NO: 48)
CDR2: LAWGGGST (SEQ ID NO: 22)
CDR3: ARQRSYSRYDIRTPQTYDY hz4E01v21:

(SEQ ID NO: 49)
EVQLLESGGGEVQPGGSLRLSCAAS`GWAFSNYG`MAWFRQAPGKEREFVSR`LAWGGGST`DYVESV
KGRFTISRDNAKNTLYLQMSSLRAEDTAVYYC`ARQRSYSRYDIRTPQTYDY`WGQGTLVTVKP (SEQ ID NO: 50)
CDR1: GWAFSNYG (SEQ ID NO: 48)
CDR2: LAWGGGST (SEQ ID NO: 22)
CDR3: ARQRSYSRYDIRTPQTYDY hz4E01v22:

(SEQ ID NO: 51)
EVQLLESGGGEVQPGGSLRLSCAAS`GWAFGNYG`MAWFRQAPGKEREFVSR`LAWSGGST`DYVESV
KGRFTISRDNAKNTLYLQMSSLRAEDTAVYYC`ARQRSYSRYGIRTPQTYDY`WGQGTLVTVKP (SEQ ID NO: 21)
CDR1: GWAFGNYG (SEQ ID NO: 52)
CDR2: LAWSGGST (SEQ ID NO: 22)
CDR3: ARQRSYSRYDIRTPQTYDY hz4E01v23:

(SEQ ID NO: 53)
EVQLLESGGGEVQPGGSLRLSCAAS`GWAFSNYG`MAWFRQAPGKEREFVSR`LAWGGST`DYVESV
KGRFTISRDNAKNTLYLQMSSLRAEDTAVYYC`ARQRSYSRYDIRTPQTYDY`WGQGTLVTVKP (SEQ ID NO: 50)
CDR1: GWAFSNYG (SEQ ID NO: 52)
CDR2: LAWSGGST (SEQ ID NO: 22)
CDR3: ARQRSYSRYDIRTPQTYDY hz4E01v24:
(SEQ ID NO: 54)
EVQLLESGGGEVQPGGSLRLSCAAS GWAFGNYG MAWFRQAPGKEREFVSR LAWGGGST DYVESV
KGRFTISRDNAKNTLYLQMSSLRAEDTAVYYC ARQRSYSGYDIRTPQTYDY WGQGTLVTVKP (SEQ ID NO: 21)
CDR1: GWAFGNYG (SEQ ID NO: 48)
CDR2: LAWGGGST (SEQ ID NO: 55)
CDR3: ARQRSYSGYDIRTPQTYDY hz4E01v25:
(SEQ ID NO: 56)
EVQLLESGGGEVQPGGSLRLSCAAS GWAFGNYG MAWFRQAPGKEREFVSR LAWGGGST DYVESV
KGRFTISRDNAKNTLYLQMSSLRAEDTAVYYC ARQRSYSRYGIRTPQTYDY WGQGTLVTVKP (SEQ ID NO: 21)
CDR1: GWAFGNYG (SEQ ID NO: 48)
CDR2: LAWGGGST (SEQ ID NO: 57)
CDR3: ARQRSYSRYGIRTPQTYDY hz4E01v26:
(SEQ ID NO: 58)
EVQLLESGGGEVQPGGSLRLSCAAS GWAFGNYG MAWFRQAPGKEREFVSR LAWGGGST DYVESV
KGRFTISRDNAKNTLYLQMSSLRAEDTAVYYC ARQRSYSGYGIRTPQTYDY WGQGTLVTVKP (SEQ ID NO: 21)
CDR1: GWAFGNYG (SEQ ID NO: 48)
CDR2: LAWGGGST (SEQ ID NO: 19)
CDR3: ARQRSYSGYGIRTPQTYDY hzRH3-v1:
(SEQ ID NO: 59)
EVQLLESGGGEVQPGGSLRLSCAAS GFSFSINA MGWYRQAPGKGLEWVAA IDSGRNT VYAESVK
GRFTISRDNAKNTLYLQMSSLRAEDTAVYYC GLLKGNRVVSPSVAY WGQGTLVTVKP (SEQ ID NO: 26)
CDR1: GFSFSINA (SEQ ID NO: 27)
CDR2: IDSGRNT (SEQ ID NO: 28)
CDR3: GLLKGNRVVSPSVAY hzRH3v5-1:
(SEQ ID NO: 60)
EVQLLESGGGEVQPGGSLRLSCAAS GFSFSINA MGWYRQAPGKRREFVAA IESGRNT VYAESVK
GRFTISRDNAKNTVYLQMSSLRAEDTAVYYC GLLKGNRVVSPSVAY WGQGTLVTVKP (SEQ ID NO: 26)
CDR1: GFSFSINA (SEQ ID NO: 61)
CDR2: IESGRNT (SEQ ID NO: 28)
CDR3: GLLKGNRVVSPSVAY hzRH3v5-2:

(SEQ ID NO: 62)
EVQLLESGGGEVQPGGSLRLSCAAS`GFSFSINA`MGWYRQAPGKRREFVAA`IYSGRNT`VYAESVK
GRFTISRDNAKNTVYLQMSSLRAEDTAVYYC`GLLKGNRVVSPSVAY`WGQGTLVTVKP (SEQ ID NO: 26)
CDR1: GFSFSINA (SEQ ID NO: 63)
CDR2: IYSGRNT (SEQ ID NO: 28)
CDR3: GLLKGNRVVSPSVAY hzRH3v5-3

(SEQ ID NO: 64)
EVQLLESGGGEVQPGGSLRLSCAAS`GFTFSINA`MGWYRQAPGKRREFVAA`IESGRNT`VYAESVK
GRFTISRDNAKNTVYLQMSSLRAEDTAVYYC`GLLKGNRVVSPSVAY`WGQGTLVTVKP (SEQ ID NO: 65)
CDR1: GFTFSINA (SEQ ID NO: 61)
CDR2: IESGRNT (SEQ ID NO: 28)
CDR3: GLLKGNRVVSPSVAY hzRH3v5-6

(SEQ ID NO: 66)
EVQLLESGGGEVQPGGSLRLSCAAS`GFSFSINA`MSWYRQAPGKRREFVAA`IESGRNT`VYAESVK
GRFTISRDNAKNTVYLQMSSLRAEDTAVYYC`GLLKGNRVVSPSVAY`WGQGTLVTVKP (SEQ ID NO: 67)
CDR1: GFSFSINA (SEQ ID NO: 61)
CDR2: IESGRNT (SEQ ID NO: 28)
CDR3: GLLKGNRVVSPSVAY hzRH3v5-8

(SEQ ID NO: 68)
EVQLLESGGGEVQPGGSLRLSCAAS`GFTFSSNA`MGWYRQAPGKRREFVAA`IESGRNT`VYAESVK
GRFTISRDNAKNTVYLQMSSLRAEDTAVYYC`GLLKGNRVVSPSVAY`WGQGTLVTVKP (SEQ ID NO: 69)
CDR1: GFTFSSNA (SEQ ID NO: 61)
CDR2: IESGRNT (SEQ ID NO: 28)
CDR3: GLLKGNRVVSPSVAY hzRH3v5-10

(SEQ ID NO: 70)
EVQLLESGGGEVQPGGSLRLSCAAS`GFSFSINA`MGWYRQAPGKRREFVAA`IESSRNT`VYAESVK
GRFTISRDNAKNTVYLQMSSLRAEDTAVYYC`GLLKGNRVVSPSVAY`WGQGTLVTVKP (SEQ ID NO: 26)
CDR1: GFSFSINA (SEQ ID NO: 71)
CDR2: IESSRNT (SEQ ID NO: 28)
CDR3: GLLKGNRVVSPSVAY hzRH3v5-12

(SEQ ID NO: 72)
EVQLLESGGGEVQPGGSLRLSCAAS`GFSFSINA`MGWYRQAPGKRREFVAA`IESGSNT`VYAESVK
GRFTISRDNAKNTVYLQMSSLRAEDTAVYYC`GLLKGNRVVSPSVAY`WGQGTLVTVKP

CDR1: GFSFSINA (SEQ ID NO: 26)

CDR2: IESGSNT (SEQ ID NO: 73)

CDR3: GLLKGNRVVSPSVAY (SEQ ID NO: 28)

hzRH3v5-14

(SEQ ID NO: 74)
EVQLLESGGGEVQPGGSLRLSCAAS`GFSFSINA`MGWYRQAPGKRREFVAA`IESGRST`VYAESVK
GRFTISRDNAKNTVYLQMSSLRAEDTAVYYC`GLLKGNRVVSPSVAY`WGQGTLVTVKP

CDR1: GFSFSINA (SEQ ID NO: 26)

CDR2: IESGRST (SEQ ID NO: 75)

CDR3: GLLKGNRVVSPSVAY (SEQ ID NO: 28)

hzRH3v5-15

(SEQ ID NO: 76)
EVQLLESGGGEVQPGGSLRLSCAAS`GFSFSINA`MGWYRQAPGKRREFVAA`IESGRNT`YYAESVK
GRFTISRDNAKNTVYLQMSSLRAEDTAVYYC`GLLKGNRVVSPSVAY`WGQGTLVTVKP

CDR1: GFSFSINA (SEQ ID NO: 26)

CDR2: IESGRNT (SEQ ID NO: 77)

CDR3: GLLKGNRVVSPSVAY (SEQ ID NO: 28)

hzRH3v5-16

(SEQ ID NO: 78)
EVQLLESGGGEVQPGGSLRLSCAAS`GFSFSINA`MGWYRQAPGKRREFVAA`IYSGSST`VYAESVK
GRFTISRDNAKNTVYLQMSSLRAEDTAVYYC`GLLKGNRVVSPSVAY`WGQGTLVTVKP

CDR1: GFSFSINA (SEQ ID NO: 26)

CDR2: IYSGSST (SEQ ID NO: 79)

CDR3: GLLKGNRVVSPSVAY (SEQ ID NO: 28)

hzRH3v7

(SEQ ID NO: 80)
EVQLLESGGGEVQPGGSLRLSCAVS`GFSFSINA`MGWYRQAPGKRREFVAA`IESGRNT`VYAESVK
GRFTISRDNAKNTVYLQMSSLRAEDTAVYYC`GLLKGNRVVSPSVAY`WGQGTLVTVKP

CDR1: GFSFSINA (SEQ ID NO: 26)

CDR2: IESGRNT (SEQ ID NO: 61)

CDR3: GLLKGNRVVSPSVAY (SEQ ID NO: 28)

hzRH3v8
(SEQ ID NO: 81)
EVQLLESGGGEVQPGGSLRLSCAAS GFSFSINA MGWYRQAPGKRREFVAA IESGRNT VYAVSVK
GRFTISRDNAKNTVYLQMSSLRAEDTAVYYC GLLKGNRVVSPSVAY WGQGTLVTVKP

CDR1: GFSFSINA (SEQ ID NO: 26)

CDR2: IESGRNT (SEQ ID NO: 61)

CDR3: GLLKGNRVVSPSVAY (SEQ ID NO: 28)

hzRH3v9
(SEQ ID NO: 82)
EVQLLESGGGEVQPGGSLRLSCAAS GFSFSINA MGWYRQAPGKGREFVAA IESGRNT VYAESVK
GRFTISRDNAKNTVYLQMSSLRAEDTAVYYC GLLKGNRVVSPSVAY WGQGTLVTVKP

CDR1: GFSFSINA (SEQ ID NO: 26)

CDR2: IESGRNT (SEQ ID NO: 61)

CDR3: GLLKGNRVVSPSVAY (SEQ ID NO: 28)

hzRH3v13
(SEQ ID NO: 83)
EVQLLESGGGEVQPGGSLRLSCAAS GFSFSINA MGWYRQAPGKRREFLAA IESGRNT VYAESVK
GRFTISRDNAKNTVYLQMSSLRAEDTAVYYC GLLKGNRVVSPSVAY WGQGTLVTVKP

CDR1: GFSFSINA (SEQ ID NO: 26)

CDR2: IESGRNT (SEQ ID NO: 61)

CDR3: GLLKGNRVVSPSVAY (SEQ ID NO: 28)

In some embodiments, the 41BB binding domain comprises or is derived from an antibody sequence or antigen-binding fragment thereof that includes a combination of a variable heavy chain (VH) sequence and a variable light chain (VL) sequence selected from the group consisting of:

VH Sequences:
(SEQ ID NO: 84)
QVQLVQSGAEVKKPGSSVKVSCKASGGTFNSYAISWVRQAPGQGLEWMG
GIIPGFGTANYAQKFQGRVTITADESTSTAYMELSSLRSEDTAVYYCAR
KNEEDGGFDHWGQGTLVTVSS (SEQ ID NO: 85)
QVQLVESGGGLVQPGGSLRLSCAASGFTFSDYYMHWVRQAPGKGLEWVS
VISGSGSNTYYADSVKGRFTISRDNSKNTLYLQMNSLRAEDTAVYYCAR
LYAQFEGDFWGQGTLVTVSS (SEQ ID NO: 86)
QVQLVQSGAEVKKPGESLKISCKGSGYSFSTYWISWVRQMPGKGLEWMG
KIYPGDSYTNYSPSFQGQVTISADKSISTAYLQWSSLKASDTAMYYCAR
GYGIFDYWGQGTLVTVSS (SEQ ID NO: 87)
EVQLVQSGAEVKKPGESLRISCKGSGYSFSTYWISWVRQMPGKGLEWMG
KIYPGDSYTNYSPSFQGQVTISADKSISTAYLQWSSLKASDTAMYYCAR
GYGIFDYWGQGTLVTVSS VL Sequences:
(SEQ ID NO: 88)
DIELTQPPSVSVAPGQTARISCSGDNLGDYYASWYQQKPGQAPVLVIYD
DSNRPSGIPERFSGSNSGNTATLTISGTQAEDEADYYCQTWDGTLHFVF
GGGTKLTVL (SEQ ID NO: 89)
DIELTQPPSVSVAPGQTARISCSGDNIGSKYVSWYQQKPGQAPVLVIYS
DSERPSGIPERFSGSNSGNTATLTISGTQAEDEADYYCQSWDGSISRVF
GGGTKLTVL (SEQ ID NO: 90)
DIELTQPPSVSVAPGQTARISCSGDNIGDQYAHWYQQKPGQAPVVVIYQ
DKNRPSGIPERFSGSNSGNTATLTISGTQAEDEADYYCATYTGFGSLAV
FGGGTKLTVL

```
                                                     (SEQ ID NO: 91)
SYELTQPPSVSVSPGQTASITCSGDNIGDQYAHWYQQKPGQSPVLVIYQ

DKNRPSGIPERFSGSNSGNTATLTISGTQAMDEADYYCATYTGFGSLAV

FGGGTKLTVL (SEQ ID NO: 92)
SYELTQPPSVSVSPGQTASITCSGDNIGDQYAHWYQQKPGQSPVVVIYQ

DKNRPSGIPERFSGSNSGNTATLTISGTQAMDEADYYCATYTGFGSLAV

FGGGTKLTVL (SEQ ID NO: 93)
DIELTQPPSVSVAPGQTARISCSGDNIGDQYAHWYQQKPGQAPVVVIYQ

DKNRPSGIPERFSGSNSGNTATLTISGTQAEDEADYYCSTYTFVGFTTV

FGGGTKLTVL (SEQ ID NO: 94)
SYELTQPPSVSVSPGQTASITCSGDNIGDQYAHWYQQKPGQSPVLVIYQ

DKNRPSGIPERFSGSNSGNTATLTISGTQAMDEADYYCSTYTFVGFTTV

FGGGTKLTVL (SEQ ID NO: 95)
SYELTQPPSVSVSPGQTASITCSGDNIGDQYAHWYQQKPGQSPVVVIYQ

DKNRPSGIPERFSGSNSGNTATLTISGTQAMDEADYYCSTYTFVGFTTV

FGGGTKLTVL
```

In some embodiments, the 41BB binding domain comprises or is derived from an antibody sequence or antigen-binding fragment thereof that includes a combination of a heavy chain (HC) sequence and a light chain (LC) sequence selected from the group consisting of:

```
HC Sequences:
                                                     (SEQ ID NO: 96)
QVQLQQWGAGLLKPSETLSLTCAVYGGSFSGYYWSWIRQSPEKGLEWIGEI

NHGGYVTYNPSLESRVTISVDTSKNQFSLKLSSVTAADTAVYYCARDYGPG

NYDWYFDLWGRGTLVTVSSASTKGPSVFPLAPCSRSTSESTAALGCLVKDY

FPEPVTVSWNSGALTSGVHTFPAVLQSSGLYSLSSVVTVPSSSLGTKTYTC

NVDHKPSNTKVDKRVESKYGPPCPPCPAPEFLGGPSVFLFPPKPKDTLMIS

RTPEVTCVVVDVSQEDPEVQFNWYVDGVEVHNAKTKPREEQFNSTYRVVSV

LTVLHQDWLNGKEYKCKVSNKGLPSSIEKTISKAKGQPREPQVYTLPPSQE

EMTKNQVSLTCLVKGFYPSDIAVEWESNGQPENNYKTTPPVLDSDGSFFLY

SRLTVDKSRWQEGNVFSCSVMHEALHNHYTQKSLSLSLGK (SEQ ID NO: 97)
QVQLQQWGAGLLKPSETLSLTCAVYGGSFSGYYWSWIRQSPEKGLEWIGEI

NHGGYVTYNPSLESRVTISVDTSKNQFSLKLSSVTAADTAVYYCARDYGPG

NYDWYFDLWGRGTLVTVSSASTKGPSVFPLAPSSKSTSGGTAALGCLVKDY

FPEPVTVSWNSGALTSGVHTFPAVLQSSGLYSLSSVVTVPSSSLGTQTYIC

NVNHKPSNTKVDKRVEPKSCDKTHTCPPCPAPELLGGPSVFLFPPKPKDTL

MISRTPEVTCVVVDVSHEDPEVKFNWYVDGVEVHNAKTKPREEQYNSTYRV

VSVLTVLHQDWLNGKEYKCKVSNKALPAPIEKTISKAKGQPREPQVYTLPP

SRDELTKNQVSLTCLVKGFYPSDIAVEWESNGQPENNYKTTPPVLDSDGSF

FLYSKLTVDKSRWQQGNVFSCSVMHEALHNHYTQKSLSLSPGK

LC Sequences:
                                                     (SEQ ID NO: 98)
EIVLTQSPATLSLSPGERATLSCRASQSVSSYLAWYQQKPGQAPRLLIYDA

SNRATGIPARFSGSGSGTDFTLTISSLEPEDFAVYYCQQRSNWPPALTFGG

GTKVEIKRTVAAPSVFIFPPSDEQLKSGTASVVCLLNNFYPREAKVQWKVD

NALQSGNSQESVIEQDSKDSTYSLSSTLTLSKADYEKHKVYACEVTHQGLS

SPVTKSFNRGEC
```

In some embodiments, the 41BB binding domain comprises or is derived from an antibody sequence or antigen-binding fragment thereof selected from the antibody sequences described in US Patent Application Publication No. 20160244528, the contents of which are hereby incorporated by reference in their entirety.

In some embodiments, the 41BB binding domain comprises or is derived from an antibody sequence or antigen-binding fragment thereof selected from the antibody sequences described in U.S. Pat. No. 8,337,850, the contents of which are hereby incorporated by reference in their entirety.

In some embodiments, the 41BB binding domain comprises or is derived from an antibody sequence or antigen-binding fragment thereof selected from the antibody sequences described in PCT Publication No. WO 2005/035584, the contents of which are hereby incorporated by reference in their entirety.

In some embodiments, the 41BB binding domain comprises or is derived from an antibody sequence or antigen-binding fragment thereof selected from the antibody sequences described in EP Patent No. EP 1670828 B1, the contents of which are hereby incorporated by reference in their entirety.

In some embodiments, the 41BB binding domain comprises or is derived from an antibody sequence or antigen-binding fragment thereof selected from the antibody sequences described in PCT Publication No. WO 2006/088447, the contents of which are hereby incorporated by reference in their entirety.

In some embodiments, the 41BB binding domain comprises or is derived from an antibody sequence or antigen-binding fragment thereof selected from the antibody sequences described in US Patent Application Publication No. 20080166336, the contents of which are hereby incorporated by reference in their entirety.

In some embodiments, the 41BB binding domain comprises or is derived from an anti-cancer fusion protein sequence or antigen-binding fragment thereof selected from the sequences described in PCT Publication No. WO 2016/177802, the contents of which are hereby incorporated by reference in their entirety. In some embodiments, the 41BB binding domain comprises or is derived from an amino acid sequence comprising:

```
                                                     (SEQ ID NO: 99)
QDSTSDLIPAPPLSKVPLQQNFQDNQFHGKWYVVGQAGNIRLREDKDPIKM

MATIYELKEDKSYDVTMVKFDDKKCMYDIWTFVPGSQPGEFTLGKIKSFPG

HTSSLVRVVSTNYNQHAMVFFKFVFQNREEFYITLYGRTKELTSELKENFI

RFSKSLGLPENHIVFPVPIDQCIDG
```

In some embodiments, the 41BB binding domain comprises or is derived from an 41BB-targeting polypeptide sequence or antigen-binding fragment thereof selected from the sequences described in PCT Publication No. WO 2016/177762, the contents of which are hereby incorporated by reference in their entirety. In some embodiments, the 41BB binding domain comprises or is derived from an amino acid sequence comprising:

PDL1 Targeting

In some embodiments, the fusion proteins are multispecific containing at least a first binding domain, e.g., a TBD, and a second binding domain directed toward Program Death Ligand 1 (PD-L1). In these, embodiments, the binding to PD-L1 is capable of providing the additional cross-linking function and TNFRSF activation is achieved with only one or two TBDs. In these embodiments, the TNFRSF signaling is enhanced and focused by the presence of a PD-L1 expressing cell.

PDL1 is a 40 kDa type I transmembrane protein that forms a complex with its receptor programmed cell death protein 1 (PD1), also known as CD279. Engagement of PDL1 with its receptor PD1 on T cells delivers a signal that inhibits TCR-mediated activation of IL-2 production and T cell proliferation. Aberrant expression and/or activity of PDL1 and PDL1-related signaling has been implicated in the pathogenesis of many diseases and disorders, such as cancer, inflammation, and autoimmunity.

In some embodiments, the PD-L1 binding portion is single domain antibody. In some embodiments, the PDL1 binding portion of the fusion blocks or dampens the interaction of PDL1 and PD-1. Exemplary PDL1-targeting single domain sequences are shown below:

```
28A10:
                                                        (SEQ ID NO: 100)
QVQLQESGGGLVQAGGSLRLACTTSGGIFNIRPISWYRQPPGMQREWVATIAFGGATNYANSIK

GRFTASRDNAKNTVYLQMNGLKPEDTAVYYCNAFEIWGQGTQVTV (SEQ ID NO: 101)
CDR1: GGIFNIRP (SEQ ID NO: 102)
CDR2: IAFGGAT (SEQ ID NO: 103)
CDR3: NAFEI

28A2:
                                                        (SEQ ID NO: 104)
QLQLQESGGGLVRAGGSLRLACTTSGGIFAIKPISWYRQPPGQEREWVTTTTSSGATNYANSIK

GRFTVARDNAKNTVYLQMNDLKLEDTAVYYCNVFEYWGQGTQVTV (SEQ ID NO: 105)
CDR1: GGIFAIKP (SEQ ID NO: 106)
CDR2: TTSSGAT (SEQ ID NO: 107)
CDR3: NVFEY

B03:
                                                        (SEQ ID NO: 108)
QVQLQESGGDLVQAGSSLRLACATSGGVFNIRPISWYRQPPGKQREWVATIASGGATNYANSIK

GRFTASRDNAKNTVYLQMNGLKPEDTAVYYCNAFEVWGQGTQVTV (SEQ ID NO: 109)
CDR1: GGVFNIRP (SEQ ID NO: 110)
CDR2: IASGGAT (SEQ ID NO: 111)
CDR3: NAFEV

B10:
                                                        (SEQ ID NO: 112)
QVQLQQSGGGLVQAGGSLRLACTTSGGIFNIRPISWYRQPPGMQREWVATIASGGATNYANSIK

GRFTASRDNAKNTVYLQMNGLKPEDTAVYYCNTLNHWGRGTQVTV (SEQ ID NO: 101)
CDR1: GGIFNIRP (SEQ ID NO: 110)
CDR2: IASGGAT
```

-continued

CDR3: NTLNF (SEQ ID NO: 113)

D02:
(SEQ ID NO: 114)
QVQLQESGGGLVQAGGSLRLACTTS`GGIFNIRP`ISWYRQPPGMQREWVAT`IASGGAT`NYANSIK
GRFTASRDNAKNTVYLMNGLKPEDTAVYYC`NVFEI`WGQGTQVTV

CDR1: GGIFNIRP (SEQ ID NO: 101)

CDR2: IASGGAT (SEQ ID NO: 110)

CDR3: NVFEI (SEQ ID NO: 115)

A03:
(SEQ ID NO: 116)
QVQLQQSGGGLVQAGGSLRLACITS`GGIFNIRP`ISWYRQPPGKQREWVAT`IASGGAA`NYANSIK
GRFTASRDNAKNTVYLMNGLKPEDTAVYYC`NAFEN`WGQGTQVTV

CDR1: GGIFNIRP (SEQ ID NO: 101)

CDR2: IASGGAA (SEQ ID NO: 117)

CDR3: NAFEN (SEQ ID NO: 118)

hz28A2v1
(SEQ ID NO: 119)
QVQLQESGGGEVQPGGSLRLSCAAS`GGIFAIKP`ISWYRQAPGKQREWVST`TTSSGAT`NYAESVK
GRFTISRDNAKNTLYLQMSSLRAEDTAVYYC`NVFEY`WGQGTLVTVKP

CDR1: GGIFAIKP (SEQ ID NO: 105)

CDR2: TTSSGAT (SEQ ID NO: 106)

CDR3: NVFEY (SEQ ID NO: 107)

hz28A2v1-1
(SEQ ID NO: 120)
EVQLQESGGGEVQPGGSLRLSCAAS`GGIFAIKP`ISWYRQAPGKQREWVST`TTSSGAT`NYAESVK
GRFTISRDNAKNTLYLQMSSLRAEDTAVYYC`NVFEY`WGQGTLVTVKP

CDR1: GGIFAIKP (SEQ ID NO: 105)

CDR2: TTSSGAT (SEQ ID NO: 106)

CDR3: NVFEY (SEQ ID NO: 107)

hz28A2v2
(SEQ ID NO: 121)
EVQLLESGGGEVQPGGSLRLSCAAS`GGIFAIKP`ISWYRQAPGKQREWVST`TTSSGAT`NYAESVK
GRFTISRDNAKNTLYLQMSSLRAEDTAVYYC`NVFEY`WGQGTLVTVKP

CDR1: GGIFAIKP (SEQ ID NO: 105)

CDR2: TTSSGAT (SEQ ID NO: 106)

CDR3: NVFEY (SEQ ID NO: 107)

hz28A2v3

(SEQ ID NO: 122)
EVQLLESGGGEVQPGGSLRLSCAAS GGIFAIKP ISWYRQAPGKQREWVST TTSSGAT NYAESVK
GRFTISRDNAKNTLYLQMSSLRAEDTAVYYC NVFEY WGQGTLVTVKP (SEQ ID NO: 105)
CDR1: GGIFAIKP (SEQ ID NO: 106)
CDR2: TTSSGAT (SEQ ID NO: 107)
CDR3: NVFEY hz28A2v4:

(SEQ ID NO: 123)
EVQLLESGGGEVQPGGSLRLSCAAS GGIFAIKP ISWYRQAPGKQREWVTT TTSSGAT NYAESVK
GRFTISRDNAKNTVYLQMSSLRAEDTAVYYC NVFEY WGQGTLVTVKP (SEQ ID NO: 105)
CDR1: GGIFAIKP (SEQ ID NO: 106)
CDR2: TTSSGAT (SEQ ID NO: 107)
CDR3: NVFEY hz28A2v5:

(SEQ ID NO: 124)
EVQLLESGGGEVQPGGSLRLSCAAS GGIFAIKP ISWYRQAPGKQREWVST TTSSGAT NYAESVK
GRFTISRDNAKNTLYLQMSSLRAEDTAVYYC NVFEY WGQGTLVTVKP (SEQ ID NO: 105)
CDR1: GGIFAIKP (SEQ ID NO: 106)
CDR2: TTSSGAT (SEQ ID NO: 107)
CDR3: NVFEY

In other embodiments, the PD-L1 binding portion is derived from the extracellular domain of PD-1 containing at least the IgV domain as shown below:

(SEQ ID NO: 125)
PTFSPALLVVTEGDNATFTCSFSNTSESFVLNWYRMSPSNQTDKLAAFPED

RSQPGQDCRFRVTQLPNGRDFHMSVVRARRNDSGTYLCGAISLAPKAQIKE

SLRAELRVT

In some embodiments, the PDL1 binding domain comprises or is derived from a known anti-PDL1 antibody sequence or antigen-binding fragment thereof. In some embodiments, the PDL1 binding domain comprises or is derived from an antibody sequence disclosed in PCT Publication No. WO 2016/149201, the contents of which are hereby incorporated by reference in their entirety.

In some embodiments, the PDL1 binding domain comprises or is derived from an antibody sequence or antigen-binding fragment thereof that includes a combination of a variable heavy chain (VH) sequence and a variable light chain (VL) sequence selected from the group consisting of:

VH Sequences:

(SEQ ID NO: 126)
QVQLVQSGAEVKKPGASVKVSCKASGYTFTDYGFSWVRQAPGQGLEWMGWI

TAYNGNTNYAQKLQGRVTMTTDTSTSTVYMELRSLRSDDTAVYYCARDYFY

GMDVWGQGTTVTVSS (SEQ ID NO: 127)
QVQLVQSGAEVKKPGSSVKVSCKTSGDTFSTYAISWVRQAPGQGLEWMGGI

IPIFGKAHYAQKFQGRVTITADESTSTAYMELSSLRSEDTAVYFCARKFHF

VSGSPFGMDVWGQGTTVTVSS (SEQ ID NO: 128)
QVQLVQSGAEVKKPGASVKVSCKASGYTFTSYDVHWVRQAPGQRLEWMGWL

HADTGITKFSQKFQGRVTITRDTSASTAYMELSSLRSEDTAVYYCARERIQ

LWFDYWGQGT (SEQ ID NO: 129)
QVQLVQSGAEVKKPGSSVKVSCKVSGGIFSTYAINWVRQAPGQGLEWMGGI

IPIFGTANHAQKFQGRVTITADESTSTAYMELSSLRSEDTAVYYCARDQGI

AAALFDYWGQGTLVTVSS (SEQ ID NO: 130)
EVQLVESGGGLVQPGRSLRLSCAVSGFTFDDYVVHWVRQAPGKGLEWVSGN

SGNIGYADSVKGRFTISRDNAKNSLYLQMNSLRAEDTALYYCAVPFDYWGQ

GTLVTVSS (SEQ ID NO: 131)
QVQLVQSGAEVKKPGSSVKVSCKTSGDTFSSYAISWVRQAPGQGLEWMGGI

IPIFGRAHYAQKFQGRVTITADESTSTAYMELSSLRSEDTAVYFCARKFHF

VSGSPFGMDVWGQGTTVTVSS (SEQ ID NO: 132)
QVQLVQSGAEVKKPGSSVKVSCKTSGGTFSSYAISWVRQAPGQGLEWMGGI

IPIFGKAHYAQKFQGRVTITADESTTTAYMELSSLRSEDTAVYYCARKYDY

VSGSPFGMDVWGQGTTVTVSS (SEQ ID NO: 133)
QVQLVQSGAEVKKPGSSVKVSCKASGGTFSSYAINWVRQAPGQGLEWMGGI

IPIFGSANYAQKFQDRVTITADESTSAAYMELSSLRSEDTAVYYCARDSSG

WSRYYMDVWGQGTTVTVSS (SEQ ID NO: 134)
QVQLVQSGAEVKEPGSSVKVSCKASGGTFNSYAISWVRQAPGQGLEWMGGI

IPLFGIAHYAQKFQGRVTITADESTNTAYMDLSSLRSEDTAVYYCARKYSY

VSGSPFGMDVWGQGTTVTVSS (SEQ ID NO: 135)
EVQLVESGGGLVQPGRSLRLSCAASGITFDDYGMHWVRQAPGKGLEWVSGI

SWNRGRIEYADSVKGRFTISRDNAKNSLYLQMNSLRAEDTALYYCAKGRFR

YFDWFLDYWGQGTLVTVSS (SEQ ID NO: 136)
QMQLVQSGGGLVQPGGSLRLSCAASGFTFSSYWMSWVRQAPGKGLEWVANI

KQDGSEKYYVDSVKGRFTISRDNAKNSLYLQMNSLRAEDTAVYYCARDYFW

SGFSAFDIWGKGTLVTVS

VL Sequences:
(SEQ ID NO: 137)
EIVLTQSPATLSLSPGERATLSCRASQSVSSYLVWYQQKPGQAPRLLIYDA

SNRATGIPARFSGSGSGTDFTLTISSLEPEDFAVYYCQQRSNWPRTFGQGT

KVEIK (SEQ ID NO: 138)
EIVLTQSPATLSLSPGERATLSCRASQSVSSYLAWYQQKPGQAPRLLIYDA

SNRATGIPARFSGSGSGTDFTLTISSLEPEDFAVYYCQQRSNWPTFGQGTK

VEIK (SEQ ID NO: 139)
DIQMTQSPSSLSASVGDRVTITCRASQGISSWLAWYQQKPEKAPKSLIYAA

SSLQSGVPSRFSGSGSGTDFTLTISSLQPEDFATYYCQQYNSYPYTFGQGT

KLEIK (SEQ ID NO: 140)
EIVLTQSPGTLSLSPGERATLSCRASQSVSSSYLAWYQQKPGQAPRLLIYG

ASSRATGIPDRFSGSGSGTDFTLTISRLEPEDFAVYYCQQYGSSPWTFGQG

TKVEIK (SEQ ID NO: 141)
EIVLTQSPGTLSLSPGERATLSCRASQSVSSSYLAWYQQKPGQAPRLLIYG

ASSRATGIPDRFSGSGSGTDFTLTISRLEPEDFAVYYCQQYGSSPFGGGTK

VEIK (SEQ ID NO: 142)
EIVLTQSPATLSLSPGERATLSCRASQSVSSYLAWYQQKPGQAPRLLIYDA

SNRATGIPARFSGSGSGTDFTLTISSLEPEDFAVYYCQQRSNWPTFGQGTR

LEIK (SEQ ID NO: 143)
AIQLTQSPSSLSASVGDRVTITCRASQGISSALAWYQQKPGKAPKLLIYDA

SSLESGVPSRFSGSGSGTDFTLTISSLQPEDFATYYCQQFNSYPFTFGPGT

KVDIK (SEQ ID NO: 144)
DIVMTQSPSTLSASVGDRVTITCRASQGISSWLAWYQQKPGRAPKVLIYKA

STLESGVPSRFSGSGSGTDFTLTISSLQPEDFATYYCQQSYSTPWTFGQGT

KLEIK

In some embodiments, the PDL1 binding domain comprises or is derived from an antibody sequence or antigen-binding fragment thereof that includes a combination of a VH sequence and a VL sequence selected from the group consisting of:

VH Sequence:
(SEQ ID NO: 145)
EVQLVESGGGLVQPGGSLRLSCAASGFTFSRYWMSWVRQAPGKGLEWVANI

KQDGSEKYYVDSVKGRFTISRDNAKNSLYLQMNSLRAEDTAVYYCAREGGW

FGELAFDYWGQGTLVTVSS

VL Sequence:
(SEQ ID NO: 146)
EIVLTQSPGTLSLSPGERATLSCRASQRVSSSYLAWYQQKPGQAPRLLIYD

ASSRATGIPDRFSGSGSGTDFTLTISRLEPEDFAVYYCQQYGSLPWTFGQG

TKVEIK

In some embodiments, the PDL1 binding domain comprises or is derived from an antibody sequence or antigen-binding fragment thereof that includes a combination of a VH sequence and a VL sequence selected from the group consisting of:

VH Sequences:
(SEQ ID NO: 147)
EVQLVESGGGLVQPGGSLRLSCAASGFTFSDSWIHWVRQAPGKGLEWVAWI

SPYGGSTYYADSVKGRFTISADTSKNTAYLQMNSLRAEDTAVYYCARRHWP

GGFDYWGQGTLVTVSA (SEQ ID NO: 148)
EVQLVESGGGLVQPGGSLRLSCAASGFTFSGSWIHWVRQAPGKGLEWVAWI

LPYGGSSYYADSVKGRFTISADTSKNTAYLQMNSLRAEDTAVYYCARRHWP

GGFDYWGQGTLVTVSA

VL Sequences:

(SEQ ID NO: 149)
DIQMTQSPSSLSASVGDRVTITCRASQDVSTAVAWYQQKPGKAPKLLIYSA
SFLYSGVPSRFSGSGSGTDFTLTISSLQPEDFATYYCQQYLYHPATFGQGT
KVEIKR (SEQ ID NO: 150)
DIQMTQSPSSLSASVGDRVTITCRASQDVSTAVAWYQQKPGKAPKLLIYSA
SFLYSGVPSRFSGSGSGTDFTLTISSLQPEDFATYYCQQYYNVPWTFGQGT
KVEIKR (SEQ ID NO: 151)
DIQMTQSPSSLSASVGDRVTITCRASQDVSTAVAWYQQKPGKAPKLLIYSA
SFLYSGVPSRFSGSGSGTDFTLTISSLQPEDFATYYCQQYYAPPWTFGQGT
KVEIKR (SEQ ID NO: 152)
DIQMTQSPSSLSASVGDRVTITCRASQDVSTAVAWYQQKPGKAPKLLIYSA
SFLYSGVPSRFSGSGSGTDFTLTISSLQPEDFATYYCQQYYTVPWTFGQGT
KVEIKR (SEQ ID NO: 153)
DIQMTQSPSSLSASVGDRVTITCRASQVINTFLAWYQQKPGKAPKLLIYSA
STLASGVPSRFSGSGSGTDFTLTISSLQPEDFATYYCQQYYTVPRTFGQGT
KVEIKR (SEQ ID NO: 154)
DIQMTQSPSSLSASVGDRVTITCRASQDVSTAVAWYQQKPGKAPKLLIYSA
SFLYSGVPSRFSGSGSGTDFTLTISSLQPEDFATYYCQQGYGVPRTFGQGT
KVEIKR (SEQ ID NO: 155)
DIQMTQSPSSLSASVGDRVTITCRASQDVSTAVAWYQQKPGKAPKLLIYSA
SFLYSGVPSRFSGSGSGTDFTLTISSLQPEDFATYYCQQYLFTPPTFGQGT
KVEIKR (SEQ ID NO: 156)
DIQMTQSPSSLSASVGDRVTITCRASQDVSTAVAWYQQKPGKAPKLLIYSA
SFLYSGVPSRFSGSGSGTDFTLTISSLQPEDFATYYCQQYFITPTTFGQGT
KVEIKR (SEQ ID NO: 157)
DIQMTQSPSSLSASVGDRVTITCRASQDVSTAVAWYQQKPGKAPKLLIYSA
SFLYSGVPSRFSGSGSGTDFTLTISSLQPEDFATYYCQQYYTPPTFGQGT
KVEIKR (SEQ ID NO: 158)
DIQMTQSPSSLSASVGDRVTITCRASQDVSTAVAWYQQKPGKAPKLLIYSA
SFLYSGVPSRFSGSGSGTDFTLTISSLQPEDFATYYCQQFFYTPPTFGQGT
KVEIKR (SEQ ID NO: 159)
DIQMTQSPSSLSASVGDRVTITCRASQDVSTAVAWYQQKPGKAPKLLIYSA
SFLYSGVPSRFSGSGSGTDFTLTISSLQPEDFATYYCQQSLFTPPTFGQGT
KVEIKR (SEQ ID NO: 160)
DIQMTQSPSSLSASVGDRVTITCRASQDVSTAVAWYQQKPGKAPKLLIYSA
SFLYSGVPSRFSGSGSGTDFTLTISSLQPEDFATYYCQQSLYTPPTFGQGT
KVEIKR (SEQ ID NO: 161)
DIQMTQSPSSLSASVGDRVTITCRASQDVSTAVAWYQQKPGKAPKLLIYSA
SFLYSGVPSRFSGSGSGTDFTLTISSLQPEDFATYYCQQSWYHPPTFGQGT
KVEIKR (SEQ ID NO: 162)
DIQMTQSPSSLSASVGDRVTITCRASQDVSTAVAWYQQKPGKAPKLLIYSA
SFLYSGVPSRFSGSGSGTDFTLTISSLQPEDFATYYCQQYFYIPPTFGQGT
KVEIKR (SEQ ID NO: 163)
DIQMTQSPSSLSASVGDRVTITCRASQDVSTAVAWYQQKPGKAPKLLIYSA
SFLYSGVPSRFSGSGSGTDFTLTISSLQPEDFATYYCQQYWYTPTTFGQGT
KVEIKR (SEQ ID NO: 164)
DIQMTQSPSSLSASVGDRVTITCRASQDVSTAVAWYQQKPGKAPKLLIYSA
SFLYSGVPSRFSGSGSGTDFTLTISSLQPEDFATYYCQQSYFIPPTFGQGT
KVEIKR

In some embodiments, the PDL1 binding domain comprises or is derived from an antibody sequence or antigen-binding fragment thereof that includes a combination of a VH sequence and a VL sequence selected from the group consisting of:

VH Sequences:

(SEQ ID NO: 165)
METGLRWLLLVAVLKGVQCLSVEESGGRLVTPGTPLTLTCTASGFTITNYH
MFWVRQAPGKGLEWIGVITSSGIGSSSTTYYATWAKGRFTISKTSTTVNLR
ITSPTTEDTATYFCARDYFTNTYYALDIWGPGTLVTVSS (SEQ ID NO: 166)
QVQLVQSGAEVKKPGSSVKVSCKTSGDTFSTYAISWVRQAPGQGLEWMGGI
IPIFGKAHYAQKFQGRVTITADESTSTAYMELSSLRSEDTAVYFCARKFHF
VSGSPFGMDVWGQGTTVTVSS (SEQ ID NO: 167)
QVQLVQSGAEVKKPGASVKVSCKASGYTFTSYDVHWVRQAPGQRLEWMGWL
HADTGITKFSQKFQGRVTITRDTSASTAYMELSSLRSEDTAVYYCARERIQ
LWFDYWGQGTLVTVSS (SEQ ID NO: 168)
QVQLVQSGAEVKKPGSSVKVSCKVSGGIFSTYAINWVRQAPGQGLEWMGGI
IPIFGTANHAQKFQGRVTITADESTSTAYMELSSLRSEDTAVYYCARDQGI
AAALFDYWGQGTLVTVSS (SEQ ID NO: 169)
EVQLVESGGGLVQPGRSLRLSCAVSGFTFDDYVVHWVRQAPGKGLEWVSGI
SGNSGNIGYADSVKGRFTISRDNAKNSLYLQMNSLRAEDTALYYCAVPFDY
WGQGTLVTVSS (SEQ ID NO: 170)
QVQLVQSGAEVKKPGSSVKVSCKTSGDTFSSYAISWVRQAPGQGLEWMGGI

IPIFGRAHYAQKFQGRVTITADESTSTAYMELSSLRSEDTAVYFCARKFHF

VSGSPFGMDVWGQGTTVTVSS (SEQ ID NO: 171)
QVQLVQSGAEVKKPGSSVKVSCKTSGGTFSSYAISWVRQAPGQGLEWMGGI

IPIFGKAHYAQKFQGRVTITADESTTTAYMELSSLRSEDTAVYYCARKYDY

VSGSPFGMDVWGQGTTVTVSS (SEQ ID NO: 172)
QVQLVQSGAEVKKPGSSVKVSCKASGGTFSSYAINWVRQAPGQGLEWMGGI

IPIFGSANYAQKFQDRVTITADESTSAAYMELSSLRSEDTAVYYCARDSSG

WSRYYMDVWGQGTTVTVSS (SEQ ID NO: 173)
QVQLVQSGAEVKEPGSSVKVSCKASGGTFNSYAISWVRQAPGQGLEWMGGI

IPLFGIAHYAQKFQGRVTITADESTNTAYMDLSSLRSEDTAVYYCARKYSY

VSGSPFGMDVWGQGTTVTVSS (SEQ ID NO: 174)
EVQLVESGGGLVQPGRSLRLSCAASGITFDDYGMHWVRQAPGKGLEWVSGI

SWNRGRIEYADSVKGRFTISRDNAKNSLYLQMNSLRAEDTALYYCAKGRFR

YFDWFLDYWGQGTLVTVSS

VL Sequences:
(SEQ ID NO: 175)
MDTRAPTQLLGLLLLWLPGARCALVMTQTPSSTSTAVGGTVTIKCQASQSI

SVYLAWYQQKPGQPPKLLIYSASTLASGVPSRFKGSRSGTEYTLTISGVQR

EDAATYYCLGSAGS (SEQ ID NO: 176)
EIVLTQSPATLSLSPGERATLSCRASQSVSSYLVWYQQKPGQAPRLLIYDA

SNRATGIPARFSGSGSGTDFTLTISSLEPEDFAVYYCQQRSNWPRTFGQGT

KVEIK (SEQ ID NO: 177)
EIVLTQSPATLSLSPGERATLSCRASQSVSSYLAWYQQKPGQAPRLLIYDA

SNRATGIPARFSGSGSGTDFTLTISSLEPEDFAVYYCQQRSNWPTFGQGTK

VEIK (SEQ ID NO: 178)
DIQMTQSPSSLSASVGDRVTITCRASQGISSWLAWYQQKPEKAPKSLIYAA

SSLQSGVPSRFSGSGSGTDFTLTISSLQPEDFATYYCQQYNSYPYTFGQGT

KLEIK (SEQ ID NO: 179)
EIVLTQSPGTLSLSPGERATLSCRASQSVSSSYLAWYQQKPGQAPRLLIYG

ASSRATGIPDRFSGSGSGTDFTLTISRLEPEDFAVYYCQQYGSSPWTFGQG

TKVEIK (SEQ ID NO: 180)
EIVLTQSPGTLSLSPGERATLSCRASQSVSSSYLAWYQQKPGQAPRLLIYG

ASSRATGIPDRFSGSGSGTDFTLTISRLEPEDFAVYYCQQYGSSPFGGGTK

VEIK (SEQ ID NO: 181)
EIVLTQSPATLSLSPGERATLSCRASQSVSSYLAWYQQKPGQAPRLLIYDA

SNRATGIPARFSGSGSGTDFTLTISSLEPEDFAVYYCQQRSNWPTFGQGTR

LEIK (SEQ ID NO: 182)
AIQLTQSPSSLSASVGDRVTITCRASQGISSALAWYQQKPGKAPKLLIYDA

SSLESGVPSRFSGSGSGTDFTLTISSLQPEDFATYYCQQFNSYPFTFGPGT

KVDIK

In some embodiments, the PDL1 binding domain comprises or is derived from an antibody sequence or antigen-binding fragment thereof that includes a combination of a VH sequence and a VL sequence selected from the group consisting of:

VH Sequences:
(SEQ ID NO: 183)
EVQLLESGGGLVQPGGSLRLSCAASGFTFSSYIMMWVRQAPGKGLEWVSSI

YPSGGITFYADTVKGRFTISRDNSKNTLYLQMNSLRAEDTAVYYCARIKLG

TVTTVDYWGQGTLVTVSS

VL Sequences:
(SEQ ID NO: 184)
QSALTQPASVSGSPGQSITISCTGTSSDVGGYNYVSWYQQHPGKAPKLMIY

DVSNRPSGVSNRFSGSKSGNTASLTISGLQAEDEADYYCSSYTSSSTRVFG

TGTKVTVL

In some embodiments, the PDL1 binding domain comprises or is derived from an antibody sequence or antigen-binding fragment thereof that includes a combination of a VH sequence and a VL sequence selected from the group consisting of:

VH Sequences:
(SEQ ID NO: 185)
EVKLQESGPSLVKPSQTLSLTCSVTGYSITSDYWNWIRKFPGNKLEYVGYISYTGSTYYNPSLK

SRISITRDTSKNQYYLQLNSVTSEDTATYYCARYGGWLSPFDYWGQGTTLTVSS (SEQ ID NO: 186)
EVQLQESGPGLVAPSQSLSITCTVSGFSLITYSINWIRQPPGKGLEWLGVMWAGGGINSNSVLK

SRLIISKDNSKSQVFLKMNSLQTDDTARYYCARYYGNSPYYAIDYWGQGTSVTVSS

-continued (SEQ ID NO: 187)
EVKLQESGPSLVKPSQTLSLTCSVTGYSIISDYWNWIRKFPGNKLEYLGYISYTGSTYYNPSLK

SRISITRDTSKNQYYLQLNSVTTEDTATYYCARRGGWLLPFDYWGQGTTLTVSS (SEQ ID NO: 188)
EVKLQESGPSLVKPGASVKLSCKASGYTFTSYDINWVKQRPGQGLEWIGWIFPRDNNTKYNENF

KGKATLTVDTSSTTAYMELHSLTSEDSAVYFCTKENWVGDFDYWGQGTTLTLSS (SEQ ID NO: 189)
EVQLQQSGPDLVTPGASVRISCQASGYTFPDYYMNWVKQSHGKSLEWIGDIDPNYGGTTYNQKF

KGKAILTVDRSSTAYMELRSLTSEDSAVYYCARGALTDWGQGTSLTVSS (SEQ ID NO: 190)
EIVLTQSPATLSLSPGERATLSCRASSSVSYTYWFQQKPGQSPRPLIYAAFNRATGIPARFSGS

GSGTDYTLTISSLEPEDFAVYYCQQWSNNPLTFGQGTKVEIK (SEQ ID NO: 191)
QVQLVQSGAEVKKPGASVKVSCKASGYTFPDYYMNWVRQAPGQGLEWMGDIDPNYGGTNYAQKF

QGRVTMTRDTSISTAYMELSRLRSDDTAVYYCARGALTDWGQGTMVTVSS (SEQ ID NO: 192)
QVQLVQSGAEVKKPGASVKVSCKASGYTFPDYYMNWVRQAPGQSLEWMGDIDPNYGGTNYNQKF

QGRVTMTRDTSISTAYMELSRLRSDDTAVYYCARGALTDWGQGTMVTVSS (SEQ ID NO: 193)
EVQLVQSGAEVKKPGASVKVSCKASGYTFPDYYMNWVRQAPGQSLEWMGDIDPNYGGTNYNQKF

QGRVTMTVDRSSTAYMELSRLRSDDTAVYYCARGALTDWGQGTMVTVSS (SEQ ID NO: 194)
EVQLVESGGGLVQPGRSLRLSCTASGYTFPDYYMNWVRQAPGKGLEWVGDIDPNYGGTTYAASV

KGRFTISVDRSKSIAYLQMSSLKTEDTAVYYCTRGALTDWGQGTMVTVSS (SEQ ID NO: 195)
EVQLVESGGGLVQPGRSLRLSCTASGYTFPDYYMNWVRQAPGKGLEWVGDIDPNYGGTTYNASV

KGRFTISVDRSKSIAYLQMSSLKTEDTAVYYCARGALTDWGQGTMVTVSS

VL Sequences:

(SEQ ID NO: 196)
DIVMTQSHKLMSTSVGDRVSITCKASQDVGTAVAWYQQKPGQSPKLLIYWASTRHTGVPDRFTG

SGSGTDFTLTISNVQSEDLADYFCQQDSSYPLTFGAGTKVELK (SEQ ID NO: 197)
DIVTTQSHKLMSTSVGDRVSITCKASQDVGTAVAWYQQKPGQSPKLLIYWASTRHTGVPDRFTG

SGSGTDFTLTISNVQSEDLADYFCQQDSSYPLTFGAGTKVELK (SEQ ID NO: 198)
DIVMTQSPSSLAVSVGEKVSMGCKSSQSLLYSSNQKNSLAWYQQKPGQSPKLLIDWASTRESGV

PDRFTGSGSGTDFTLTISSVKAEDLAVYYCQQYYGYPLTFGAGTKLELK (SEQ ID NO: 199)
DIVMTQSPAIMSASPGEKVTMTCSASSSIRYMHWYQQKPGTSPKRWISDTSKLTSGVPARFSGS

GSGTSYALTISSMEAEDAATYYCHQRSSYPWTFGGGTKLEIK (SEQ ID NO: 200)
QIVLSQSPAILSASPGEKVTMTCRASSSVSYTYWFQQKPGSSPKPWIYATFNLASGVPARFSGS

GSGTSYSLTISRVETEDAATYYCQQWSNNPLTFGAGTKLELK (SEQ ID NO: 201)
EIVLTQSPATLSLSPGERATLSCRASSSVSYTYWFQQKPGQAPRLLIYAAFNRATGIPARFSGS

GSGTDYTLTISSLEPEDFAVYYCQQWSNNPLTFGQGTKVEIK (SEQ ID NO: 202)
QIVLTQSPATLSLSPGERATLSCRASSSVSYTYWFQQKPGQSPRPLIYATFNLASGIPARFSGS

GSGTSYTLTISRLEPEDFAVYYCQQWSNNPLTFGQGTKVEIK

```
                                                 (SEQ ID NO: 203)
DIQLTQSPSSLSASVGDRVTITCRASSGVSYTYWFQQKPGKAPKLLIYAAFNLASGVPSRFSGS

GSGTEYTLTISSLQPEDFATYYCQQWSNNPLTFGQGTKVEIK (SEQ ID NO: 204)
DIQLTQSPSSLSASVGDRVTITCRASSGVSYTYWFQQKPGKAPKPLIYAAFNLASGVPSRFSGS

GSGTEYTLTISSLQPEDFATYYCQQWSNNPLTFGQGTKVEIK (SEQ ID NO: 205)
DIQLTQSPSILSASVGDRVTITCRASSSVSYTYWFQQKPGKAPKPLIYATFNLASGVPSRFSGS

GSGTSYTLTISSLQPEDFATYYCQQWSNNPLTFGQGTKVEIK
```

In some embodiments, the PDL1 binding domain comprises or is derived from an antibody sequence or antigen-binding fragment thereof that includes a combination of a VH sequence and a VL sequence selected from the group consisting of:

```
VH Sequences:
                                                 (SEQ ID NO: 206)
QVQLVQSGAEVKKPGASVKVSCKASGYTFTSYGISWVRQAPGQGLEWMGWISAYNGNTNYAQKL

QGRVTMTTDTSTSTAYMELRSLRSDDTAVYYCARALPSGTILVGGWFDPWGQGTLVTVSS (SEQ ID NO: 207)
EVQLVQSGGGVVQPGRSLRLSCAASGFTFSSYALSWVRQAPGKGLEWVSAISGGGGSTYYADSV

KGRFTISRDNSKNTLYLQMNSLRAEDTAVYYCAKDVFPETFSMNYGMDVWGQGTLVTVSS (SEQ ID NO: 208)
QVQLVQSGGGVVQPGGSLRLSCAASGFTFDDYAMHWVRQAPGKGLEWVSLISGDGGSTYYADSV

KGRFTISRDNSKNSLYLQMNSLRTEDTALYYCAKVLLPCSSTSCYGSVGAFDIWGQGTTVTVSS (SEQ ID NO: 209)
QVQLVQSGGSVVRPGESLRLSCVASGFIFDNYDMSWVRQVPGKGLEWVSRVNWNGGSTTYADAV

KGRFTISRDNTKNSLYLQMNNLRAEDTAVYYCVREFVGAYDLWGQGTTVTVSS (SEQ ID NO: 210)
QVQLVQSGAEVKKPGATVKVSCKVFGDTFRGLYIHWVRQAPGQGLEWMGGIIPIFGTANYAQKF

QGRVTITTDESTSTAYMELSSLRSEDTAVYYCASGLRWGIWGWFDPWGQGTLVTVSS (SEQ ID NO: 211)
EVQLVQSGAELKKPGSSVKVSCKAFGGIFSDNAISWVRQAPGQGPEWMGGIIPIFGKPNYAQKF

QGRVTITADESTSTAYMVLSSLRSEDTAVYYCARTMVRGFLGVMDVWGQGTTVTVSS (SEQ ID NO: 212)
QVQLVQSGGGLVQPGGSLRLSCAASGFTFSSYAMSWVRQAPGKGLEWVSAISGSGGSTYYADSV

KGRFTISRDNSKNTLYLQMNSLRAEDTAVYYCAKDQFVTIFGVPRYGMDVWGQGTTVTVSS (SEQ ID NO: 213)
QVQLVQSGAEVKKPGSSVKVSCKASGGIFSSYAISWVRQAPGQGLEWMGGIIPIFGTANYAQKF

QGRVTITADKSTSTAYMELSSLRSEDTAVYYCARGRQMFGAGIDFWGPGTLVTVSS (SEQ ID NO: 214)
EVQLVESGAEVKKPGSSVKVSCKVSGGTFGTYALNWVRQAPGQGLEWMGRIVPLIGLVNYAHNF

EGRISITADKSTGTAYMELSNLRSDDTAVYYCAREVYGGNSDYWGQGTLVTVSS (SEQ ID NO: 215)
QVQLVQSGGEVKKPGASVKVSCKASGYTLSSHGITWVRQAPGQGLEWMGWISAHNGHASNAQKV

EDRVTMTTDTSTNTAYMELRSLTADDTAVYYCARVHAALYYGMDVWGQGTLVTVSS (SEQ ID NO: 216)
QVQLQESGGGVVQPGRSLRLSCSASGFTFSRHGMHWVRQAPGKGLEWVAVISHDGSVKYYADSM

KGRFSISRDNSNNTLYLQMDSLRADDTAVYYCARGLSYQVSGWFDPWGQGTLVTVSS
```

```
                                                    (SEQ ID NO: 217)
NFMLTQPHSVSESPGKTVTISCTRSSGSIASNYVQWYQQRPGSSPTTVIYEDNQRPSGVPDRFS

GSIDTSSNSASLTISGLKTKDEADYYCQSYDGITVIFGGGTKLTVL (SEQ ID NO: 218)
NFMLTQPHSVSGSPGKTVTLPCTRSSGSIASHYVQWYQQRPGSAPTTVIYEDNKRPSGVPDRFS

GSIDSSSNSASLSISGLKTEDEADYYCQSYDSSNRWVFGGGTKLTVL (SEQ ID NO: 219)
LPVLTQPASLSASPGASASLTCTLRSGLNVGSYRIYWYQQKPGSRPQYLLNYKSDSNKQQASGV

PSRFSGSKDASANAGILLISGLQSEDEADYYCMIWYSSAVVFGGGTKLTVL

VL Sequences:
                                                    (SEQ ID NO: 220)
NFMLTQPHSVSESPGKTVTISCTRSSGNIASNYVQWYQQRPGSAPTTVIYEDNQRPSGVPDRFS

GSIDSSSNSASLTISGLKTEDEADYYCQSYDSSNLWVFGGGTKLTVL (SEQ ID NO: 221)
SSELTQDPAVSVALGQTVRITCQGDSLRSYYASWYQQKPGQAPVLVIYGKNNRPSGIPDRFSGS

SSGNTASLTITGAQAEDEADYYCNSRDSSGNHYVFGTGTKVTVL (SEQ ID NO: 222)
LPVLTQAPSVSVAPGKTARITCGGSDIGRKSVHWYQQKPGQAPALVIYSDRDRPSGISERFSGS

NSGNTATLTISRVEAGDEADYYCQVWDNNSDHYVFGAGTELIVL (SEQ ID NO: 223)
QSALTQPASVSGSPGQSITISCIGTSSDVGGYNYVSWYQQHPGKAPKLMIYDVSNRPSGVSNRF

SGSKSGNTASLTISGLQAEDEADYYCSSYTSSTLPFGGGTKLTVL (SEQ ID NO: 224)
EIVLTQSPATLSLSPGERATLSCRASQSIGNSLAWYQQKPGQAPRLLMYGASSRATGIPDRFSG

SGAGTDFTLTISSLEPEDFATYYCQQHTIPTFSFGPGTKVEVK (SEQ ID NO: 225)
DIVMTQTPSFLSASIGDRVTITCRASQGIGSYLAWYQQRPGEAPKLLIYAASTLQSGVPSRFSG

SGSGTDFTLTISNLQPEDFATYYCQQLNNYPITFGQGTRLEIK (SEQ ID NO: 226)
QSALTQPPSVSVSPGQTANIPCSGDKLGNKYAYWYQQKPGQSPVLLIYQDIKRPSRIPERFSGS

NSADTATLTISGTQAMDEADYYCQTWDNSVVFGGGTKLTVL (SEQ ID NO: 227)
NFMLTQPHSVSESPGKTVTISCTRSSGSIDSNYVQWYQQRPGSAPTTVIYEDNQRPSGVPDRFS

GSIDSSSNSASLTISGLKTEDEADYYCQSYDSNNRHVIFGGGTKLTVL (SEQ ID NO: 228)
NFMLTQPHSVSESPGKTVTISCTRSSGNIGTNYVQWYQQRPGSAPVALIYEDYRRPSGVPDRFS

GSIDSSSNSASLIISGLKPEDEADYYCQSYHSSGWEFGGGTKLTVL (SEQ ID NO: 229)
QSVLTQPPSVSVAPGQTARITCGGNNIGSKGVHWYQQKPGQAPVLVVYDDSDRPSGIPERFSGS

NSGNTATLTISRVEAGDEADYYCQVWDSSSDHWVFGGGTKLTVL (SEQ ID NO: 230)
NFMLTQPHSVSESPGKTVTISCTRSSGSIASNYVQWYQQRPGSAPTTVIYEDNQRPSGVPDRFS

GSIDSSSNSASLTISGLKTEDEADYYCQSYDSTTPSVFGGGTKLTVL (SEQ ID NO: 231)
QVQLVQSGAEVKKPGASVKVSCKASGYTFTSYGISWVRQAPGQGLEWMGWTSPHNGLTAFAQIL

EGRVTMTTDTSTNTAYMELRNLTFDDTAVYFCAKVHPVFSYALDVWGQGTLVTSS (SEQ ID NO: 232)
EVQLVESGAEVMNPGSSVRVSCRGSGGDFSTYAFSWVRQAPGQGLEWMGRIIPILGIANYAQKF

QGRVTITADKSTSTAYMELSSLRSDDTAVYYCARDGYGSDPVLWGQGTLVTSS
```

```
                                                     (SEQ ID NO: 233)
EVQLVQSGAEVKKPGASVKVSCKASGYTFTNYGISWVRQAPGQGLEWMGWISAYNGNTNYAQKV

QGRVTMTTDTSTSTGYMELRSLRSDDTAVYYCARGDFRKPFDYWGQGTLVTVSS
```

In some embodiments, the PDL1 binding domain comprises or is derived from an antibody sequence or antigen-binding fragment thereof that includes a combination of a VH sequence and a VL sequence selected from the group consisting of:

```
VH Sequences:
                                                     (SEQ ID NO: 234)
EVQLVQSGPELKKPGASVKMSCKASGYTFTSYVMHWVKQAPGQRLEWIGYV

NPFNDGTKYNEMFKGRATLTSDKSTSTAYMELSSLRSEDSAVYYCARQAWG

YPWGQGTLVTVSS
                                                     (SEQ ID NO: 235)
EVQLVQSGAEVKKPGASVKMSCKASGYTFTSYVMHWVKQAPGQRLEWIGYV

NPFNDGTKYNEMFKGRATLTSDKSTSTAYMELSSLRSEDTAVYYCARQAWG

YPWGQGTLVTVSS
                                                     (SEQ ID NO: 236)
EVQLVQSGAEVKKPGASVKMSCKASGYTFTSYVMHWVRQAPGQRLEWIGYV

NPFNDGTKYNEMFKGRATLTSDKSTSTAYMELSSLRSEDTAVYYCARQAWG

YPWGQGTLVTVSS
                                                     (SEQ ID NO: 237)
EVQLVQSGAEVKKPGASVKVSCKASGYTFTSYVMHWVRQAPGQRLEWIGYV

NPFNDGTKYNEMFKGRATLTSDKSTSTAYMELSSLRSEDTAVYYCARQAWG

YPWGQGTLVTVSS
                                                     (SEQ ID NO: 238)
EVQLVQSGAEVKKPGASVKVSCKASGYTFTSYVMHWVRQAPGQRLEWIGYV

NPFNDGTKYNEMFKGRATITSDKSTSTAYMELSSLRSEDTAVYYCARQAWG

YPWGQGTLVTVSS

VL Sequences:
                                                     (SEQ ID NO: 239)
DIVLTQSPASLALSPGERATLSCRATESVEYYGTSLVQWYQQKPGQPPKLL

IYAASSVDSGVPSRFSGSGSGTDFTLTINSLEEEDAAMYFCQQSRRVPYTF

GQGTKLEIK
                                                     (SEQ ID NO: 240)
DIVLTQSPATLSLSPGERATLSCRATESVEYYGTSLVQWYQQKPGQPPKLL

IYAASSVDSGVPSRFSGSGSGTDFTLTINSLEAEDAAMYFCQQSRRVPYTF

GQGTKLEIK
                                                     (SEQ ID NO: 241)
EIVLTQSPATLSLSPGERATLSCRATESVEYYGTSLVQWYQQKPGQPPKLL

IYAASSVDSGVPSRFSGSGSGTDFTLTINSLEAEDAAMYFCQQSRRVPYTF

GQGTKLEIK
                                                     (SEQ ID NO: 242)
DIVLTQSPATLSLSPGERATLSCRATESVEYYGTSLVQWYQQKPGQPPKLL

IYAASSVDSGVPSRFSGSGSGTDFTLTINSLEAEDAATYFCQQSRRVPYTF

GQGTKLEIK
```

In some embodiments, the PDL1 binding domain comprises or is derived from an antibody sequence or antigen-binding fragment thereof that includes a combination of a VH sequence and a VL sequence selected from the group consisting of:

```
VH Sequences:
                                                     (SEQ ID NO: 243)
EVQLVQSGAEVKKPGSSVKVSCKASGGTFSSYAISWVRQAPGQGLEWMGGIIPIFGTANYAQKF QGRVTITADKSTSTAYMELSSLRSEDTAVYYCAREGTIYDSSGYSFDYWGQGTLVTVSS
                                                     (SEQ ID NO: 244)
EVQLVQSGAEVKKPGSSVKVSCKASGGTFSSYAISWVRQAPGQGLEWMGIINPSGGSTSYAQKF QGRVSMTRDTSTSTVYMELSSLTSEDTAVYYCARDLFPHIYGNYYGMDIWGQGTTVTVSS
                                                     (SEQ ID NO: 245)
QVQLVQSGAEVKKPGSSVKVSCKASGGTFSSYAISWVRQAPGQGLEWMGGIIPIFGTANYAQKF QGRVTITADKSTSTAYMELSSLRSEDTAVYYCARLAVPGAFDIWGQGTMVTVSS
                                                     (SEQ ID NO: 246)
EVQLVESGGGVVQPGRSLRLSCAASGFTFSSYAMHWVRQAPGKGLAVISYDGSNKYYADSVKGR FTISRDNSKNTLYLQMNSLRAEDTAVYYCARGQWLVTELDYWGQGTLVTVSS
                                                     (SEQ ID NO: 247)
EVQLVESGSEVEKPGSSVKVSCKASGGTFSDSGISWVRQAPGQGLEWMGGIIPMFATPYYAQKF QDRVTITADESTSTVYMELSGLRSDDTAVFYCARDRGRGHLPWYFDLWGRGTLVTVSS
                                                     (SEQ ID NO: 248)
EVQLVESGAEVKKPGSSVKVSCKASGGTFSSYAISWVRQAPGQGLEWMGGIIPIFGTANYAQKF

QGRVTITADESTSTAYMELSSLRSEDTAVYYCARAPYYYYMDVWGQGTTVTVSS
```

-continued

```
                                            (SEQ ID NO: 249)
EVQLLESGAEVKKPGSSVKVSCKASGGTLSRYALSWVRQAPGQGPEWVGAIIPIFGTPHYSKKF

QDRVIITVDTSTNTAFMELSSLRFEDTALYFCARGHDEYDISGYHRLDYWGQGTLVTVSS (SEQ ID NO: 250)
QVQLVQSGSELKKPGSSVKVSCKASGYSFSGYYTHWVRQAPGQGLEWMGWIDPNSGVTNYVRRF

QGRVTMTRDTSLSTAYMELSGLTADDTAVYYCARDENLWQFGYLDYWGQGTLVTVSS (SEQ ID NO: 251)
QVQLVQSGAEVKKPGSSVKVSCKASGGTFSRYGVHWVRQAPGQGLEWMGRLIPIVSMTNYAQKF

QDRVSITTDKSTGTAYMELRSLTSEDTALYYCASVGQQLPWVFFAWGQGTLVTVSS (SEQ ID NO: 252)
QVQLVESGGGVVQPGRSLRLSCAASGFTFSSYAMHWVRQAPGKGLEWVAVISFDGSNKYYADSV

RGRFTISRDNSKNTLYLQMNSLRTEDTAVYYCARGWLDRDIDYWGQGTLVTVSS (SEQ ID NO: 253)
EVQLVESGGGVVQPGRSLRLSCAASGFTFSSYAMHWVRQAPGKGLEWVAVISFDGSNKYYADSV

RGRFTISRDNSKNTLYLQMNSLRTEDTAVYYCARGWLDRDIDYWGQGTLVTVSS (SEQ ID NO: 254)
EVQLVQSGGGLVQPGGSLRLSCAASGFTFSDYGMHWVRQFPGKGLEWLAVISYDGSYKIHADSV

QGRFTISRDNAKNSVFLQMNSLKTEDTAVYYCTTDRKWLAWHGMDVWGQGTTVTVSS (SEQ ID NO: 255)
EVQLVQSGAEVKKPGSSVKVSCKASGGTFSSYAISWVRQAPGQGLEWMGGIIPIFGTANYAQKF

QGRVTITADESTSTAYMELSSLRSEDTAVYYCARDGIVADFQHWGQGTLVTVSS (SEQ ID NO: 256)
EVQLVESGAEVKKPGASVKVSCKASGDTFSRYGITWVRQAPGRGLEWMGNIVPFFGATNYAQKF

QGRLTITADKSSYTSYMDLSSLRSDDTAVYYCARDHFYGSGGYFDYWGQGTLVTVSS (SEQ ID NO: 257)
EVQLLESGAEVKKPGASVKVSCKASGYTFNSYDINWVRQAPGQGLEWMGGIIPVFGTANYAESF

QGRVTMTADHSTSTAYMELNNLRSEDTAVYYCARDRWHYESRPMDVWGQGTTVTVSS (SEQ ID NO: 258)
EVQLVESGGGLVRPGGSLRLACAASGFSFSDYYMTWIRQAPGRGLEWIAYISDSGQTVHYADSV

KGRFTISRDNTKNSLFLQVNTLRAEDTAVYYCAREDLLGYYLQSWGQGTLVTVSS (SEQ ID NO: 259)
QVQLQQSGPGLVKPSQTLSLTCAISGDSVSSNSAAWNWIRQSPSRGLEWLGRTYYRSKWYNDYA

VSVKSRITINPDTSKNQFSLQLNSVTPEDTAVYYCARDEPRAVAGSQAYYYYGMDVWGQGTTVT

VSS (SEQ ID NO: 260)
EVQLVQSGAEVKKPGASVKVSCKASGYTFTSYYMHWVRQAPGQGLEWMGIINPSDGSTSYAQKF

QGRVTMTRDTSTSTVHMELSSLRSEDTAVYYCARDLFPHIYGNYYGMDIWGQGTTVTVSS (SEQ ID NO: 261)
QMQLVQSGGGVVQPGRSLRLSCAASGFTFSSYAMHWVRQAPGKGLEWVAVISFDGSNKYYADSV

RGRFTISRDNSKNTLYLQMNSLRTEDTAVYYCARGWLDRDIDYWGQGTLVTVSS (SEQ ID NO: 262)
QVQLVQSGGGVVQPGRSLRLSCAASGFTFSSYAMHWVRQAPGKGLEWVAVISFDGSNKYYADSV

RGRFTISRDNSKNTLYLQMNSLRTEDTAVYYCARGWLDRDIDYWGQGTLVTVSS

VL Sequences:
                                            (SEQ ID NO: 263)
QSVLTQPPSVSAAPGQKVTISCSGNNSNIANNYVSWYQQLPGTAPKLLIYDNNYRPSGIPDRFS

GSKSGTSATLDITGLQTGDEADYYCGVWDGSLTTGVFGGGTKLTVL
```

```
                                                            (SEQ ID NO: 264)
AIQMTQSPSSLSASVGDRVTITCRASQGISNYLAWYQQKPGKVPKLLIYAASTLESGVPSRFSG

SGSGTDFTLTISSLQPEDLATYYCQQLHTFPLTFGGGTKVEIK (SEQ ID NO: 265)
QPVLTQPPSASGSPGQSVTISCTGTSSDVGAYNFVSWYRQHPGKAPKLMIYEVNKRPSGVPDRF

SGSKSGNTASLTVSGLQAEDEADYYCSSYAGTNSLGIFGTGTKLTVL (SEQ ID NO: 266)
QSVVTQPPSVSAAPGQKVTISCSGSSSDIGNHYVSWYQQLPGTAPKLLIYDNNQRPSGIPDRFS

GSKSGTSATLAITGLQTGDEADYYCGTWDNSLSPHLLFGGGTKLTVL (SEQ ID NO: 267)
QSVLTQPPSVSAAPGQKVTISCSGSSSNMGNNYVSWYKQVPGTAPKLLIYENDKRPSGIPDRFS

GSKSGTSATLGITGLQTGDEADYYCGTWDNSLSGFVFASGTKVTVL (SEQ ID NO: 268)
QSALTQPASVSGSLGQSVTISCTGSSSDVGSYNLVSWYQQHPGKAPNLMIYDVSKRSGVSNRFS

GSKSGNTASLTISGLQAEDEADYYCSSYTGISTVVFGGGTKLTVL (SEQ ID NO: 269)
QSVLTQPASVSGSPGQSITISCTGTSSDVGSYNLVSWYQQHPGKAPKLMIYEVSKRPSGVSNRF

SGSKSGNTASLTISGLQAEDEADYYCSSYGGFNNLLFGGGTKLTVL (SEQ ID NO: 270)
DIVMTQSPSSLSASIGDRVTITCRASQRISAYVNWYQQKPGKAPKVLIYAASSLRSGVPSRFSG

SGSGTDFTLTISSLQPEDFATYYCQQTYSSPWTFGQGTKVEIK (SEQ ID NO: 271)
QSVLTQPPSASGSPGQSVTISCTGTSSDIGGYDSVSWYQQHPGKAPKLMIYDVSKRPSGVSNRF

SGSKSGNTASLTISGLQAEDEADYYCSSYTSSSIFFYVFGTGTKVTVL (SEQ ID NO: 272)
LPVLTQPASVSGSPGQSITISCTGTTSDIGGYDYVSWYQQHPGKAPKLMIYDVSKRPSGVSNRF

SGSKSGNTASLTISGLQAEDEADYYCSSYTSSSTHVFGTGTKLTVL (SEQ ID NO: 273)
QSALTQPASVSGSPGQSITISCTGTSSDVGGYNYVSWYQQHPGKAPKLMIYDVSNRPSGVSNRF

SGSKSGNTASLTISGLQAEDEADYYCSSYRSSTLGPVFGGGTKLTVL (SEQ ID NO: 274)
QAGLTQPPSVSEAPRQRVTISCSGSSSNIGNNAVNWYQQLPGKAPKLLIYYDDLLPSGVSDRFS

GSKSGTSASLAISGLQSEDEADYYCAAWDDSLNGYVFGTGTKLTVL (SEQ ID NO: 275)
QSALTQPRSVSGSPGQSVTISCTGTSSDVGGYNYVSWYQQHPGKAPKLMIYDVSKRPSGVPDRF

SGSKSGNTASLTISGLQAEDEADYYCSSYTSSTTHVFGTGTKVTVL (SEQ ID NO: 276)
QSVVTQPPSVSAAPGQKVTISCSGSSSNIGNNYVSWYQQLPGTAPKLLIYDNNKRPSGIPDRFS

GSKSGTSATLGITGLQTGDEADYYCGTWDSSLSVWVFGGGTQLTVL (SEQ ID NO: 277)
QSVLTQPASVSGSPGQSITISCTGTSSDVGGYNYVSWYQQHPGRAPRLMIYDVSNRPSGVSNRF

SGSKSGNTASLTISGLQAEDEGDYYCSSYTSGGTLGPVFGGGTKLTVL (SEQ ID NO: 278)
QAGLTQPPSASGTPGQRVTISCSGSSSNIGSNTVNWYQQLPGTAPKLLIYSNNQRPSGVPDRFS

GSKSGTSASLAISGLQSEDEADYYCAAWDDSLNGWVFGGGTKLTVL (SEQ ID NO: 279)
AIRMTQSPSSLSASVGDRVTITCRASQSISNYLNWYQQRPGKAPNLLIYAASSLQSGVPSRFSG

SGSGTDFTLTISSLQPEDFATYYCQQTYSTPYTFGQGTKLEIK
```

-continued (SEQ ID NO: 280)
QSVLTQPASVSGSPGQSITISCTGTSSDVGGYNYVSWYRQHPGKAPKLMIYDVSYRPSGVSNRF

SGSKSGNTASLTISGLQAEDEADYYCSSYTDSSTRYVFGTGTKLTVL (SEQ ID NO: 281)
QPVLTQPPSASGTPGQRVAISCSGSRSNIEINSVNWYQQLPGTAPKLLIYDNNKRPSGIPDRFS

GSKSGTSATLGITGLQTGDEADYYCGSWDSSLSADVFGTGTKLTVL (SEQ ID NO: 282)
QSVLTQPPSVSAAPGKKVTISCSGSSSNIGNNYVSWYQQLPGTAPKLLIYRNNQRPSGVPDRFS

GSKSGTSASLAISGLQSEDEADYYCATWDDSLNGWVFGGGTKLTVL (SEQ ID NO: 283)
QSVVTQPPSVSGAPGQRVTISCIGSSSNIGAGYDVHWYQQLPGTAPKLLIYGNNNRHSGVPDRF

SGSKSGTSASLAITGLQAEDEAEFFCGTWDSRLTTYVFGSGTKLTVL (SEQ ID NO: 284)
QSVVTQPPSVSAAPGQKVTISCSGSSSNIGNNYVSWYQQLPGTAPKLLIYDNNKRPSGIPDRFS

GSKSGTSATLGITGLQTGDEADYYCGTWDSSLSAVVFGGGTKLTVL (SEQ ID NO: 285)
VIWMTQSPSSLSASVGDRVTITCAASSLQSWYQQKPGKAPKLLIYEASTLESGVPSRFSGSGSG

TEFTLTISSLQPEDFATYYCQQSYSTPYTFGQGTKLEIK (SEQ ID NO: 286)
QSVVTQPPSVSAAPGQKVTISCSGSSSNIGNNYVSWYQQVPGTAPKLLIYDNNKRPSGIPDRFS

GSNSDTSATLGITGLQTGDEADYYCGTWDSSLSAWVFGGGTKLTVL (SEQ ID NO: 287)
QSVVTQPPSVSAAPGQKVTISCSGSSSNIGNNYVSWYQQLPGTAPKLLIYDNNKRPSGIPDRFS

GSKSGTSATLGITGLQTGDEADYYCGTWDSSLSAGSVVFGGGTKLTVL (SEQ ID NO: 288)
SYELMQPPSVSVAPGKTATIACGGENIGRKTVHWYQQKPGQAPVLVIYYDSDRPSGIPERFSGS

NSGNTATLTISRVEAGDEADYYCLVWDSSSDHRIFGGGTKLTVL (SEQ ID NO: 289)
SYELMQPPSVSVAPGKTATIACGGENIGRKTVHWYQQKPGQAPVLVIYYDSDRPSGIPERFSGS

NSGNTATLTISRVEAGDEADYYCQVWDSSSDHRIFGGGTKLTVL (SEQ ID NO: 290)
SYELMQPPSVSVAPGKTATIACGGENIGRKTVHWYQQKPGQAPVLVIYYDSDRPSGIPERFSGS

NSGNTATLTISRVEAGDEADYYCQVWDSSSDHRIFGGGTKLTVL (SEQ ID NO: 291)
SYELMQPPSVSVAPGKTATIACGGENIGRKTVHWYQQKPGQAPVLVIYYDSDRPSGIPERFSGS

NSGNTATLTISRVEAGDEADYYCQVWDSSSDHRIFGGGTKLTVL

In some embodiments, the PDL1 binding domain comprises or is derived from an antibody sequence or antigen-binding fragment thereof that includes a combination of a heavy chain (HC) and a light chain sequence (LC) selected from the group consisting of:

HC Sequences:

(SEQ ID NO: 292)
QVQLVQSGVEVKKPGASVKVSCKASGYTFTNYYMYWVRQAPGQGLEWMGG

INPSNGGTNFNEKFKNRVTLTTDSSTTTAYMELKSLQFDDTAVYYCARRD

YRFDMGFDYWGQGTTVTVSSASTKGPSVFPLAPCSRSTSESTAALGCLVK

DYFPEPVTVSWNSGALTSGVHTFPAVLQSSGLYSLSSVVTVPSSSLGTKT

YTCNVDHKPSNTKVDKRVESKYGPPCPPCPAPEFLGGPSVFLFPPKPKDT

-continued

LMISRTPEVTCVVVDVSQEDPEVQFNWYVDGVEVHNAKTKPREEQFNSTY

RVVSVLTVLHQDWLNGKEYKCKVSNKGLPSSIEKTISKAKGQPREPQVYT

LPPSQEEMTKNQVSLTCLVKGFYPSDIAVEWESNGQPENNYKTTPPVLDS

DGSFFLYSRLTVDKSRWQEGNVFSCSVMHEALHNHYTQKSLSLSLGK (SEQ ID NO: 293)
QVQLVESGGGVVQPGRSLRLDCKASGITFSNSGMHWVRQAPGKGLEWVAV

IWYDGSKRYYADSVKGRFTISRDNSKNTLFLQMNSLRAEDTAVYYCATND

DYWGQGTLVTVSSASTKGPSVFPLAPCSRSTSESTAALGCLVKDYFPEPV

TVSWNSGALTSGVHTFPAVLQSSGLYSLSSVVTVPSSSLGTKTYTCNVDH

```
KPSNTKVDKRVESKYGPPCPPCPAPEFLGGPSVFLFPPKPKDTLMISRTP

EVTCVVVDVSQEDPEVQFNWYVDGVEVHNAKTKPREEQFNSTYRVVSVLT

VLHQDWLNGKEYKCKVSNKGLPSSIEKTISKAKGQPREPQVYTLPPSQEE

MTKNQVSLTCLVKGFYPSDIAVEWESNGQPENNYKTTPPVLDSDGSFFLY

SRLTVDKSRWQEGNVFSCSVMHEALHNHYTQKSLSLSLGK

LC Sequences:
                                   (SEQ ID NO: 294)
EIVLTQSPATLSLSPGERATLSCRASKGVSTSGYSYLHWYQQKPGQAPRL

LIYLASYLESGVPARFSGSGSGTDFTLTISSLEPEDFAVYYCQHSRDLPL

TFGGGTKVEIKRTVAAPSVFIFPPSDEQLKSGTASVVCLLNNFYPREAKV

QWKVDNALQSGNSQESVTEQDSKDSTYSLSSTLTLSKADYEKHKVYACEV

THQGLSSPVTKSFNRGEC (SEQ ID NO: 295)
EIVLTQSPATLSLSPGERATLSCRASQSVSSYLAWYQQKPGQAPRLLIYD

ASNRATGIPARFSGSGSGTDFTLTISSLEPEDFAVYYCQQSSNWPRTFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
```

In some embodiments, the PDL1 binding domain comprises or is derived from an antibody sequence or antigen-binding fragment thereof that includes a combination of a VH sequence and a VL sequence selected from the group consisting of:

```
VH Sequences:
                                   (SEQ ID NO: 296)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSSASTK (SEQ ID NO: 297)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSS

HC Sequences:
                                   (SEQ ID NO: 298)
EVQLVESGGGLVQPGGSLRLSCAASGFTFSDSWIHWVRQAPGKGLEWVAW

ISPYGGSTYYADSVKGRFTISADTSKNTAYLQMNSLRAEDTAVYYCARRH

WPGGFDYWGQGTLVTVSSASTKGPSVFPLAPSSKSTSGGTAALGCLVKDY

FPEPVTVSWNSGALTSGVHTFPAVLQSSGLYSLSSVVTVPSSSLGTQTYI

CNVNHKPSNTKVDKKVEPKSCDKTHTCPPCPAPELLGGPSVFLFPPKPKD

TLMISRTPEVTCVVVDVSHEDPEVKFNWYVDGVEVHNAKTKPREEQYAST

YRVVSVLTVLHQDWLNGKEYKCKVSNKALPAPIEKTISKAKGQPREPQVY

TLPPSREEMTKNQVSLTCLVKGFYPSDIAVEWESNGQPENNYKTTPPVLD

SDGSFFLYSKLTVDKSRWQQGNVFSCSVMHEALHNHYTQKSLSLSPG

VL Sequences:
                                   (SEQ ID NO: 299)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKR

LC Sequences:
                                   (SEQ ID NO: 300)
DIQMTQSPSSLSASVGDRVTITCRASQDVSTAVAWYQQKPGKAPKLLIYS

ASFLYSGVPSRFSGSGSGTDFTLTISSLQPEDFATYYCQQYLYHPATFGQ

GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
```

In some embodiments, the PDL1 binding domain comprises or is derived from an antibody sequence or antigen-binding fragment thereof that includes a combination of a VH sequence and a VL sequence selected from the group consisting of:

```
VH Sequences:
                                   (SEQ ID NO: 301)
EVQLVESGGGLVQPGGSLRLSCAASGFTFSRFWMSWVRQAPGKGLEWVAN

INQDGTEKYYVDSVKGRFTISRDNAKNSLYLQMNSLRAGDTAVYYCANTY

YDFWSGHFDYWGQGTLVTVSS (SEQ ID NO: 302)
QEHLVESGGGVVQPGRSLRLSCEASGFTFSNFGMHWVRQAPGKGLEWVAA

LWSDGSNKYYADSVKGRVTISRDNSKNTLYLQMNSLRAEDTAVYYCARGR

GAPGIPIFGYWGQGTLVTVSS (SEQ ID NO: 303)
EVQLVESGGGLVKPGGSLRLSCAASGFTFSNAWMSWVRQAPGKGLEWVGR

IKRKTDGGTTDYAAPVKGRFTISRDDSKNTLHLQMNSLKTEDTAVYYCTT

DDIVVVPAVMREYYFGMDVWGQGTTVTVSS (SEQ ID NO: 304)
QVQLVQSGAEVKKPGASVQVSCKASGYSFTGYYIHWVRQAPGQGLEWMGW

INPNSGTKKYAHKFQGRVTMTRDTSIDTAYMILSSLISDDTAVYYCARDE

DWNFGSWFDSWGQGTLVTVSS (SEQ ID NO: 305)
QVHLVQSGAEVKKPGASVKVSCKASGYTFTGYYIHWVRQAPGHGLEWMGW

LNPNTGTTKYIQNFQGRVTMTRDTSSSTAYMELTRLRSDDTAVYYCARDE

DWNYGSWFDTWGQGTLVTVSS (SEQ ID NO: 306)
EVQLVESGGGVVRPGGSLRLSCAASGFTFDDYGMTWVRQAPGRGLEWVSG

IHWHGKRTGYADSVKGRFTISRDNAKKSLYLQMNSLKGEDTALYHCVRGG

MSTGDWFDPWGQGTLVIVSS (SEQ ID NO: 307)
EVQLVESGGGVVRPGGSLRLSCAASGFTFDDYGMTWVRQVPGKGLEWVSG

IHWSGRSTGYADSVKGRFTISRDNAKNSLYLQMNSLRAEDTALYYCARGG

MSTGDWFDPWGQGTLVTVSS
```

(SEQ ID NO: 308)
EVQLVESGGGLVQPGGSLRLSCAASGFTVGSNYMNWVRQAPGKGLEWVSV
IYSGGSTYYADSVKGRFTISRLTSKNTLYLQMSSLRPEDTAVYYCARGIR
GLDVWGQGTTVTVSS (SEQ ID NO: 309)
EERLVESGGDLVQPGGSLRLSCAASGITVGTNYMNWVRQAPGKGLEWVSV
ISSGGNTHYADSVKGRFIMSRQTSKNTLYLQMNSLETEDTAVYYCARGIR
GLDVWGQGTMVTVSS (SEQ ID NO: 310)
QVQLVQSGAEVKMPGSSVRVSCKASGGIFSSSTISWVRQAPGQGLEWMGE
IIPVFGTVNYAQKFQDRVIFTADESTTTAYMELSSLKSGDTAVYFCARNW
GLGSFYIWGQGTMVTVSS (SEQ ID NO: 311)
EVQLVESGGDLVHPGRSLRLSCAASGFPFDEYAMHWVRQVPGKGLEWVSG
ISWSNNNIGYADSVKGRFTISRDNAKNSLYLQMNSLRPEDTAFYYCAKSG
IFDSWGQGTLVTVSS (SEQ ID NO: 312)
EVQLVESGGGVVQPGRSLRLSCAASGFTFSSYGMHWVRQAPGKGLEWVTL
ISYEGRNKYYADSVKGRFTISRDNSKNTLYLQMNSLRAEDTAVYYCAKDR
TLYGMDVWGQGTTVTVSS (SEQ ID NO: 313)
QVTLRESGPALVKTTQTLTLTCTFSGFSLSTNRMCVTWIRQPPGKALEWL
ARIDWDGVKYYNTSLKTRLTISKDTSKNQVVLTMTNMDPVDTATFYCARS
TSLTFYYFDYWGQGTLVTVSS (SEQ ID NO: 314)
EVQLVESGGGLVQPGGSLRLSCAASEFTVGTNHMNWVRQAPGKGLEWVSV
IYSGGNTFYADSVKGRFTISRHTSKNTLYLQMNSLTAEDTAVYYCARGLG
GMDVWGQGTTVTVSS (SEQ ID NO: 315)
EVQLVESGGGLVQRGESLRLYCAASGFTFSKYWMNWVRQAPGKGLEWVAN
IKGDGSEKYYVDSVKGRFTISRDNAKNSLYLQMNSLRAEDTAVYYCARDY
WGSGYYFDFWGQGTLVTVSS (SEQ ID NO: 316)
EVQLVESGGGLVQSGGSLRLSCAASGFTFSSYWMSWVRQAPGKGLEWVAN
IKQDGSEKYYVDSVKGRFTISRDNAKNSLYLQMNSLRADDTAVYYCARDD
IVVVPAPMGYYYYFGMDVWGQGTTVTVSS (SEQ ID NO: 317)
EVQLVESGGGLVQPGRSLRLSCAASGFTFDDFAMHWVRQAPGKGLEWVSG
ISWTGGNMDYANSVKGRFTISREDAKNSLYLQMNSLRAADTALYYCVKDI
RGIVATGGAFDIWGRGTMVTVSS (SEQ ID NO: 318)
EVQLVESGGGLVQPGGSLRLSCAASGFTVGTNYMNWVRQAPGKGLEWISV
IYSGGSTFYADSVKGRFTISRQTSQNTLYLQMNSLRPEDTAVYYCARGIR
GFDIWGQGTMVTVSS (SEQ ID NO: 319)
EVQLVESGGGLVQPGGSLRLSCAASGFTISTNYMNWVRQAPGKGLEWVAV
IYSSGSTYYIDSVKGRFTISRLTSKNTVYLQMSSLNSEDTAVYYCARGIR
GFDIWGQGTMVTVSS (SEQ ID NO: 320)
EVQLVESGGGLVQPGRSLRLSCAASGFTIDDSAMHWVRQTPGKGLEWVSG
ISWKSGSIGYADSVRGRFTISRDNAKNSLYLQMNSLRVEDTALYYCVKDI
RGNWNYGGNWFDPWGQGTLVTVSS (SEQ ID NO: 321)
EVQLVESGGGLVQPGGSLRLSCEASGFTVGVNHMNWVRQAPGKGLEWVSV
IFSSGRTFYGDYVKGRLTIFRQTSQNTVYLQMNSLRSEDTAIYYCARGIG
GLDIWGRGTMVTVSS (SEQ ID NO: 322)
EVQLVESGGGLVQPGRSLRLSCAASGFTFDDYALHWVRQAPGKGLEWVSG
ISWTGGTIDYADSVKGRFTISRDNAKNSLYLQMSSLRTEDTAIYYCTRDI
RGNWKYGGWFDPWGQGTLVTVSS (SEQ ID NO: 323)
QVQLVQSGTEVKKPGASVKVSCKASGYTFTAYYMHWVRQAPGQGLDWMGW
ISPNSGFTNYAQKFQGRVTMTRDTSINTFYMELSGLRSDDTAVYYCAREG
STHHNSFDPWGQGTLVTVSS (SEQ ID NO: 324)
EVQLVESGGGLVQPGGSLRLSCAASGFTVGTNFMNWVRQAPGKGLEWVSA
IYSGGTANYADSVKGRFTISRDTSRNTLYLQMNSLRTEDTAVYYCARGGG
MDVWGQGTTVTVSS (SEQ ID NO: 325)
QVQLVQSGAEVKKPGSSVKVSCKASGGTFNTYVLSWVRQAPGQGLEWMGE
IIPILGAANYAQNFQGRVTFTTDESTNTAYMDLSSLRSEDTAVYYCARDR
TSGGFDPWGQGTLVTVSS (SEQ ID NO: 326)
QVQLVQSGAEVEKPGASVKVSCKASGYIFTHYGISWVRQAPGQGLEWVGW
ISPYNGYTDYAQKLQGRVTLTTDTSTTTAYMELRNLRSDDTAMYYCSRGR
GPYWSFDLWGRGTLVTVSS

VL Sequences:
(SEQ ID NO: 327)
DIQMTQSPSTLSASVGDRVTITCRASQSISNWLAWYQQKPGKAPKLLIYK
ASSLESGVPSRFSGSGSGTEFTLTISSLQPDDFATYYCQQYHSYSYTFGQ
GTKEIK (SEQ ID NO: 328)
DIQMTQSPSSLSASVGDRVTITCRASQGIRNDLGWYQQKPGKAPKRLIYT
ASSLQSGVPSRFSGSGSGTEFTLTISSLQPEDFATYYCLQHNSYPLTFGG
GTKVAIK (SEQ ID NO: 329)
DIQMTQSPSSLSASVGDRVTITCRTSQGIRNDLGWYQQKPGKAPKRLIYA
ASSLQSGVPSRFSGSGSGTEFTLTISSLQPEDFATYYCLQHNNYPYTFGQ
GTKLEIK -continued (SEQ ID NO: 330)
DIVMTQTPLSSPVTLGQPASISCRSSQTLVHGDGNTYLSWIQQRPGQPPR
LLIYKVSNQFSGVPDRFSGSGAGTDFTLKISRVEAEDVGLYFCMQATHFP
ITFGQGTRLEIK (SEQ ID NO: 331)
DIVMTQTPLSSPVTLGQPASISCRSSPSLVHSDGNTYLSWLQQRPGQPPR
LLIYKISNRFSGVPDRFSGSGAGTDFTLKISRVEAEDVGVYYCMQATHFP
ITFGQGTRLEIR (SEQ ID NO: 332)
DIQMTQSPSSLSASLGDRVTITCRASQSINSYLNWYQQKPGKAPKLLIYV
ASSLQSGVPSRFSGSGSGTEFTLTISNLQPEDFATYYCQQSYSTPPITFG
QGTRLEIK (SEQ ID NO: 333)
DIQMTQSPSSLSASVGDRVTITCRASQSISSYLNWYQQKPGKAPKLLIYV
ASSLQSGVPSRFSGSGSGTDFTLTISSLQPEDFATYYCQQSYSTPPITFG
QGTRLEIK (SEQ ID NO: 334)
DIQMTQSPSSLSASVGDRVTITCRASQTINTYLNWYQQKPGRAPRLLIYA
ASSLQSGVPSRFSGSGSGTDFTLTISSLQPEDFATYYCHQSYSTPPITFG
QGTRLEIK (SEQ ID NO: 335)
DIQMTQSPSSLSASVGDRVTITCRASQSMSSYLNWYQQKPGRAPKLLIFA
ASSLQSGVPSRFSGSGSGTDFTLTISSLQPEDFATYYCQQSYSTPPITFG
QGTRLEIK (SEQ ID NO: 336)
EIVLTQSPGTLSLSPGERATLSCRASQSFNFNYLAWYQQKPGQAPRLLIY
GASSRATGIPDRFSGSGSGTDFTLTINRLEPEDFGVFYCQQYESAPWTFG
QGTKVEIK (SEQ ID NO: 337)
DIQMTQSPSSLSASVGDRVTITCRASQSISSYLNWYQQKPGKLLIYAASS
LQSGVPSRFSGGGSGTDFTLTISSLRPEDFATYYCQQSYCTPPITFGQGT
RLEIK (SEQ ID NO: 338)
DIQMTQSPSSLSASVGDRVTITCRASQSISSYLNWYQQKPGKAPKLLIYA
ASSLQSGVPSRFSGSGSGTDFTLTISSLQPEDFATYYCQQSYSTPPITFG
QGTRLEIK (SEQ ID NO: 339)
DRVTITCRASQVISNYLAWYQQKPGKVPRLLIYAASTLQSGVPSRFSGSG
SGTDFTLTISSLQPEDVATYYCQKYNSAPRTFGQGTKVEIK (SEQ ID NO: 340)
DIQMTQSPSSLSASVGDRVTITCRASQNINNYLNWYQQKPGKAPKLLIYA
ASSFQNAVPSRFSGSGSGTDFTLTISSLQPEDFATYYCQQSYNTPLTFGG
GTKVEIK (SEQ ID NO: 341)
DIQMTQSPSSLSASVGDRVTITCRASQGIRNDLGWYQQKPGKAPKRLIYA
ASSLQSGVPSRFSGSGSGTEFTLTISSLQPEDFATYYCLQHNSYPYTFGQ
GTKLEIK (SEQ ID NO: 342)
DIQMTQSPSSLSASVGDRVTITCRASQSISSYLNWYQQKPGKAPKLLIYA
ASSLQSGVPSRFSGSGSGTDFTLTISSLQPEDFATYYCQQSYSTPPITFG
QGTRLEIK In some embodiments, the PDL1 binding domain comprises or is derived from an antibody sequence or antigen-binding fragment thereof that includes a combination of a VH sequence and a VL sequence selected from the group consisting of:

VH Sequences:
(SEQ ID NO: 343)
QSLEESGGRLVKPDETLTITCTVSGIDLSSNGLTWVRQAPGEGLEWIGTI
NKDASAYYASWAKGRLTISKPSSTKVDLKITSPTTEDTATYFCGRIAFKT
GTSIWGPGTLVTVSS VL Sequences:
(SEQ ID NO: 344)
AIVMTQTPSPVSAAVGGTVTINCQASESVYSNNYLSWFQQKPGQPPKLLI
YLASTLASGVPSRFKGSGSGTQFTLTISGVQCDDAATYYCIGGKSSSTDG
NAFGGGTEVVVR In some embodiments, the PDL1 binding domain comprises or is derived from an antibody sequence or antigen-binding fragment thereof that includes a combination of a VH sequence and a VL sequence selected from the group consisting of:

VH Sequences:
(SEQ ID NO: 345)
QMQLVQSGAEVKKPGSSVKVSCKASGGTFSSYAISWVRQAPGQGLEWMGG
IIPIFGTANYAQKFQGRVTITADESTSTAYMELSSLRSEDTAVYYCARGN
IVATITPLDYWGQGTLVTVSS (SEQ ID NO: 346)
QPVLTQFPSVSAAPGQKVTISCSGSSSNIANNYVSWYQQLPGTAPKLLIF
ANNKRPSGIPDRFSGSKSGTSAALDITGLQTGDEADYYCGTWDSDLRAGV
FGGGTKLTVL (SEQ ID NO: 347)
EVQLVQSGAEVKKPGSSVKVSCKASGGTFSSYAISWVRQAPGQGLEWMGG
IIPIFGTANYAQKFQGRVTITADKSTSTAYMELSSLRSEDTAVYYCAREG
TIYDSSGYSFDYWGQGTLVTVSS (SEQ ID NO: 348)
QVQLVESGGGVVQPGRSLRLSCAASGFTFSSYAMHWVRQAPGKGLEWVAV
ISFDGSNKYYADSVRGRFTISRDNSKNTLYLQMNSLRTEDTAVYYCARGW
LDRDIDYWGQGTLVTVSS (SEQ ID NO: 349)
EVQLVESGGGVVQPGRSLRLSCAASGFTFSSYAMHWVRQAPGKGLEWVAV
ISFDGSNKYYADSVRGRFTISRDNSKNTLYLQMNSLRTEDTAVYYCARGW
LDRDIDYWGQGTLVTVSS

```
                                            (SEQ ID NO: 350)
QVQLVESGGGVVQPGRSLRLSCAASGFTFSSYAMHWVRQAPGKGLEWVAV
ISFDGSNKYYADSVRGRFTISRDNSKNTLYLQMNSLRTEDTAVYYCARGW
LDRDIDYWGQGTLVTVSS (SEQ ID NO: 351)
EVQLVESGGGVVQPGRSLRLSCAASGFTFSSYAMHWVRQAPGKGLEWVAV
ISFDGSNKYYADSVRGRFTISRDNSKNTLYLQMNSLRTEDTAVYYCARGW
LDRDIDYWGQGTLVTVSS (SEQ ID NO: 352)
EVQLVESGGGVVQPGRSLRLSCAASGFTFSSYAMHWVRQAPGKGLEWVAV
ISFDGSNKYYADSVRGRFTISRDNSKNTLYLQMNSLRTEDTAVYYCARGW
LDRDIDYWGQGTLVTVSS (SEQ ID NO: 353)
QVQLVESGGGVVQPGRSLRLSCAASGFTFSSYAMHWVRQAPGKGLEWVAV
ISFDGSNKYYADSVRGRFTISRDNSKNTLYLQMNSLRTEDTAVYYCARGW
LDRDIDYWGQGTLVTVSS (SEQ ID NO: 354)
QVQLVQSGAEVKKPGSSVKVSCKASGGTFSRYGVHWVRQAPGQGLEWMGR
LIPIVSMTNYAQKFQDRVSITTDKSTGTAYMELRSLTSEDTALYYCASVG
QQLPWVFFAWGQGTLVTVSS (SEQ ID NO: 355)
QMQLVQSGGGVVQPGRSLRLSCAASGFTFSSYAMHWVRQAPGKGLEWVAV
ISFDGSNKYYADSVRGRFTISRDNSKNTLYLQMNSLRTEDTAVYYCARGW
LDRDIDYWGQGTLVTVSS (SEQ ID NO: 356)
QVQLVQSGGGVVQPGRSLRLSCAASGFTFSSYAMHWVRQAPGKGLEWVAV
ISFDGSNKYYADSVRGRFTISRDNSKNTLYLQMNSLRTEDTAVYYCARGW
LDRDIDYWGQGTLVTVSS (SEQ ID NO: 357)
QMQLVQSGAEVKKPGSSVKVSCKASGGTFSSYAYSWVRQAPGQGLEWMGG
IIPSFGTANYAQKFQGRVTITADESTSTAYMELSSLRSEDTAVYYCARGP
IVATITPLDYWGQGTLVTVSS (SEQ ID NO: 358)
QMQLVQSGAEVKKPGSSVKVSCKASGGTFSSYAYSWVRQAPGQGLEWMGG
IIPIFGTANYAQKFQGRVTITADESTSTAYMELSSLRSEDTAVYYCARGP
IVATITPLDYWGQGTLVTVSS (SEQ ID NO: 359)
QMQLVQSGAEVKKPGSSVKVSCKASGGTFSSYAYSWVRQAPGQGLEWMGG
IIPSFGTANYAQKFQGRVTITADESTSTAYMELSSLRSEDTAVYYCARGP
IVATITPLDYWGQGTLVTVSS (SEQ ID NO: 360)
QMQLVQSGAEVKKPGSSVKVSCKASGGTFSSYAISWVRQAPGQGLEWMGG
IIPAFGTANYAQKFQGRVTITADESTSTAYMELSSLRSEDTAVYYCARGP
IVATITPLDYWGQGTLVTVSS
```

VL Sequences:
```
                                            (SEQ ID NO: 361)
SYELMQPPSVSVAPGKTATIACGGENIGRKTVHWYQQKPGQAPVLVIYYD
SDRPSGIPERFSGSNSGNTATLTISRVEAGDEADYYCQVWDSSSDHRIFG
GGTKLTVL (SEQ ID NO: 362)
AIRMTQSPSSLSASVGDRVTITCRASQSISSYLNWYQQKPGKAPKLLIYT
TSSLKSGVPSRFSGSGSGTDFTLTISRLQPEDFATYYCQQSYSSTWTFGR
GTKVEIK (SEQ ID NO: 363)
QSVLTQPPSVSAAPGQKVTISCSGNNSNIANNYVSWYQQLPGTAPKLLIY
DNNYRPSGIPDRFSGSKSGTSATLDITGLQTGDEADYYCGVWDGSLTTGV
FGGGTKLTVL (SEQ ID NO: 364)
LPVLTQPASVSGSPGQSITISCTGTTSDIGGYDYVSWYQQHPGKAPKLMI
YDVSKRPSGVSNRFSGSKSGNTASLTISGLQAEDEADYYCSSYTSSSTHV
FGTGTKLTVL (SEQ ID NO: 365)
QSALTQPASVSGSPGQSITISCTGTSSDVGGYNYVSWYQQHPGKAPKLMI
YDVSNRPSGVSNRFSGSKSGNTASLTISGLQAEDEADYYCSSYRSSTLGP
VFGGGTKLTVL (SEQ ID NO: 366)
QAGLTQPPSVSEAPRQRVTISCSGSSSNIGNNAVNWYQQLPGKAPKLLIY
YDDLLPSGVSDRFSGSKSGTSASLAISGLQSEDEADYYCAAWDDSLNGYV
FGTGTKLTVL (SEQ ID NO: 367)
QSALTQPRSVSGSPGQSVTISCTGTSSDVGGYNYVSWYQQHPGKAPKLMI
YDVSKRPSGVPDRFSGSKSGNTASLTISGLQAEDEADYYCSSYTSSTTHV
FGTGTKVTVL (SEQ ID NO: 368)
QSVVTQPPSVSAAPGQKVTISCSGSSSNIGNNYVSWYQQLPGTAPKLLIY
DNNKRPSGIPDRFSGSKSGTSATLGITGLQTGDEADYYCGTWDSSLSVWV
FGGGTQLTVL (SEQ ID NO: 369)
QSVLTQPASVSGSPGQSITISCTGTSSDVGGYNYVSWYQQHPGRAPRLMI
YDVSNRPSGVSNRFSGSKSGNTASLTISGLQAEDEGDYYCSSYTSGGTLG
PVFGGGTKLTVL (SEQ ID NO: 370)
QSVVTQPPSVSAAPGQKVTISCSGSSSNIGNNYVSWYQQLPGTAPKLLIY
DNNKRPSGIPDRFSGSKSGTSATLGITGLQTGDEADYYCGTWDSSLSAVV
FGGGTKLTVL (SEQ ID NO: 371)
QSVVTQPPSVSAAPGQKVTISCSGSSSNIGNNYVSWYQQVPGTAPKLLIY
DNNKRPSGIPDRFSGSNSDTSATLGITGLQTGDEADYYCGTWDSSLSAWV
FGGGTKLTVL
```

(SEQ ID NO: 372)
QSVVTQPPSVSAAPGQKVTISCSGSSSNIGNNYVSWYQQLPGTAPKLLIY

DNNKRPSGIPDRFSGSKSGTSATLGITGLQTGDEADYYCGTWDSSLSAGS

VVFGGGTKLTVL (SEQ ID NO: 373)
SYELMQPPSVSVAPGKTATIACGGENIGRKTVHWYQQKPGQAPVLVIYYD

SDRPSGIPERFSGSNSGNTATLTISRVEAGDEADYYCLVWDSSSDHRIFG

GGTKLTVL (SEQ ID NO: 374)
SYELMQPPSVSVAPGKTATIACGGENIGRKTVHWYQQKPGQAPVLVIYYD

SDRPSGIPERFSGSNSGNTATLTISRVEAGDEADYYCQVWDSSSDHRIFG

GGTKLTVL (SEQ ID NO: 375)
SYELMQPPSVSVAPGKTATIACGGENIGRKTVHWYQQKPGQAPVLVIYYD

SDRPSGIPERFSGSNSGNTATLTISRVEAGDEADYYCQVWDSSSDHRIFG

GGTKLTVL (SEQ ID NO: 376)
SYELMQPPSVSVAPGKTATIACGGENIGRKTVHWYQQKPGQAPVLVIYYD

SDRPSGIPERFSGSNSGNTATLTISRVEAGDEADYYCQVWDSSSDHRIFG

GGTKLTVL

In some embodiments, the PDL1 binding domain comprises or is derived from an antibody sequence or antigen-binding fragment thereof that includes a combination of a VH sequence and a VL sequence selected from the group consisting of:

VH Sequences:
(SEQ ID NO: 377)
QVQLVQSGSEVKKSGSSVKVSCKTSGGTFSITNYAINWVRQAPGQGLEWM

GGILPIFGAAKYAQKFQDRVTITADESTNTAYLELSSLTSEDTAMYYCAR

GKRWLQSDLQYWGQGTLVTVSS

VL Sequences:
(SEQ ID NO: 378)
QPVLTQPASVSGSPGQSITISCTGSSSDVGSYDLVSWYQQSPGKVPKLLI

YEGVKRPSGVSNRFSGSKSGNTASLTISGLQAEDEADYYCSSYAGTRNFV

FGGGTQLTVL

In some embodiments, the PDL1 binding domain comprises or is derived from an antibody sequence or antigen-binding fragment thereof that includes a combination of a VH sequence and a VL sequence selected from the group consisting of:

VH Sequences:
(SEQ ID NO: 379)
EVQLLESGGGLVQPGGSLRLSCAASGFTFSSYAMSWVRQAPGKGLEWVSS

IYSTGGATAYADSVKGRFTISRDNSKNTLYLQMNSLRAEDTAVYYCAKSS

AGQSRPGFDYWGQGTLVTVSS (SEQ ID NO: 380)
EVQLLESGGGLVQPGGSLRLSCAASGFTFSSYAMSWVRQAPGKGLEWVSS

IYSTGGATAYADSVKGRFTISRDNSKNTLYLQMNSLRAEDTAVYYCAKSS

AGQSWPGFDYWGQGTLVTVSS (SEQ ID NO: 381)
EVQLLESGGGLVQPGGSLRLSCAASGFTFSSYAMSWVRQAPGKGLEWVSS

IYSTGGATAYADSVKGRFTISRDNSKNTLYLQMNSLRAEDTAVYYCAKSS

AGQSFPGFDYWGQGTLVTVSS (SEQ ID NO: 382)
EVQLLESGGGLVQPGGSLRLSCAASGFTFSSYAMSWVRQAPGKGLEWVSS

IYSTGGATAYADSVKGRFTISRDNSKNTLYLQMNSLRAEDTAVYYCAKWS

AAFDYWGQGTLVTSS (SEQ ID NO: 383)
EVQLLESGGGLVQPGGSLRLSCAASGFTFSSYAMSWVRQAPGKGLEWVSS

IYSTGGATAYADSVKGRFTISRDNSKNTLYLQMNSLRAEDTAVYYCAKWS

AGYDYWGQGTLVTVSS (SEQ ID NO: 384)
EVQLLESGGGLVQPGGSLRLSCAASGFTFSSYAMSWVRQAPGKGLEWVSS

IYSTGGATAYADSVKGRFTISRDNSKNTLYLQMNSLRAEDTAVYYCAKWS

KGFDYWGQGTLVTVSS (SEQ ID NO: 385)
EVQLLESGGGLVQPGGSLRLSCAASGFTFSSYAMSWVRQAPGKGLEWVSS

IWKQGIVTVYDSVKGRFTISRDNSKNTLYLQMNSLRAEDTAVYYCAKSSA

GFDYWGQGTLVTV (SEQ ID NO: 386)
EVQLLESGGGLVQPGGSLRLSCAASGFTFSSYAMSWVRQAPGKGLEWVSS

IWRNGIVTVYDSVKGRFTISRDNSKNTLYLQMNSLRAEDTAVYYCAKSSA

GFDYWGQGTLVTVSS (SEQ ID NO: 387)
EVQLLESGGGLVQPGGSLRLSCAASGFTFSSYAMSWVRQAPGKGLEWVSD

IWKQGMVTVYDSVKGRFTISRDNSKNTLYLQMNSLRAEDTAVYYCAKSSA

GFDYWGQGTLVTVSS (SEQ ID NO: 388)
EVQLLESGGGLVQPGGSLRLSCAASGFTFSSYAMSWVRQAPGKGLEWVSS

IWRQGLATAYDSVKGRFTISRDNSKNTLYLQMNSLRAEDTAVYYCAKSSA

GFDYWGQGTLVTVSS (SEQ ID NO: 389)
EVQLLESGGGLVQPGGSLRLSCAASGFTFSSYAMSWVRQAPGKGLEWVSE

IVATGILTSYDSVKGRFTISRDNSKNTLYLQMNSLRAEDTAVYYCAKSSA

GFDYWGQGTLVTVSS (SEQ ID NO: 390)
EVQLLESGGGLVQPGGSLRLSCAASGFTFSSYAMSWVRQAPGKGLEWVSS

IGRQGLITVYDSVKGRFTISRDNSKNTLYLQMNSLRAEDTAVYYCAKSSA

GFDYWGQGTLVTVSS (SEQ ID NO: 391)
EVQLLESGGGLVQPGGSLRLSCAASGFTFSSYAMSWVRQAPGKGLEWVSS
IWYQGLVTVYDSVKGRFTISRDNSKNTLYLQMNSLRAEDTAVYYCAKSSA
GFDYWGQGTLVTVSS (SEQ ID NO: 392)
EVQLLESGGGLVQPGGSLRLSCAASGFTFSSYAMSWVRQAPGKGLEWVSD
IWKQGFATADSVKGRFTISRDNSKNTLYLQMNSLRAEDTAVYYCAKSSAG
FDYWGQGTLVTVSS (SEQ ID NO: 393)
EVQLLESGGGLVQPGGSLRLSCAASGFTFSSYAMSWVRQAPGKGLEWVSS
IWKQGIVTVYDSVKGRFTISRDNSKNTLYLQMNSLRAEDTAVYYCAKSSA
GFDYWGQGTLVTVSS (SEQ ID NO: 394)
EVQLLESGGGLVQPGGSLRLSCAASGFTFSSYAMSWVRQAPGKGLEWVSS
IWRQGLATAYDSVKGRFTISRDNSKNTLYLQMNSLRAEDTAVYYCAKSSA
GFDYWGQGTLVTVSS (SEQ ID NO: 395)
EVQLLESGGGLVQPGGSLRLSCAASGFTFSSYAMSWVRQAPGKGLEWVSS
IWRNGIVTVYADSVKGRFTISRDNSKNTLYLQMNSLRAEDTAVYYCAKWS
AAFDYWGQGTLVTVSS (SEQ ID NO: 396)
EVQLLESGGGLVQPGGSLRLSCAASGFTFSSYAMSWVRQAPGKGLEWVSS
IWRNGIVTVYADSVKGRFTISRDNSKNTLYLQMNSLRAEDTAVYYCAKWS
AGYDYWGQGTLVTVSS (SEQ ID NO: 397)
EVQLLESGGGLVQPGGSLRLSCAASGFTFSSYAMSWVRQAPGKGLEWVSS
IWRNGIVTVYADSVKGRFTISRDNSKNTLYLQMNSLRAEDTAVYYCAKWS
KGFDYWGQGTLVTVSS (SEQ ID NO: 398)
EVQLLESGGGLVQPGGSLRLSCAASGFTFSSYAMetSWVRQAPGKGLEWV
SSIWYQGLVTVYADSVKGRFTISRDNSKNTLYLQMetNSLRAEDTAVYYC
AKWSAAFDYWGQGTLVTVSS (SEQ ID NO: 399)
EVQLLESGGGLVQPGGSLRLSCAASGFTFSSYAMSWVRQAPGKGLEWVSS
IWYQGLVTVYADSVKGRFTISRDNSKNTLYLQMNSLRAEDTAVYYCAKWS
AGYDYWGQGTLVTVSS (SEQ ID NO: 400)
EVQLLESGGGLVQPGGSLRLSCAASGFTFSSYAMSWVRQAPGKGLEWVSS
IWYQGLVTVYADSVKGRFTISRDNSKNTLYLQMNSLRAEDTAVYYCAKWS
KGFDYWGQGTLVTVSS

VL Sequences:
(SEQ ID NO: 401)
DIQMTQSPSSLSASVGDRVTITCRASQSISSYLNWYQQKPGKAPKLLIYY
ASTLQSGVPSRFSGSGSGTDFTLTISSLQPEDFATYYCQQDNGYPSTFGQ
GTKVEIKR (SEQ ID NO: 402)
DIQMTQSPSSLSASVGDRVTITCRASQSISSYLNWYQQKPGKAPKLLIYY
ASTLQSGVPSRFSGSGSGTDFTLTISSLQPEDFATYYCQQDNGYPSTFGQ
GTKVEIKR (SEQ ID NO: 403)
DIQMTQSPSSLSASVGDRVTITCRASQSISSYLNWYQQKPGKAPKLLIYA
ASSLQSGVPSRFSGSGSGTDFTLTISSLQPEDFATYYCQQDNGYPSTFGG
GTKVEIKR In some embodiments, the PDL1 binding domain comprises or is derived from an antibody sequence or antigen-binding fragment thereof that includes a single chain Fv (scFv) sequence selected from the group consisting of:

(SEQ ID NO: 404)
EVQLLESGGGLVQPGGSLRLSCAASGFTFSSYAMSWVRQAPGKGLEWVSD
ITASGQRTTYADSVKGRFTISRDNSKNTLYLQMNSLRAEDTAVYYCARSK
IAFDYWGQGTLVTVSSGGGGSGGGGSGGGGSTDIQMTQSPSSLSASVGDR
VTITCRASQSISSYLNWYQQKPGKAPKLLIYKASRLQSGVPSRFSGSGSG
TDFTLTISSLQPEDFATYYCQQRALKPVTFGQGTKVEIKR (SEQ ID NO: 405)
EVQLLESGGGLVQPGGSLRLSCAASGFTFSSYAMSWVRQAPGKGLEWVSS
INKDGHYTSYADSVKGRFTISRDNSKNTLYLQMNSLRAEDTAVYYCAKNL
DEFDYWGQGTLVTVSSGGGGSGGGGSGGGGSTDIQMTQSPSSLSASVGDR
VTITCRASQSISSYLNWYQQKPGKAPKLLIYAASSLQSGVPSRFSGSGSG
TDFTLTISSLQPEDFATYYCQQSYSTPNTFGQGTKVEIKR (SEQ ID NO: 406)
EVQLLESGGGLVQPGGSLRLSCAASGFTFSSYAMSWVRQAPGKGLEWVSS
IMATGAGTLYADSVKGRFTISRDNSKNTLYLQMNSLRAEDTAVYYCAKDG
AGFDYWGQGTLVTVSSGGGGSGGGGSGGGGSTDIQMTQSPSSLSASVGDR
VTITCRASQSISSYLNWYQQKPGKAPKLLIYSASQLQSGVPSRFSGSGSG
TDFTLTISSLQPEDFATYYCQQANSRPSTFGQGTKVEIKR (SEQ ID NO: 407)
EVQLLESGGGLVQPGGSLRLSCAASGFTFSSYAMSWVRQAPGKGLQWVST
ITSSGAATYYADSVKGRFTISRDNSKNTLYLQMNSLRAEDTAVYYCAKNY
TGFDYWGQGTLVTVSSGGGGSGGGGSGGGGSTDIQMTQSPSSLSASVGDR
VTITCRASQSISSYLNWYQQKPGKAPKLLIYNASSLQSGVPSRFSGSGSG
TDFTLTISSLQPEDFATYYCQQYTYGPGTFGQGTKVEIKR (SEQ ID NO: 408)
EVQLLESGGGLVQPGGSLRLSCAASGFTFSSYAMSWVRQAPGKGLEWVSS
IYSTGGATAYADSVKGRFTISRDNSKNTLYLQMNSLRAEDTAVYYCAKSS
AGFDYWGQGTLVTVSSGGGGSGGGGSGGGGSTDIQMTQSPSSLSASVGDR
VTITCRASQSISSYLNWYQQKPGKAPKLLIYYASTLQSGVPSRFSGSGSG
TDFTLTISSLQPEDFATYYCQQDNGYPSTFGQGTKVEIKR

PDL1×41BB Dual Targeting

In some embodiments, the fusion proteins are bispecific molecules that include a TBD that binds 41BB and a binding domain directed toward PDL1. In these, embodiments, the binding to PDL1 is capable of providing the additional crosslinking function and TNFRSF activation can be achieved with only one or two anti-41BB TBDs. In these embodiments, the TNFRSF signaling is enhanced and focused by the presence of a PDL1 expressing cell.

```
Tetravalent 41BB agonist: hzRH3v5-1
                                 (SEQ ID NO: 448)
EVQLLESGGGEVQPGGSLRLSCAASGFSFSINAMGWYRQAPGKRREFVAA
IESGRNTVYAESVKGRFTISRDNAKNTVYLQMSSLRAEDTAVYYCGLLKG
NRVVSPSVAYWGQGTLVTVKPGGGGDKTHTCPPCPAPGGPSVFLFPPKPK
DTLMISRTPEVTCVVVDVSHEDPEVKFNWYVDGVEVHNAKTKPREEQYNS
TYRVVSVLTVLHQDWLNGKEYKCKVSNKALPAPIEKTISKAKGQPREPQV
YTLPPSRDELTKNQVSLTCLVKGFYPSDIAVEWESNGQPENNYKTTPPVL
DSDGSFFLYSKLTVDKSRWQQGNVFSCSVMHEALHNHYTQKSLSLSPGSG
GGGSGGGGSEVQLLESGGGEVQPGGSLRLSCAASGFSFSINAMGWYRQAPG
KRREFVAAIESGRNTVYAESVKGRFTISRDNAKNTVYLQMSSLRAED
TAVYYCGLLKGNRVVSPSVAYWGQGTLVTVKPGG Bispecific PDL1 × 41BB: hz28A2v5 × hzRH3v5-1
                                 (SEQ ID NO: 449)
EVQLLESGGGEVQPGGSLRLSCAASGGIFAIKPISWYRQAPGKQREWVST
TTSSGATNYAESVKGRFTISRDNAKNTLYLQMSSLRAEDTAVYYCNVFEY
WGQGTLVTVKPGGSGGSEVQLLESGGGEVQPGGSLRLSCAASGFSFSINA
MGWYRQAPGKRREFVAAIESGRNTVYAESVKGRFTISRDNAKNTVYLQMS
SLRAEDTAVYYCGLLKGNRVVSPSVAYWGQGTLVTVKPGGGGDKTHTCPP
CPAPGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAVEW
ESNGQPENNYKTTPPVLDSDGSFFLYSKLTVDKSRWQQGNVFSCSVMHEA
LHNHYTQKSLSLSPGK Bispecific PDL1 × 41BB: hz28A2v5 × hzRH3v5-2
                                 (SEQ ID NO: 450)
EVQLLESGGGEVQPGGSLRLSCAASGGIFAIKPISWYRQAPGKQREWVST
TTSSGATNYAESVKGRFTISRDNAKNTLYLQMSSLRAEDTAVYYCNVFEY
WGQGTLVTVKPGGSGGSEVQLLESGGGEVQPGGSLRLSCAASGFSFSINA
MGWYRQAPGKRREFVAAIYSGRNTVYAESVKGRFTISRDNAKNTVYLQMS
SLRAEDTAVYYCGLLKGNRVVSPSVAYWGQGTLVTVKPGGGGDKTHTCPP
CPAPGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAVEW
ESNGQPENNYKTTPPVLDSDGSFFLYSKLTVDKSRWQQGNVFSCSVMHEA
LHNHYTQKSLSLSPGK Bispecific PDL1 × 41BB: hz28A2v5 × hzRH3v5-16
                                 (SEQ ID NO: 451)
EVQLLESGGGEVQPGGSLRLSCAASGGIFAIKPISWYRQAPGKQREWVST
TTSSGATNYAESVKGRFTISRDNAKNTLYLQMSSLRAEDTAVYYCNVFEY
WGQGTLVTVKPGGSGGSEVQLLESGGGEVQPGGSLRLSCAASGFSFSINA
MGWYRQAPGKRREFVAAIYSGSSTVYAESVKGRFTISRDNAKNTVYLQMS
SLRAEDTAVYYCGLLKGNRVVSPSVAYWGQGTLVTVKPGGGGDKIHTCPP
CPAPGGPSVFLFPPKPKDTLMISRTPEVTCVVVDVSHEDPEVKFNWYVDG
VEVHNAKTKPREEQYNSTYRVVSVLTVLHQDWLNGKEYKCKVSNKALPAP
IEKTISKAKGQPREPQVYTLPPSRDELTKNQVSLTCLVKGFYPSDIAVEW
ESNGQPENNYKTTPPVLDSDGSFFLYSKLTVDKSRWQQGNVFSCSVMHEA
LHNHYTQKSLSLSPGK Bispecific PDL1 × 41BB: hz28A2v5 × hz4E01v16
                                 (SEQ ID NO: 452)
EVQLLESGGGEVQPGGSLRLSCAASGGIFAIKPISWYRQAPGKQREWVST
TTSSGATNYAESVKGRFTISRDNAKNTLYLQMSSLRAEDTAVYYCNVFEY
WGQGTLVTVKPGGSGGSEVQLLESGGGEVQLLESGGGEVQPGGSLRLSCA
ASGWAFGNYGMAWFRQAPGKEREFVSRLAWQGGSTDYVESVKGRFTISRD
NAKNTLYLQMSSLRAEDTAVYYCARQRSYSRYDIRTPQTYDYWGQGTLVT
VKPGGGGDKTHTCPPCPAPGGPSVFLFPPKPKDTLMISRTPEVTCVVVDV
SHEDPEVKFNWYVDGVEVHNAKTKPREEQYNSTYRVVSVLTVLHQDWLNG
KEYKCKVSNKALPAPIEKTISKAKGQPREPQVYTLPPSRDELTKNQVSLT
CLVKGFYPSDIAVEWESNGQPENNYKTTPPVLDSDGSFFLYSKLTVDKSR
WQQGNVFSCSVMHEALHNHYTQKSLSLSPGK Bispecific PDL1 × 41BB: hz28A2v5 × hz4E01v18
                                 (SEQ ID NO: 453)
EVQLLESGGGEVQPGGSLRLSCAASGGIFAIKPISWYRQAPGKQREWVST
TTSSGATNYAESVKGRFTISRDNAKNTLYLQMSSLRAEDTAVYYCNVFEY
WGQGTLVTVKPGGSGGSEVQLLESGGGEVQLLESGGGEVQPGGSLRLSCA
ASGWAFGNYGMAWFRQAPGKEREFVSRLAWGGGSTDYVESVKGRFTISRD
NAKNTLYLQMSSLRAEDTAVYYCARQRSYSRYDIRTPQTYDYWGQGTLVT
VKPGGGGDKTHTCPPCPAPGGPSVFLFPPKPKDTLMISRTPEVTCVVVDV
SHEDPEVKFNWYVDGVEVHNAKTKPREEQYNSTYRVVSVLTVLHQDWLNG
KEYKCKVSNKALPAPIEKTISKAKGQPREPQVYTLPPSRDELTKNQVSLT
CLVKGFYPSDIAVEWESNGQPENNYKTTPPVLDSDGSFFLYSKLTVDKSR
WQQGNVFSCSVMHEALHNHYTQKSLSLSPGK Bispecific PDL1 × 41BB: hz28A2v5 × hz4E01v21
                                 (SEQ ID NO: 454)
EVQLLESGGGEVQPGGSLRLSCAASGGIFAIKPISWYRQAPGKQREWVST
TTSSGATNYAESVKGRFTISRDNAKNTLYLQMSSLRAEDTAVYYCNVFEY
WGQGTLVTVKPGGSGGSEVQLLESGGGEVQLLESGGGEVQPGGSLRLSCA
ASGWAFSNYGMAWFRQAPGKEREFVSRLAWGGGSTDYVESVKGRFTISRD
NAKNTLYLQMSSLRAEDTAVYYCARQRSYSRYDIRTPQTYDYWGQGTLVT
VKPGGGGDKTHTCPPCPAPGGPSVFLFPPKPKDTLMISRTPEVTCVVVDV
SHEDPEVKFNWYVDGVEVHNAKTKPREEQYNSTYRVVSVLTVLHQDWLNG
KEYKCKVSNKALPAPIEKTISKAKGQPREPQVYTLPPSRDELTKNQVSLT
CLVKGFYPSDIAVEWESNGQPENNYKTTPPVLDSDGSFFLYSKLTVDKSR
WQQGNVFSCSVMHEALHNHYTQKSLSLSPGK
```

Bispecific PDL1 x 41BB: hz28A2v5 x hz4E01v22
(SEQ ID NO: 455)
EVQLLESGGGEVQPGGSLRLSCAASGGIFAIKPISWYRQAPGKQREWVST

TTSSGATNYAESVKGRFTISRDNAKNTLYLQMSSLRAEDTAVYYCNVFEY

WGQGTLVTVKPGGSGGSEVQLLESGGGEVQLLESGGGEVQPGGSLRLSCA

ASGWAFGNYGMAWFRQAPGKEREFVSRLAWSGGSTDYVESVKGRFTISRD

NAKNTLYLQMSSLRAEDTAVYYCARQRSYSRYDIRTPQTYDYWGQGTLVT

VKPGGGGDKTHTCPPCPAPGGPSVFLFPPKPKDTLMISRTPEVTCVVVDV

SHEDPEVKFNWYVDGVEVHNAKTKPREEQYNSTYRVVSVLTVLHQDWLNG

KEYKCKVSNKALPAPIEKTISKAKGQPREPQVYTLPPSRDELTKNQVSLT

CLVKGFYPSDIAVEWESNGQPENNYKTTPPVLDSDGSFFLYSKLTVDKSR

WQQGNVFSCSVMHEALHNHYTQKSLSLSPGK

Bispecific PDL1 x 41BB: hz28A2v5 x hz4E01v23
(SEQ ID NO: 456)
EVQLLESGGGEVQPGGSLRLSCAASGGIFAIKPISWYRQAPGKQREWVST

TTSSGATNYAESVKGRFTISRDNAKNTLYLQMSSLRAEDTAVYYCNVFEY

WGQGTLVTVKPGGSGGSEVQLLESGGGEVQLLESGGGEVQPGGSLRLSCA

ASGWAFSNYGMAWFRQAPGKEREFVSRLAWSGGSTDYVESVKGRFTISRD

NAKNTLYLQMSSLRAEDTAVYYCARQRSYSRYDIRTPQTYDYWGQGTLVT

VKPGGGGDKTHTCPPCPAPGGPSVFLFPPKPKDTLMISRTPEVTCVVVDV

SHEDPEVKFNWYVDGVEVHNAKTKPREEQYNSTYRVVSVLTVLHQDWLNG

KEYKCKVSNKALPAPIEKTISKAKGQPREPQVYTLPPSRDELTKNQVSLT

CLVKGFYPSDIAVEWESNGQPENNYKTTPPVLDSDGSFFLYSKLTVDKSR

WQQGNVFSCSVMHEALHNHYTQKSLSLSPGK

Folate Receptor Alpha (FRα) Targeting

In some embodiments, the fusion proteins are multispecific containing a TBD and a binding domain directed toward Folate Receptor Alpha (FRα). In these, embodiments, the binding to FRα is capable of providing the additional crosslinking function and TNFRSF activation can be achieved with only one or two TBDs. In these embodiments, the TNFRSF signaling is enhanced and focused by the presence of a FRα expressing cell.

Exemplary FRα-targeting single domain sequences are shown below:

```
Fra-5:
                                              (SEQ ID NO: 409)
QLQLQESGGGLVQAGGSLRLSCAASGIMFYISDMGWYRQAPGKQREFVATITSGGTTNYADSVE

GRFSISRDNAKNTVYLQMNSLEPEDTAVYYCTAHGPTYGSTWDDLWGQGTQVTVKPGG (SEQ ID NO: 410)
CDR1: GIMFYISD (SEQ ID NO: 411)
CDR2: TITSGGTTNY (SEQ ID NO: 412)
CDR3: TAHGPTYGSTWDDL

Fra-6:
                                              (SEQ ID NO: 413)
QLQLQESGGGLVQAGGSLRLSCAASETFGVVFTLGWYRQTPGKQREFVARVTGTDTVDYADSVK

GRFTISSDFARNTVYLQMNNLKPEDTAVYYCNTGAYWGQGTQVTVKPGG (SEQ ID NO: 414)
CDR1: TFGVVFT (SEQ ID NO: 415)
CDR2: VTGTDTV (SEQ ID NO: 416)
CDR3: NTGAY

Fra-57:
                                              (SEQ ID NO: 417)
QVQLVQSGGGLVQTGGSLRLSCAASGRTASTYSMGWFRQAPGKERQFVARIIWSTGSTYYTNSV

EGRFTISRDIAKNTLYLQMNSLEPEDTAVYYCTAREPTGYDYWGQGTQVTVKPGG (SEQ ID NO: 418)
CDR1: GRTASTYS (SEQ ID NO: 419)
CDR2: IWSTGST (SEQ ID NO: 420)
CDR3: TAREPTGYDY
```

-continued

1A3:
(SEQ ID NO: 421)
QLQLQESGGGLVQAGGSLGLSCAAS GSIFRFGA RGWYRQAPGKQRELVAI ITSGGST NYADSVQ

GRFTISRDNAKNMVYLQMNGLKSGDTAVYYC AADRSDAVGVGWDY WGQGTQVTVKPGG (SEQ ID NO: 422)
CDR1: GSIFRFGA (SEQ ID NO: 423)
CDR2: ITSGGST (SEQ ID NO: 424)
CDR3: AADRSDAVGVGWDY

1F3:
(SEQ ID NO: 425)
QVQLQQSGGGLVQTGGSLRLSCAAS GRTASTYS MGWFRQAPGKERQFVAR IIWSTGST YYTNSV

EGRFTISRDIAKNTLYLQMNSLEPEDTAVYYC TARDPTGYDY WGQGTQVTVKPGG (SEQ ID NO: 418)
CDR1: GRTASTYS (SEQ ID NO: 426)
CDR2: IIWSTGST (SEQ ID NO: 427)
CDR3: TARDPTGYDY

1G10:
(SEQ ID NO: 428)
QLQLQESGGGLVQAGGSLGLSCAAS GSIFSIDA TAWYRQAPGKQRELVAI ITSSGST NYPDSVK

GRFTISRDNAKNTVYLQMNSLNPEDTALYSC NAITRMGGSTYDF WGQGTQVTVKPGG (SEQ ID NO: 429)
CDR1: GSIFSIDA (SEQ ID NO: 430)
CDR2: ITSSGST (SEQ ID NO: 431)
CDR3: NAITRMGGSTYDF

The disclosure will be further described in the following examples, which do not limit the scope of the disclosure described in the claims.

EXAMPLES

Example 1. 41BB-Targeting Single Domain Antibodies Bind 41BB

Figure 1:
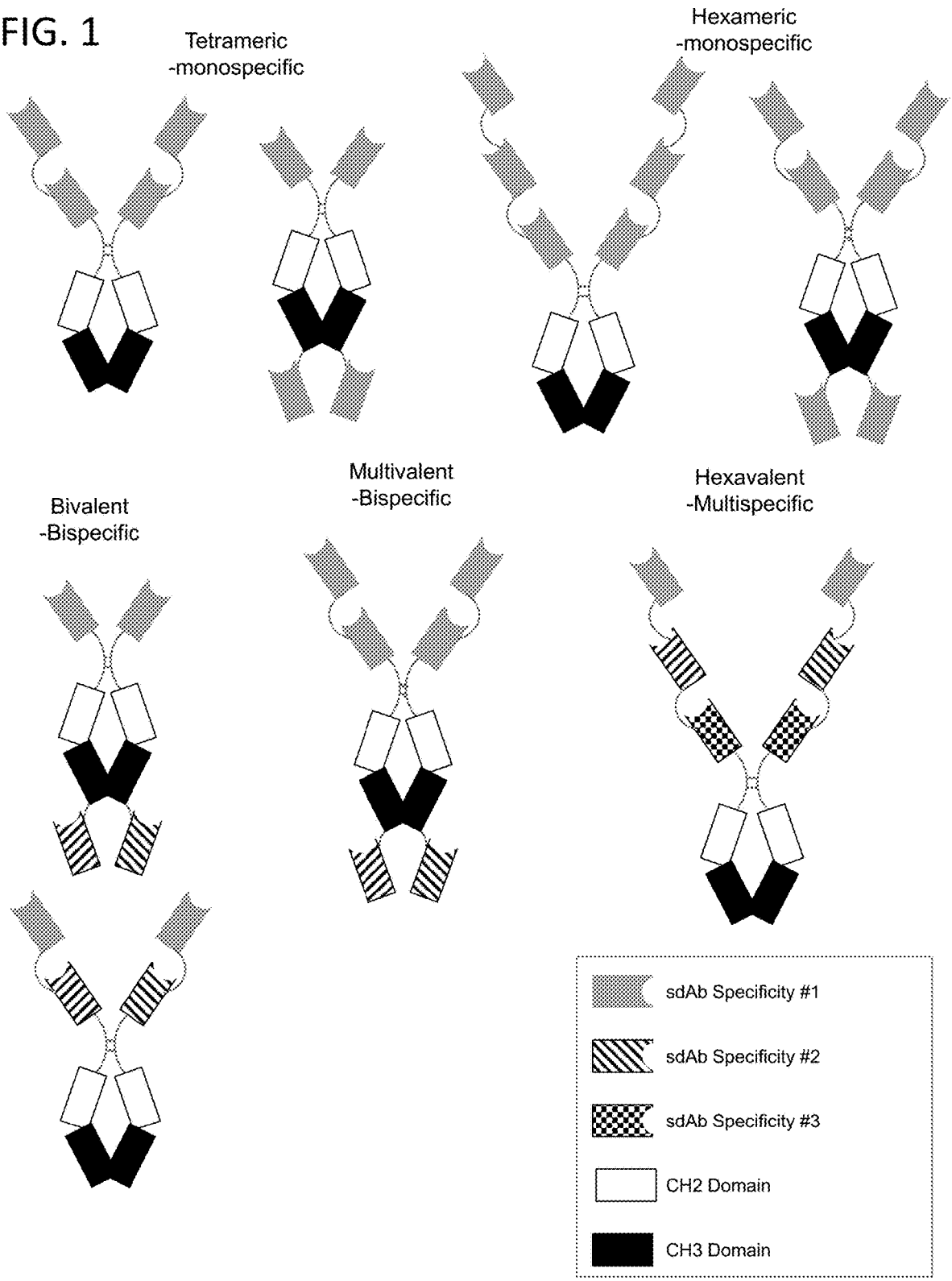
FIG. 1 is schematic of exemplary multivalent and multi-specific fusion proteins of the present disclosure.
Figure 2A:
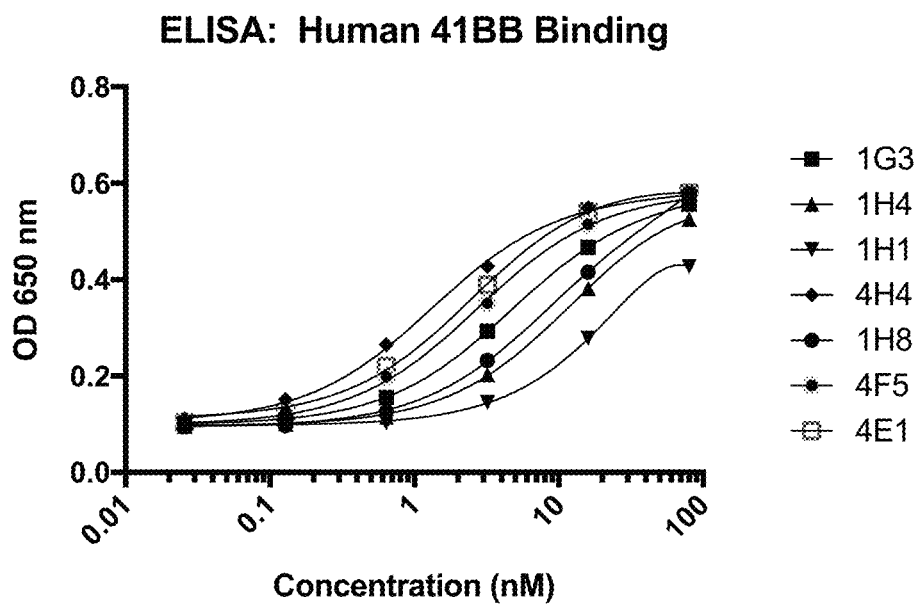
FIGS. 2A and 2B are a pair of graphs demonstrating the ability of 41BB single domain antibodies (sdAbs) to bind recombinant human 41BB (FIG. 2A) or cyno 41BB (FIG. 2B). Binding was assessed by ELISA wherein recombinant 41BB-mFc protein was immobilized on a Medisorp 96 well plate.
Figure 2B:
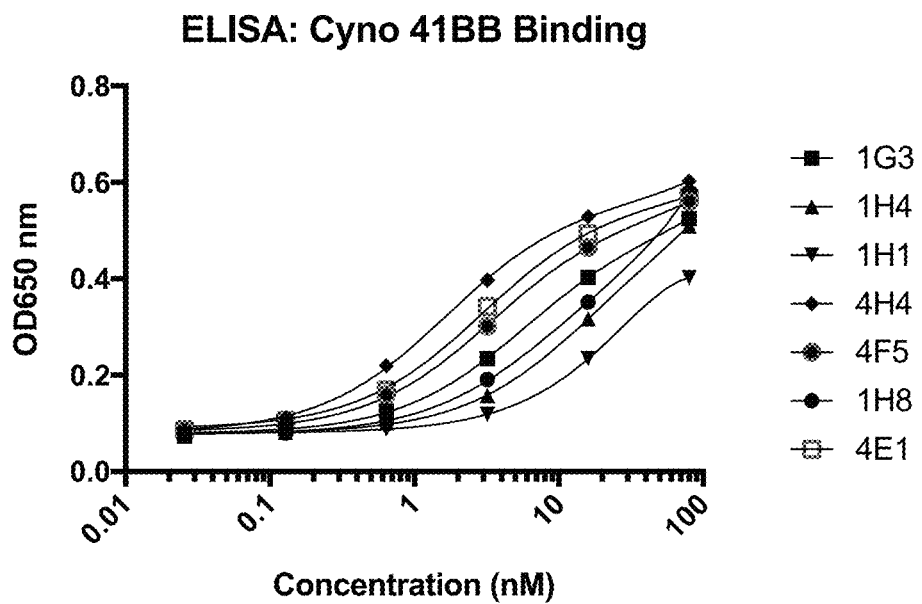
Figure 3:
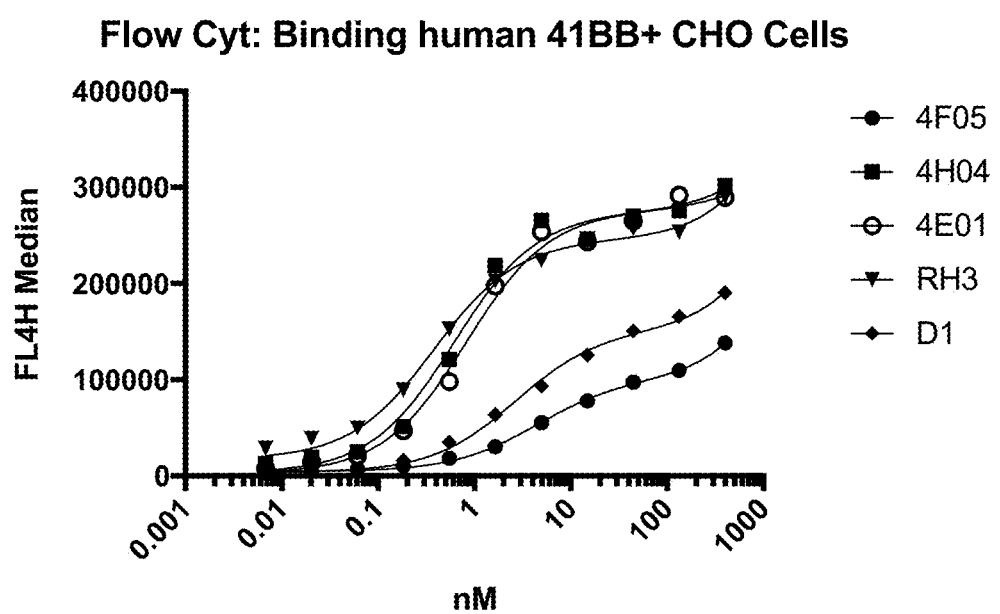
FIG. 3 is a graph demonstrating the ability of 41BB single domain antibodies (sdAbs) to bind cell surface 41BB. Binding was assessed by flow cytometry using 41BB expressing CHO cells and data is presented as median fluorescence intensity.
Figure 4:
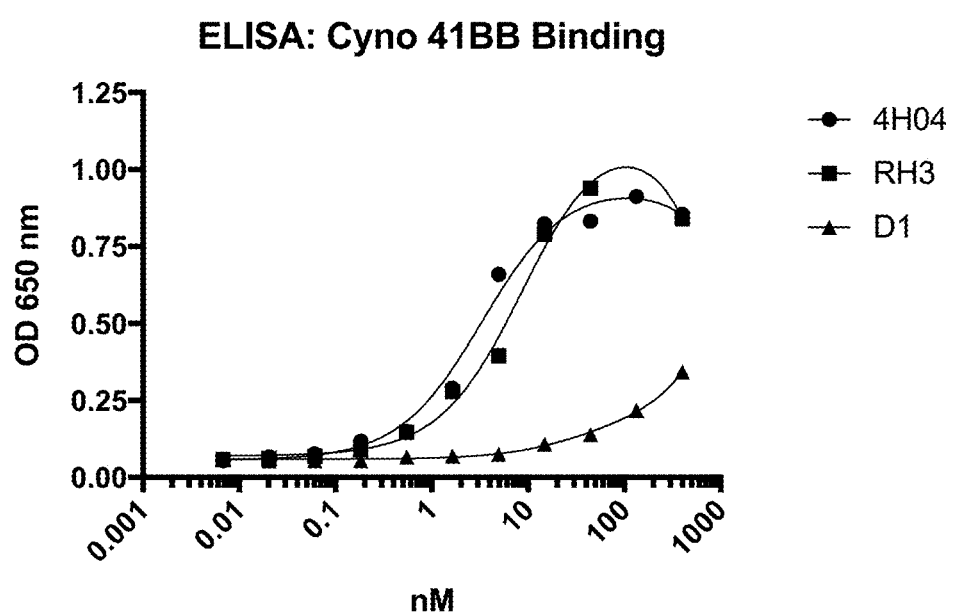
FIG. 4 is a graph demonstrating the ability of 41BB single domain antibodies, RH3 and 4H04 to bind cynomolgus monkey 41BB. Binding was assessed by ELISA wherein recombinant 41BB-mFc protein was immobilized on a Medisorp 96 well plate.
Figure 5:
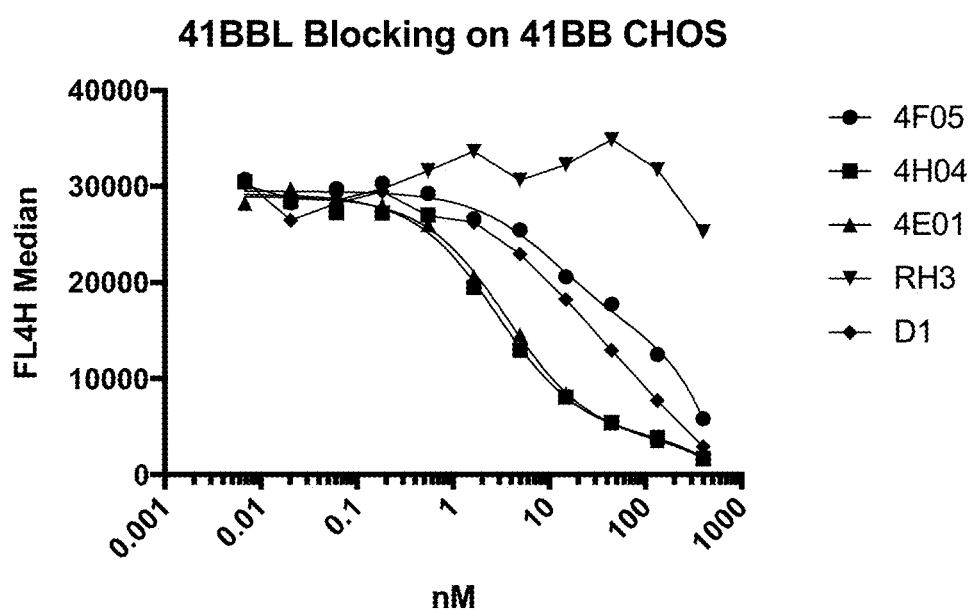
FIG. 5 is a graph demonstrating the capacity of 41BB single domain antibodies (VHHs) to block the interaction between 41BB and 41BBL. All single domain antibodies tested, with the exception of RH3 blocks the interaction between 41BB and 41BBL. Blocking was assessed by flow cytometry using a recombinant 41BB fusion protein and 41BB expressing CHO cells, data is presented as median fluorescence intensity.

The 41BB-targeting single domain antibodies (sdAbs) referred to herein as 1G3 (SEQ ID NO: 432), 1H4 (SEQ ID NO: 436), 1H1 (SEQ ID NO: 440), 4H4 (SEQ ID NO: 16), 1H8 (SEQ ID NO: 444), 4F5 (SEQ ID NO: 23), and 4E1 (SEQ ID NO: 20) bind recombinant human 41BB (FIG. 2A), cynomolgus 41BB (FIG. 2B). The 41BB-targeting single domain antibodies (sdAbs) referred to herein as 4F5 (SEQ ID NO: 23), 4H04 (SEQ ID NO: 16), 4E01 (SEQ ID NO: 20), RH03 (SEQ ID NO: 25), and D1 (SEQ ID NO: 29) bind human 41BB expressed on the cell surface of CHO cells (FIG. 3). The 41BB-targeting sdAbs referred to herein as 4H04, RH03, and bind cynomolgus 41BB. For FIG. 2A, FIG. 2B, and FIG. 4, binding was assessed by ELISA wherein recombinant 41BB-mFc fusion protein (a fusion protein containing 41BB operably linked to a mouse Fc region) was immobilized on a Medisorp 96 well plate. For FIG. 3, binding was assessed by flow cytometry using 41BB expressing CHO cells, and the data is presented as median fluorescence intensity.

Example 2. 41BB-Targeting Single Domain Antibodies Block 41BB

The 41BB-targeting single domain antibodies (sdAbs) referred to herein as 4F05 (SEQ ID NO: 23), 4H04 (SEQ ID NO: 16), 4E01 (SEQ ID NO: 20), RH03 (SEQ ID NO: 25), and D1 (SEQ ID NO: 29) block the interaction between 41BB and its ligand 41BBL. All single domain antibodies tested, with the exception of RH3 blocks the interaction between 41BB and 41BBL. Blocking was assessed by flow cytometry using a recombinant 41BB fusion protein and 41BB expressing CHO cells, data is presented as median fluorescence intensity.

Figure 6:
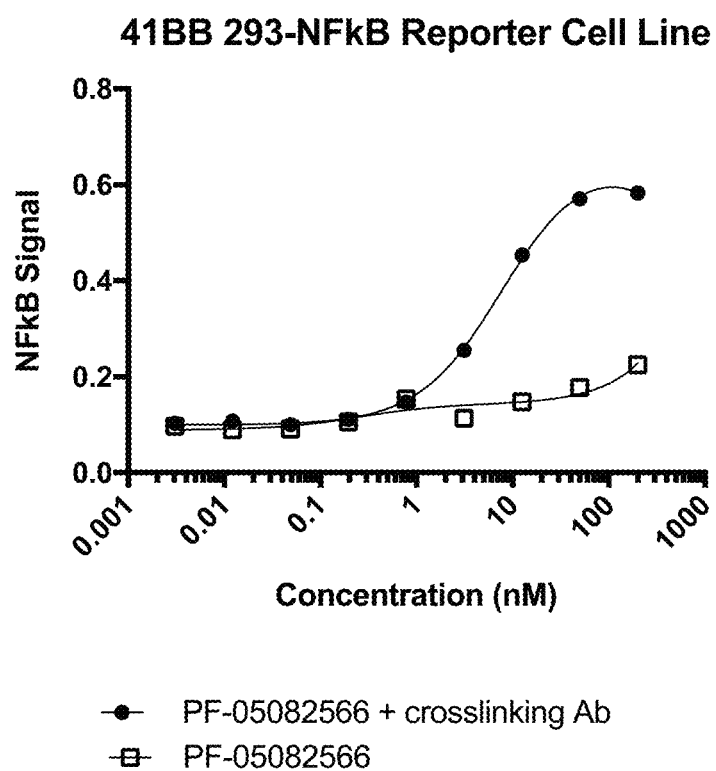
FIG. 6 is a graph demonstrating the inability of a conventional bivalent anti-41BB antibody PF-05082566 to induce 41BB signaling unless further clustered with an exogenous crosslinking anti-human IgG antibody. 41BB signaling was monitored using a NF-kB reporter 293 cell line expressing 41BB.

In contrast to the 41BB sdAbs of the disclosure, conventional bivalent anti-41BB antibodies do not induce 41BB signaling unless further clustered with an exogenous cross-linking anti-human IgG antibody. FIG. 6 demonstrates the inability of a conventional bivalent anti-41BB antibody PF-05082566, which is disclosed in U.S. Pat. No. 8,337,850, to induce 41BB signaling unless further clustered with an exogenous crosslinking anti-human IgG antibody. In FIG. 6, 41BB signaling was monitored using a NF-kB reporter 293 cell line expressing 41BB.

Example 3. PDL1-Targeting Single Domain Antibodies Bind PDL1 and Block the Interaction Between PLD1 and PD1

Figure 7A:
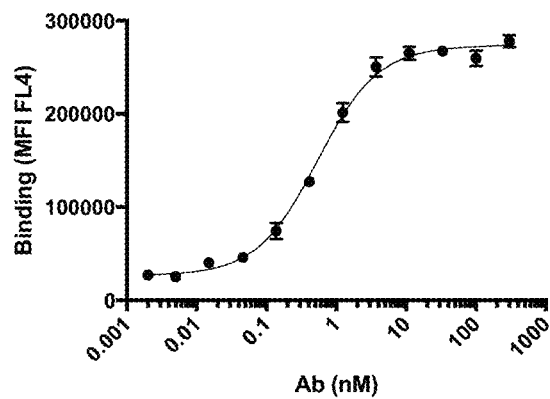
FIGS. 7A and 7B are a pair of graphs demonstrating the capacity of an exemplary PDL1 single domain antibody (28A10) to bind cell surface PDL1 and to block the interaction with PD1. Binding (FIG. 7A) was assessed by flow cytometry on PDL1 expressing CHO cells. Blocking (FIG. 7B) was assessed by flow cytometry using a recombinant PD1 fusion protein and PDL1 expressing CHO cells, data is presented as median fluorescence intensity.
Figure 7B:
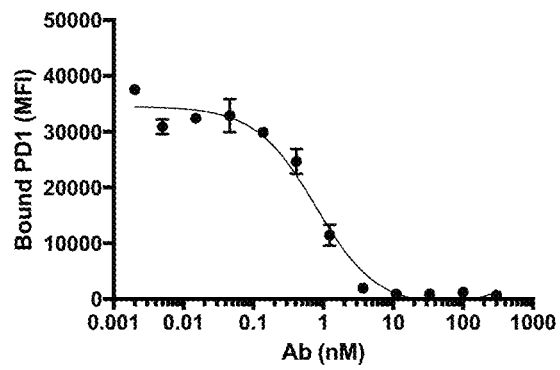

The studies presented herein use an exemplary PDL1 single domain antibody (sdAb), referred to herein as 28A10 (SEQ ID NO: 100) to demonstrate that the PDL1-targeting sdAbs of the disclosure bind cell surface PDL1 (FIG. 7A) and block the interaction of PDL1 with PD1 (FIG. 7B). Binding was assessed by flow cytometry on PDL1 expressing CHO cells, and blocking was assessed by flow cytometry using a recombinant PD1 fusion protein and PDL1 expressing CHO cells. The data presented in FIGS. 7A and 7B are presented as median fluorescence intensity.

Example 4. PDL1-41BB Targeting Fusion Proteins

Figure 8A:
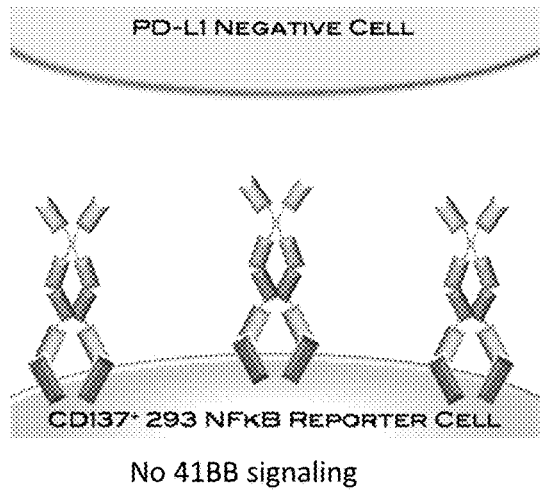
FIGS. 8A, 8B, and 8C are a series of illustrations and a graph depicting PDL1-dependent 41BB agonism mediated by bispecific PDL1-41BB targeting fusion proteins of the present disclosure.
Figure 8B:
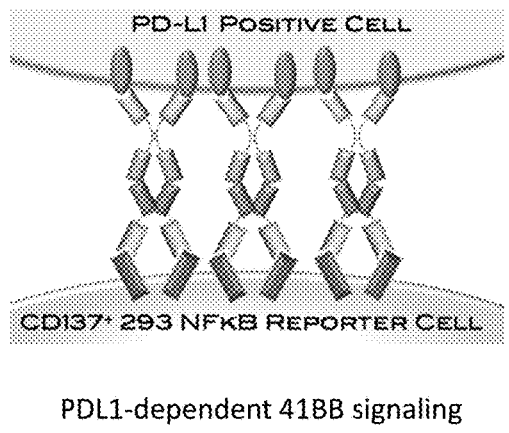
Figure 8C:
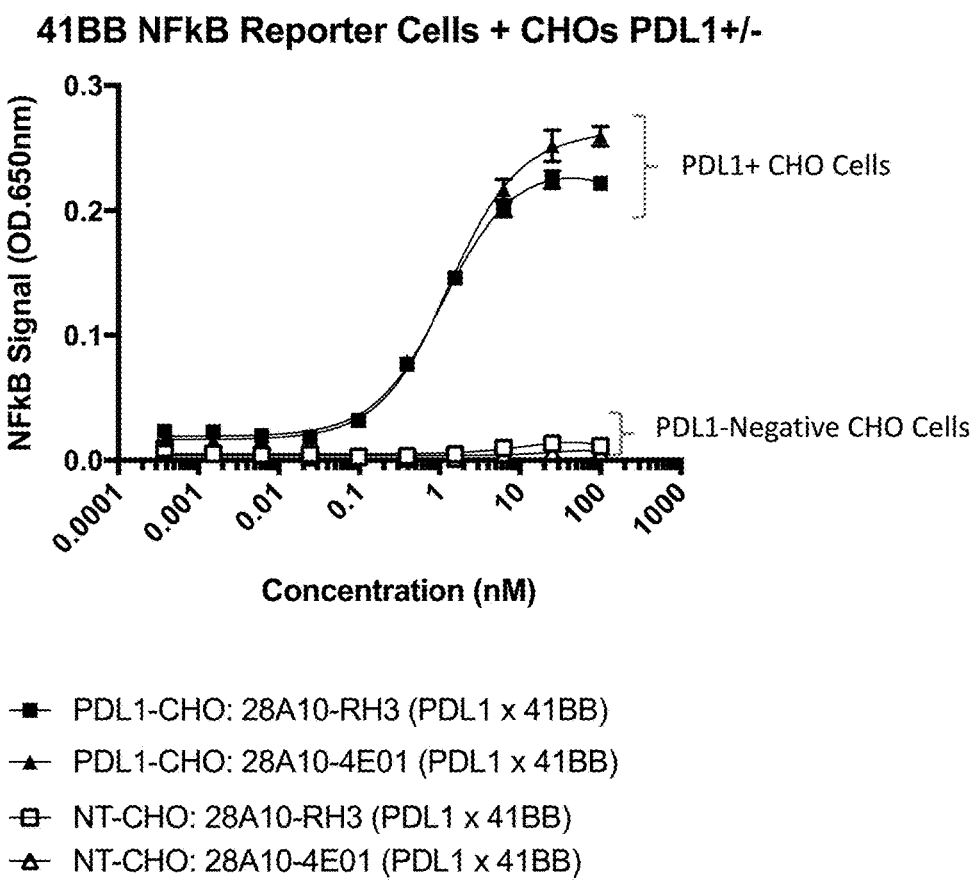

The disclosure provides fusion proteins that target at least PDL1 and 41BB. These bispecific PDL1-41BB targeting fusion proteins are agonists of PDL1-dependent 41BB mediated signaling. FIGS. 8A and 8B are conceptual schematics wherein the bispecific fusion proteins have minimal 41BB agonistic properties (FIG. 8A) unless bound by a PD-L1 expressing cell (FIG. 8B). FIG. 8C demonstrates the ability of a PDL1-positive cell, in this case, a population of PDL1 transfected CHO cells, to mediate 41BB signaling and the inability of PDL1-negative cell, in this case, a population of untransfected CHO cells, to mediate 41BB signaling. Two distinct bispecific fusion proteins are shown in this figure, each containing a distinct 41BB binding VHH (e.g., 4E01 or RH3) and the same PD-L1 VHH, 28A10. 41BB signaling was monitored using a NF-kB reporter 293 cell line expressing 41BB. This reporter cell line implements an NF-kB driven secreted alkaline phosphatase, to monitor NF-kB signaling.

Figure 9A:
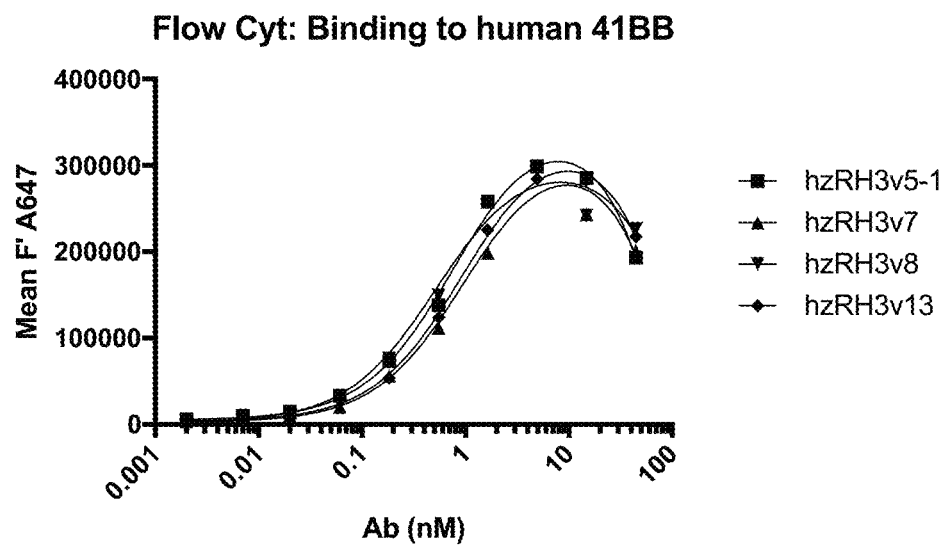
FIGS. 9A, 9B, 9C, 9D, and 9E are a series of graphs demonstrating the binding to human (FIG. 9A and FIG. 9C) or cynomolgus monkey (FIG. 9B and FIG. 9D) 41BB of humanized RH3 variants. Binding was assessed by flow cytometry on 41BB expressing 293freestyle cells.
Figure 9B:
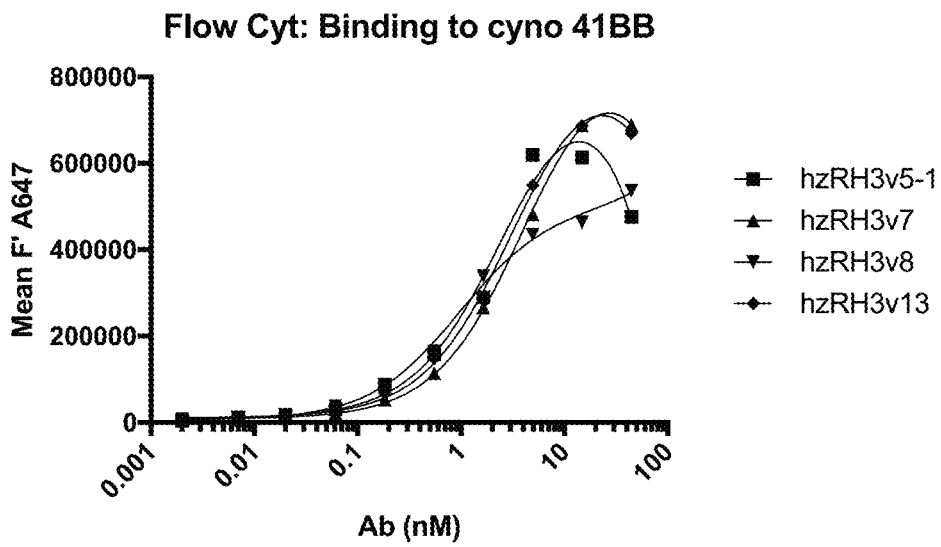
Figure 9C:
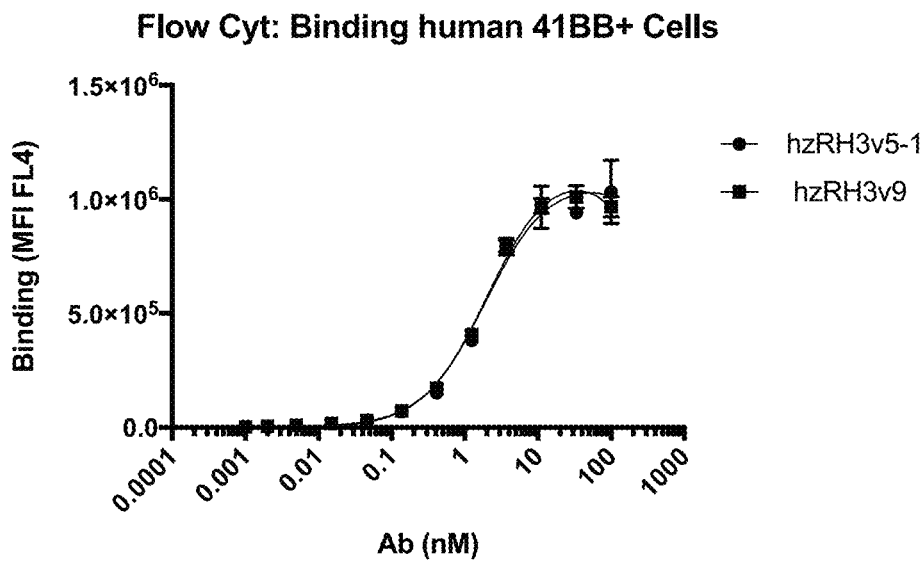
Figure 9D:
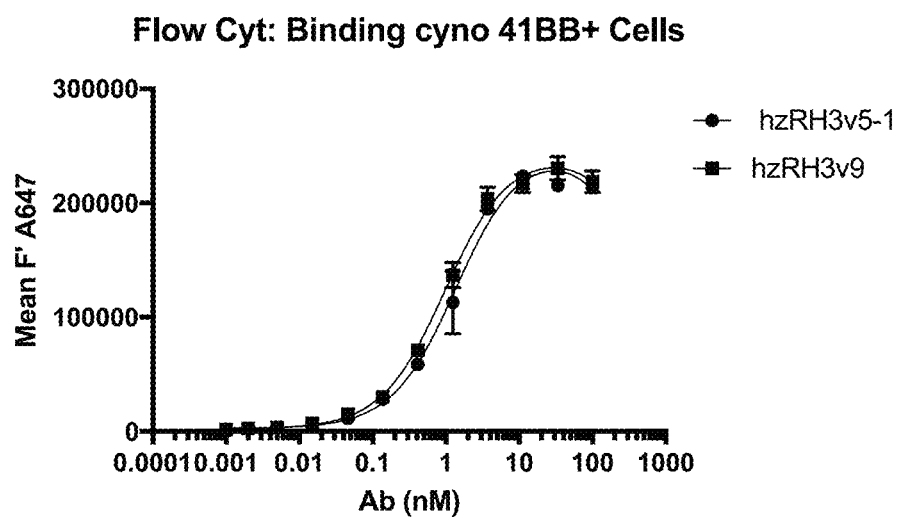

The PDL1-41BB targeting fusion proteins of the disclosure include a humanized anti-41BB sequence. In the studies presented herein, the PDL1-41BB targeting fusion proteins of the disclosure include a humanized anti-41BB sequence such as hzRH3v5-1 (SEQ ID NO: 30) and/or hzRH3v9 (SEQ ID NO: 82) bind both human and cynomolgus 41BB (FIGS. 9A, 9B), including human 41BB and cynomolgus 41BB expressed on the surface of CHO cells (FIGS. 9C, 9D). Binding was assessed by flow cytometry on 41BB expressing 293freestyle cells.

Figure 9E:
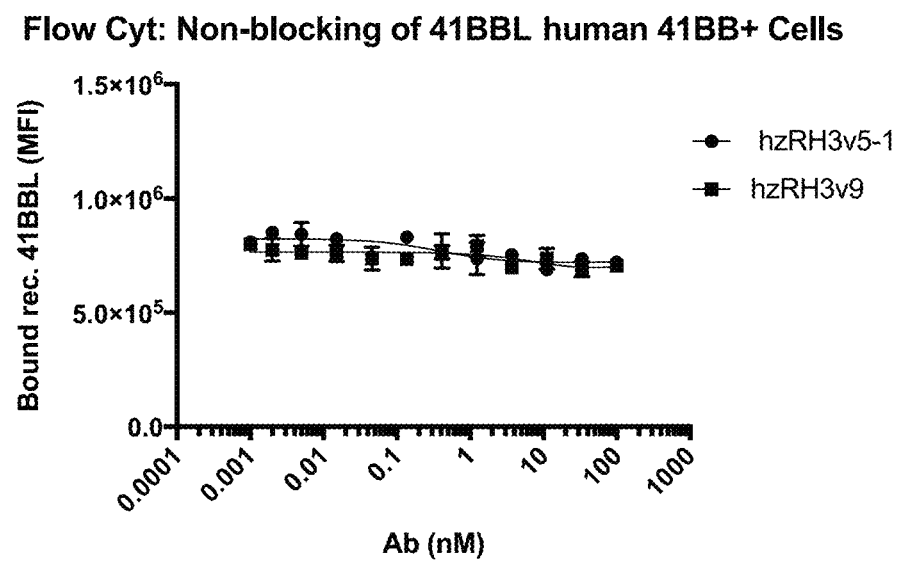
Figure 10:
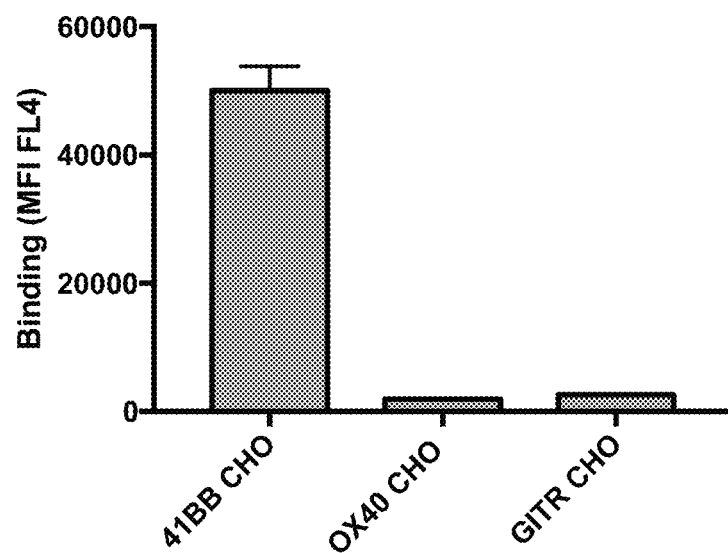
FIG. 10 is a graph demonstrating the specific binding of hzRH3v5-1 (40 nM) to 41BB compared to other TNFRSF members OX40 and GITR. Binding was assessed by flow cytometry using CHO cells expressing the given TNFRSF member.

The humanized variants hzRH3v5-1 and hzRH3v9 do not block binding of 41BBL to cell surface 41BB as shown in FIG. 9E. In these studies, a recombinant fusion protein 41BBL-mFc, containing a mouse Fc region, was used, and bound 41BBL was detected The humanized variant hzRH3v5-1 specifically binds 41BB as compared to the other TNFRSF members OX40 and GITR (FIG. 10). Binding was assessed by flow cytometry using CHO cells expressing the given TNFRSF member.

Figure 11A:
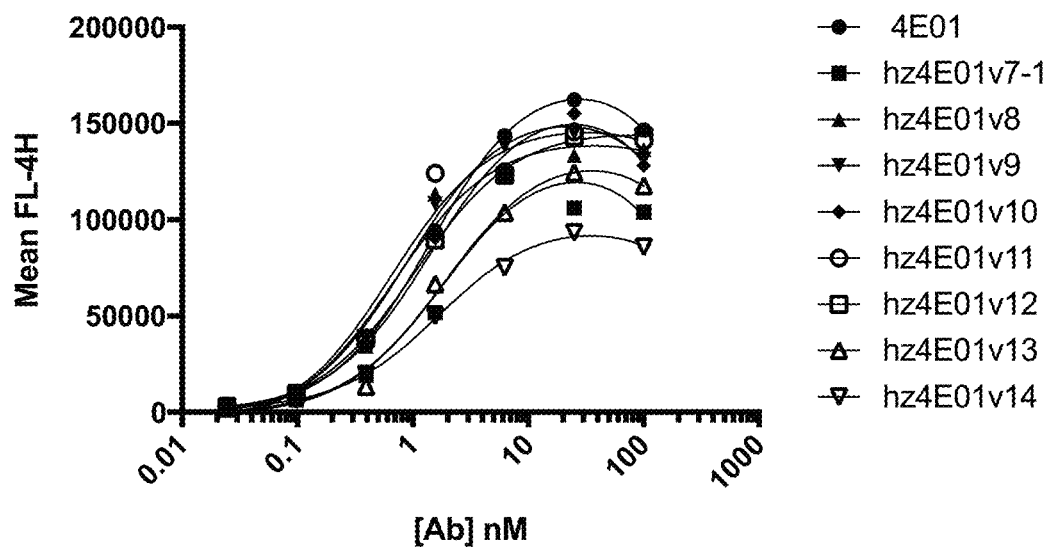
FIGS. 11A, 11B, 11C, and 11D are a series of graphs demonstrating the binding to human (FIG. 11A and FIG. 11C) or cynomolgus monkey (FIG. 11B) 41BB of humanized 4E01 variants. Binding was assessed by flow cytometry on 41BB expressing 293freestyle cells.
Figure 11B:
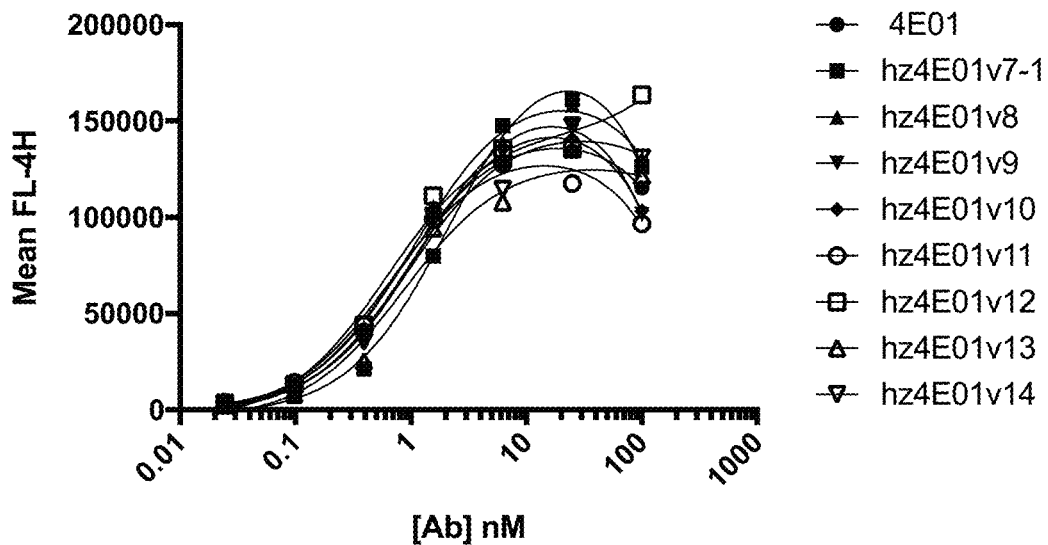
Figure 11C:
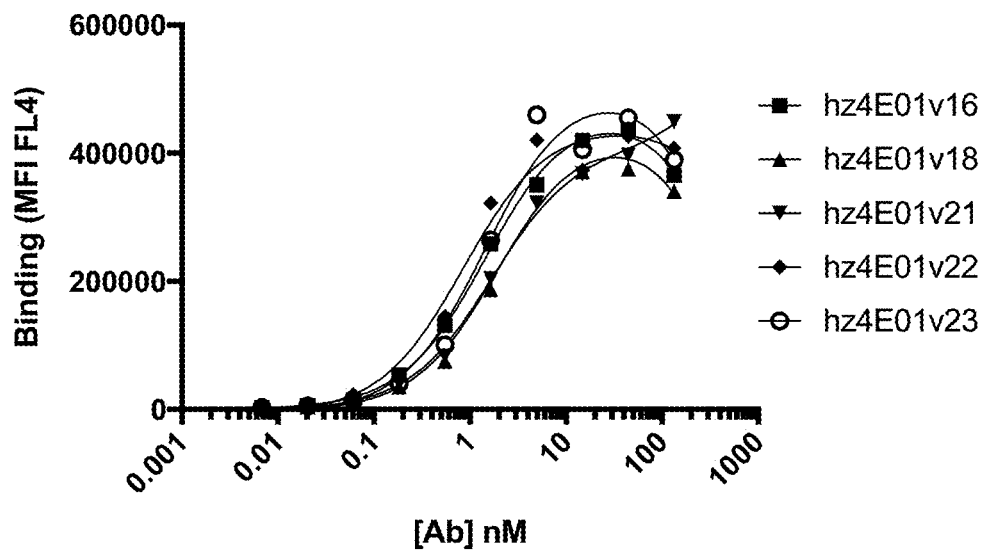
Figure 11D:
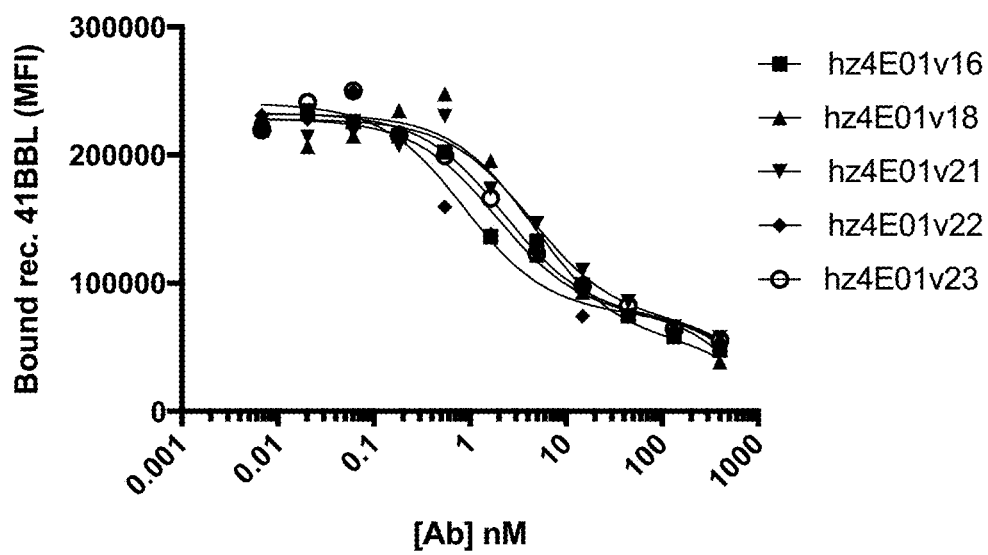

Additional humanized 41BB variants were analyzed. FIGS. 11A, 11B, 11C, and 11D demonstrate the binding to human (FIG. 11A and FIG. 11C) or cynomolgus monkey (FIG. 11B) 41BB of the humanized 4E01 variants. Binding was assessed by flow cytometry on 41BB expressing 293freestyle cells. FIG. 11D demonstrates that the humanized variants hz4E01v16, hz4E01v18, hz4E01v21, hz4E01v22 and hz4E01v23 block binding of 41BBL to cell surface 41BB. In these studies, a recombinant fusion protein 41BBL-mFc, containing a mouse Fc region was used and bound 41BBL was detected using an anti-mouse IgG-Fc specific secondary antibody.

Figure 12:
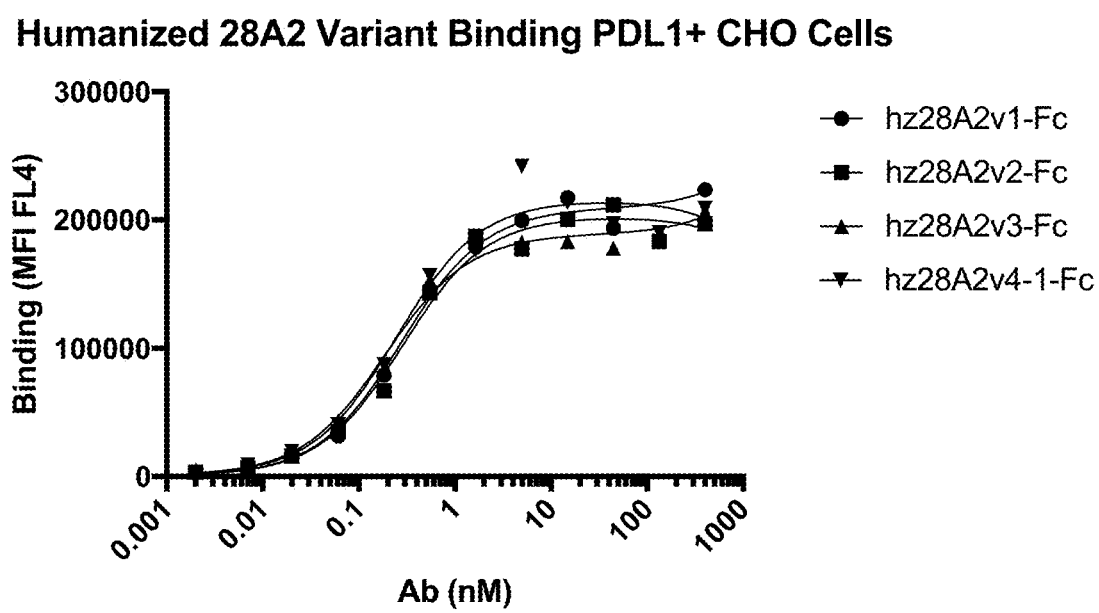
FIG. 12 is a graph demonstrating binding of humanized single domain antibodies targeting PDL1. Binding was assessed by flow cytometry on PDL1-expressing CHO cells.

The PDL1-41BB targeting fusion proteins of the disclosure also include a humanized anti-PDL1 sequence. In the studies presented herein, the PDL1-41BB targeting fusion proteins of the disclosure include a humanized anti-PDL1 sequence such as hz28A2v1 (SEQ ID NO: 120), hz28A2v2 (SEQ ID NO: 121), hz28A2v3 (SEQ ID NO: 122), and hz28A2v4-1 (SEQ ID NO: 123). FIG. 12 demonstrates binding of humanized single domain antibodies targeting PDL1. Binding was assessed by flow cytometry on PDL1-expressing CHO cells.

Figure 13:
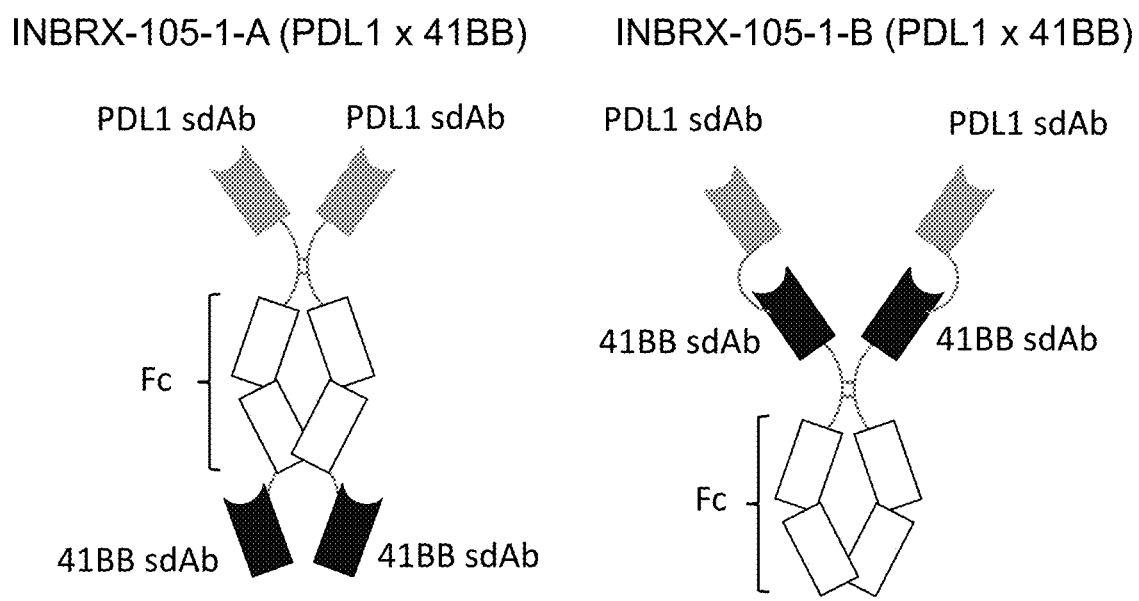
FIG. 13 is a schematic of two exemplary formats of a PDL1×41BB bispecific, INBRX-105-1. INBRX-105-1-A (left) has the PDL1 and 41BB binding domains, located at opposing terminal positions with a central Fc region, whereas INBRX-105-1-B (right) has the PDL1 and 41BB binding domains positioned in tandem, N-terminal to an Fc region.

FIG. 13 is a schematic of two exemplary formats of a PDL1×41BB bispecific fusion protein of the disclosure, referred to herein as INBRX-105-1. INBRX-105-1-A (left) has the PDL1 and 41BB binding domains located at opposing terminal positions with a central Fc region, whereas INBRX-105-1-B (right) has the PDL1 and 41BB binding domains positioned in tandem, N-terminal to an Fc region.

These two formats were further evaluated for their ability to bind human or cynomolgus monkey 41BB, to block the interaction between 41BB and 41BBL, to bind PDL1, and to block the interaction between PDL1 and PD1.

Figure 14A:
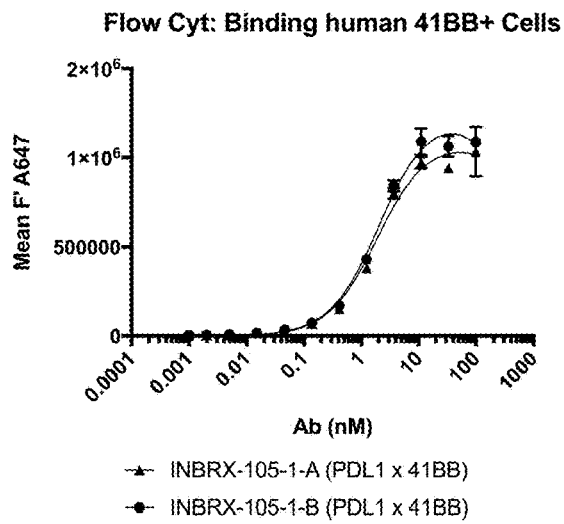
FIGS. 14A, 14B, and 14C are a series of graphs demonstrating the equivalent binding to human (FIG. 14A) or cynomolgus monkey (FIG. 14B) 41BB by the two distinct formats of a bispecific fusion protein targeting PDL1 and 41BB referred to herein as INBRX-105-1-A and INBRX-105-1-B. Binding was assessed by flow cytometry on 41BB expressing 293freestyle cells.
Figure 14B:
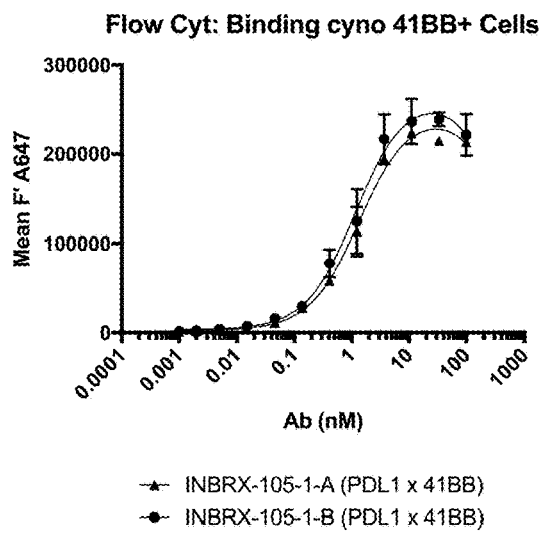
Figure 14C:
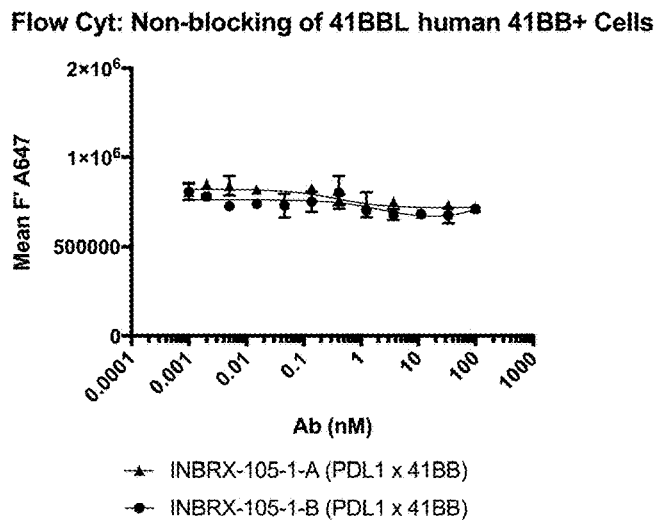

In particular, FIGS. 14A, 14B, and 14C demonstrate the equivalent binding to human (FIG. 14A) or cynomolgus monkey (FIG. 14B) 41BB by the two distinct formats of a bispecific fusion protein targeting PDL1 and 41BB referred to herein as INBRX-105-1-A and INBRX-105-1-B and illustrated in FIG. 13. Binding was assessed by flow cytometry on 41BB expressing 293freestyle cells. In the studies presented herein, hzRH3v5-1 (SEQ ID NO: 124) is the 41BB binding domain used in both formats. As shown in FIG. 14C, the bispecific fusion protein containing hzRh3v5-1 does not block 41BBL binding to cell surface 41BB. In these studies, a recombinant fusion protein of 41BBL and a mouse Fc region was used, and bound 41BBL was detected using an anti-mouse IgG-Fc specific secondary antibody.

Furthermore, FIGS. 15A, 15B, 15C, and 15D demonstrate the equivalent binding (FIG. 15A and FIG. 15C) and PD1 blocking (FIG. 15B and FIG. 15D) by the two distinct formats of a bispecific fusion protein targeting PDL1 and 41BB referred to herein as INBRX-105-1-A and INBRX-105-1-B. Binding was assessed by flow cytometry on human (FIG. 15A) or cynomolgus monkey (FIG. 15C) PDL1 expressing 293freestyle cells. Blocking was assessed by flow cytometry using on human (FIG. 15B) or cynomolgus monkey (FIG. 15D) PDL1 expressing 293freestyle cells with either recombinant human (FIG. 15B) or cynomolgus monkey (FIG. 15D) PD1-mFc fusion protein. Bound PD1 was detected using an anti-mouse IgG-Fc specific secondary antibody. In the studies presented herein, hz28A2v5 is the PDL1-binding domain used in both formats.

The PDL1×41BB bispecific fusion proteins were evaluated for their ability to induce PDL1-dependent 41BB agonism. FIG. 16 demonstrates the ability of humanized versions of a PDL1×41BB bispecific fusion protein (INBRX-105-1) to induce PDL1-dependent 41BB agonism. Compared herein are two distinct formats, INBRX-105-1-A vs INBRX-105-1-B, having the PDL1 and 41BB binding domains positioned at opposite termini or in tandem within the fusion protein, respectively. Notably, INBRX-105-1-A vs INBRX-105-1-B demonstrate equivalent PDL1-dependent agonistic activities. A 41BB-expressing HEK293 NF-kB reporter cell line was used to assess 41BB signaling and a PDL1-expressing CHO cell line was used as the source of PDL1. This reporter cell line implements an NF-kB driven secreted alkaline phosphatase, to monitor NF-kB signaling.

The ability of the 41BB-specific binding and the PDL1-specific binding by the binding domains in the PDL1×41BB bispecific fusion proteins was evaluated. FIGS. 17A and 17B demonstrate the 41BB-specific binding by the 41BB-binding portion of a PDL1×41BB bispecific fusion protein (INBRX-105-1) of the present disclosure. Binding was assessed on 41BB (FIG. 17A) or the closest homolog, TNFRSF21/DR6 (FIG. 17B), expressing 293freestyle cells by flow cytometry. An anti-DR6 antibody (Invitrogen) was used to as positive control for DR6 expression. In addition, FIGS. 18A, 18B, and 18C demonstrate the PDL1-specific binding by the PDL1-binding portion of a PDL1×41BB bispecific fusion protein (INBRX-105-1) of the present disclosure. Binding was assessed on PDL1 (FIG. 18A), the closest homologs PDL2 (FIG. 18B) or VISTA/PDL3 (FIG. 18C), expressing 293freestyle cells by flow cytometry. An anti-PDL2 antibody and an anti-VISTA antibody known as VSTB174, which is disclosed in PCT Publication No. WO 2015/097536, were used to as positive controls for PDL2 and PDL3 expression respectively.

The ability of the PDL1×41BB bispecific fusion proteins to simultaneously bind both 41BB and PDL1 was evaluated. FIGS. 19A and 19B demonstrate the ability of a PDL1×41BB bispecific fusion protein to simultaneously bind PDL1 and 41BB. INBRX-105-1 was titrated onto PDL1 expressing K562 cells and 25 nM recombinant 41BB-mFc proteins was added. Bound 41BB was detected using an anti-mouse IgG-Fc specific secondary antibody. FIG. 19A. is a graph showing the binding of INBRX-105-1 to the PDL1 expressing K562 cells. FIG. 19B is a graph showing the binding of recombinant 41BB to INBRX-105-1 on the PDL1 expressing cells.

FIG. 20 demonstrates the ability of a PDL1×41BB bispecific fusion protein to simultaneously bind recombinant PDL1 and recombinant 41BB in an ELISA. INBRX-105-1 was titrated on to immobilized (Medisorp plate) recombinant PDL1, subsequently either 2 or biotinylated-recombinant 41BB (His-tagged) was added. Bound recombinant 41BB was detected via streptavidin-HRP.

The effect of the PDL1×41BB bispecific fusion proteins to on T-cell activation and proliferation was evaluated. FIGS. 21A, 21B, and 21C demonstrate the effect of a PDL1×41BB bispecific fusion protein (INBRX-105-1) of the present disclosure on T-cell activation and proliferation. Herein an autologous in vitro co-culture system implementing immature DC (iDC) and donor matched T-cells was conducted for 7 days. PDL1$^+$ iDC were derived by enriching the monocyte population (EasySep™ Human Monocyte Enrichment Kit, STEMCELL Technologies Inc.) from human donor PBMCs and culturing them in 500 U/ml GM-CSF and 250 U/ml IL-4 for 7 days. Autologous T-cells were enriched at the same time (EasySep™ Human T-cell Enrichment Kit, STEMCELL Technologies Inc.) and cryopreserved until iDC derivation was complete. Enriched T-cells were added to iDC at approximately 20:1 (T-cell: iDC) and co-cultured for at least 7 days in the presence of IL-7. The PDL1×41BB bispecific, INBRX-105-1, is superior to the monospecific PDL1 sdAb-Fc fusion protein (hz28A2v5-Fc), the 41BB sdAb-Fc fusion protein (hzRH3v5-1-Fc), the combination of the hz28A2v5-Fc and hzRH3v5-1-Fc, the anti-PDL1 antibody Atezolizumab, the anti-41BB antibody, Utomilumab (PF-05082566, disclosed in U.S. Pat. No. 8,337,850), or the anti-PD1 antibody Prembrolizumab, and combinations thereof, at inducing INFγ (FIG. 21A) or mediating CD8$^+$ T-cell proliferation (FIG. 21B) and activation (FIG. 21C). INFγ production in the cell supernatant was monitored using an ELISA and normalized to the standard curve. T-cell proliferation was monitored by flow cytometry using CTV labeling of T-cells. T-cell activation was assessed by the presence of the activation marker CD25 monitored by flow cytometry. Antibodies were used at 10 nM. INBRX-105-1 seemingly augments low level and/or tonic T-cell activation/signaling events that is dampened by the PDL1:PD1 interaction.

FIGS. 22A and 22B demonstrate PDL1-dependent 41BB agonism mediated by a PDL1×41BB bispecific fusion protein (INBRX-105-1) of the present disclosure. In these studies, T-cells were cultured alone or with autologous immature DCs (iDC, PDL1-expressing), a PDL1-expressing K562 cell line or the parental K562 cell line (PDL1-negative) in the presence or absence of 10 nM INBRX-105-1 for 7 days. CD8$^+$ T-cell proliferation (FIG. 22A) was monitored using CTV labeling and INFγ production (FIG. 22B) in the cell supernatant was monitored using an ELISA and normalized to the standard curve.

FIG. 23 demonstrates the capacity of a PDL1×41BB bispecific fusion protein (INBRX-105-1) of the present disclosure to enhance the Th1 lineage defining transcription factor, T-bet, expression in T-cell populations. Herein T-cells were co-cultured with autologous immature DCs for 7 days in the presence or absence of INBRX-105-1. T-bet expression was assessed on CD4$^+$ and CD8$^+$ T-cell population by flow cytometry via intracellular staining following fixation and permeabilization. INBRX-105-1 has a more dramatic effect on T-bet expression in CD8$^+$ T-cells.

The PDL1×41BB bispecific fusion proteins of the disclosure were compared to various known monospecific antibodies. FIGS. 24A and 24B contrast the capacity of a PDL1×41BB bispecific fusion protein (INBRX-105-1) of the present disclosure and the combination of monospecific antibodies Atezolizumab (anti-PDL1) and Utomilumab (anti-41BB) to induce INFγ (FIG. 24A) or TNFα (FIG. 24B) production from CD4$^+$ or CD8$^+$ T-cells. Herein T-cells were co-cultured with autologous immature DCs for 7 days in the presence or absence of INBRX-105-1 or the combination of the monospecific antibodies. INBRX-105-1 is far superior at T-cell co-stimulation compared to monospecific antibodies targeting the same antigens. Cytokine expression was assessed on CD4$^+$ and CD8$^+$ T-cell population by flow cytometry via intracellular staining following fixation and permeabilization.

FIGS. 25A and 25B demonstrate the agonistic capacity of a tetravalent 41BB-binding fusion protein and PDL1×41BB bispecific fusion proteins of the present disclosure in the presence of an additional PDL1 positive (FIG. 25A) or negative (FIG. 25B) cell line. Notably only the tetravalent 41BB binding fusion protein is capable of inducing 41BB signaling in the absence of a PDL1 expressing cell line. The bispecific PDL1×41BB fusion proteins (INBRX-105-1, INBRX-105-2 and INBRX-105-16) only induced 41BB signaling when bound to cell surface PDL1 as shown in FIG. 25A. This demonstrates that bivalent engagement of 41BB, as is the case of INBRX-105, is insufficient to effectively cluster and mediate productive 41BB signaling. Engagement of a second cell surface antigen, PDL1 as in the present example, enables further clustering of 41BB and productive signaling. Herein a 41BB-expressing HEK293 NF-kB reporter cell was used and co-incubated with either the PDL1-negative K562 cell line (FIG. 25B) or a stably transfected, PDL1-expressing K562 cell line (FIG. 25A). INBRX-105-1 incorporates the 41BB-targeting sdAb: hzRH3v5-1, INBRX-105-2 incorporates the 41BB-targeting sdAb: hzRH3v5-2 and INBRX-105-16 incorporates the 41BB-targeting sdAb: hzRH3v5-16 and all incorporate the hz28A2v5 PDL1-targeting sdAb. The tetravalent 41BB-targeting fusion protein used herein has the following format comprising hzRH3v5-1-Fc-hzRH3v5-1.

```
                          SEQUENCE LISTING

Sequence total quantity: 456
SEQ ID NO: 1           moltype = AA  length = 218
FEATURE                Location/Qualifiers
REGION                 1..218
                       note = chemically synthesized
source                 1..218
                       mol_type = protein
                       organism = synthetic construct
SEQUENCE: 1
PAPELLGGPS VFLFPPKPKD TLMISRTPEV TCVVVDVSHE DPEVKFNWYV DGVEVHNAKT    60
KPREEQYNST YRVVSVLTVL HQDWLNGKEY KCKVSNKALP APIEKTISKA KGQPREPQVY   120
TLPPSRDELT KNQVSLTCLV KGFYPSDIAV EWESNGQPEN NYKTTPPVLD SDGSFFLYSK   180
LTVDKSRWQQ GNVFSCSVMH EALHNHYTQK SLSLSPGK                           218

SEQ ID NO: 2           moltype = AA  length = 215
FEATURE                Location/Qualifiers
REGION                 1..215
                       note = chemically synthesized
source                 1..215
                       mol_type = protein
                       organism = synthetic construct
SEQUENCE: 2
PAPGGPSVFL FPPKPKDTLM ISRTPEVTCV VVDVSHEDPE VKFNWYVDGV EVHNAKTKPR    60
EEQYNSTYRV VSVLTVLHQD WLNGKEYKCK VSNKALPAPI EKTISKAKGQ PREPQVYTLP   120
PSRDELTKNQ VSLTCLVKGF YPSDIAVEWE SNGQPENNYK TTPPVLDSDG SFFLYSKLTV   180
DKSRWQQGNV FSCSVMHEAL HNHYTQKSLS LSPGK                              215

SEQ ID NO: 3           moltype = AA  length = 217
FEATURE                Location/Qualifiers
REGION                 1..217
                       note = chemically synthesized
source                 1..217
                       mol_type = protein
                       organism = synthetic construct
SEQUENCE: 3
PAPPVAGPSV FLFPPKPKDT LMISRTPEVT CVVVDVSHED PEVQFNWYVD GVEVHNAKTK    60
PREEQFNSTF RVVSVLTVVH QDWLNGKEYK CKVSNKGLPA PIEKTISKTK GQPREPQVYT   120
LPPSREEMTK NQVSLTCLVK GFYPSDISVE WESNGQPENN YKTTPPMLDS DGSFFLYSKL   180
TVDKSRWQQG NVFSCSVMHE ALHNHYTQKS LSLSPGK                            217

SEQ ID NO: 4           moltype = AA  length = 218
FEATURE                Location/Qualifiers
REGION                 1..218
                       note = chemically synthesized
source                 1..218
                       mol_type = protein
                       organism = synthetic construct
SEQUENCE: 4
PAPELLGGPS VFLFPPKPKD TLMISRTPEV TCVVVDVSHE DPEVQFKWYV DGVEVHNAKT    60
KPREEQYNST FRVVSVLTVL HQDWLNGKEY KCKVSNKALP APIEKTISKT KGQPREPQVY   120
TLPPSREEMT KNQVSLTCLV KGFYPSDIAV EWESSGQPEN NYNTTPPMLD SDGSFFLYSK   180
LTVDKSRWQQ GNIFSCSVMH EALHNRFTQK SLSLSPGK                           218

SEQ ID NO: 5           moltype = AA  length = 218
FEATURE                Location/Qualifiers
REGION                 1..218
                       note = chemically synthesized
source                 1..218
                       mol_type = protein
                       organism = synthetic construct
SEQUENCE: 5
PAPEFLGGPS VFLFPPKPKD TLMISRTPEV TCVVVDVSQE DPEVQFNWYV DGVEVHNAKT    60
KPREEQFNST YRVVSVLTVL HQDWLNGKEY KCKVSNKGLP SSIEKTISKA KGQPREPQVY   120
TLPPSQEEMT KNQVSLTCLV KGFYPSDIAV EWESNGQPEN NYKTTPPVLD SDGSFFLYSR   180
LTVDKSRWQE GNVFSCSVMH EALHNHYTQK SLSLSLGK                           218

SEQ ID NO: 6           moltype = AA  length = 218
FEATURE                Location/Qualifiers
REGION                 1..218
                       note = chemically synthesized
source                 1..218
                       mol_type = protein
                       organism = synthetic construct
SEQUENCE: 6
PAPELLGGPS VFLFPPKPKD TLMISRTPEV TCVVVDVSQE DPEVQFNWYV DGVEVHNAKT    60
```

```
KPREEQFNST YRVVSVLTVL HQDWLNGKEY KCKVSNKGLP SSIEKTISKA KGQPREPQVY    120
TLPPSQEEMT KNQVSLTCLV KGFYPSDIAV EWESNGQPEN NYKTTPPVLD SDGSFFLYSR    180
LTVDKSRWQE GNVFSCSVMH EALHNHYTQK SLSLSLGK                            218

SEQ ID NO: 7              moltype = AA   length = 14
FEATURE                   Location/Qualifiers
REGION                    1..14
                          note = chemically synthesized
source                    1..14
                          mol_type = protein
                          organism = synthetic construct
SEQUENCE: 7
EPKSSDKTHT CPPC                                                      14

SEQ ID NO: 8              moltype = AA   length = 9
FEATURE                   Location/Qualifiers
REGION                    1..9
                          note = chemically synthesized
source                    1..9
                          mol_type = protein
                          organism = synthetic construct
SEQUENCE: 8
DKTHTCPPC                                                             9

SEQ ID NO: 9              moltype = AA   length = 11
FEATURE                   Location/Qualifiers
REGION                    1..11
                          note = chemically synthesized
source                    1..11
                          mol_type = protein
                          organism = synthetic construct
SEQUENCE: 9
ESKYGPPCPP C                                                         11

SEQ ID NO: 10             moltype = AA   length = 6
FEATURE                   Location/Qualifiers
REGION                    1..6
                          note = chemically synthesized
source                    1..6
                          mol_type = protein
                          organism = synthetic construct
SEQUENCE: 10
GGSGGS                                                                6

SEQ ID NO: 11             moltype = AA   length = 9
FEATURE                   Location/Qualifiers
REGION                    1..9
                          note = chemically synthesized
source                    1..9
                          mol_type = protein
                          organism = synthetic construct
SEQUENCE: 11
GGSGGSGGS                                                             9

SEQ ID NO: 12             moltype = AA   length = 12
FEATURE                   Location/Qualifiers
REGION                    1..12
                          note = chemically synthesized
source                    1..12
                          mol_type = protein
                          organism = synthetic construct
SEQUENCE: 12
GGSGGSGGSG GS                                                        12

SEQ ID NO: 13             moltype = AA   length = 15
FEATURE                   Location/Qualifiers
REGION                    1..15
                          note = chemically synthesized
source                    1..15
                          mol_type = protein
                          organism = synthetic construct
SEQUENCE: 13
GGSGGSGGSG GSGGS                                                     15

SEQ ID NO: 14             moltype = AA   length = 12
FEATURE                   Location/Qualifiers
REGION                    1..12
                          note = chemically synthesized
source                    1..12
```

```
                            mol_type = protein
                            organism = synthetic construct
SEQUENCE: 14
GQGTLVTVKP GG                                                                     12

SEQ ID NO: 15               moltype = AA   length = 12
FEATURE                     Location/Qualifiers
REGION                      1..12
                            note = chemically synthesized
source                      1..12
                            mol_type = protein
                            organism = synthetic construct
SEQUENCE: 15
GQGTLVTVEP GG                                                                     12

SEQ ID NO: 16               moltype = AA   length = 123
FEATURE                     Location/Qualifiers
REGION                      1..123
                            note = chemically synthesized
source                      1..123
                            mol_type = protein
                            organism = synthetic construct
SEQUENCE: 16
QVQLQESGGG LVQAGDSLRL SCAASGWAFD NYGMAWFRQA PGKEREFIGR LAWNGGSTDY                 60
ADSVKGRFTI SRDNPKNTLY LQMNNLKPED TAVYYCARQR SYSGYGIRTP QTYDYWGQGT                120
QVT                                                                             123

SEQ ID NO: 17               moltype = AA   length = 8
FEATURE                     Location/Qualifiers
REGION                      1..8
                            note = chemically synthesized
source                      1..8
                            mol_type = protein
                            organism = synthetic construct
SEQUENCE: 17
GWAFDNYG                                                                           8

SEQ ID NO: 18               moltype = AA   length = 8
FEATURE                     Location/Qualifiers
REGION                      1..8
                            note = chemically synthesized
source                      1..8
                            mol_type = protein
                            organism = synthetic construct
SEQUENCE: 18
LAWNGGST                                                                           8

SEQ ID NO: 19               moltype = AA   length = 19
FEATURE                     Location/Qualifiers
REGION                      1..19
                            note = chemically synthesized
source                      1..19
                            mol_type = protein
                            organism = synthetic construct
SEQUENCE: 19
ARQRSYSGYG IRTPQTYDY                                                              19

SEQ ID NO: 20               moltype = AA   length = 123
FEATURE                     Location/Qualifiers
REGION                      1..123
                            note = chemically synthesized
source                      1..123
                            mol_type = protein
                            organism = synthetic construct
SEQUENCE: 20
QVQLQQSGGG LVQAGDSLRL SCAASGWAFG NYGMAWFRRA PGKEREFIGR LAWNGGSTDY                 60
VDSVKGRFTI SRDNPKNTLY LQMNNLKPDD TAVYYCARQR SYSRYDIRTP QTYDYWGQGT                120
QVT                                                                             123

SEQ ID NO: 21               moltype = AA   length = 8
FEATURE                     Location/Qualifiers
REGION                      1..8
                            note = chemically synthesized
source                      1..8
                            mol_type = protein
                            organism = synthetic construct
SEQUENCE: 21
GWAFGNYG                                                                           8
```

```
SEQ ID NO: 22              moltype = AA  length = 19
FEATURE                    Location/Qualifiers
REGION                     1..19
                           note = chemically synthesized
source                     1..19
                           mol_type = protein
                           organism = synthetic construct
SEQUENCE: 22
ARQRSYSRYD IRTPQTYDY                                                   19

SEQ ID NO: 23              moltype = AA  length = 123
FEATURE                    Location/Qualifiers
REGION                     1..123
                           note = chemically synthesized
source                     1..123
                           mol_type = protein
                           organism = synthetic construct
SEQUENCE: 23
QVQLVQSGGG LVQPGGSLRL SCAASGWAFD NYGMAWFRQA PGKEREFIGR LAWNGGSTDY       60
ADSVKGRFTI SRDNPKNTLY LQMNSLKPED TAVYYCARQR SYSRYGIRAP QTYDYWGQGT      120
QVT                                                                   123

SEQ ID NO: 24              moltype = AA  length = 19
FEATURE                    Location/Qualifiers
REGION                     1..19
                           note = chemically synthesized
source                     1..19
                           mol_type = protein
                           organism = synthetic construct
SEQUENCE: 24
ARQRSYSRYG IRAPQTYDY                                                   19

SEQ ID NO: 25              moltype = AA  length = 118
FEATURE                    Location/Qualifiers
REGION                     1..118
                           note = chemically synthesized
source                     1..118
                           mol_type = protein
                           organism = synthetic construct
SEQUENCE: 25
QVQLQESGGG LVQPGGSLRL SCAVSGFSFS INAMGWYRQA PGKRREFLAA IDSGRNTVYA       60
VSVKGRFTIS RDNAKNTVYL QMNSLKPEDT AIYYCGLLKG NRVVSPSVAY WGQGTQVT        118

SEQ ID NO: 26              moltype = AA  length = 8
FEATURE                    Location/Qualifiers
REGION                     1..8
                           note = chemically synthesized
source                     1..8
                           mol_type = protein
                           organism = synthetic construct
SEQUENCE: 26
GFSFSINA                                                                8

SEQ ID NO: 27              moltype = AA  length = 7
FEATURE                    Location/Qualifiers
REGION                     1..7
                           note = chemically synthesized
source                     1..7
                           mol_type = protein
                           organism = synthetic construct
SEQUENCE: 27
IDSGRNT                                                                 7

SEQ ID NO: 28              moltype = AA  length = 15
FEATURE                    Location/Qualifiers
REGION                     1..15
                           note = chemically synthesized
source                     1..15
                           mol_type = protein
                           organism = synthetic construct
SEQUENCE: 28
GLLKGNRVVS PSVAY                                                       15

SEQ ID NO: 29              moltype = AA  length = 120
FEATURE                    Location/Qualifiers
REGION                     1..120
                           note = chemically synthesized
source                     1..120
                           mol_type = protein
```

```
                        organism = synthetic construct
SEQUENCE: 29
EVQPVQSGGG LVQAGESLRL SCAASATIFS NNAMGWYRQA PGKQRELVAT ITTGGFTNYR     60
DSVKGRFDIS RDNAKNTVYL QMNNLKPEDT AVYYCNVVLR YSRDYSYTTV KEYWGQGTQV    120

SEQ ID NO: 30           moltype = AA  length = 8
FEATURE                 Location/Qualifiers
REGION                  1..8
                        note = chemically synthesized
source                  1..8
                        mol_type = protein
                        organism = synthetic construct
SEQUENCE: 30
ATIFSNNA                                                               8

SEQ ID NO: 31           moltype = AA  length = 7
FEATURE                 Location/Qualifiers
REGION                  1..7
                        note = chemically synthesized
source                  1..7
                        mol_type = protein
                        organism = synthetic construct
SEQUENCE: 31
ITTGGFT                                                                7

SEQ ID NO: 32           moltype = AA  length = 18
FEATURE                 Location/Qualifiers
REGION                  1..18
                        note = chemically synthesized
source                  1..18
                        mol_type = protein
                        organism = synthetic construct
SEQUENCE: 32
NVVLRYSRDY SYTTVKEY                                                   18

SEQ ID NO: 33           moltype = AA  length = 126
FEATURE                 Location/Qualifiers
REGION                  1..126
                        note = chemically synthesized
source                  1..126
                        mol_type = protein
                        organism = synthetic construct
SEQUENCE: 33
EVQLLESGGG EVQPGGSLRL SCAASGWAFG NYGMAWFRQA PGKGLEWVAR LAWNGGSTDY     60
AESVKGRFTI SRDNAKNTLY LQMSSLRAED TAVYYCARQR SYSRYDIRTP QTYDYWGQGT    120
LVTVKP                                                               126

SEQ ID NO: 34           moltype = AA  length = 126
FEATURE                 Location/Qualifiers
REGION                  1..126
                        note = chemically synthesized
source                  1..126
                        mol_type = protein
                        organism = synthetic construct
SEQUENCE: 34
EVQLLESGGG EVQPGGSLRL SCAASGWAFG NYGMAWFRQA PGKGREFVAR LAWNGGSTDY     60
AESVKGRFTI SRDNAKNTLY LQMSSLRAED TAVYYCARQR SYSRYDIRTP QTYDYWGQGT    120
LVTVKP                                                               126

SEQ ID NO: 35           moltype = AA  length = 126
FEATURE                 Location/Qualifiers
REGION                  1..126
                        note = chemically synthesized
source                  1..126
                        mol_type = protein
                        organism = synthetic construct
SEQUENCE: 35
EVQLLESGGG EVQPGGSLRL SCAASGWAFG NYGMAWFRQA PGKEREFVSR LAWNGGSTDY     60
VAESVKGRFT ISRDNAKNTL YLQMSSLRAE DTAVYYCARQ RSYSRYDIRT PQTYDYWGQG    120
TLVTVK                                                               126

SEQ ID NO: 36           moltype = AA  length = 126
FEATURE                 Location/Qualifiers
REGION                  1..126
                        note = chemically synthesized
source                  1..126
                        mol_type = protein
                        organism = synthetic construct
SEQUENCE: 36
```

```
EVQLLESGGG EVQPGGSLRL SCAASGWAFG NYGMAWFRQA PGKEREFIGR LAWNGGSTDY    60
VESVKGRFTI SRDNPKNTLY LQMSSLRAED TAVYYCARQR SYSRYDIRTP QTYDYWGQGT   120
LVTVKP                                                             126

SEQ ID NO: 37           moltype = AA   length = 126
FEATURE                 Location/Qualifiers
REGION                  1..126
                        note = chemically synthesized
source                  1..126
                        mol_type = protein
                        organism = synthetic construct
SEQUENCE: 37
EVQLLESGGG EVQPGGSLRL SCAASGWAFG NYGMAWFRQA PGKEREFVSR LAWNGGSTDY    60
VESVKGRFTI SRDNAKNTLY LQMSSLRAED TAVYYCARQR SYSRYDIRTP QTYDYWGQGT   120
LVTVKP                                                             126

SEQ ID NO: 38           moltype = AA   length = 126
FEATURE                 Location/Qualifiers
REGION                  1..126
                        note = chemically synthesized
source                  1..126
                        mol_type = protein
                        organism = synthetic construct
SEQUENCE: 38
EVQLLESGGG EVQPGGSLRL SCAASGWAFG NYGMAWFRQA PGKEREFVSR LAWNGGSTDY    60
VESVKGRFTI SRDNPKNTLY LQMSSLRAED TAVYYCARQR SYSRYDIRTP QTYDYWGQGT   120
LVTVKP                                                             126

SEQ ID NO: 39           moltype = AA   length = 126
FEATURE                 Location/Qualifiers
REGION                  1..126
                        note = chemically synthesized
source                  1..126
                        mol_type = protein
                        organism = synthetic construct
SEQUENCE: 39
EVQLLESGGG EVQPGGSLRL SCAASGWAFG NYGMAWFRQA PGKEREFIGR LAWNGGSTDY    60
VESVKGRFTI SRDNAKNTLY LQMSSLRAED TAVYYCARQR SYSRYDIRTP QTYDYWGQGT   120
LVTVKP                                                             126

SEQ ID NO: 40           moltype = AA   length = 126
FEATURE                 Location/Qualifiers
REGION                  1..126
                        note = chemically synthesized
source                  1..126
                        mol_type = protein
                        organism = synthetic construct
SEQUENCE: 40
EVQLLESGGG EVQPGGSLRL SCAASGWAFG NYGMAWFRQA PGKEREFIGR LAWNGGSTDY    60
VESVKGRFTI SRDNPKNTLY LQMSSLRAED TAVYYCARQR SYSRYDIRTP QTYDYWGQGT   120
LVTVKP                                                             126

SEQ ID NO: 41           moltype = AA   length = 126
FEATURE                 Location/Qualifiers
REGION                  1..126
                        note = chemically synthesized
source                  1..126
                        mol_type = protein
                        organism = synthetic construct
SEQUENCE: 41
EVQLLESGGG EVQPGGSLRL SCAASGWAFG NYGMAWFRQA PGKEREFIGR LAWQGGSTDY    60
VESVKGRFTI SRDNPKNTLY LQMSSLRAED TAVYYCARQR SYSRYDIRTP QTYDYWGQGT   120
LVTVKP                                                             126

SEQ ID NO: 42           moltype = AA   length = 8
FEATURE                 Location/Qualifiers
REGION                  1..8
                        note = chemically synthesized
source                  1..8
                        mol_type = protein
                        organism = synthetic construct
SEQUENCE: 42
LAWQGGST                                                             8

SEQ ID NO: 43           moltype = AA   length = 126
FEATURE                 Location/Qualifiers
REGION                  1..126
                        note = chemically synthesized
source                  1..126
```

```
                            mol_type = protein
                            organism = synthetic construct
SEQUENCE: 43
EVQLLESGGG EVQPGGSLRL SCAASGWAFG NYGMAWFRQA PGKEREFIGR LAWNAGSTDY   60
VESVKGRFTI SRDNPKNTLY LQMSSLRAED TAVYYCARQR SYSRYDIRTP QTYDYWGQGT  120
LVTVKP                                                            126

SEQ ID NO: 44               moltype = AA  length = 8
FEATURE                     Location/Qualifiers
REGION                      1..8
                            note = chemically synthesized
source                      1..8
                            mol_type = protein
                            organism = synthetic construct
SEQUENCE: 44
LAWNAGST                                                            8

SEQ ID NO: 45               moltype = AA  length = 126
FEATURE                     Location/Qualifiers
REGION                      1..126
                            note = chemically synthesized
source                      1..126
                            mol_type = protein
                            organism = synthetic construct
SEQUENCE: 45
EVQLLESGGG EVQPGGSLRL SCAASGWAFG NYGMAWFRQA PGKEREFVSR LAWQGGSTDY   60
VESVKGRFTI SRDNAKNTLY LQMSSLRAED TAVYYCARQR SYSRYDIRTP QTYDYWGQGT  120
LVTVKP                                                            126

SEQ ID NO: 46               moltype = AA  length = 126
FEATURE                     Location/Qualifiers
REGION                      1..126
                            note = chemically synthesized
source                      1..126
                            mol_type = protein
                            organism = synthetic construct
SEQUENCE: 46
EVQLLESGGG EVQPGGSLRL SCAASGWAFG NYGMAWFRQA PGKEREFVSR LAWNAGSTDY   60
VESVKGRFTI SRDNAKNTLY LQMSSLRAED TAVYYCARQR SYSRYDIRTP QTYDYWGQGT  120
LVTVKP                                                            126

SEQ ID NO: 47               moltype = AA  length = 126
FEATURE                     Location/Qualifiers
REGION                      1..126
                            note = chemically synthesized
source                      1..126
                            mol_type = protein
                            organism = synthetic construct
SEQUENCE: 47
EVQLLESGGG EVQPGGSLRL SCAASGWAFG NYGMAWFRQA PGKEREFVSR LAWGGGSTDY   60
VESVKGRFTI SRDNAKNTLY LQMSSLRAED TAVYYCARQR SYSRYDIRTP QTYDYWGQGT  120
LVTVKP                                                            126

SEQ ID NO: 48               moltype = AA  length = 8
FEATURE                     Location/Qualifiers
REGION                      1..8
                            note = chemically synthesized
source                      1..8
                            mol_type = protein
                            organism = synthetic construct
SEQUENCE: 48
LAWGGGST                                                            8

SEQ ID NO: 49               moltype = AA  length = 126
FEATURE                     Location/Qualifiers
REGION                      1..126
                            note = chemically synthesized
source                      1..126
                            mol_type = protein
                            organism = synthetic construct
SEQUENCE: 49
EVQLLESGGG EVQPGGSLRL SCAASGWAFS NYGMAWFRQA PGKEREFVSR LAWGGGSTDY   60
VESVKGRFTI SRDNAKNTLY LQMSSLRAED TAVYYCARQR SYSRYDIRTP QTYDYWGQGT  120
LVTVKP                                                            126

SEQ ID NO: 50               moltype = AA  length = 8
FEATURE                     Location/Qualifiers
REGION                      1..8
                            note = chemically synthesized
```

```
source                  1..8
                        mol_type = protein
                        organism = synthetic construct
SEQUENCE: 50
GWAFSNYG                                                                     8

SEQ ID NO: 51           moltype = AA  length = 126
FEATURE                 Location/Qualifiers
REGION                  1..126
                        note = chemically synthesized
source                  1..126
                        mol_type = protein
                        organism = synthetic construct
SEQUENCE: 51
EVQLLESGGG EVQPGGSLRL SCAASGWAFG NYGMAWFRQA PGKEREFVSR LAWSGGSTDY             60
VESVKGRFTI SRDNAKNTLY LQMSSLRAED TAVYYCARQR SYSRYDIRTP QTYDYWGQGT            120
LVTVKP                                                                     126

SEQ ID NO: 52           moltype = AA  length = 8
FEATURE                 Location/Qualifiers
REGION                  1..8
                        note = chemically synthesized
source                  1..8
                        mol_type = protein
                        organism = synthetic construct
SEQUENCE: 52
LAWSGGST                                                                     8

SEQ ID NO: 53           moltype = AA  length = 126
FEATURE                 Location/Qualifiers
REGION                  1..126
                        note = chemically synthesized
source                  1..126
                        mol_type = protein
                        organism = synthetic construct
SEQUENCE: 53
EVQLLESGGG EVQPGGSLRL SCAASGWAFS NYGMAWFRQA PGKEREFVSR LAWSGGSTDY             60
VESVKGRFTI SRDNAKNTLY LQMSSLRAED TAVYYCARQR SYSRYDIRTP QTYDYWGQGT            120
LVTVKP                                                                     126

SEQ ID NO: 54           moltype = AA  length = 126
FEATURE                 Location/Qualifiers
REGION                  1..126
                        note = chemically synthesized
source                  1..126
                        mol_type = protein
                        organism = synthetic construct
SEQUENCE: 54
EVQLLESGGG EVQPGGSLRL SCAASGWAFG NYGMAWFRQA PGKEREFVSR LAWGGGSTDY             60
VESVKGRFTI SRDNAKNTLY LQMSSLRAED TAVYYCARQR SYSGYDIRTP QTYDYWGQGT            120
LVTVKP                                                                     126

SEQ ID NO: 55           moltype = AA  length = 19
FEATURE                 Location/Qualifiers
REGION                  1..19
                        note = chemically synthesized
source                  1..19
                        mol_type = protein
                        organism = synthetic construct
SEQUENCE: 55
ARQRSYSGYD IRTPQTYDY                                                        19

SEQ ID NO: 56           moltype = AA  length = 126
FEATURE                 Location/Qualifiers
REGION                  1..126
                        note = chemically synthesized
source                  1..126
                        mol_type = protein
                        organism = synthetic construct
SEQUENCE: 56
EVQLLESGGG EVQPGGSLRL SCAASGWAFG NYGMAWFRQA PGKEREFVSR LAWGGGSTDY             60
VESVKGRFTI SRDNAKNTLY LQMSSLRAED TAVYYCARQR SYSRYGIRTP QTYDYWGQGT            120
LVTVKP                                                                     126

SEQ ID NO: 57           moltype = AA  length = 19
FEATURE                 Location/Qualifiers
REGION                  1..19
                        note = chemically synthesized
source                  1..19
```

```
                          mol_type = protein
                          organism = synthetic construct
SEQUENCE: 57
ARQRSYSRYG IRTPQTYDY                                                  19

SEQ ID NO: 58             moltype = AA  length = 126
FEATURE                   Location/Qualifiers
REGION                    1..126
                          note = chemically synthesized
source                    1..126
                          mol_type = protein
                          organism = synthetic construct
SEQUENCE: 58
EVQLLESGGG EVQPGGSLRL SCAASGWAFG NYGMAWFRQA PGKEREFVSR LAWGGGSTDY      60
VESVKGRFTI SRDNAKNTLY LQMSSLRAED TAVYYCARQR SYSGYGIRTP QTYDYWGQGT      120
LVTVKP                                                                126

SEQ ID NO: 59             moltype = AA  length = 121
FEATURE                   Location/Qualifiers
REGION                    1..121
                          note = chemically synthesized
source                    1..121
                          mol_type = protein
                          organism = synthetic construct
SEQUENCE: 59
EVQLLESGGG EVQPGGSLRL SCAASGFSFS INAMGWYRQA PGKGLEWVAA IDSGRNTVYA      60
ESVKGRFTIS RDNAKNTLYL QMSSLRAEDT AVYYCGLLKG NRVVSPSVAY WGQGTLVTVK      120
P                                                                     121

SEQ ID NO: 60             moltype = AA  length = 121
FEATURE                   Location/Qualifiers
REGION                    1..121
                          note = chemically synthesized
source                    1..121
                          mol_type = protein
                          organism = synthetic construct
SEQUENCE: 60
EVQLLESGGG EVQPGGSLRL SCAASGFSFS INAMGWYRQA PGKRREFVAA IESGRNTVYA      60
ESVKGRFTIS RDNAKNTVYL QMSSLRAEDT AVYYCGLLKG NRVVSPSVAY WGQGTLVTVK      120
P                                                                     121

SEQ ID NO: 61             moltype = AA  length = 7
FEATURE                   Location/Qualifiers
REGION                    1..7
                          note = chemically synthesized
source                    1..7
                          mol_type = protein
                          organism = synthetic construct
SEQUENCE: 61
IESGRNT                                                               7

SEQ ID NO: 62             moltype = AA  length = 121
FEATURE                   Location/Qualifiers
REGION                    1..121
                          note = chemically synthesized
source                    1..121
                          mol_type = protein
                          organism = synthetic construct
SEQUENCE: 62
EVQLLESGGG EVQPGGSLRL SCAASGFSFS INAMGWYRQA PGKRREFVAA IYSGRNTVYA      60
ESVKGRFTIS RDNAKNTVYL QMSSLRAEDT AVYYCGLLKG NRVVSPSVAY WGQGTLVTVK      120
P                                                                     121

SEQ ID NO: 63             moltype = AA  length = 7
FEATURE                   Location/Qualifiers
REGION                    1..7
                          note = chemically synthesized
source                    1..7
                          mol_type = protein
                          organism = synthetic construct
SEQUENCE: 63
IYSGRNT                                                               7

SEQ ID NO: 64             moltype = AA  length = 121
FEATURE                   Location/Qualifiers
REGION                    1..121
                          note = chemically synthesized
source                    1..121
                          mol_type = protein
```

```
                                organism = synthetic construct
SEQUENCE: 64
EVQLLESGGG EVQPGGSLRL SCAASGFTFS INAMGWYRQA PGKRREFVAA IESGRNTVYA    60
ESVKGRFTIS RDNAKNTVYL QMSSLRAEDT AVYYCGLLKG NRVVSPSVAY WGQGTLVTVK   120
P                                                                   121

SEQ ID NO: 65           moltype = AA  length = 8
FEATURE                 Location/Qualifiers
REGION                  1..8
                        note = chemically synthesized
source                  1..8
                        mol_type = protein
                        organism = synthetic construct
SEQUENCE: 65
GFTFSINA                                                              8

SEQ ID NO: 66           moltype = AA  length = 121
FEATURE                 Location/Qualifiers
REGION                  1..121
                        note = chemically synthesized
source                  1..121
                        mol_type = protein
                        organism = synthetic construct
SEQUENCE: 66
EVQLLESGGG EVQPGGSLRL SCAASGFSFS INAMSWYRQA PGKRREFVAA IESGRNTVYA    60
ESVKGRFTIS RDNAKNTVYL QMSSLRAEDT AVYYCGLLKG NRVVSPSVAY WGQGTLVTVK   120
P                                                                   121

SEQ ID NO: 67           moltype = AA  length = 8
FEATURE                 Location/Qualifiers
REGION                  1..8
                        note = chemically synthesized
source                  1..8
                        mol_type = protein
                        organism = synthetic construct
SEQUENCE: 67
GFSFSINA                                                              8

SEQ ID NO: 68           moltype = AA  length = 121
FEATURE                 Location/Qualifiers
REGION                  1..121
                        note = chemically synthesized
source                  1..121
                        mol_type = protein
                        organism = synthetic construct
SEQUENCE: 68
EVQLLESGGG EVQPGGSLRL SCAASGFTFS SNAMGWYRQA PGKRREFVAA IESGRNTVYA    60
ESVKGRFTIS RDNAKNTVYL QMSSLRAEDT AVYYCGLLKG NRVVSPSVAY WGQGTLVTVK   120
P                                                                   121

SEQ ID NO: 69           moltype = AA  length = 8
FEATURE                 Location/Qualifiers
REGION                  1..8
                        note = chemically synthesized
source                  1..8
                        mol_type = protein
                        organism = synthetic construct
SEQUENCE: 69
GFTFSSNA                                                              8

SEQ ID NO: 70           moltype = AA  length = 121
FEATURE                 Location/Qualifiers
REGION                  1..121
                        note = chemically synthesized
source                  1..121
                        mol_type = protein
                        organism = synthetic construct
SEQUENCE: 70
EVQLLESGGG EVQPGGSLRL SCAASGFSFS INAMGWYRQA PGKRREFVAA IESSRNTVYA    60
ESVKGRFTIS RDNAKNTVYL QMSSLRAEDT AVYYCGLLKG NRVVSPSVAY WGQGTLVTVK   120
P                                                                   121

SEQ ID NO: 71           moltype = AA  length = 7
FEATURE                 Location/Qualifiers
REGION                  1..7
                        note = chemically synthesized
source                  1..7
                        mol_type = protein
                        organism = synthetic construct
```

```
SEQUENCE: 71
IESSRNT                                                                        7

SEQ ID NO: 72           moltype = AA  length = 121
FEATURE                 Location/Qualifiers
REGION                  1..121
                        note = chemically synthesized
source                  1..121
                        mol_type = protein
                        organism = synthetic construct
SEQUENCE: 72
EVQLLESGGG EVQPGGSLRL SCAASGFSFS INAMGWYRQA PGKRREFVAA IESGSNTVYA    60
ESVKGRFTIS RDNAKNTVYL QMSSLRAEDT AVYYCGLLKG NRVVSPSVAY WGQGTLVTVK   120
P                                                                   121

SEQ ID NO: 73           moltype = AA  length = 7
FEATURE                 Location/Qualifiers
REGION                  1..7
                        note = chemically synthesized
source                  1..7
                        mol_type = protein
                        organism = synthetic construct
SEQUENCE: 73
IESGSNT                                                                        7

SEQ ID NO: 74           moltype = AA  length = 121
FEATURE                 Location/Qualifiers
REGION                  1..121
                        note = chemically synthesized
source                  1..121
                        mol_type = protein
                        organism = synthetic construct
SEQUENCE: 74
EVQLLESGGG EVQPGGSLRL SCAASGFSFS INAMGWYRQA PGKRREFVAA IESGRSTVYA    60
ESVKGRFTIS RDNAKNTVYL QMSSLRAEDT AVYYCGLLKG NRVVSPSVAY WGQGTLVTVK   120
P                                                                   121

SEQ ID NO: 75           moltype = AA  length = 7
FEATURE                 Location/Qualifiers
REGION                  1..7
                        note = chemically synthesized
source                  1..7
                        mol_type = protein
                        organism = synthetic construct
SEQUENCE: 75
IESGRST                                                                        7

SEQ ID NO: 76           moltype = AA  length = 121
FEATURE                 Location/Qualifiers
REGION                  1..121
                        note = chemically synthesized
source                  1..121
                        mol_type = protein
                        organism = synthetic construct
SEQUENCE: 76
EVQLLESGGG EVQPGGSLRL SCAASGFSFS INAMGWYRQA PGKRREFVAA IESGRNTYYA    60
ESVKGRFTIS RDNAKNTVYL QMSSLRAEDT AVYYCGLLKG NRVVSPSVAY WGQGTLVTVK   120
P                                                                   121

SEQ ID NO: 77           moltype = AA  length = 7
FEATURE                 Location/Qualifiers
REGION                  1..7
                        note = chemically synthesized
source                  1..7
                        mol_type = protein
                        organism = synthetic construct
SEQUENCE: 77
IESGRNT                                                                        7

SEQ ID NO: 78           moltype = AA  length = 121
FEATURE                 Location/Qualifiers
REGION                  1..121
                        note = chemically synthesized
source                  1..121
                        mol_type = protein
                        organism = synthetic construct
SEQUENCE: 78
EVQLLESGGG EVQPGGSLRL SCAASGFSFS INAMGWYRQA PGKRREFVAA IYSGSSTVYA    60
ESVKGRFTIS RDNAKNTVYL QMSSLRAEDT AVYYCGLLKG NRVVSPSVAY WGQGTLVTVK   120
```

```
                                                       P                                        121

SEQ ID NO: 79           moltype = AA   length = 7
FEATURE                 Location/Qualifiers
REGION                  1..7
                        note = chemically synthesized
source                  1..7
                        mol_type = protein
                        organism = synthetic construct
SEQUENCE: 79
IYSGSST                                                                                         7

SEQ ID NO: 80           moltype = AA   length = 121
FEATURE                 Location/Qualifiers
REGION                  1..121
                        note = chemically synthesized
source                  1..121
                        mol_type = protein
                        organism = synthetic construct
SEQUENCE: 80
EVQLLESGGG EVQPGGSLRL SCAVSGFSFS INAMGWYRQA PGKRREFVAA IESGRNTVYA                                60
ESVKGRFTIS RDNAKNTVYL QMSSLRAEDT AVYYCGLLKG NRVVSPSVAY WGQGTLVTVK                                120
P                                                                                               121

SEQ ID NO: 81           moltype = AA   length = 121
FEATURE                 Location/Qualifiers
REGION                  1..121
                        note = chemically synthesized
source                  1..121
                        mol_type = protein
                        organism = synthetic construct
SEQUENCE: 81
EVQLLESGGG EVQPGGSLRL SCAASGFSFS INAMGWYRQA PGKRREFVAA IESGRNTVYA                                60
VSVKGRFTIS RDNAKNTVYL QMSSLRAEDT AVYYCGLLKG NRVVSPSVAY WGQGTLVTVK                                120
P                                                                                               121

SEQ ID NO: 82           moltype = AA   length = 121
FEATURE                 Location/Qualifiers
REGION                  1..121
                        note = chemically synthesized
source                  1..121
                        mol_type = protein
                        organism = synthetic construct
SEQUENCE: 82
EVQLLESGGG EVQPGGSLRL SCAASGFSFS INAMGWYRQA PGKGREFVAA IESGRNTVYA                                60
ESVKGRFTIS RDNAKNTVYL QMSSLRAEDT AVYYCGLLKG NRVVSPSVAY WGQGTLVTVK                                120
P                                                                                               121

SEQ ID NO: 83           moltype = AA   length = 121
FEATURE                 Location/Qualifiers
REGION                  1..121
                        note = chemically synthesized
source                  1..121
                        mol_type = protein
                        organism = synthetic construct
SEQUENCE: 83
EVQLLESGGG EVQPGGSLRL SCAASGFSFS INAMGWYRQA PGKRREFLAA IESGRNTVYA                                60
ESVKGRFTIS RDNAKNTVYL QMSSLRAEDT AVYYCGLLKG NRVVSPSVAY WGQGTLVTVK                                120
P                                                                                               121

SEQ ID NO: 84           moltype = AA   length = 119
FEATURE                 Location/Qualifiers
REGION                  1..119
                        note = chemically synthesized
source                  1..119
                        mol_type = protein
                        organism = synthetic construct
SEQUENCE: 84
QVQLVQSGAE VKKPGSSVKV SCKASGGTFN SYAISWVRQA PGQGLEWMGG IIPGFGTANY                                60
AQKFQGRVTI TADESTSTAY MELSSLRSED TAVYYCARKN EEDGGFDHWG QGTLVTVSS                                 119

SEQ ID NO: 85           moltype = AA   length = 118
FEATURE                 Location/Qualifiers
REGION                  1..118
                        note = chemically synthesized
source                  1..118
                        mol_type = protein
                        organism = synthetic construct
SEQUENCE: 85
```

```
QVQLVESGGG LVQPGGSLRL SCAASGFTFS DYYMHWVRQA PGKGLEWVSV ISGSGSNTYY      60
ADSVKGRFTI SRDNSKNTLY LQMNSLRAED TAVYYCARLY AQFEGDFWGQ GTLVTVSS      118

SEQ ID NO: 86              moltype = AA  length = 116
FEATURE                    Location/Qualifiers
REGION                     1..116
                           note = chemically synthesized
source                     1..116
                           mol_type = protein
                           organism = synthetic construct
SEQUENCE: 86
QVQLVQSGAE VKKPGESLKI SCKGSGYSFS TYWISWVRQM PGKGLEWMGK IYPGDSYTNY      60
SPSFQGQVTI SADKSISTAY LQWSSLKASD TAMYYCARGY GIFDYWGQGT LVTVSS         116

SEQ ID NO: 87              moltype = AA  length = 116
FEATURE                    Location/Qualifiers
REGION                     1..116
                           note = chemically synthesized
source                     1..116
                           mol_type = protein
                           organism = synthetic construct
SEQUENCE: 87
EVQLVQSGAE VKKPGESLRI SCKGSGYSFS TYWISWVRQM PGKGLEWMGK IYPGDSYTNY      60
SPSFQGQVTI SADKSISTAY LQWSSLKASD TAMYYCARGY GIFDYWGQGT LVTVSS         116

SEQ ID NO: 88              moltype = AA  length = 107
FEATURE                    Location/Qualifiers
REGION                     1..107
                           note = chemically synthesized
source                     1..107
                           mol_type = protein
                           organism = synthetic construct
SEQUENCE: 88
DIELTQPPSV SVAPGQTARI SCSGDNLGDY YASWYQQKPG QAPVLVIYDD SNRPSGIPER      60
FSGSNSGNTA TLTISGTQAE DEADYYCQTW DGTLHFVFGG GTKLTVL                  107

SEQ ID NO: 89              moltype = AA  length = 107
FEATURE                    Location/Qualifiers
REGION                     1..107
                           note = chemically synthesized
source                     1..107
                           mol_type = protein
                           organism = synthetic construct
SEQUENCE: 89
DIELTQPPSV SVAPGQTARI SCSGDNIGSK YVSWYQQKPG QAPVLVIYSD SERPSGIPER      60
FSGSNSGNTA TLTISGTQAE DEADYYCQSW DGSISRVFGG GTKLTVL                  107

SEQ ID NO: 90              moltype = AA  length = 108
FEATURE                    Location/Qualifiers
REGION                     1..108
                           note = chemically synthesized
source                     1..108
                           mol_type = protein
                           organism = synthetic construct
SEQUENCE: 90
DIELTQPPSV SVAPGQTARI SCSGDNIGDQ YAHWYQQKPG QAPVVVIYQD KNRPSGIPER      60
FSGSNSGNTA TLTISGTQAE DEADYYCATY TGFGSLAVFG GGTKLTVL                 108

SEQ ID NO: 91              moltype = AA  length = 108
FEATURE                    Location/Qualifiers
REGION                     1..108
                           note = chemically synthesized
source                     1..108
                           mol_type = protein
                           organism = synthetic construct
SEQUENCE: 91
SYELTQPPSV SVSPGQTASI TCSGDNIGDQ YAHWYQQKPG QSPVLVIYQD KNRPSGIPER      60
FSGSNSGNTA TLTISGTQAM DEADYYCATY TGFGSLAVFG GGTKLTVL                 108

SEQ ID NO: 92              moltype = AA  length = 108
FEATURE                    Location/Qualifiers
REGION                     1..108
                           note = chemically synthesized
source                     1..108
                           mol_type = protein
                           organism = synthetic construct
SEQUENCE: 92
SYELTQPPSV SVSPGQTASI TCSGDNIGDQ YAHWYQQKPG QSPVVVIYQD KNRPSGIPER      60
FSGSNSGNTA TLTISGTQAM DEADYYCATY TGFGSLAVFG GGTKLTVL                 108
```

```
SEQ ID NO: 93          moltype = AA  length = 108
FEATURE                Location/Qualifiers
REGION                 1..108
                       note = chemically synthesized
source                 1..108
                       mol_type = protein
                       organism = synthetic construct
SEQUENCE: 93
DIELTQPPSV SVAPGQTARI SCSGDNIGDQ YAHWYQQKPG QAPVVVIYQD KNRPSGIPER    60
FSGSNSGNTA TLTISGTQAE DEADYYCSTY TFVGFTTVFG GGTKLTVL                108

SEQ ID NO: 94          moltype = AA  length = 108
FEATURE                Location/Qualifiers
REGION                 1..108
                       note = chemically synthesized
source                 1..108
                       mol_type = protein
                       organism = synthetic construct
SEQUENCE: 94
SYELTQPPSV SVSPGQTASI TCSGDNIGDQ YAHWYQQKPG QSPVLVIYQD KNRPSGIPER    60
FSGSNSGNTA TLTISGTQAM DEADYYCSTY TFVGFTTVFG GGTKLTVL                108

SEQ ID NO: 95          moltype = AA  length = 108
FEATURE                Location/Qualifiers
REGION                 1..108
                       note = chemically synthesized
source                 1..108
                       mol_type = protein
                       organism = synthetic construct
SEQUENCE: 95
SYELTQPPSV SVSPGQTASI TCSGDNIGDQ YAHWYQQKPG QSPVVVIYQD KNRPSGIPER    60
FSGSNSGNTA TLTISGTQAM DEADYYCSTY TFVGFTTVFG GGTKLTVL                108

SEQ ID NO: 96          moltype = AA  length = 448
FEATURE                Location/Qualifiers
REGION                 1..448
                       note = chemically synthesized
source                 1..448
                       mol_type = protein
                       organism = synthetic construct
SEQUENCE: 96
QVQLQQWGAG LLKPSETLSL TCAVYGGSFS GYYWSWIRQS PEKGLEWIGE INHGGYVTYN    60
PSLESRVTIS VDTSKNQFSL KLSSVTAADT AVYYCARDYG PGNYDWYFDL WGRGTLVTVS   120
SASTKGPSVF PLAPCSRSTS ESTAALGCLV KDYFPEPVTV SWNSGALTSG VHTFPAVLQS   180
SGLYSLSSVV TVPSSSLGTK TYTCNVDHKP SNTKVDKRVE SKYGPPCPPC PAPEFLGGPS   240
VFLFPPKPKD TLMISRTPEV TCVVVDVSQE DPEVQFNWYV DGVEVHNAKT KPREEQFNST   300
YRVVSVLTVL HQDWLNGKEY KCKVSNKGLP SSIEKTISKA KGQPREPQVY TLPPSQEEMT   360
KNQVSLTCLV KGFYPSDIAV EWESNGQPEN NYKTTPPVLD SDGSFFLYSR LTVDKSRWQE   420
GNVFSCSVMH EALHNHYTQK SLSLSLGK                                     448

SEQ ID NO: 97          moltype = AA  length = 451
FEATURE                Location/Qualifiers
REGION                 1..451
                       note = chemically synthesized
source                 1..451
                       mol_type = protein
                       organism = synthetic construct
SEQUENCE: 97
QVQLQQWGAG LLKPSETLSL TCAVYGGSFS GYYWSWIRQS PEKGLEWIGE INHGGYVTYN    60
PSLESRVTIS VDTSKNQFSL KLSSVTAADT AVYYCARDYG PGNYDWYFDL WGRGTLVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKRVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRD   360
ELTKNQVSLT CLVKGFYPSD IAVEWESNGQ PENNYKTTPP VLDSDGSFFL YSKLTVDKSR   420
WQQGNVFSCS VMHEALHNHY TQKSLSLSPG K                                 451

SEQ ID NO: 98          moltype = AA  length = 216
FEATURE                Location/Qualifiers
REGION                 1..216
                       note = chemically synthesized
source                 1..216
                       mol_type = protein
                       organism = synthetic construct
SEQUENCE: 98
EIVLTQSPAT LSLSPGERAT LSCRASQSVS SYLAWYQQKP GQAPRLLIYD ASNRATGIPA    60
RFSGSGSGTD FTLTISSLEP EDFAVYYCQQ RSNWPPALTF GGGTKVEIKR TVAAPSVFIF   120
PPSDEQLKSG TASVVCLLNN FYPREAKVQW KVDNALQSGN SQESVTEQDS KDSTYSLSST   180
```

```
LTLSKADYEK HKVYACEVTH QGLSSPVTKS FNRGEC                            216

SEQ ID NO: 99            moltype = AA  length = 178
FEATURE                  Location/Qualifiers
REGION                   1..178
                         note = chemically synthesized
source                   1..178
                         mol_type = protein
                         organism = synthetic construct
SEQUENCE: 99
QDSTSDLIPA PPLSKVPLQQ NFQDNQFHGK WYVVGQAGNI RLREDKDPIK MMATIYELKE   60
DKSYDVTMVK FDDKKCMYDI WTFVPGSQPG EFTLGKIKSF PGHTSSLVRV VSTNYNQHAM  120
VFFKFVFQNR EEFYITLYGR TKELTSELKE NFIRFSKSLG LPENHIVFPV PIDQCIDG    178

SEQ ID NO: 100           moltype = AA  length = 109
FEATURE                  Location/Qualifiers
REGION                   1..109
                         note = chemically synthesized
source                   1..109
                         mol_type = protein
                         organism = synthetic construct
SEQUENCE: 100
QVQLQESGGG LVQAGGSLRL ACTTSGGIFN IRPISWYRQP PGMQREWVAT IAFGGATNYA   60
NSIKGRFTAS RDNAKNTVYL QMNGLKPEDT AVYYCNAFEI WGQGTQVTV              109

SEQ ID NO: 101           moltype = AA  length = 8
FEATURE                  Location/Qualifiers
REGION                   1..8
                         note = chemically synthesized
source                   1..8
                         mol_type = protein
                         organism = synthetic construct
SEQUENCE: 101
GGIFNIRP                                                             8

SEQ ID NO: 102           moltype = AA  length = 7
FEATURE                  Location/Qualifiers
REGION                   1..7
                         note = chemically synthesized
source                   1..7
                         mol_type = protein
                         organism = synthetic construct
SEQUENCE: 102
IAFGGAT                                                              7

SEQ ID NO: 103           moltype = AA  length = 5
FEATURE                  Location/Qualifiers
REGION                   1..5
                         note = chemically synthesized
source                   1..5
                         mol_type = protein
                         organism = synthetic construct
SEQUENCE: 103
NAFEI                                                                5

SEQ ID NO: 104           moltype = AA  length = 109
FEATURE                  Location/Qualifiers
REGION                   1..109
                         note = chemically synthesized
source                   1..109
                         mol_type = protein
                         organism = synthetic construct
SEQUENCE: 104
QLQLQESGGG LVRAGGSLRL ACTTSGGIFA IKPISWYRQP PGQEREWVTT TTSSGATNYA   60
NSIKGRFTVA RDNAKNTVYL QMNDLKLEDT AVYYCNVFEY WGQGTQVTV              109

SEQ ID NO: 105           moltype = AA  length = 8
FEATURE                  Location/Qualifiers
REGION                   1..8
                         note = chemically synthesized
source                   1..8
                         mol_type = protein
                         organism = synthetic construct
SEQUENCE: 105
GGIFAIKP                                                             8

SEQ ID NO: 106           moltype = AA  length = 7
FEATURE                  Location/Qualifiers
REGION                   1..7
```

```
                        note = chemically synthesized
source                  1..7
                        mol_type = protein
                        organism = synthetic construct
SEQUENCE: 106
TTSSGAT                                                                        7

SEQ ID NO: 107          moltype = AA  length = 5
FEATURE                 Location/Qualifiers
REGION                  1..5
                        note = chemically synthesized
source                  1..5
                        mol_type = protein
                        organism = synthetic construct
SEQUENCE: 107
NVFEY                                                                          5

SEQ ID NO: 108          moltype = AA  length = 109
FEATURE                 Location/Qualifiers
REGION                  1..109
                        note = chemically synthesized
source                  1..109
                        mol_type = protein
                        organism = synthetic construct
SEQUENCE: 108
QVQLQESGGD LVQAGSSLRL ACATSGGVFN IRPISWYRQP PGKQREWVAT IASGGATNYA              60
NSIKGRFTAS RDNAKNTVYL QMNGLKPEDT AVYYCNAFEV WGQGTQVTV                         109

SEQ ID NO: 109          moltype = AA  length = 8
FEATURE                 Location/Qualifiers
REGION                  1..8
                        note = chemically synthesized
source                  1..8
                        mol_type = protein
                        organism = synthetic construct
SEQUENCE: 109
GGVFNIRP                                                                       8

SEQ ID NO: 110          moltype = AA  length = 7
FEATURE                 Location/Qualifiers
REGION                  1..7
                        note = chemically synthesized
source                  1..7
                        mol_type = protein
                        organism = synthetic construct
SEQUENCE: 110
IASGGAT                                                                        7

SEQ ID NO: 111          moltype = AA  length = 5
FEATURE                 Location/Qualifiers
REGION                  1..5
                        note = chemically synthesized
source                  1..5
                        mol_type = protein
                        organism = synthetic construct
SEQUENCE: 111
NAFEV                                                                          5

SEQ ID NO: 112          moltype = AA  length = 109
FEATURE                 Location/Qualifiers
REGION                  1..109
                        note = chemically synthesized
source                  1..109
                        mol_type = protein
                        organism = synthetic construct
SEQUENCE: 112
QVQLQQSGGG LVQAGGSLRL ACTTSGGIFN IRPISWYRQP PGMQREWVAT IASGGATNYA              60
NSIKGRFTAS RDNAKNTVYL QMNGLKPEDT AVYYCNTLNF WGRGTQVTV                         109

SEQ ID NO: 113          moltype = AA  length = 5
FEATURE                 Location/Qualifiers
REGION                  1..5
                        note = chemically synthesized
source                  1..5
                        mol_type = protein
                        organism = synthetic construct
SEQUENCE: 113
NTLNF                                                                          5
```

| | | |
|---|---|---|
| SEQ ID NO: 114 | moltype = AA length = 109 | |
| FEATURE | Location/Qualifiers | |
| REGION | 1..109 | |
| | note = chemically synthesized | |
| source | 1..109 | |
| | mol_type = protein | |
| | organism = synthetic construct | |
| SEQUENCE: 114 | | |
| QVQLQESGGG LVQAGGSLRL ACTTSGGIFN IRPISWYRQP PGMQREWVAT IASGGATNYA | | 60 |
| NSIKGRFTAS RDNAKNTVYL QMNGLKPEDT AVYYCNVFEI WGQGTQVTV | | 109 |
| | | |
| SEQ ID NO: 115 | moltype = AA length = 5 | |
| FEATURE | Location/Qualifiers | |
| REGION | 1..5 | |
| | note = chemically synthesized | |
| source | 1..5 | |
| | mol_type = protein | |
| | organism = synthetic construct | |
| SEQUENCE: 115 | | |
| NVFEI | | 5 |
| | | |
| SEQ ID NO: 116 | moltype = AA length = 109 | |
| FEATURE | Location/Qualifiers | |
| REGION | 1..109 | |
| | note = chemically synthesized | |
| source | 1..109 | |
| | mol_type = protein | |
| | organism = synthetic construct | |
| SEQUENCE: 116 | | |
| QVQLQQSGGG LVQAGGSLRL ACITSGGIFN IRPISWYRQP PGKQREWVAT IASGGAANYA | | 60 |
| NSIKGRFTAS RDNAKNTVYL QMNGLKPEDT AVYYCNAFEN WGQGTQVTV | | 109 |
| | | |
| SEQ ID NO: 117 | moltype = AA length = 7 | |
| FEATURE | Location/Qualifiers | |
| REGION | 1..7 | |
| | note = chemically synthesized | |
| source | 1..7 | |
| | mol_type = protein | |
| | organism = synthetic construct | |
| SEQUENCE: 117 | | |
| IASGGAA | | 7 |
| | | |
| SEQ ID NO: 118 | moltype = AA length = 5 | |
| FEATURE | Location/Qualifiers | |
| REGION | 1..5 | |
| | note = chemically synthesized | |
| source | 1..5 | |
| | mol_type = protein | |
| | organism = synthetic construct | |
| SEQUENCE: 118 | | |
| NAFEN | | 5 |
| | | |
| SEQ ID NO: 119 | moltype = AA length = 111 | |
| FEATURE | Location/Qualifiers | |
| REGION | 1..111 | |
| | note = chemically synthesized | |
| source | 1..111 | |
| | mol_type = protein | |
| | organism = synthetic construct | |
| SEQUENCE: 119 | | |
| QVQLQESGGG EVQPGGSLRL SCAASGGIFA IKPISWYRQA PGKQREWVST TTSSGATNYA | | 60 |
| ESVKGRFTIS RDNAKNTLYL QMSSLRAEDT AVYYCNVFEY WGQGTLVTVK P | | 111 |
| | | |
| SEQ ID NO: 120 | moltype = AA length = 111 | |
| FEATURE | Location/Qualifiers | |
| REGION | 1..111 | |
| | note = chemically synthesized | |
| source | 1..111 | |
| | mol_type = protein | |
| | organism = synthetic construct | |
| SEQUENCE: 120 | | |
| EVQLQESGGG EVQPGGSLRL SCAASGGIFA IKPISWYRQA PGKQREWVST TTSSGATNYA | | 60 |
| ESVKGRFTIS RDNAKNTLYL QMSSLRAEDT AVYYCNVFEY WGQGTLVTVK P | | 111 |
| | | |
| SEQ ID NO: 121 | moltype = AA length = 111 | |
| FEATURE | Location/Qualifiers | |
| REGION | 1..111 | |
| | note = chemically synthesized | |
| source | 1..111 | |

```
                            mol_type = protein
                            organism = synthetic construct
SEQUENCE: 121
EVQLLESGGG EVQPGGSLRL SCAASGGIFA IKPISWYRQA PGKQREWVST TTSSGATNYA    60
ESVKGRFTIS RDNAKNTLYL QMSSLRAEDT AVYYCNVFEY WGQGTLVTVK P           111

SEQ ID NO: 122          moltype = AA  length = 111
FEATURE                 Location/Qualifiers
REGION                  1..111
                        note = chemically synthesized
source                  1..111
                        mol_type = protein
                        organism = synthetic construct
SEQUENCE: 122
EVQLLESGGG EVQPGGSLRL SCAASGGIFA IKPISWYRQA PGKQREWVST TTSSGATNYA    60
ESVKGRFTIS RDNAKNTLYL QMSSLRAEDT AVYYCNVFEY WGQGTLVTVK P           111

SEQ ID NO: 123          moltype = AA  length = 111
FEATURE                 Location/Qualifiers
REGION                  1..111
                        note = chemically synthesized
source                  1..111
                        mol_type = protein
                        organism = synthetic construct
SEQUENCE: 123
EVQLLESGGG EVQPGGSLRL SCAASGGIFA IKPISWYRQA PGKQREWVTT TTSSGATNYA    60
ESVKGRFTIS RDNAKNTVYL QMSSLRAEDT AVYYCNVFEY WGQGTLVTVK P           111

SEQ ID NO: 124          moltype = AA  length = 111
FEATURE                 Location/Qualifiers
REGION                  1..111
                        note = chemically synthesized
source                  1..111
                        mol_type = protein
                        organism = synthetic construct
SEQUENCE: 124
EVQLLESGGG EVQPGGSLRL SCAASGGIFA IKPISWYRQA PGKQREWVST TTSSGATNYA    60
ESVKGRFTIS RDNAKNTLYL QMSSLRAEDT AVYYCNVFEY WGQGTLVTVK P           111

SEQ ID NO: 125          moltype = AA  length = 111
FEATURE                 Location/Qualifiers
REGION                  1..111
                        note = chemically synthesized
source                  1..111
                        mol_type = protein
                        organism = synthetic construct
SEQUENCE: 125
PTFSPALLVV TEGDNATFTC SFSNTSESFV LNWYRMSPSN QTDKLAAFPE DRSQPGQDCR    60
FRVTQLPNGR DFHMSVVRAR RNDSGTYLCG AISLAPKAQI KESLRAELRV T           111

SEQ ID NO: 126          moltype = AA  length = 117
FEATURE                 Location/Qualifiers
REGION                  1..117
                        note = chemically synthesized
source                  1..117
                        mol_type = protein
                        organism = synthetic construct
SEQUENCE: 126
QVQLVQSGAE VKKPGASVKV SCKASGYTFT DYGFSWVRQA PGQGLEWMGW ITAYNGNTNY    60
AQKLQGRVTM TTDTSTSTVY MELRSLRSDD TAVYYCARDY FYGMDVWGQG TTVTVSS    117

SEQ ID NO: 127          moltype = AA  length = 123
FEATURE                 Location/Qualifiers
REGION                  1..123
                        note = chemically synthesized
source                  1..123
                        mol_type = protein
                        organism = synthetic construct
SEQUENCE: 127
QVQLVQSGAE VKKPGSSVKV SCKTSGDTFS TYAISWVRQA PGQGLEWMGG IIPIFGKAHY    60
AQKFQGRVTI TADESTSTAY MELSSLRSED TAVYFCARKF HFVSGSPFGM DVWGQGTTVT  120
VSS                                                                123

SEQ ID NO: 128          moltype = AA  length = 112
FEATURE                 Location/Qualifiers
REGION                  1..112
                        note = chemically synthesized
source                  1..112
                        mol_type = protein
```

```
                        organism = synthetic construct
SEQUENCE: 128
QVQLVQSGAE VKKPGASVKV SCKASGYTFT SYDVHWVRQA PGQRLEWMGW LHADTGITKF    60
SQKFQGRVTI TRDTSASTAY MELSSLRSED TAVYYCARER IQLWFDYWGQ GT           112

SEQ ID NO: 129          moltype = AA   length = 120
FEATURE                 Location/Qualifiers
REGION                  1..120
                        note = chemically synthesized
source                  1..120
                        mol_type = protein
                        organism = synthetic construct
SEQUENCE: 129
QVQLVQSGAE VKKPGSSVKV SCKVSGGIFS TYAINWVRQA PGQGLEWMGG IIPIFGTANH    60
AQKFQGRVTI TADESTSTAY MELSSLRSED TAVYYCARDQ GIAAALFDYW GQGTLVTVSS   120

SEQ ID NO: 130          moltype = AA   length = 110
FEATURE                 Location/Qualifiers
REGION                  1..110
                        note = chemically synthesized
source                  1..110
                        mol_type = protein
                        organism = synthetic construct
SEQUENCE: 130
EVQLVESGGG LVQPGRSLRL SCAVSGFTFD DYVVHWVRQA PGKGLEWVSG NSGNIGYADS    60
VKGRFTISRD NAKNSLYLQM NSLRAEDTAL YYCAVPFDYW GQGTLVTVSS              110

SEQ ID NO: 131          moltype = AA   length = 123
FEATURE                 Location/Qualifiers
REGION                  1..123
                        note = chemically synthesized
source                  1..123
                        mol_type = protein
                        organism = synthetic construct
SEQUENCE: 131
QVQLVQSGAE VKKPGSSVKV SCKTSGDTFS SYAISWVRQA PGQGLEWMGG IIPIFGRAHY    60
AQKFQGRVTI TADESTSTAY MELSSLRSED TAVYFCARKF HFVSGSPFGM DVWGQGTTVT   120
VSS                                                                 123

SEQ ID NO: 132          moltype = AA   length = 123
FEATURE                 Location/Qualifiers
REGION                  1..123
                        note = chemically synthesized
source                  1..123
                        mol_type = protein
                        organism = synthetic construct
SEQUENCE: 132
QVQLVQSGAE VKKPGSSVKV SCKTSGGTFS SYAISWVRQA PGQGLEWMGG IIPIFGKAHY    60
AQKFQGRVTI TADESTTTAY MELSSLRSED TAVYYCARKY DYVSGSPFGM DVWGQGTTVT   120
VSS                                                                 123

SEQ ID NO: 133          moltype = AA   length = 121
FEATURE                 Location/Qualifiers
REGION                  1..121
                        note = chemically synthesized
source                  1..121
                        mol_type = protein
                        organism = synthetic construct
SEQUENCE: 133
QVQLVQSGAE VKKPGSSVKV SCKASGGTFS SYAINWVRQA PGQGLEWMGG IIPIFGSANY    60
AQKFQDRVTI TADESTSAAY MELSSLRSED TAVYYCARDS SGWSRYYMDV WGQGTTVTVS   120
S                                                                   121

SEQ ID NO: 134          moltype = AA   length = 123
FEATURE                 Location/Qualifiers
REGION                  1..123
                        note = chemically synthesized
source                  1..123
                        mol_type = protein
                        organism = synthetic construct
SEQUENCE: 134
QVQLVQSGAE VKEPGSSVKV SCKASGGTFN SYAISWVRQA PGQGLEWMGG IIPLFGIAHY    60
AQKFQGRVTI TADESTNTAY MDLSSLRSED TAVYYCARKY SYVSGSPFGM DVWGQGTTVT   120
VSS                                                                 123

SEQ ID NO: 135          moltype = AA   length = 121
FEATURE                 Location/Qualifiers
REGION                  1..121
                        note = chemically synthesized
```

```
source                  1..121
                        mol_type = protein
                        organism = synthetic construct
SEQUENCE: 135
EVQLVESGGG LVQPGRSLRL SCAASGITFD DYGMHWVRQA PGKGLEWVSG ISWNRGRIEY    60
ADSVKGRFTI SRDNAKNSLY LQMNSLRAED TALYYCAKGR FRYFDWFLDY WGQGTLVTVS   120
S                                                                   121

SEQ ID NO: 136          moltype = AA   length = 120
FEATURE                 Location/Qualifiers
REGION                  1..120
                        note = chemically synthesized
source                  1..120
                        mol_type = protein
                        organism = synthetic construct
SEQUENCE: 136
QMQLVQSGGG LVQPGGSLRL SCAASGFTFS SYWMSWVRQA PGKGLEWVAN IKQDGSEKYY    60
VDSVKGRFTI SRDNAKNSLY LQMNSLRAED TAVYYCARDY FWSGFSAFDI WGKGTLVTVS   120

SEQ ID NO: 137          moltype = AA   length = 107
FEATURE                 Location/Qualifiers
REGION                  1..107
                        note = chemically synthesized
source                  1..107
                        mol_type = protein
                        organism = synthetic construct
SEQUENCE: 137
EIVLTQSPAT LSLSPGERAT LSCRASQSVS SYLVWYQQKP GQAPRLLIYD ASNRATGIPA    60
RFSGSGSGTD FTLTISSLEP EDFAVYYCQQ RSNWPRTFGQ GTKVEIK                 107

SEQ ID NO: 138          moltype = AA   length = 106
FEATURE                 Location/Qualifiers
REGION                  1..106
                        note = chemically synthesized
source                  1..106
                        mol_type = protein
                        organism = synthetic construct
SEQUENCE: 138
EIVLTQSPAT LSLSPGERAT LSCRASQSVS SYLAWYQQKP GQAPRLLIYD ASNRATGIPA    60
RFSGSGSGTD FTLTISSLEP EDFAVYYCQQ RSNWPTFGQG TKVEIK                  106

SEQ ID NO: 139          moltype = AA   length = 107
FEATURE                 Location/Qualifiers
REGION                  1..107
                        note = chemically synthesized
source                  1..107
                        mol_type = protein
                        organism = synthetic construct
SEQUENCE: 139
DIQMTQSPSS LSASVGDRVT ITCRASQGIS SWLAWYQQKP EKAPKSLIYA ASSLQSGVPS    60
RFSGSGSGTD FTLTISSLQP EDFATYYCQQ YNSYPYTFGQ GTKLEIK                 107

SEQ ID NO: 140          moltype = AA   length = 108
FEATURE                 Location/Qualifiers
REGION                  1..108
                        note = chemically synthesized
source                  1..108
                        mol_type = protein
                        organism = synthetic construct
SEQUENCE: 140
EIVLTQSPGT LSLSPGERAT LSCRASQSVS SSYLAWYQQK PGQAPRLLIY GASSRATGIP    60
DRFSGSGSGT DFTLTISRLE PEDFAVYYCQ QYGSSPWTFG QGTKVEIK                108

SEQ ID NO: 141          moltype = AA   length = 106
FEATURE                 Location/Qualifiers
REGION                  1..106
                        note = chemically synthesized
source                  1..106
                        mol_type = protein
                        organism = synthetic construct
SEQUENCE: 141
EIVLTQSPGT LSLSPGERAT LSCRASQSVS SSYLAWYQQK PGQAPRLLIY GASSRATGIP    60
DRFSGSGSGT DFTLTISRLE PEDFAVYYCQ QYGSSPFGGG TKVEIK                  106

SEQ ID NO: 142          moltype = AA   length = 106
FEATURE                 Location/Qualifiers
REGION                  1..106
                        note = chemically synthesized
source                  1..106
```

```
                         mol_type = protein
                         organism = synthetic construct
SEQUENCE: 142
EIVLTQSPAT LSLSPGERAT LSCRASQSVS SYLAWYQQKP GQAPRLLIYD ASNRATGIPA    60
RFSGSGSGTD FTLTISSLEP EDFAVYYCQQ RSNWPTFGQG TRLEIK                  106

SEQ ID NO: 143           moltype = AA  length = 107
FEATURE                  Location/Qualifiers
REGION                   1..107
                         note = chemically synthesized
source                   1..107
                         mol_type = protein
                         organism = synthetic construct
SEQUENCE: 143
AIQLTQSPSS LSASVGDRVT ITCRASQGIS SALAWYQQKP GKAPKLLIYD ASSLESGVPS    60
RFSGSGSGTD FTLTISSLQP EDFATYYCQQ FNSYPFTFGP GTKVDIK                 107

SEQ ID NO: 144           moltype = AA  length = 107
FEATURE                  Location/Qualifiers
REGION                   1..107
                         note = chemically synthesized
source                   1..107
                         mol_type = protein
                         organism = synthetic construct
SEQUENCE: 144
DIVMTQSPST LSASVGDRVT ITCRASQGIS SWLAWYQQKP GRAPKVLIYK ASTLESGVPS    60
RFSGSGSGTD FTLTISSLQP EDFATYYCQQ SYSTPWTFGQ GTKLEIK                 107

SEQ ID NO: 145           moltype = AA  length = 121
FEATURE                  Location/Qualifiers
REGION                   1..121
                         note = chemically synthesized
source                   1..121
                         mol_type = protein
                         organism = synthetic construct
SEQUENCE: 145
EVQLVESGGG LVQPGGSLRL SCAASGFTFS RYWMSWVRQA PGKGLEWVAN IKQDGSEKYY    60
VDSVKGRFTI SRDNAKNSLY LQMNSLRAED TAVYYCAREG GWFGELAFDY WGQGTLVTVS   120
S                                                                  121

SEQ ID NO: 146           moltype = AA  length = 108
FEATURE                  Location/Qualifiers
REGION                   1..108
                         note = chemically synthesized
source                   1..108
                         mol_type = protein
                         organism = synthetic construct
SEQUENCE: 146
EIVLTQSPGT LSLSPGERAT LSCRASQRVS SSYLAWYQQK PGQAPRLLIY DASSRATGIP    60
DRFSGSGSGT DFTLTISRLE PEDFAVYYCQ QYGSLPWTFG QGTKVEIK                108

SEQ ID NO: 147           moltype = AA  length = 118
FEATURE                  Location/Qualifiers
REGION                   1..118
                         note = chemically synthesized
source                   1..118
                         mol_type = protein
                         organism = synthetic construct
SEQUENCE: 147
EVQLVESGGG LVQPGGSLRL SCAASGFTFS DSWIHWVRQA PGKGLEWVAW ISPYGGSTYY    60
ADSVKGRFTI SADTSKNTAY LQMNSLRAED TAVYYCARRH WPGGFDYWGQ GTLVTVSA    118

SEQ ID NO: 148           moltype = AA  length = 118
FEATURE                  Location/Qualifiers
REGION                   1..118
                         note = chemically synthesized
source                   1..118
                         mol_type = protein
                         organism = synthetic construct
SEQUENCE: 148
EVQLVESGGG LVQPGGSLRL SCAASGFTFS GSWIHWVRQA PGKGLEWVAW ILPYGGSSYY    60
ADSVKGRFTI SADTSKNTAY LQMNSLRAED TAVYYCARRH WPGGFDYWGQ GTLVTVSA    118

SEQ ID NO: 149           moltype = AA  length = 108
FEATURE                  Location/Qualifiers
REGION                   1..108
                         note = chemically synthesized
source                   1..108
                         mol_type = protein
```

```
                        organism = synthetic construct
SEQUENCE: 149
DIQMTQSPSS LSASVGDRVT ITCRASQDVS TAVAWYQQKP GKAPKLLIYS ASFLYSGVPS    60
RFSGSGSGTD FTLTISSLQP EDFATYYCQQ YLYHPATFGQ GTKVEIKR                108

SEQ ID NO: 150          moltype = AA   length = 108
FEATURE                 Location/Qualifiers
REGION                  1..108
                        note = chemically synthesized
source                  1..108
                        mol_type = protein
                        organism = synthetic construct
SEQUENCE: 150
DIQMTQSPSS LSASVGDRVT ITCRASQDVS TAVAWYQQKP GKAPKLLIYS ASFLYSGVPS    60
RFSGSGSGTD FTLTISSLQP EDFATYYCQQ YYNVPWTFGQ GTKVEIKR                108

SEQ ID NO: 151          moltype = AA   length = 108
FEATURE                 Location/Qualifiers
REGION                  1..108
                        note = chemically synthesized
source                  1..108
                        mol_type = protein
                        organism = synthetic construct
SEQUENCE: 151
DIQMTQSPSS LSASVGDRVT ITCRASQDVS TAVAWYQQKP GKAPKLLIYS ASFLYSGVPS    60
RFSGSGSGTD FTLTISSLQP EDFATYYCQQ YYAPPWTFGQ GTKVEIKR                108

SEQ ID NO: 152          moltype = AA   length = 108
FEATURE                 Location/Qualifiers
REGION                  1..108
                        note = chemically synthesized
source                  1..108
                        mol_type = protein
                        organism = synthetic construct
SEQUENCE: 152
DIQMTQSPSS LSASVGDRVT ITCRASQDVS TAVAWYQQKP GKAPKLLIYS ASFLYSGVPS    60
RFSGSGSGTD FTLTISSLQP EDFATYYCQQ YYTVPWTFGQ GTKVEIKR                108

SEQ ID NO: 153          moltype = AA   length = 108
FEATURE                 Location/Qualifiers
REGION                  1..108
                        note = chemically synthesized
source                  1..108
                        mol_type = protein
                        organism = synthetic construct
SEQUENCE: 153
DIQMTQSPSS LSASVGDRVT ITCRASQVIN TFLAWYQQKP GKAPKLLIYS ASTLASGVPS    60
RFSGSGSGTD FTLTISSLQP EDFATYYCQQ YYTVPRTFGQ GTKVEIKR                108

SEQ ID NO: 154          moltype = AA   length = 108
FEATURE                 Location/Qualifiers
REGION                  1..108
                        note = chemically synthesized
source                  1..108
                        mol_type = protein
                        organism = synthetic construct
SEQUENCE: 154
DIQMTQSPSS LSASVGDRVT ITCRASQDVS TAVAWYQQKP GKAPKLLIYS ASFLYSGVPS    60
RFSGSGSGTD FTLTISSLQP EDFATYYCQQ GYGVPRTFGQ GTKVEIKR                108

SEQ ID NO: 155          moltype = AA   length = 108
FEATURE                 Location/Qualifiers
REGION                  1..108
                        note = chemically synthesized
source                  1..108
                        mol_type = protein
                        organism = synthetic construct
SEQUENCE: 155
DIQMTQSPSS LSASVGDRVT ITCRASQDVS TAVAWYQQKP GKAPKLLIYS ASFLYSGVPS    60
RFSGSGSGTD FTLTISSLQP EDFATYYCQQ YLFTPPTFGQ GTKVEIKR                108

SEQ ID NO: 156          moltype = AA   length = 108
FEATURE                 Location/Qualifiers
REGION                  1..108
                        note = chemically synthesized
source                  1..108
                        mol_type = protein
                        organism = synthetic construct
SEQUENCE: 156
```

```
DIQMTQSPSS LSASVGDRVT ITCRASQDVS TAVAWYQQKP GKAPKLLIYS ASFLYSGVPS    60
RFSGSGSGTD FTLTISSLQP EDFATYYCQQ YFITPTTFGQ GTKVEIKR               108

SEQ ID NO: 157          moltype = AA   length = 108
FEATURE                 Location/Qualifiers
REGION                  1..108
                        note = chemically synthesized
source                  1..108
                        mol_type = protein
                        organism = synthetic construct
SEQUENCE: 157
DIQMTQSPSS LSASVGDRVT ITCRASQDVS TAVAWYQQKP GKAPKLLIYS ASFLYSGVPS    60
RFSGSGSGTD FTLTISSLQP EDFATYYCQQ YYYTPPTFGQ GTKVEIKR               108

SEQ ID NO: 158          moltype = AA   length = 108
FEATURE                 Location/Qualifiers
REGION                  1..108
                        note = chemically synthesized
source                  1..108
                        mol_type = protein
                        organism = synthetic construct
SEQUENCE: 158
DIQMTQSPSS LSASVGDRVT ITCRASQDVS TAVAWYQQKP GKAPKLLIYS ASFLYSGVPS    60
RFSGSGSGTD FTLTISSLQP EDFATYYCQQ FFYTPPTFGQ GTKVEIKR               108

SEQ ID NO: 159          moltype = AA   length = 108
FEATURE                 Location/Qualifiers
REGION                  1..108
                        note = chemically synthesized
source                  1..108
                        mol_type = protein
                        organism = synthetic construct
SEQUENCE: 159
DIQMTQSPSS LSASVGDRVT ITCRASQDVS TAVAWYQQKP GKAPKLLIYS ASFLYSGVPS    60
RFSGSGSGTD FTLTISSLQP EDFATYYCQQ SLFTPPTFGQ GTKVEIKR               108

SEQ ID NO: 160          moltype = AA   length = 108
FEATURE                 Location/Qualifiers
REGION                  1..108
                        note = chemically synthesized
source                  1..108
                        mol_type = protein
                        organism = synthetic construct
SEQUENCE: 160
DIQMTQSPSS LSASVGDRVT ITCRASQDVS TAVAWYQQKP GKAPKLLIYS ASFLYSGVPS    60
RFSGSGSGTD FTLTISSLQP EDFATYYCQQ SLYTPPTFGQ GTKVEIKR               108

SEQ ID NO: 161          moltype = AA   length = 108
FEATURE                 Location/Qualifiers
REGION                  1..108
                        note = chemically synthesized
source                  1..108
                        mol_type = protein
                        organism = synthetic construct
SEQUENCE: 161
DIQMTQSPSS LSASVGDRVT ITCRASQDVS TAVAWYQQKP GKAPKLLIYS ASFLYSGVPS    60
RFSGSGSGTD FTLTISSLQP EDFATYYCQQ SWYHPPTFGQ GTKVEIKR               108

SEQ ID NO: 162          moltype = AA   length = 108
FEATURE                 Location/Qualifiers
REGION                  1..108
                        note = chemically synthesized
source                  1..108
                        mol_type = protein
                        organism = synthetic construct
SEQUENCE: 162
DIQMTQSPSS LSASVGDRVT ITCRASQDVS TAVAWYQQKP GKAPKLLIYS ASFLYSGVPS    60
RFSGSGSGTD FTLTISSLQP EDFATYYCQQ YFYIPPTFGQ GTKVEIKR               108

SEQ ID NO: 163          moltype = AA   length = 108
FEATURE                 Location/Qualifiers
REGION                  1..108
                        note = chemically synthesized
source                  1..108
                        mol_type = protein
                        organism = synthetic construct
SEQUENCE: 163
DIQMTQSPSS LSASVGDRVT ITCRASQDVS TAVAWYQQKP GKAPKLLIYS ASFLYSGVPS    60
RFSGSGSGTD FTLTISSLQP EDFATYYCQQ YWYTPTTFGQ GTKVEIKR               108
```

```
SEQ ID NO: 164          moltype = AA  length = 108
FEATURE                 Location/Qualifiers
REGION                  1..108
                        note = chemically synthesized
source                  1..108
                        mol_type = protein
                        organism = synthetic construct
SEQUENCE: 164
DIQMTQSPSS LSASVGDRVT ITCRASQDVS TAVAWYQQKP GKAPKLLIYS ASFLYSGVPS    60
RFSGSGSGTD FTLTISSLQP EDFATYYCQQ SYFIPPTFGQ GTKVEIKR                 108

SEQ ID NO: 165          moltype = AA  length = 141
FEATURE                 Location/Qualifiers
REGION                  1..141
                        note = chemically synthesized
source                  1..141
                        mol_type = protein
                        organism = synthetic construct
SEQUENCE: 165
METGLRWLLL VAVLKGVQCL SVEESGGRLV TPGTPLTLTC TASGFTITNY HMFWVRQAPG    60
KGLEWIGVIT SSGIGSSSTT YYATWAKGRF TISKTSTTVN LRITSPTTED TATYFCARDY    120
FTNTYYALDI WGPGTLVTVS S                                              141

SEQ ID NO: 166          moltype = AA  length = 123
FEATURE                 Location/Qualifiers
REGION                  1..123
                        note = chemically synthesized
source                  1..123
                        mol_type = protein
                        organism = synthetic construct
SEQUENCE: 166
QVQLVQSGAE VKKPGSSVKV SCKTSGDTFS TYAISWVRQA PGQGLEWMGG IIPIFGKAHY    60
AQKFQGRVTI TADESTSTAY MELSSLRSED TAVYFCARKF HFVSGSPFGM DVWGQGTTVT    120
VSS                                                                  123

SEQ ID NO: 167          moltype = AA  length = 118
FEATURE                 Location/Qualifiers
REGION                  1..118
                        note = chemically synthesized
source                  1..118
                        mol_type = protein
                        organism = synthetic construct
SEQUENCE: 167
QVQLVQSGAE VKKPGASVKV SCKASGYTFT SYDVHWVRQA PGQRLEWMGW LHADTGITKF    60
SQKFQGRVTI TRDTSASTAY MELSSLRSED TAVYYCARER IQLWFDYWGQ GTLVTVSS      118

SEQ ID NO: 168          moltype = AA  length = 120
FEATURE                 Location/Qualifiers
REGION                  1..120
                        note = chemically synthesized
source                  1..120
                        mol_type = protein
                        organism = synthetic construct
SEQUENCE: 168
QVQLVQSGAE VKKPGSSVKV SCKVSGGIFS TYAINWVRQA PGQGLEWMGG IIPIFGTANH    60
AQKFQGRVTI TADESTSTAY MELSSLRSED TAVYYCARDQ GIAAALFDYW GQGTLVTVSS    120

SEQ ID NO: 169          moltype = AA  length = 113
FEATURE                 Location/Qualifiers
REGION                  1..113
                        note = chemically synthesized
source                  1..113
                        mol_type = protein
                        organism = synthetic construct
SEQUENCE: 169
EVQLVESGGG LVQPGRSLRL SCAVSGFTFD DYVVHWVRQA PGKGLEWVSG ISGNSGNIGY    60
ADSVKGRFTI SRDNAKNSLY LQMNSLRAED TALYYCAVPF DYWGQGTLVT VSS           113

SEQ ID NO: 170          moltype = AA  length = 123
FEATURE                 Location/Qualifiers
REGION                  1..123
                        note = chemically synthesized
source                  1..123
                        mol_type = protein
                        organism = synthetic construct
SEQUENCE: 170
QVQLVQSGAE VKKPGSSVKV SCKTSGDTFS SYAISWVRQA PGQGLEWMGG IIPIFGRAHY    60
AQKFQGRVTI TADESTSTAY MELSSLRSED TAVYFCARKF HFVSGSPFGM DVWGQGTTVT    120
```

```
VSS                                                                       123

SEQ ID NO: 171          moltype = AA  length = 123
FEATURE                 Location/Qualifiers
REGION                  1..123
                        note = chemically synthesized
source                  1..123
                        mol_type = protein
                        organism = synthetic construct
SEQUENCE: 171
QVQLVQSGAE VKKPGSSVKV SCKTSGGTFS SYAISWVRQA PGQGLEWMGG IIPIFGKAHY         60
AQKFQGRVTI TADESTTTAY MELSSLRSED TAVYYCARKY DYVSGSPFGM DVWGQGTTVT         120
VSS                                                                       123

SEQ ID NO: 172          moltype = AA  length = 121
FEATURE                 Location/Qualifiers
REGION                  1..121
                        note = chemically synthesized
source                  1..121
                        mol_type = protein
                        organism = synthetic construct
SEQUENCE: 172
QVQLVQSGAE VKKPGSSVKV SCKASGGTFS SYAINWVRQA PGQGLEWMGG IIPIFGSANY         60
AQKFQDRVTI TADESTSAAY MELSSLRSED TAVYYCARDS SGWSRYYMDV WGQGTTVTVS         120
S                                                                         121

SEQ ID NO: 173          moltype = AA  length = 123
FEATURE                 Location/Qualifiers
REGION                  1..123
                        note = chemically synthesized
source                  1..123
                        mol_type = protein
                        organism = synthetic construct
SEQUENCE: 173
QVQLVQSGAE VKEPGSSVKV SCKASGGTFN SYAISWVRQA PGQGLEWMGG IIPLFGIAHY         60
AQKFQGRVTI TADESTNTAY MDLSSLRSED TAVYYCARKY SYVSGSPFGM DVWGQGTTVT         120
VSS                                                                       123

SEQ ID NO: 174          moltype = AA  length = 121
FEATURE                 Location/Qualifiers
REGION                  1..121
                        note = chemically synthesized
source                  1..121
                        mol_type = protein
                        organism = synthetic construct
SEQUENCE: 174
EVQLVESGGG LVQPGRSLRL SCAASGITFD DYGMHWVRQA PGKGLEWVSG ISWNRGRIEY         60
ADSVKGRFTI SRDNAKNSLY LQMNSLRAED TALYYCAKGR FRYFDWFLDY WGQGTLVTVS         120
S                                                                         121

SEQ ID NO: 175          moltype = AA  length = 116
FEATURE                 Location/Qualifiers
REGION                  1..116
                        note = chemically synthesized
source                  1..116
                        mol_type = protein
                        organism = synthetic construct
SEQUENCE: 175
MDTRAPTQLL GLLLLWLPGA RCALVMTQTP SSTSTAVGGT VTIKCQASQS ISVYLAWYQQ         60
KPGQPPKLLI YSASTLASGV PSRFKGSRSG TEYTLTISGV QREDAATYYC LGSAGS            116

SEQ ID NO: 176          moltype = AA  length = 107
FEATURE                 Location/Qualifiers
REGION                  1..107
                        note = chemically synthesized
source                  1..107
                        mol_type = protein
                        organism = synthetic construct
SEQUENCE: 176
EIVLTQSPAT LSLSPGERAT LSCRASQSVS SYLVWYQQKP GQAPRLLIYD ASNRATGIPA         60
RFSGSGSGTD FTLTISSLEP EDFAVYYCQQ RSNWPRTFGQ GTKVEIK                      107

SEQ ID NO: 177          moltype = AA  length = 106
FEATURE                 Location/Qualifiers
REGION                  1..106
                        note = chemically synthesized
source                  1..106
                        mol_type = protein
                        organism = synthetic construct
```

```
SEQUENCE: 177
EIVLTQSPAT LSLSPGERAT LSCRASQSVS SYLAWYQQKP GQAPRLLIYD ASNRATGIPA    60
RFSGSGSGTD FTLTISSLEP EDFAVYYCQQ RSNWPTFGQG TKVEIK                  106

SEQ ID NO: 178           moltype = AA   length = 107
FEATURE                  Location/Qualifiers
REGION                   1..107
                         note = chemically synthesized
source                   1..107
                         mol_type = protein
                         organism = synthetic construct
SEQUENCE: 178
DIQMTQSPSS LSASVGDRVT ITCRASQGIS SWLAWYQQKP EKAPKSLIYA ASSLQSGVPS    60
RFSGSGSGTD FTLTISSLQP EDFATYYCQQ YNSYPYTFGQ GTKLEIK                 107

SEQ ID NO: 179           moltype = AA   length = 108
FEATURE                  Location/Qualifiers
REGION                   1..108
                         note = chemically synthesized
source                   1..108
                         mol_type = protein
                         organism = synthetic construct
SEQUENCE: 179
EIVLTQSPGT LSLSPGERAT LSCRASQSVS SSYLAWYQQK PGQAPRLLIY GASSRATGIP    60
DRFSGSGSGT DFTLTISRLE PEDFAVYYCQ QYGSSPWTFG QGTKVEIK                108

SEQ ID NO: 180           moltype = AA   length = 106
FEATURE                  Location/Qualifiers
REGION                   1..106
                         note = chemically synthesized
source                   1..106
                         mol_type = protein
                         organism = synthetic construct
SEQUENCE: 180
EIVLTQSPGT LSLSPGERAT LSCRASQSVS SSYLAWYQQK PGQAPRLLIY GASSRATGIP    60
DRFSGSGSGT DFTLTISRLE PEDFAVYYCQ QYGSSPFGGG TKVEIK                  106

SEQ ID NO: 181           moltype = AA   length = 106
FEATURE                  Location/Qualifiers
REGION                   1..106
                         note = chemically synthesized
source                   1..106
                         mol_type = protein
                         organism = synthetic construct
SEQUENCE: 181
EIVLTQSPAT LSLSPGERAT LSCRASQSVS SYLAWYQQKP GQAPRLLIYD ASNRATGIPA    60
RFSGSGSGTD FTLTISSLEP EDFAVYYCQQ RSNWPTFGQG TRLEIK                  106

SEQ ID NO: 182           moltype = AA   length = 107
FEATURE                  Location/Qualifiers
REGION                   1..107
                         note = chemically synthesized
source                   1..107
                         mol_type = protein
                         organism = synthetic construct
SEQUENCE: 182
AIQLTQSPSS LSASVGDRVT ITCRASQGIS SALAWYQQKP GKAPKLLIYD ASSLESGVPS    60
RFSGSGSGTD FTLTISSLQP EDFATYYCQQ FNSYPFTFGP GTKVDIK                 107

SEQ ID NO: 183           moltype = AA   length = 120
FEATURE                  Location/Qualifiers
REGION                   1..120
                         note = chemically synthesized
source                   1..120
                         mol_type = protein
                         organism = synthetic construct
SEQUENCE: 183
EVQLLESGGG LVQPGGSLRL SCAASGFTFS SYIMMWVRQA PGKGLEWVSS IYPSGGITFY    60
ADTVKGRFTI SRDNSKNTLY LQMNSLRAED TAVYYCARIK LGTVTTVDYW GQGTLVTVSS  120

SEQ ID NO: 184           moltype = AA   length = 110
FEATURE                  Location/Qualifiers
REGION                   1..110
                         note = chemically synthesized
source                   1..110
                         mol_type = protein
                         organism = synthetic construct
SEQUENCE: 184
QSALTQPASV SGSPGQSITI SCTGTSSDVG GYNYVSWYQQ HPGKAPKLMI YDVSNRPSGV    60
```

```
SNRFSGSKSG NTASLTISGL QAEDEADYYC SSYTSSSTRV FGTGTKVTVL            110

SEQ ID NO: 185          moltype = AA   length = 118
FEATURE                 Location/Qualifiers
REGION                  1..118
                        note = chemically synthesized
source                  1..118
                        mol_type = protein
                        organism = synthetic construct
SEQUENCE: 185
EVKLQESGPS LVKPSQTLSL TCSVTGYSIT SDYWNWIRKF PGNKLEYVGY ISYTGSTYYN   60
PSLKSRISIT RDTSKNQYYL QLNSVTSEDT ATYYCARYGG WLSPFDYWGQ GTTLTVSS    118

SEQ ID NO: 186          moltype = AA   length = 120
FEATURE                 Location/Qualifiers
REGION                  1..120
                        note = chemically synthesized
source                  1..120
                        mol_type = protein
                        organism = synthetic construct
SEQUENCE: 186
EVQLQESGPG LVAPSQSLSI TCTVSGFSLT TYSINWIRQP PGKGLEWLGV MWAGGGTNSN   60
SVLKSRLIIS KDNSKSQVFL KMNSLQTDDT ARYYCARYYG NSPYYAIDYW GQGTSVTVSS  120

SEQ ID NO: 187          moltype = AA   length = 118
FEATURE                 Location/Qualifiers
REGION                  1..118
                        note = chemically synthesized
source                  1..118
                        mol_type = protein
                        organism = synthetic construct
SEQUENCE: 187
EVKLQESGPS LVKPSQTLSL TCSVTGYSII SDYWNWIRKF PGNKLEYLGY ISYTGSTYYN   60
PSLKSRISIT RDTSKNQYYL QLNSVTTEDT ATYYCARRGG WLLPFDYWGQ GTTLTVSS    118

SEQ ID NO: 188          moltype = AA   length = 118
FEATURE                 Location/Qualifiers
REGION                  1..118
                        note = chemically synthesized
source                  1..118
                        mol_type = protein
                        organism = synthetic construct
SEQUENCE: 188
EVKLQESGPS LVKPGASVKL SCKASGYTFT SYDINWVKQR PGQGLEWIGW IFPRDNNTKY   60
NENFKGKATL TVDTSSTTAY MELHSLTSED SAVYFCTKEN WVGDFDYWGQ GTTLTLSS    118

SEQ ID NO: 189          moltype = AA   length = 114
FEATURE                 Location/Qualifiers
REGION                  1..114
                        note = chemically synthesized
source                  1..114
                        mol_type = protein
                        organism = synthetic construct
SEQUENCE: 189
EVQLQQSGPD LVTPGASVRI SCQASGYTFP DYYMNWVKQS HGKSLEWIGD IDPNYGGTTY   60
NQKFKGKAIL TVDRSSTAY MELRSLTSED SAVYYCARGA LTDWGQGTSL TVSS         114

SEQ ID NO: 190          moltype = AA   length = 106
FEATURE                 Location/Qualifiers
REGION                  1..106
                        note = chemically synthesized
source                  1..106
                        mol_type = protein
                        organism = synthetic construct
SEQUENCE: 190
EIVLTQSPAT LSLSPGERAT LSCRASSSVS YIYWFQQKPG QSPRPLIYAA FNRATGIPAR   60
FSGSGSGTDY TLTISSLEPE DFAVYYCQQW SNNPLTFGQG TKVEIK                 106

SEQ ID NO: 191          moltype = AA   length = 114
FEATURE                 Location/Qualifiers
REGION                  1..114
                        note = chemically synthesized
source                  1..114
                        mol_type = protein
                        organism = synthetic construct
SEQUENCE: 191
QVQLVQSGAE VKKPGASVKV SCKASGYTFP DYYMNWVRQA PGQGLEWMGD IDPNYGGTNY   60
AQKFQGRVTM TRDTSISTAY MELSRLRSDD TAVYYCARGA LTDWGQGTMV TVSS        114
```

```
SEQ ID NO: 192            moltype = AA   length = 114
FEATURE                   Location/Qualifiers
REGION                    1..114
                          note = chemically synthesized
source                    1..114
                          mol_type = protein
                          organism = synthetic construct
SEQUENCE: 192
QVQLVQSGAE VKKPGASVKV SCKASGYTFP DYYMNWVRQA PGQSLEWMGD IDPNYGGTNY    60
NQKFQGRVTM TRDTSISTAY MELSRLRSDD TAVYYCARGA LTDWGQGTMV TVSS         114

SEQ ID NO: 193            moltype = AA   length = 114
FEATURE                   Location/Qualifiers
REGION                    1..114
                          note = chemically synthesized
source                    1..114
                          mol_type = protein
                          organism = synthetic construct
SEQUENCE: 193
EVQLVQSGAE VKKPGASVKV SCKASGYTFP DYYMNWVRQA PGQSLEWMGD IDPNYGGTNY    60
NQKFQGRVTM TVDRSSSTAY MELSRLRSDD TAVYYCARGA LTDWGQGTMV TVSS         114

SEQ ID NO: 194            moltype = AA   length = 114
FEATURE                   Location/Qualifiers
REGION                    1..114
                          note = chemically synthesized
source                    1..114
                          mol_type = protein
                          organism = synthetic construct
SEQUENCE: 194
EVQLVESGGG LVQPGRSLRL SCTASGYTFP DYYMNWVRQA PGKGLEWVGD IDPNYGGTTY    60
AASVKGRFTI SVDRSKSIAY LQMSSLKTED TAVYYCTRGA LTDWGQGTMV TVSS         114

SEQ ID NO: 195            moltype = AA   length = 114
FEATURE                   Location/Qualifiers
REGION                    1..114
                          note = chemically synthesized
source                    1..114
                          mol_type = protein
                          organism = synthetic construct
SEQUENCE: 195
EVQLVESGGG LVQPGRSLRL SCTASGYTFP DYYMNWVRQA PGKGLEWVGD IDPNYGGTTY    60
NASVKGRFTI SVDRSKSIAY LQMSSLKTED TAVYYCARGA LTDWGQGTMV TVSS         114

SEQ ID NO: 196            moltype = AA   length = 107
FEATURE                   Location/Qualifiers
REGION                    1..107
                          note = chemically synthesized
source                    1..107
                          mol_type = protein
                          organism = synthetic construct
SEQUENCE: 196
DIVMTQSHKL MSTSVGDRVS ITCKASQDVG TAVAWYQQKP GQSPKLLIYW ASTRHTGVPD    60
RFTGSGSGTD FTLTISNVQS EDLADYFCQQ DSSYPLTFGA GTKVELK                107

SEQ ID NO: 197            moltype = AA   length = 107
FEATURE                   Location/Qualifiers
REGION                    1..107
                          note = chemically synthesized
source                    1..107
                          mol_type = protein
                          organism = synthetic construct
SEQUENCE: 197
DIVTTQSHKL MSTSVGDRVS ITCKASQDVG TAVAWYQQKP GQSPKLLIYW ASTRHTGVPD    60
RFTGSGSGTD FTLTISNVQS EDLADYFCQQ DSSYPLTFGA GTKVELK                107

SEQ ID NO: 198            moltype = AA   length = 113
FEATURE                   Location/Qualifiers
REGION                    1..113
                          note = chemically synthesized
source                    1..113
                          mol_type = protein
                          organism = synthetic construct
SEQUENCE: 198
DIVMTQSPSS LAVSVGEKVS MGCKSSQSLL YSSNQKNSLA WYQQKPGQSP KLLIDWASTR    60
ESGVPDRFTG SGSGTDFTLT ISSVKAEDLA VYYCQQYYGY PLTFGAGTKL ELK         113

SEQ ID NO: 199            moltype = AA   length = 106
FEATURE                   Location/Qualifiers
```

```
REGION                      1..106
                            note = chemically synthesized
source                      1..106
                            mol_type = protein
                            organism = synthetic construct
SEQUENCE: 199
DIVMTQSPAI MSASPGEKVT MTCSASSSIR YMHWYQQKPG TSPKRWISDT SKLTSGVPAR    60
FSGSGSGTSY ALTISSMEAE DAATYYCHQR SSYPWTFGGG TKLEIK                 106

SEQ ID NO: 200              moltype = AA   length = 106
FEATURE                     Location/Qualifiers
REGION                      1..106
                            note = chemically synthesized
source                      1..106
                            mol_type = protein
                            organism = synthetic construct
SEQUENCE: 200
QIVLSQSPAI LSASPGEKVT MTCRASSSVS YIYWFQQKPG SSPKPWIYAT FNLASGVPAR    60
FSGSGSGTSY SLTISRVETE DAATYYCQQW SNNPLTFGAG TKLELK                 106

SEQ ID NO: 201              moltype = AA   length = 106
FEATURE                     Location/Qualifiers
REGION                      1..106
                            note = chemically synthesized
source                      1..106
                            mol_type = protein
                            organism = synthetic construct
SEQUENCE: 201
EIVLTQSPAT LSLSPGERAT LSCRASSSVS YIYWFQQKPG QAPRLLIYAA FNRATGIPAR    60
FSGSGSGTDY TLTISSLEPE DFAVYYCQQW SNNPLTFGQG TKVEIK                 106

SEQ ID NO: 202              moltype = AA   length = 106
FEATURE                     Location/Qualifiers
REGION                      1..106
                            note = chemically synthesized
source                      1..106
                            mol_type = protein
                            organism = synthetic construct
SEQUENCE: 202
QIVLTQSPAT LSLSPGERAT LSCRASSSVS YIYWFQQKPG QSPRPLIYAT FNLASGIPAR    60
FSGSGSGTSY TLTISRLEPE DFAVYYCQQW SNNPLTFGQG TKVEIK                 106

SEQ ID NO: 203              moltype = AA   length = 106
FEATURE                     Location/Qualifiers
REGION                      1..106
                            note = chemically synthesized
source                      1..106
                            mol_type = protein
                            organism = synthetic construct
SEQUENCE: 203
DIQLTQSPSS LSASVGDRVT ITCRASSGVS YIYWFQQKPG KAPKLLIYAA FNLASGVPSR    60
FSGSGSGTEY TLTISSLQPE DFATYYCQQW SNNPLTFGQG TKVEIK                 106

SEQ ID NO: 204              moltype = AA   length = 106
FEATURE                     Location/Qualifiers
REGION                      1..106
                            note = chemically synthesized
source                      1..106
                            mol_type = protein
                            organism = synthetic construct
SEQUENCE: 204
DIQLTQSPSS LSASVGDRVT ITCRASSGVS YIYWFQQKPG KAPKPLIYAA FNLASGVPSR    60
FSGSGSGTEY TLTISSLQPE DFATYYCQQW SNNPLTFGQG TKVEIK                 106

SEQ ID NO: 205              moltype = AA   length = 106
FEATURE                     Location/Qualifiers
REGION                      1..106
                            note = chemically synthesized
source                      1..106
                            mol_type = protein
                            organism = synthetic construct
SEQUENCE: 205
DIQLTQSPSI LSASVGDRVT ITCRASSSVS YIYWFQQKPG KAPKPLIYAT FNLASGVPSR    60
FSGSGSGTSY TLTISSLQPE DFATYYCQQW SNNPLTFGQG TKVEIK                 106

SEQ ID NO: 206              moltype = AA   length = 124
FEATURE                     Location/Qualifiers
REGION                      1..124
                            note = chemically synthesized
```

```
source                  1..124
                        mol_type = protein
                        organism = synthetic construct
SEQUENCE: 206
QVQLVQSGAE VKKPGASVKV SCKASGYTFT SYGISWVRQA PGQGLEWMGW ISAYNGNTNY    60
AQKLQGRVTM TTDTSTSTAY MELRSLRSDD TAVYYCARAL PSGTILVGGW FDPWGQGTLV   120
TVSS                                                                124

SEQ ID NO: 207          moltype = AA   length = 124
FEATURE                 Location/Qualifiers
REGION                  1..124
                        note = chemically synthesized
source                  1..124
                        mol_type = protein
                        organism = synthetic construct
SEQUENCE: 207
EVQLVQSGGG VVQPGRSLRL SCAASGFTFS SYALSWVRQA PGKGLEWVSA ISGGGGSTYY    60
ADSVKGRFTI SRDNSKNTLY LQMNSLRAED TAVYYCAKDV FPETFSMNYG MDVWGQGTLV   120
TVSS                                                                124

SEQ ID NO: 208          moltype = AA   length = 128
FEATURE                 Location/Qualifiers
REGION                  1..128
                        note = chemically synthesized
source                  1..128
                        mol_type = protein
                        organism = synthetic construct
SEQUENCE: 208
QVQLVQSGGG VVQPGGSLRL SCAASGFTFD DYAMHWVRQA PGKGLEWVSL ISGDGGSTYY    60
ADSVKGRFTI SRDNSKNSLY LQMNSLRTED TALYYCAKVL LPCSSTSCYG SVGAFDIWGQ   120
GTTVTVSS                                                            128

SEQ ID NO: 209          moltype = AA   length = 117
FEATURE                 Location/Qualifiers
REGION                  1..117
                        note = chemically synthesized
source                  1..117
                        mol_type = protein
                        organism = synthetic construct
SEQUENCE: 209
QVQLVQSGGS VVRPGESLRL SCVASGFIFD NYDMSWVRQV PGKGLEWVSR VNWNGGSTTY    60
ADAVKGRFTI SRDNTKNSLY LQMNNLRAED TAVYYCVREF VGAYDLWGQG TTVTVSS      117

SEQ ID NO: 210          moltype = AA   length = 121
FEATURE                 Location/Qualifiers
REGION                  1..121
                        note = chemically synthesized
source                  1..121
                        mol_type = protein
                        organism = synthetic construct
SEQUENCE: 210
QVQLVQSGAE VKKPGATVKV SCKVFGDTFR GLYIHWVRQA PGQGLEWMGG IIPIFGTANY    60
AQKFQGRVTI TTDESTSTAY MELSSLRSED TAVYYCASGL RWGIWGWFDP WGQGTLVTVS   120
S                                                                   121

SEQ ID NO: 211          moltype = AA   length = 121
FEATURE                 Location/Qualifiers
REGION                  1..121
                        note = chemically synthesized
source                  1..121
                        mol_type = protein
                        organism = synthetic construct
SEQUENCE: 211
EVQLVQSGAE LKKPGSSVKV SCKAFGGTFS DNAISWVRQA PGQGPEWMGG IIPIFGKPNY    60
AQKFQGRVTI TADESTSTAY MVLSSLRSED TAVYYCARTM VRGFLGVMDV WGQGTTVTVS   120
S                                                                   121

SEQ ID NO: 212          moltype = AA   length = 125
FEATURE                 Location/Qualifiers
REGION                  1..125
                        note = chemically synthesized
source                  1..125
                        mol_type = protein
                        organism = synthetic construct
SEQUENCE: 212
QVQLVQSGGG LVQPGGSLRL SCAASGFTFS SYAMSWVRQA PGKGLEWVSA ISGSGGSTYY    60
ADSVKGRFTI SRDNSKNTLY LQMNSLRAED TAVYYCAKDQ FVTIFGVPRY GMDVWGQGTT   120
VTVSS                                                               125
```

```
SEQ ID NO: 213            moltype = AA   length = 120
FEATURE                   Location/Qualifiers
REGION                    1..120
                          note = chemically synthesized
source                    1..120
                          mol_type = protein
                          organism = synthetic construct
SEQUENCE: 213
QVQLVQSGAE VKKPGSSVKV SCKASGGTFS SYAISWVRQA PGQGLEWMGG IIPIFGTANY     60
AQKFQGRVTI TADKSTSTAY MELSSLRSED TAVYYCARGR QMFGAGIDFW GPGTLVTVSS    120

SEQ ID NO: 214            moltype = AA   length = 118
FEATURE                   Location/Qualifiers
REGION                    1..118
                          note = chemically synthesized
source                    1..118
                          mol_type = protein
                          organism = synthetic construct
SEQUENCE: 214
EVQLVESGAE VKKPGSSVKV SCKVSGGTFG TYALNWVRQA PGQGLEWMGR IVPLIGLVNY     60
AHNFEGRISI TADKSTGTAY MELSNLRSDD TAVYYCAREV YGGNSDYWGQ GTLVTVSS      118

SEQ ID NO: 215            moltype = AA   length = 120
FEATURE                   Location/Qualifiers
REGION                    1..120
                          note = chemically synthesized
source                    1..120
                          mol_type = protein
                          organism = synthetic construct
SEQUENCE: 215
QVQLVQSGGE VKKPGASVKV SCKASGYTLS SHGITWVRQA PGQGLEWMGW ISAHNGHASN     60
AQKVEDRVTM TTDTSTNTAY MELRSLTADD TAVYYCARVH AALYYGMDVW GQGTLVTVSS    120

SEQ ID NO: 216            moltype = AA   length = 121
FEATURE                   Location/Qualifiers
REGION                    1..121
                          note = chemically synthesized
source                    1..121
                          mol_type = protein
                          organism = synthetic construct
SEQUENCE: 216
QVQLQESGGG VVQPGRSLRL SCSASGFTFS RHGMHWVRQA PGKGLEWVAV ISHDGSVKYY     60
ADSMKGRFSI SRDNSNNTLY LQMDSLRADD TAVYYCARGL SYQVSGWFDP WGQGTLVTVS    120
S                                                                   121

SEQ ID NO: 217            moltype = AA   length = 110
FEATURE                   Location/Qualifiers
REGION                    1..110
                          note = chemically synthesized
source                    1..110
                          mol_type = protein
                          organism = synthetic construct
SEQUENCE: 217
NFMLTQPHSV SESPGKTVTI SCTRSSGSIA SNYVQWYQQR PGSSPTTVIY EDNQRPSGVP     60
DRFSGSIDTS SNSASLTISG LKTKDEADYY CQSYDGITVI FGGGTKLTVL              110

SEQ ID NO: 218            moltype = AA   length = 111
FEATURE                   Location/Qualifiers
REGION                    1..111
                          note = chemically synthesized
source                    1..111
                          mol_type = protein
                          organism = synthetic construct
SEQUENCE: 218
NFMLTQPHSV SGSPGKTVTL PCTRSSGSIA SHYVQWYQQR PGSAPTTVIY EDNKRPSGVP     60
DRFSGSIDSS SNSASLSISG LKTEDEADYY CQSYDSSNRW VFGGGTKLTV L             111

SEQ ID NO: 219            moltype = AA   length = 115
FEATURE                   Location/Qualifiers
REGION                    1..115
                          note = chemically synthesized
source                    1..115
                          mol_type = protein
                          organism = synthetic construct
SEQUENCE: 219
LPVLTQPASL SASPGASASL TCTLRSGLNV GSYRIYWYQQ KPGSRPQYLL NYKSDSNKQQ     60
ASGVPSRFSG SKDASANAGI LLISGLQSED EADYYCMIWY SSAVFGGGT KLTVL          115

SEQ ID NO: 220            moltype = AA   length = 111
```

```
                            -continued

FEATURE              Location/Qualifiers
REGION               1..111
                     note = chemically synthesized
source               1..111
                     mol_type = protein
                     organism = synthetic construct
SEQUENCE: 220
NFMLTQPHSV SESPGKTVTI SCTRSSGNIA SNYVQWYQQR PGSAPTTVIY EDNQRPSGVP    60
DRFSGSIDSS NSASLTISG LKTEDEADYY CQSYDSSNLW VFGGGTKLTV L             111

SEQ ID NO: 221       moltype = AA   length = 108
FEATURE              Location/Qualifiers
REGION               1..108
                     note = chemically synthesized
source               1..108
                     mol_type = protein
                     organism = synthetic construct
SEQUENCE: 221
SSELTQDPAV SVALGQTVRI TCQGDSLRSY YASWYQQKPG QAPVLVIYGK NNRPSGIPDR    60
FSGSSSGNTA SLTITGAQAE DEADYYCNSR DSSGNHYVFG TGTKVTVL               108

SEQ ID NO: 222       moltype = AA   length = 108
FEATURE              Location/Qualifiers
REGION               1..108
                     note = chemically synthesized
source               1..108
                     mol_type = protein
                     organism = synthetic construct
SEQUENCE: 222
LPVLTQAPSV SVAPGKTARI TCGGSDIGRK SVHWYQQKPG QAPALVIYSD RDRPSGISER    60
FSGSNSGNTA TLTISRVEAG DEADYYCQVW DNNSDHYVFG AGTELIVL               108

SEQ ID NO: 223       moltype = AA   length = 109
FEATURE              Location/Qualifiers
REGION               1..109
                     note = chemically synthesized
source               1..109
                     mol_type = protein
                     organism = synthetic construct
SEQUENCE: 223
QSALTQPASV SGSPGQSITI SCTGTSSDVG GYNYVSWYQQ HPGKAPKLMI YDVSNRPSGV    60
SNRFSGSKSG NTASLTISGL QAEDEADYYC SSYTSSTLPF GGGTKLTVL              109

SEQ ID NO: 224       moltype = AA   length = 107
FEATURE              Location/Qualifiers
REGION               1..107
                     note = chemically synthesized
source               1..107
                     mol_type = protein
                     organism = synthetic construct
SEQUENCE: 224
EIVLTQSPAT LSLSPGERAT LSCRASQSIG NSLAWYQQKP GQAPRLLMYG ASSRATGIPD    60
RFSGSGAGTD FTLTISSLEP EDFATYYCQQ HTIPTFSFGP GTKVEVK                107

SEQ ID NO: 225       moltype = AA   length = 107
FEATURE              Location/Qualifiers
REGION               1..107
                     note = chemically synthesized
source               1..107
                     mol_type = protein
                     organism = synthetic construct
SEQUENCE: 225
DIVMTQTPSF LSASIGDRVT ITCRASQGIG SYLAWYQQRP GEAPKLLIYA ASTLQSGVPS    60
RFSGSGSGTD FTLTISNLQP EDFATYYCQQ LNNYPITFGQ GTRLEIK                107

SEQ ID NO: 226       moltype = AA   length = 105
FEATURE              Location/Qualifiers
REGION               1..105
                     note = chemically synthesized
source               1..105
                     mol_type = protein
                     organism = synthetic construct
SEQUENCE: 226
QSALTQPPSV SVSPGQTANI PCSGDKLGNK YAYWYQQKPG QSPVLLIYQD IKRPSRIPER    60
FSGSNSADTA TLTISGTQAM DEADYYCQTW DNSVVFGGGT KLTVL                  105

SEQ ID NO: 227       moltype = AA   length = 112
FEATURE              Location/Qualifiers
REGION               1..112
```

|  |  |
|---|---|
| | note = chemically synthesized |
| source | 1..112 |
| | mol_type = protein |
| | organism = synthetic construct |

SEQUENCE: 227
NFMLTQPHSV SESPGKTVTI SCTRSSGSID SNYVQWYQQR PGSAPTTVIY EDNQRPSGVP   60
DRFSGSIDSS SNSASLTISG LKTEDEADYY CQSYDSNNRH VIFGGGTKLT VL           112

| SEQ ID NO: 228 | moltype = AA length = 110 |
|---|---|
| FEATURE | Location/Qualifiers |
| REGION | 1..110 |
| | note = chemically synthesized |
| source | 1..110 |
| | mol_type = protein |
| | organism = synthetic construct |

SEQUENCE: 228
NFMLTQPHSV SESPGKTVTI SCTRSSGNIG TNYVQWYQQR PGSAPVALIY EDYRRPSGVP   60
DRFSGSIDSS SNSASLIISG LKPEDEADYY CQSYHSSGWE FGGGTKLTVL             110

| SEQ ID NO: 229 | moltype = AA length = 108 |
|---|---|
| FEATURE | Location/Qualifiers |
| REGION | 1..108 |
| | note = chemically synthesized |
| source | 1..108 |
| | mol_type = protein |
| | organism = synthetic construct |

SEQUENCE: 229
QSVLTQPPSV SVAPGQTARI TCGGNNIGSK GVHWYQQKPG QAPVLVVYDD SDRPSGIPER   60
FSGSNSGNTA TLTISRVEAG DEADYYCQVW DSSSDHWVFG GGTKLTVL               108

| SEQ ID NO: 230 | moltype = AA length = 111 |
|---|---|
| FEATURE | Location/Qualifiers |
| REGION | 1..111 |
| | note = chemically synthesized |
| source | 1..111 |
| | mol_type = protein |
| | organism = synthetic construct |

SEQUENCE: 230
NFMLTQPHSV SESPGKTVTI SCTRSSGSIA SNYVQWYQQR PGSAPTTVIY EDNQRPSGVP   60
DRFSGSIDSS SNSASLTISG LKTEDEADYY CQSYDSTTPS VFGGGTKLTV L           111

| SEQ ID NO: 231 | moltype = AA length = 120 |
|---|---|
| FEATURE | Location/Qualifiers |
| REGION | 1..120 |
| | note = chemically synthesized |
| source | 1..120 |
| | mol_type = protein |
| | organism = synthetic construct |

SEQUENCE: 231
QVQLVQSGAE VKKPGASVKV SCKASGYTFT SYGISWVRQA PGQGLEWMGW TSPHNGLTAF   60
AQILEGRVTM TTDTSTNTAY MELRNLTFDD TAVYFCAKVH PVFSYALDVW GQGTLVTVSS   120

| SEQ ID NO: 232 | moltype = AA length = 118 |
|---|---|
| FEATURE | Location/Qualifiers |
| REGION | 1..118 |
| | note = chemically synthesized |
| source | 1..118 |
| | mol_type = protein |
| | organism = synthetic construct |

SEQUENCE: 232
EVQLVESGAE VMNPGSSVRV SCRGSGGDFS TYAFSWVRQA PGQGLEWMGR IIPILGIANY   60
AQKFQGRVTI TADKSTSTAY MELSSLRSDD TAVYYCARDG YGSDPVLWGQ GTLVTVSS     118

| SEQ ID NO: 233 | moltype = AA length = 118 |
|---|---|
| FEATURE | Location/Qualifiers |
| REGION | 1..118 |
| | note = chemically synthesized |
| source | 1..118 |
| | mol_type = protein |
| | organism = synthetic construct |

SEQUENCE: 233
EVQLVQSGAE VKKPGASVKV SCKASGYTFT NYGISWVRQA PGQGLEWMGW ISAYNGNTNY   60
AQKVQGRVTM TTDTSTSTGY MELRSLRSDD TAVYYCARGD FRKPFDYWGQ GTLVTVSS     118

| SEQ ID NO: 234 | moltype = AA length = 115 |
|---|---|
| FEATURE | Location/Qualifiers |
| REGION | 1..115 |
| | note = chemically synthesized |
| source | 1..115 |

```
                              mol_type = protein
                              organism = synthetic construct
SEQUENCE: 234
EVQLVQSGPE LKKPGASVKM SCKASGYTFT SYVMHWVKQA PGQRLEWIGY VNPFNDGTKY    60
NEMFKGRATL TSDKSTSTAY MELSSLRSED SAVYYCARQA WGYPWGQGTL VTVSS        115

SEQ ID NO: 235          moltype = AA  length = 115
FEATURE                 Location/Qualifiers
REGION                  1..115
                        note = chemically synthesized
source                  1..115
                        mol_type = protein
                        organism = synthetic construct
SEQUENCE: 235
EVQLVQSGAE VKKPGASVKM SCKASGYTFT SYVMHWVKQA PGQRLEWIGY VNPFNDGTKY    60
NEMFKGRATL TSDKSTSTAY MELSSLRSED TAVYYCARQA WGYPWGQGTL VTVSS        115

SEQ ID NO: 236          moltype = AA  length = 115
FEATURE                 Location/Qualifiers
REGION                  1..115
                        note = chemically synthesized
source                  1..115
                        mol_type = protein
                        organism = synthetic construct
SEQUENCE: 236
EVQLVQSGAE VKKPGASVKM SCKASGYTFT SYVMHWVRQA PGQRLEWIGY VNPFNDGTKY    60
NEMFKGRATL TSDKSTSTAY MELSSLRSED TAVYYCARQA WGYPWGQGTL VTVSS        115

SEQ ID NO: 237          moltype = AA  length = 115
FEATURE                 Location/Qualifiers
REGION                  1..115
                        note = chemically synthesized
source                  1..115
                        mol_type = protein
                        organism = synthetic construct
SEQUENCE: 237
EVQLVQSGAE VKKPGASVKV SCKASGYTFT SYVMHWVRQA PGQRLEWIGY VNPFNDGTKY    60
NEMFKGRATL TSDKSTSTAY MELSSLRSED TAVYYCARQA WGYPWGQGTL VTVSS        115

SEQ ID NO: 238          moltype = AA  length = 115
FEATURE                 Location/Qualifiers
REGION                  1..115
                        note = chemically synthesized
source                  1..115
                        mol_type = protein
                        organism = synthetic construct
SEQUENCE: 238
EVQLVQSGAE VKKPGASVKV SCKASGYTFT SYVMHWVRQA PGQRLEWIGY VNPFNDGTKY    60
NEMFKGRATI TSDKSTSTAY MELSSLRSED TAVYYCARQA WGYPWGQGTL VTVSS        115

SEQ ID NO: 239          moltype = AA  length = 111
FEATURE                 Location/Qualifiers
REGION                  1..111
                        note = chemically synthesized
source                  1..111
                        mol_type = protein
                        organism = synthetic construct
SEQUENCE: 239
DIVLTQSPAS LALSPGERAT LSCRATESVE YYGTSLVQWY QQKPGQPPKL LIYAASSVDS    60
GVPSRFSGSG SGTDFTLTIN SLEEEDAAMY FCQQSRRVPY TFGQGTKLEI K           111

SEQ ID NO: 240          moltype = AA  length = 111
FEATURE                 Location/Qualifiers
REGION                  1..111
                        note = chemically synthesized
source                  1..111
                        mol_type = protein
                        organism = synthetic construct
SEQUENCE: 240
DIVLTQSPAT LSLSPGERAT LSCRATESVE YYGTSLVQWY QQKPGQPPKL LIYAASSVDS    60
GVPSRFSGSG SGTDFTLTIN SLEAEDAAMY FCQQSRRVPY TFGQGTKLEI K           111

SEQ ID NO: 241          moltype = AA  length = 111
FEATURE                 Location/Qualifiers
REGION                  1..111
                        note = chemically synthesized
source                  1..111
                        mol_type = protein
                        organism = synthetic construct
```

```
SEQUENCE: 241
EIVLTQSPAT LSLSPGERAT LSCRATESVE YYGTSLVQWY QQKPGQPPKL LIYAASSVDS    60
GVPSRFSGSG SGTDFTLTIN SLEAEDAAMY FCQQSRRVPY TFGQGTKLEI K           111

SEQ ID NO: 242          moltype = AA   length = 111
FEATURE                 Location/Qualifiers
REGION                  1..111
                        note = chemically synthesized
source                  1..111
                        mol_type = protein
                        organism = synthetic construct
SEQUENCE: 242
DIVLTQSPAT LSLSPGERAT LSCRATESVE YYGTSLVQWY QQKPGQPPKL LIYAASSVDS    60
GVPSRFSGSG SGTDFTLTIN SLEAEDAATY FCQQSRRVPY TFGQGTKLEI K           111

SEQ ID NO: 243          moltype = AA   length = 123
FEATURE                 Location/Qualifiers
REGION                  1..123
                        note = chemically synthesized
source                  1..123
                        mol_type = protein
                        organism = synthetic construct
SEQUENCE: 243
EVQLVQSGAE VKKPGSSVKV SCKASGGTFS SYAISWVRQA PGQGLEWMGG IIPIFGTANY    60
AQKFQGRVTI TADKSTSTAY MELSSLRSED TAVYYCAREG TIYDSSGYSF DYWGQGTLVT   120
VSS                                                                123

SEQ ID NO: 244          moltype = AA   length = 124
FEATURE                 Location/Qualifiers
REGION                  1..124
                        note = chemically synthesized
source                  1..124
                        mol_type = protein
                        organism = synthetic construct
SEQUENCE: 244
EVQLVQSGAE VKKPGSSVKV SCKASGGTFS SYAISWVRQA PGQGLEWMGI INPSGGSTSY    60
AQKFQGRVSM TRDTSTSTVY MELSSLTSED TAVYYCARDL FPHIYGNYYG MDIWGQGTTV   120
TVSS                                                               124

SEQ ID NO: 245          moltype = AA   length = 118
FEATURE                 Location/Qualifiers
REGION                  1..118
                        note = chemically synthesized
source                  1..118
                        mol_type = protein
                        organism = synthetic construct
SEQUENCE: 245
QVQLVQSGAE VKKPGSSVKV SCKASGGTFS SYAISWVRQA PGQGLEWMGG IIPIFGTANY    60
AQKFQGRVTI TADKSTSTAY MELSSLRSED TAVYYCARLA VPGAFDIWGQ GTMVTVSS    118

SEQ ID NO: 246          moltype = AA   length = 116
FEATURE                 Location/Qualifiers
REGION                  1..116
                        note = chemically synthesized
source                  1..116
                        mol_type = protein
                        organism = synthetic construct
SEQUENCE: 246
EVQLVESGGG VVQPGRSLRL SCAASGFTFS SYAMHWVRQA PGKGLAVISY DGSNKYYADS    60
VKGRFTISRD NSKNTLYLQM NSLRAEDTAV YYCARGQWLV TELDYWGQGT LVTVSS      116

SEQ ID NO: 247          moltype = AA   length = 122
FEATURE                 Location/Qualifiers
REGION                  1..122
                        note = chemically synthesized
source                  1..122
                        mol_type = protein
                        organism = synthetic construct
SEQUENCE: 247
EVQLVESGSE VEKPGSSVKV SCKASGGTFS DSGISWVRQA PGQGLEWMGG IIPMFATPYY    60
AQKFQDRVTI TADESTSTVY MELSGLRSDD TAVFYCARDR GRGHLPWYFD LWGRGTLVTV   120
SS                                                                 122

SEQ ID NO: 248          moltype = AA   length = 119
FEATURE                 Location/Qualifiers
REGION                  1..119
                        note = chemically synthesized
source                  1..119
                        mol_type = protein
```

```
                           organism = synthetic construct
SEQUENCE: 248
EVQLVESGAE VKKPGSSVKV SCKASGGTFS SYAISWVRQA PGQGLEWMGG IIPIFGTANY    60
AQKFQGRVTI TADESTSTAY MELSSLRSED TAVYYCARAP YYYYYMDVWG QGTTVTVSS    119

SEQ ID NO: 249             moltype = AA   length = 124
FEATURE                    Location/Qualifiers
REGION                     1..124
                           note = chemically synthesized
source                     1..124
                           mol_type = protein
                           organism = synthetic construct
SEQUENCE: 249
EVQLLESGAE VKKPGSSVKV SCKASGGTLS RYALSWVRQA PGQGPEWVGA IIPIFGTPHY    60
SKKFQDRVII TVDTSTNTAF MELSSLRFED TALYFCARGH DEYDISGYHR LDYWGQGTLV   120
TVSS                                                                124

SEQ ID NO: 250             moltype = AA   length = 121
FEATURE                    Location/Qualifiers
REGION                     1..121
                           note = chemically synthesized
source                     1..121
                           mol_type = protein
                           organism = synthetic construct
SEQUENCE: 250
QVQLVQSGSE LKKPGSSVKV SCKASGYSFS GYYIHWVRQA PGQGLEWMGW IDPNSGVTNY    60
VRRFQGRVTM TRDTSLSTAY MELSGLTADD TAVYYCARDE NLWQFGYLDY WGQGTLVTVS   120
S                                                                   121

SEQ ID NO: 251             moltype = AA   length = 120
FEATURE                    Location/Qualifiers
REGION                     1..120
                           note = chemically synthesized
source                     1..120
                           mol_type = protein
                           organism = synthetic construct
SEQUENCE: 251
QVQLVQSGAE VKKPGSSVKV SCKASGGTFS RYGVHWVRQA PGQGLEWMGR LIPIVSMTNY    60
AQKFQDRVSI TTDKSTGTAY MELRSLTSED TALYYCASVG QQLPWVFFAW GQGTLVTVSS   120

SEQ ID NO: 252             moltype = AA   length = 118
FEATURE                    Location/Qualifiers
REGION                     1..118
                           note = chemically synthesized
source                     1..118
                           mol_type = protein
                           organism = synthetic construct
SEQUENCE: 252
QVQLVESGGG VVQPGRSLRL SCAASGFTFS SYAMHWVRQA PGKGLEWVAV ISFDGSNKYY    60
ADSVRGRFTI SRDNSKNTLY LQMNSLRTED TAVYYCARGW LDRDIDYWGQ GTLVTVSS    118

SEQ ID NO: 253             moltype = AA   length = 118
FEATURE                    Location/Qualifiers
REGION                     1..118
                           note = chemically synthesized
source                     1..118
                           mol_type = protein
                           organism = synthetic construct
SEQUENCE: 253
EVQLVESGGG VVQPGRSLRL SCAASGFTFS SYAMHWVRQA PGKGLEWVAV ISFDGSNKYY    60
ADSVRGRFTI SRDNSKNTLY LQMNSLRTED TAVYYCARGW LDRDIDYWGQ GTLVTVSS    118

SEQ ID NO: 254             moltype = AA   length = 121
FEATURE                    Location/Qualifiers
REGION                     1..121
                           note = chemically synthesized
source                     1..121
                           mol_type = protein
                           organism = synthetic construct
SEQUENCE: 254
EVQLVQSGGG LVQPGGSLRL SCAASGFTFS DYGMHWVRQP PGKGLEWLAV ISYDGSYKIH    60
ADSVQGRFTI SRDNAKNSVF LQMNSLKTED TAVYYCTTDR KWLAWHGMDV WGQGTTVTVS   120
S                                                                   121

SEQ ID NO: 255             moltype = AA   length = 118
FEATURE                    Location/Qualifiers
REGION                     1..118
                           note = chemically synthesized
source                     1..118
```

```
                        mol_type = protein
                        organism = synthetic construct
SEQUENCE: 255
EVQLVQSGAE VKKPGSSVKV SCKASGGTFS SYAISWVRQA PGQGLEWMGG IIPIFGTANY     60
AQKFQGRVTI TADESTSTAY MELSSLRSED TAVYYCARDG IVADFQHWGQ GTLVTVSS     118

SEQ ID NO: 256          moltype = AA  length = 121
FEATURE                 Location/Qualifiers
REGION                  1..121
                        note = chemically synthesized
source                  1..121
                        mol_type = protein
                        organism = synthetic construct
SEQUENCE: 256
EVQLVESGAE VKKPGASVKV SCKASGDTFS RYGITWVRQA PGRGLEWMGN IVPFFGATNY     60
AQKFQGRLTI TADKSSYTSY MDLSSLRSDD TAVYYCARDH FYGSGGYFDY WGQGTLVTVS    120
S                                                                   121

SEQ ID NO: 257          moltype = AA  length = 121
FEATURE                 Location/Qualifiers
REGION                  1..121
                        note = chemically synthesized
source                  1..121
                        mol_type = protein
                        organism = synthetic construct
SEQUENCE: 257
EVQLLESGAE VKKPGASVKV SCKASGYTFN SYDINWVRQA PGQGLEWMGG IIPVFGTANY     60
AESFQGRVTM TADHSTSTAY MELNNLRSED TAVYYCARDR WHYESRPMDV WGQGTTVTVS    120
S                                                                   121

SEQ ID NO: 258          moltype = AA  length = 119
FEATURE                 Location/Qualifiers
REGION                  1..119
                        note = chemically synthesized
source                  1..119
                        mol_type = protein
                        organism = synthetic construct
SEQUENCE: 258
EVQLVESGGG LVRPGGSLRL ACAASGFSFS DYYMTWIRQA PGRGLEWIAY ISDSGQTVHY     60
ADSVKGRFTI SRDNTKNSLF LQVNTLRAED TAVYYCARED LLGYYLQSWG QGTLVTVSS    119

SEQ ID NO: 259          moltype = AA  length = 131
FEATURE                 Location/Qualifiers
REGION                  1..131
                        note = chemically synthesized
source                  1..131
                        mol_type = protein
                        organism = synthetic construct
SEQUENCE: 259
QVQLQQSGPG LVKPSQTLSL TCAISGDSVS SNSAAWNWIR QSPSRGLEWL GRTYYRSKWY     60
NDYAVSVKSR ITINPDTSKN QFSLQLNSVT PEDTAVYYCA RDEPRAVAGS QAYYYYGMDV    120
WGQGTTVTVS S                                                        131

SEQ ID NO: 260          moltype = AA  length = 124
FEATURE                 Location/Qualifiers
REGION                  1..124
                        note = chemically synthesized
source                  1..124
                        mol_type = protein
                        organism = synthetic construct
SEQUENCE: 260
EVQLVQSGAE VKKPGASVKV SCKASGYTFT SYYMHWVRQA PGQGLEWMGI INPSDGSTSY     60
AQKFQGRVTM TRDTSTSTVH MELSSLRSED TAVYYCARDL FPHIYGNYYG MDIWGQGTTV    120
TVSS                                                                124

SEQ ID NO: 261          moltype = AA  length = 118
FEATURE                 Location/Qualifiers
REGION                  1..118
                        note = chemically synthesized
source                  1..118
                        mol_type = protein
                        organism = synthetic construct
SEQUENCE: 261
QMQLVQSGGG VVQPGRSLRL SCAASGFTFS SYAMHWVRQA PGKGLEWVAV ISFDGSNKYY     60
ADSVRGRFTI SRDNSKNTLY LQMNSLRTED TAVYYCARGW LDRDIDYWGQ GTLVTVSS     118

SEQ ID NO: 262          moltype = AA  length = 118
FEATURE                 Location/Qualifiers
REGION                  1..118
```

```
                        note = chemically synthesized
source                  1..118
                        mol_type = protein
                        organism = synthetic construct
SEQUENCE: 262
QVQLVQSGGG VVQPGRSLRL SCAASGFTFS SYAMHWVRQA PGKGLEWVAV ISFDGSNKYY    60
ADSVRGRFTI SRDNSKNTLY LQMNSLRTED TAVYYCARGW LDRDIDYWGQ GTLVTVSS    118

SEQ ID NO: 263          moltype = AA   length = 110
FEATURE                 Location/Qualifiers
REGION                  1..110
                        note = chemically synthesized
source                  1..110
                        mol_type = protein
                        organism = synthetic construct
SEQUENCE: 263
QSVLTQPPSV SAAPGQKVTI SCSGNNSNIA NNYVSWYQQL PGTAPKLLIY DNNYRPSGIP    60
DRFSGSKSGT SATLDITGLQ TGDEADYYCG VWDGSLTTGV FGGGTKLTVL              110

SEQ ID NO: 264          moltype = AA   length = 107
FEATURE                 Location/Qualifiers
REGION                  1..107
                        note = chemically synthesized
source                  1..107
                        mol_type = protein
                        organism = synthetic construct
SEQUENCE: 264
AIQMTQSPSS LSASVGDRVT ITCRASQGIS NYLAWYQQKP GKVPKLLIYA ASTLESGVPS    60
RFSGSGSGTD FTLTISSLQP EDLATYYCQQ LHTFPLTFGG GTKVEIK                 107

SEQ ID NO: 265          moltype = AA   length = 111
FEATURE                 Location/Qualifiers
REGION                  1..111
                        note = chemically synthesized
source                  1..111
                        mol_type = protein
                        organism = synthetic construct
SEQUENCE: 265
QPVLTQPPSA SGSPGQSVTI SCTGTSSDVG AYNFVSWYRQ HPGKAPKLMI YEVNKRPSGV    60
PDRFSGSKSG NTASLTVSGL QAEDEADYYC SSYAGTNSLG IFGTGTKLTV L            111

SEQ ID NO: 266          moltype = AA   length = 111
FEATURE                 Location/Qualifiers
REGION                  1..111
                        note = chemically synthesized
source                  1..111
                        mol_type = protein
                        organism = synthetic construct
SEQUENCE: 266
QSVVTQPPSV SAAPGQKVTI SCSGSSSDIG NHYVSWYQQL PGTAPKLLIY DNNQRPSGIP    60
DRFSGSKSGT SATLAITGLQ TGDEADYYCG TWDNSLSPHL LFGGGTKLTV L            111

SEQ ID NO: 267          moltype = AA   length = 110
FEATURE                 Location/Qualifiers
REGION                  1..110
                        note = chemically synthesized
source                  1..110
                        mol_type = protein
                        organism = synthetic construct
SEQUENCE: 267
QSVLTQPPSV SAAPGQKVTI SCSGSSSNMG NNYVSWYKQV PGTAPKLLIY ENDKRPSGIP    60
DRFSGSKSGT SATLGITGLQ TGDEADYYCG TWDNSLSGFV FASGTKVTVL              110

SEQ ID NO: 268          moltype = AA   length = 109
FEATURE                 Location/Qualifiers
REGION                  1..109
                        note = chemically synthesized
source                  1..109
                        mol_type = protein
                        organism = synthetic construct
SEQUENCE: 268
QSALTQPASV SGSLGQSVTI SCTGSSSDVG SYNLVSWYQQ HPGKAPNLMI YDVSKRSGVS    60
NRFSGSKSGN TASLTISGLQ AEDEADYYCS SYTGISTVVF GGGTKLTVL               109

SEQ ID NO: 269          moltype = AA   length = 110
FEATURE                 Location/Qualifiers
REGION                  1..110
                        note = chemically synthesized
source                  1..110
```

```
                        mol_type = protein
                        organism = synthetic construct
SEQUENCE: 269
QSVLTQPASV SGSPGQSITI SCTGTSSDVG SYNLVSWYQQ HPGKAPKLMI YEVSKRPSGV    60
SNRFSGSKSG NTASLTISGL QAEDEADYYC SSYGGFNNLL FGGGTKLTVL              110

SEQ ID NO: 270          moltype = AA   length = 107
FEATURE                 Location/Qualifiers
REGION                  1..107
                        note = chemically synthesized
source                  1..107
                        mol_type = protein
                        organism = synthetic construct
SEQUENCE: 270
DIVMTQSPSS LSASIGDRVT ITCRASQRIS AYVNWYQQKP GKAPKVLIYA ASSLRSGVPS    60
RFSGSGSGTD FTLTISSLQP EDFATYYCQQ TYSSPWTFGQ GTKVEIK                 107

SEQ ID NO: 271          moltype = AA   length = 112
FEATURE                 Location/Qualifiers
REGION                  1..112
                        note = chemically synthesized
source                  1..112
                        mol_type = protein
                        organism = synthetic construct
SEQUENCE: 271
QSVLTQPPSA SGSPGQSVTI SCTGTSSDIG GYDSVSWYQQ HPGKAPKLMI YDVSKRPSGV    60
SNRFSGSKSG NTASLTISGL QAEDEADYYC SSYTSSSIFF YVFGTGTKVT VL           112

SEQ ID NO: 272          moltype = AA   length = 110
FEATURE                 Location/Qualifiers
REGION                  1..110
                        note = chemically synthesized
source                  1..110
                        mol_type = protein
                        organism = synthetic construct
SEQUENCE: 272
LPVLTQPASV SGSPGQSITI SCTGTTSDIG GYDYVSWYQQ HPGKAPKLMI YDVSKRPSGV    60
SNRFSGSKSG NTASLTISGL QAEDEADYYC SSYTSSSTHV FGTGTKLTVL              110

SEQ ID NO: 273          moltype = AA   length = 111
FEATURE                 Location/Qualifiers
REGION                  1..111
                        note = chemically synthesized
source                  1..111
                        mol_type = protein
                        organism = synthetic construct
SEQUENCE: 273
QSALTQPASV SGSPGQSITI SCTGTSSDVG GYNYVSWYQQ HPGKAPKLMI YDVSNRPSGV    60
SNRFSGSKSG NTASLTISGL QAEDEADYYC SSYRSSTLGP VFGGGTKLTV L            111

SEQ ID NO: 274          moltype = AA   length = 110
FEATURE                 Location/Qualifiers
REGION                  1..110
                        note = chemically synthesized
source                  1..110
                        mol_type = protein
                        organism = synthetic construct
SEQUENCE: 274
QAGLTQPPSV SEAPRQRVTI SCSGSSSNIG NNAVNWYQQL PGKAPKLLIY YDDLLPSGVS    60
DRFSGSKSGT SASLAISGLQ SEDEADYYCA AWDDSLNGYV FGTGTKLTVL              110

SEQ ID NO: 275          moltype = AA   length = 110
FEATURE                 Location/Qualifiers
REGION                  1..110
                        note = chemically synthesized
source                  1..110
                        mol_type = protein
                        organism = synthetic construct
SEQUENCE: 275
QSALTQPRSV SGSPGQSVTI SCTGTSSDVG GYNYVSWYQQ HPGKAPKLMI YDVSKRPSGV    60
PDRFSGSKSG NTASLTISGL QAEDEADYYC SSYTSSTTHV FGTGTKVTVL              110

SEQ ID NO: 276          moltype = AA   length = 110
FEATURE                 Location/Qualifiers
REGION                  1..110
                        note = chemically synthesized
source                  1..110
                        mol_type = protein
                        organism = synthetic construct
```

```
SEQUENCE: 276
QSVVTQPPSV SAAPGQKVTI SCSGSSSNIG NNYVSWYQQL PGTAPKLLIY DNNKRPSGIP    60
DRFSGSKSGT SATLGITGLQ TGDEADYYCG TWDSSLSVWV FGGGTQLTVL              110

SEQ ID NO: 277              moltype = AA   length = 112
FEATURE                     Location/Qualifiers
REGION                      1..112
                            note = chemically synthesized
source                      1..112
                            mol_type = protein
                            organism = synthetic construct
SEQUENCE: 277
QSVLTQPASV SGSPGQSITI SCTGTSSDVG GYNYVSWYQQ HPGRAPRLMI YDVSNRPSGV    60
SNRFSGSKSG NTASLTISGL QAEDEGDYYC SSYTSGGTLP PVFGGGTKLT VL           112

SEQ ID NO: 278              moltype = AA   length = 110
FEATURE                     Location/Qualifiers
REGION                      1..110
                            note = chemically synthesized
source                      1..110
                            mol_type = protein
                            organism = synthetic construct
SEQUENCE: 278
QAGLTQPPSA SGTPGQRVTI SCSGSSSNIG SNTVNWYQQL PGTAPKLLIY SNNQRPSGVP    60
DRFSGSKSGT SASLAISGLQ SEDEADYYCA AWDDSLNGWV FGGGTKLTVL              110

SEQ ID NO: 279              moltype = AA   length = 107
FEATURE                     Location/Qualifiers
REGION                      1..107
                            note = chemically synthesized
source                      1..107
                            mol_type = protein
                            organism = synthetic construct
SEQUENCE: 279
AIRMTQSPSS LSASVGDRVT ITCRASQSIS NYLNWYQQRP GKAPNLLIYA ASSLQSGVPS    60
RFSGSGSGTD FTLTISSLQP EDFATYYCQQ TYSTPYTFGQ GTKLEIK                 107

SEQ ID NO: 280              moltype = AA   length = 111
FEATURE                     Location/Qualifiers
REGION                      1..111
                            note = chemically synthesized
source                      1..111
                            mol_type = protein
                            organism = synthetic construct
SEQUENCE: 280
QSVLTQPASV SGSPGQSITI SCTGTSSDVG GYNYVSWYRQ HPGKAPKLMI YDVSYRPSGV    60
SNRFSGSKSG NTASLTISGL QAEDEADYYC SSYTDSSTRY VFGTGTKLTV L            111

SEQ ID NO: 281              moltype = AA   length = 110
FEATURE                     Location/Qualifiers
REGION                      1..110
                            note = chemically synthesized
source                      1..110
                            mol_type = protein
                            organism = synthetic construct
SEQUENCE: 281
QPVLTQPPSA SGTPGQRVAI SCSGSRSNIE INSVNWYQQL PGTAPKLLIY DNNKRPSGIP    60
DRFSGSKSGT SATLGITGLQ TGDEADYYCG SWDSSLSADV FGTGTKLTVL              110

SEQ ID NO: 282              moltype = AA   length = 110
FEATURE                     Location/Qualifiers
REGION                      1..110
                            note = chemically synthesized
source                      1..110
                            mol_type = protein
                            organism = synthetic construct
SEQUENCE: 282
QSVLTQPPSV SAAPGKKVTI SCSGSSSNIG NNYVSWYQQL PGTAPKLLIY RNNQRPSGVP    60
DRFSGSKSGT SASLAISGLQ SEDEADYYCA TWDDSLNGWV FGGGTKLTVL              110

SEQ ID NO: 283              moltype = AA   length = 111
FEATURE                     Location/Qualifiers
REGION                      1..111
                            note = chemically synthesized
source                      1..111
                            mol_type = protein
                            organism = synthetic construct
SEQUENCE: 283
QSVVTQPPSV SGAPGQRVTI SCTGSSSNIG AGYDVHWYQQ LPGTAPKLLI YGNNNRHSGV    60
```

```
PDRFSGSKSG TSASLAITGL QAEDEAEFFC GTWDSRLTTY VFGSGTKLTV L              111

SEQ ID NO: 284           moltype = AA  length = 110
FEATURE                  Location/Qualifiers
REGION                   1..110
                         note = chemically synthesized
source                   1..110
                         mol_type = protein
                         organism = synthetic construct
SEQUENCE: 284
QSVVTQPPSV SAAPGQKVTI SCSGSSSNIG NNYVSWYQQL PGTAPKLLIY DNNKRPSGIP     60
DRFSGSKSGT SATLGITGLQ TGDEADYYCG TWDSSLSAVV FGGGTKLTVL               110

SEQ ID NO: 285           moltype = AA  length = 103
FEATURE                  Location/Qualifiers
REGION                   1..103
                         note = chemically synthesized
source                   1..103
                         mol_type = protein
                         organism = synthetic construct
SEQUENCE: 285
VIWMTQSPSS LSASVGDRVT ITCAASSLQS WYQQKPGKAP KLLIYEASTL ESGVPSRFSG     60
SGSGTEFTLT ISSLQPEDFA TYYCQQSYST PYTFGQGTKL EIK                      103

SEQ ID NO: 286           moltype = AA  length = 110
FEATURE                  Location/Qualifiers
REGION                   1..110
                         note = chemically synthesized
source                   1..110
                         mol_type = protein
                         organism = synthetic construct
SEQUENCE: 286
QSVVTQPPSV SAAPGQKVTI SCSGSSSNIG NNYVSWYQQV PGTAPKLLIY DNNKRPSGIP     60
DRFSGSNSDT SATLGITGLQ TGDEADYYCG TWDSSLSAWV FGGGTKLTVL               110

SEQ ID NO: 287           moltype = AA  length = 112
FEATURE                  Location/Qualifiers
REGION                   1..112
                         note = chemically synthesized
source                   1..112
                         mol_type = protein
                         organism = synthetic construct
SEQUENCE: 287
QSVVTQPPSV SAAPGQKVTI SCSGSSSNIG NNYVSWYQQL PGTAPKLLIY DNNKRPSGIP     60
DRFSGSKSGT SATLGITGLQ TGDEADYYCG TWDSSLSAGS VVFGGGTKLT VL            112

SEQ ID NO: 288           moltype = AA  length = 108
FEATURE                  Location/Qualifiers
REGION                   1..108
                         note = chemically synthesized
source                   1..108
                         mol_type = protein
                         organism = synthetic construct
SEQUENCE: 288
SYELMQPPSV SVAPGKTATI ACGGENIGRK TVHWYQQKPG QAPVLVIYYD SDRPSGIPER     60
FSGSNSGNTA TLTISRVEAG DEADYYCLVW DSSSDHRIFG GGTKLTVL                 108

SEQ ID NO: 289           moltype = AA  length = 108
FEATURE                  Location/Qualifiers
REGION                   1..108
                         note = chemically synthesized
source                   1..108
                         mol_type = protein
                         organism = synthetic construct
SEQUENCE: 289
SYELMQPPSV SVAPGKTATI ACGGENIGRK TVHWYQQKPG QAPVLVIYYD SDRPSGIPER     60
FSGSNSGNTA TLTISRVEAG DEADYYCQVW DSSSDHRIFG GGTKLTVL                 108

SEQ ID NO: 290           moltype = AA  length = 108
FEATURE                  Location/Qualifiers
REGION                   1..108
                         note = chemically synthesized
source                   1..108
                         mol_type = protein
                         organism = synthetic construct
SEQUENCE: 290
SYELMQPPSV SVAPGKTATI ACGGENIGRK TVHWYQQKPG QAPVLVIYYD SDRPSGIPER     60
FSGSNSGNTA TLTISRVEAG DEADYYCQVW DSSSDHRIFG GGTKLTVL                 108
```

| | | |
|---|---|---|
| SEQ ID NO: 291 | moltype = AA length = 108 | |
| FEATURE | Location/Qualifiers | |
| REGION | 1..108 | |
| | note = chemically synthesized | |
| source | 1..108 | |
| | mol_type = protein | |
| | organism = synthetic construct | |

SEQUENCE: 291
SYELMQPPSV SVAPGKTATI ACGGENIGRK TVHWYQQKPG QAPVLVIYYD SDRPSGIPER   60
FSGSNSGNTA TLTISRVEAG DEADYYCQVW DSSSDHRIFG GGTKLTVL               108

| | | |
|---|---|---|
| SEQ ID NO: 292 | moltype = AA length = 447 | |
| FEATURE | Location/Qualifiers | |
| REGION | 1..447 | |
| | note = chemically synthesized | |
| source | 1..447 | |
| | mol_type = protein | |
| | organism = synthetic construct | |

SEQUENCE: 292
QVQLVQSGVE VKKPGASVKV SCKASGYTFT NYYMYWVRQA PGQGLEWMGG INPSNGGTNF   60
NEKFKNRVTL TTDSSTTTAY MELKSLQFDD TAVYYCARRD YRFDMGFDYW GQGTTVTVSS  120
ASTKGPSVFP LAPCSRSTSE STAALGCLVK DYFPEPVTVS WNSGALTSGV HTFPAVLQSS  180
GLYSLSSVVT VPSSSLGTKT YTCNVDHKPS NTKVDKRVES KYGPPCPPCP APEFLGGPSV  240
FLFPPKPKDT LMISRTPEVT CVVVDVSQED PEVQFNWYVD GVEVHNAKTK PREEQFNSTY  300
RVVSVLTVLH QDWLNGKEYK CKVSNKGLPS SIEKTISKAK GQPREPQVYT LPPSQEEMTK  360
NQVSLTCLVK GFYPSDIAVE WESNGQPENN YKTTPPVLDS DGSFFLYSRL TVDKSRWQEG  420
NVFSCSVMHE ALHNHYTQKS LSLSLGK                                     447

| | | |
|---|---|---|
| SEQ ID NO: 293 | moltype = AA length = 440 | |
| FEATURE | Location/Qualifiers | |
| REGION | 1..440 | |
| | note = chemically synthesized | |
| source | 1..440 | |
| | mol_type = protein | |
| | organism = synthetic construct | |

SEQUENCE: 293
QVQLVESGGG VVQPGRSLRL DCKASGITFS NSGMHWVRQA PGKGLEWVAV IWYDGSKRYY   60
ADSVKGRFTI SRDNSKNTLF LQMNSLRAED TAVYYCATND DYWGQGTLVT VSSASTKGPS  120
VFPLAPCSRS TSESTAALGC LVKDYFPEPV TVSWNSGALT SGVHTFPAVL QSSGLYSLSS  180
VVTVPSSSLG TKTYTCNVDH KPSNTKVDKR VESKYGPPCP PCPAPEFLGG PSVFLFPPKP  240
KDTLMISRTP EVTCVVVDVS QEDPEVQFNW YVDGVEVHNA KTKPREEQFN STYRVVSVLT  300
VLHQDWLNGK EYKCKVSNKG LPSSIEKTIS KAKGQPREPQ VYTLPPSQEE MTKNQVSLTC  360
LVKGFYPSDI AVEWESNGQP ENNYKTTPPV LDSDGSFFLY SRLTVDKSRW QEGNVFSCSV  420
MHEALHNHYT QKSLSLSLGK                                             440

| | | |
|---|---|---|
| SEQ ID NO: 294 | moltype = AA length = 218 | |
| FEATURE | Location/Qualifiers | |
| REGION | 1..218 | |
| | note = chemically synthesized | |
| source | 1..218 | |
| | mol_type = protein | |
| | organism = synthetic construct | |

SEQUENCE: 294
EIVLTQSPAT LSLSPGERAT LSCRASKGVS TSGYSYLHWY QQKPGQAPRL LIYLASYLES   60
GVPARFSGSG SGTDFTLTIS SLEPEDFAVY YCQHSRDLPL TFGGGTKVEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                         218

| | | |
|---|---|---|
| SEQ ID NO: 295 | moltype = AA length = 214 | |
| FEATURE | Location/Qualifiers | |
| REGION | 1..214 | |
| | note = chemically synthesized | |
| source | 1..214 | |
| | mol_type = protein | |
| | organism = synthetic construct | |

SEQUENCE: 295
EIVLTQSPAT LSLSPGERAT LSCRASQSVS SYLAWYQQKP GQAPRLLIYD ASNRATGIPA   60
RFSGSGSGTD FTLTISSLEP EDFAVYYCQQ SSNWPRTFGQ GTKVEIKRTV AAPSVFIFPP  120
SDEQLKSGTA SVVCLLNNFY PREAKVQWKV DNALQSGNSQ ESVTEQDSKD STYSLSSTLT  180
LSKADYEKHK VYACEVTHQG LSSPVTKSFN RGEC                             214

| | | |
|---|---|---|
| SEQ ID NO: 296 | moltype = AA length = 122 | |
| FEATURE | Location/Qualifiers | |
| REGION | 1..122 | |
| | note = chemically synthesized | |
| source | 1..122 | |
| | mol_type = protein | |
| | organism = synthetic construct | |

SEQUENCE: 296

```
EVQLVESGGG LVQPGGSLRL SCAASGFTFS DSWIHWVRQA PGKGLEWVAW ISPYGGSTYY    60
ADSVKGRFTI SADTSKNTAY LQMNSLRAED TAVYYCARRH WPGGFDYWGQ GTLVTVSSAS   120
TK                                                                 122

SEQ ID NO: 297          moltype = AA   length = 118
FEATURE                 Location/Qualifiers
REGION                  1..118
                        note = chemically synthesized
source                  1..118
                        mol_type = protein
                        organism = synthetic construct
SEQUENCE: 297
EVQLVESGGG LVQPGGSLRL SCAASGFTFS DSWIHWVRQA PGKGLEWVAW ISPYGGSTYY    60
ADSVKGRFTI SADTSKNTAY LQMNSLRAED TAVYYCARRH WPGGFDYWGQ GTLVTVSS     118

SEQ ID NO: 298          moltype = AA   length = 447
FEATURE                 Location/Qualifiers
REGION                  1..447
                        note = chemically synthesized
source                  1..447
                        mol_type = protein
                        organism = synthetic construct
SEQUENCE: 298
EVQLVESGGG LVQPGGSLRL SCAASGFTFS DSWIHWVRQA PGKGLEWVAW ISPYGGSTYY    60
ADSVKGRFTI SADTSKNTAY LQMNSLRAED TAVYYCARRH WPGGFDYWGQ GTLVTVSSAS   120
TKGPSVFPLA PSSKSTSGGT AALGCLVKDY FPEPVTVSWN SGALTSGVHT FPAVLQSSGL   180
YSLSSVVTVP SSSLGTQTYI CNVNHKPSNT KVDKKVEPKS CDKTHTCPPC PAPELLGGPS   240
VFLFPPKPKD TLMISRTPEV TCVVVDVSHE DPEVKFNWYV DGVEVHNAKT KPREEQYAST   300
YRVVSVLTVL HQDWLNGKEY KCKVSNKALP APIEKTISKA KGQPREPQVY TLPPSREEMT   360
KNQVSLTCLV KGFYPSDIAV EWESNGQPEN NYKTTPPVLD SDGSFFLYSK LTVDKSRWQQ   420
GNVFSCSVMH EALHNHYTQK SLSLSPG                                      447

SEQ ID NO: 299          moltype = AA   length = 108
FEATURE                 Location/Qualifiers
REGION                  1..108
                        note = chemically synthesized
source                  1..108
                        mol_type = protein
                        organism = synthetic construct
SEQUENCE: 299
DIQMTQSPSS LSASVGDRVT ITCRASQDVS TAVAWYQQKP GKAPKLLIYS ASFLYSGVPS    60
RFSGSGSGTD FTLTISSLQP EDFATYYCQQ YLYHPATFGQ GTKVEIKR                108

SEQ ID NO: 300          moltype = AA   length = 214
FEATURE                 Location/Qualifiers
REGION                  1..214
                        note = chemically synthesized
source                  1..214
                        mol_type = protein
                        organism = synthetic construct
SEQUENCE: 300
DIQMTQSPSS LSASVGDRVT ITCRASQDVS TAVAWYQQKP GKAPKLLIYS ASFLYSGVPS    60
RFSGSGSGTD FTLTISSLQP EDFATYYCQQ YLYHPATFGQ GTKVEIKRTV AAPSVFIFPP   120
SDEQLKSGTA SVVCLLNNFY PREAKVQWKV DNALQSGNSQ ESVTEQDSKD STYSLSSTLT   180
LSKADYEKHK VYACEVTHQG LSSPVTKSFN RGEC                              214

SEQ ID NO: 301          moltype = AA   length = 121
FEATURE                 Location/Qualifiers
REGION                  1..121
                        note = chemically synthesized
source                  1..121
                        mol_type = protein
                        organism = synthetic construct
SEQUENCE: 301
EVQLVESGGG LVQPGGSLRL SCAASGFTFS RFWMSWVRQA PGKGLEWVAN INQDGTEKYY    60
VDSVKGRFTI SRDNAKNSLY LQMNSLRAGD TAVYYCANTY YDFWSGHFDY WGQGTLVTVS   120
S                                                                  121

SEQ ID NO: 302          moltype = AA   length = 121
FEATURE                 Location/Qualifiers
REGION                  1..121
                        note = chemically synthesized
source                  1..121
                        mol_type = protein
                        organism = synthetic construct
SEQUENCE: 302
QEHLVESGGG VVQPGRSLRL SCEASGFTFS NFGMHWVRQA PGKGLEWVAA LWSDGSNKYY    60
ADSVKGRVTI SRDNSKNTLY LQMNSLRAED TAVYYCARGR GAPGIPIFGY WGQGTLVTVS   120
S                                                                  121
```

```
SEQ ID NO: 303           moltype = AA  length = 130
FEATURE                  Location/Qualifiers
REGION                   1..130
                         note = chemically synthesized
source                   1..130
                         mol_type = protein
                         organism = synthetic construct
SEQUENCE: 303
EVQLVESGGG LVKPGGSLRL SCAASGFTFS NAWMSWVRQA PGKGLEWVGR IKRKTDGGTT    60
DYAAPVKGRF TISRDDSKNT LHLQMNSLKT EDTAVYYCTT DDIVVVPAVM REYYFGMDVW   120
GQGTTVTVSS                                                          130

SEQ ID NO: 304           moltype = AA  length = 121
FEATURE                  Location/Qualifiers
REGION                   1..121
                         note = chemically synthesized
source                   1..121
                         mol_type = protein
                         organism = synthetic construct
SEQUENCE: 304
QVQLVQSGAE VKKPGASVQV SCKASGYSFT GYYIHWVRQA PGQGLEWMGW INPNSGTKKY    60
AHKFQGRVTM TRDTSIDTAY MILSSLISDD TAVYYCARDE DWNFGSWFDS WGQGTLVTVS   120
S                                                                   121

SEQ ID NO: 305           moltype = AA  length = 121
FEATURE                  Location/Qualifiers
REGION                   1..121
                         note = chemically synthesized
source                   1..121
                         mol_type = protein
                         organism = synthetic construct
SEQUENCE: 305
QVHLVQSGAE VKKPGASVKV SCKASGYTFT GYYIHWVRQA PGHGLEWMGW LNPNTGTTKY    60
IQNFQGRVTM TRDTSSSTAY MELTRLRSDD TAVYYCARDE DWNYGSWFDT WGQGTLVTVS   120
S                                                                   121

SEQ ID NO: 306           moltype = AA  length = 120
FEATURE                  Location/Qualifiers
REGION                   1..120
                         note = chemically synthesized
source                   1..120
                         mol_type = protein
                         organism = synthetic construct
SEQUENCE: 306
EVQLVESGGG VVRPGGSLRL SCAASGFTFD DYGMTWVRQA PGRGLEWVSG IHWHGKRTGY    60
ADSVKGRFTI SRDNAKKSLY LQMNSLKGED TALYHCVRGG MSTGDWFDPW GQGTLVIVSS   120

SEQ ID NO: 307           moltype = AA  length = 120
FEATURE                  Location/Qualifiers
REGION                   1..120
                         note = chemically synthesized
source                   1..120
                         mol_type = protein
                         organism = synthetic construct
SEQUENCE: 307
EVQLVESGGG VVRPGGSLRL SCAASGFTFD DYGMTWVRQV PGKGLEWVSG IHWSGRSTGY    60
ADSVKGRFTI SRDNAKNSLY LQMNSLRAED TALYYCARGG MSTGDWFDPW GQGTLVTVSS   120

SEQ ID NO: 308           moltype = AA  length = 115
FEATURE                  Location/Qualifiers
REGION                   1..115
                         note = chemically synthesized
source                   1..115
                         mol_type = protein
                         organism = synthetic construct
SEQUENCE: 308
EVQLVESGGG LVQPGGSLRL SCAASGFTVG SNYMNWVRQA PGKGLEWVSV IYSGGSTYYA    60
DSVKGRFTIS RLTSKNTLYL QMSSLRPEDT AVYYCARGIR GLDVWGQGTT VTVSS        115

SEQ ID NO: 309           moltype = AA  length = 115
FEATURE                  Location/Qualifiers
REGION                   1..115
                         note = chemically synthesized
source                   1..115
                         mol_type = protein
                         organism = synthetic construct
SEQUENCE: 309
EERLVESGGD LVQPGGSLRL SCAASGITVG TNYMNWVRQA PGKGLEWVSV ISSGGNTHYA    60
```

```
DSVKGRFIMS RQTSKNTLYL QMNSLETEDT AVYYCARGIR GLDVWGQGTM VTVSS         115

SEQ ID NO: 310              moltype = AA  length = 118
FEATURE                     Location/Qualifiers
REGION                      1..118
                            note = chemically synthesized
source                      1..118
                            mol_type = protein
                            organism = synthetic construct
SEQUENCE: 310
QVQLVQSGAE VKMPGSSVRV SCKASGGIFS SSTISWVRQA PGQGLEWMGE IIPVFGTVNY    60
AQKFQDRVIF TADESTTTAY MELSSLKSGD TAVYFCARNW GLGSFYIWGQ GTMVTVSS     118

SEQ ID NO: 311              moltype = AA  length = 115
FEATURE                     Location/Qualifiers
REGION                      1..115
                            note = chemically synthesized
source                      1..115
                            mol_type = protein
                            organism = synthetic construct
SEQUENCE: 311
EVQLVESGGD LVHPGRSLRL SCAASGFPFD EYAMHWVRQV PGKGLEWVSG ISWSNNNIGY    60
ADSVKGRFTI SRDNAKNSLY LQMNSLRPED TAFYYCAKSG IFDSWGQGTL VTVSS        115

SEQ ID NO: 312              moltype = AA  length = 118
FEATURE                     Location/Qualifiers
REGION                      1..118
                            note = chemically synthesized
source                      1..118
                            mol_type = protein
                            organism = synthetic construct
SEQUENCE: 312
EVQLVESGGG VVQPGRSLRL SCAASGFTFS SYGMHWVRQA PGKGLEWVTL ISYEGRNKYY    60
ADSVKGRFTI SRDNSKNTLY LQMNSLRAED TAVYYCAKDR TLYGMDVWGQ GTTVTVSS     118

SEQ ID NO: 313              moltype = AA  length = 121
FEATURE                     Location/Qualifiers
REGION                      1..121
                            note = chemically synthesized
source                      1..121
                            mol_type = protein
                            organism = synthetic construct
SEQUENCE: 313
QVTLRESGPA LVKTTQTLTL TCTFSGFSLS TNRMCVTWIR QPPGKALEWL ARIDWDGVKY    60
YNTSLKTRLT ISKDTSKNQV VLTMTNMDPV DTATFYCARS TSLTFYYFDY WGQGTLVTVS   120
S                                                                 121

SEQ ID NO: 314              moltype = AA  length = 115
FEATURE                     Location/Qualifiers
REGION                      1..115
                            note = chemically synthesized
source                      1..115
                            mol_type = protein
                            organism = synthetic construct
SEQUENCE: 314
EVQLVESGGG LVQPGGSLRL SCAASEFTVG TNHMNWVRQA PGKGLEWVSV IYSGGNTFYA    60
DSVKGRFTIS RHTSKNTLYL QMNSLTAEDT AVYYCARGLG GMDVWGQGTT VTVSS        115

SEQ ID NO: 315              moltype = AA  length = 120
FEATURE                     Location/Qualifiers
REGION                      1..120
                            note = chemically synthesized
source                      1..120
                            mol_type = protein
                            organism = synthetic construct
SEQUENCE: 315
EVQLVESGGG LVQRGESLRL YCAASGFTFS KYWMNWVRQA PGKGLEWVAN IKGDGSEKYY    60
VDSVKGRFTI SRDNAKNSLY LQMNSLRAED TAVYYCARDY WGSGYYFDFW GQGTLVTVSS   120

SEQ ID NO: 316              moltype = AA  length = 130
FEATURE                     Location/Qualifiers
REGION                      1..130
                            note = chemically synthesized
source                      1..130
                            mol_type = protein
                            organism = synthetic construct
SEQUENCE: 316
EVQLVESGGG LVQSGGSLRL SCAASGFTFS SYWMSWVRQA PGKGLEWVAN IKQDGSEKYY    60
VDSVKGRFTI SRDNAKNSLY LQMNSLRADD TAVYYCARDD IVVVPAPMGY YYYFGMDVW    120
```

```
GQGTTVTVSS                                                                  130

SEQ ID NO: 318          moltype = AA  length = 123
FEATURE                 Location/Qualifiers
REGION                  1..123
                        note = chemically synthesized
source                  1..123
                        mol_type = protein
                        organism = synthetic construct
SEQUENCE: 317
EVQLVESGGG LVQPGRSLRL SCAASGFTFD DFAMHWVRQA PGKGLEWVSG ISWTGGNMDY   60
ANSVKGRFTI SREDAKNSLY LQMNSLRAAD TALYYCVKDI RGIVATGGAF DIWGRGTMVT  120
VSS                                                                123

SEQ ID NO: 318          moltype = AA  length = 115
FEATURE                 Location/Qualifiers
REGION                  1..115
                        note = chemically synthesized
source                  1..115
                        mol_type = protein
                        organism = synthetic construct
SEQUENCE: 318
EVQLVESGGG LVQPGGSLRL SCAASGFTVG TNYMNWVRQA PGKGLEWISV IYSGGSTFYA   60
DSVKGRFTIS RQTSQNTLYL QMNSLRPEDT AVYYCARGIR GFDIWGQGTM VTVSS       115

SEQ ID NO: 319          moltype = AA  length = 115
FEATURE                 Location/Qualifiers
REGION                  1..115
                        note = chemically synthesized
source                  1..115
                        mol_type = protein
                        organism = synthetic construct
SEQUENCE: 319
EVQLVESGGG LVQPGGSLRL SCAASGFTIS TNYMNWVRQA PGKGLEWVAV IYSSGSTYYI   60
DSVKGRFTIS RLTSKNTVYL QMSSLNSEDT AVYYCARGIR GFDIWGQGTM VTVSS       115

SEQ ID NO: 320          moltype = AA  length = 124
FEATURE                 Location/Qualifiers
REGION                  1..124
                        note = chemically synthesized
source                  1..124
                        mol_type = protein
                        organism = synthetic construct
SEQUENCE: 320
EVQLVESGGG LVQPGRSLRL SCAASGFTID DSAMHWVRQT PGKGLEWVSG ISWKSGSIGY   60
ADSVRGRFTI SRDNAKNSLY LQMNSLRVED TALYYCVKDI RGNWNYGGNW FDPWGQGTLV  120
TVSS                                                               124

SEQ ID NO: 321          moltype = AA  length = 115
FEATURE                 Location/Qualifiers
REGION                  1..115
                        note = chemically synthesized
source                  1..115
                        mol_type = protein
                        organism = synthetic construct
SEQUENCE: 321
EVQLVESGGG LVQPGGSLRL SCEASGFTVG VNHMNWVRQA PGKGLEWVSV IFSSGRTFYG   60
DYVKGRLTIF RQTSQNTVYL QMNSLRSEDT AIYYCARGIG GLDIWGRGTM VTVSS       115

SEQ ID NO: 322          moltype = AA  length = 123
FEATURE                 Location/Qualifiers
REGION                  1..123
                        note = chemically synthesized
source                  1..123
                        mol_type = protein
                        organism = synthetic construct
SEQUENCE: 322
EVQLVESGGG LVQPGRSLRL SCAASGFTFD DYALHWVRQA PGKGLEWVSG ISWTGGTIDY   60
ADSVKGRFTI SRDNAKNSLY LQMSSLRTED TAIYYCTRDI RGNWKYGGWF DPWGQGTLVT  120
VSS                                                                123

SEQ ID NO: 323          moltype = AA  length = 120
FEATURE                 Location/Qualifiers
REGION                  1..120
                        note = chemically synthesized
source                  1..120
                        mol_type = protein
                        organism = synthetic construct
SEQUENCE: 323
```

```
QVQLVQSGTE VKKPGASVKV SCKASGYTFT AYYMHWVRQA PGQGLDWMGW ISPNSGFTNY    60
AQKFQGRVTM TRDTSINTFY MELSGLRSDD TAVYYCAREG STHHNSFDPW GQGTLVTVSS   120

SEQ ID NO: 324          moltype = AA  length = 114
FEATURE                 Location/Qualifiers
REGION                  1..114
                        note = chemically synthesized
source                  1..114
                        mol_type = protein
                        organism = synthetic construct
SEQUENCE: 324
EVQLVESGGG LVQPGGSLRL SCAASGFTVG TNFMNWVRQA PGKGLEWVSA IYSGGTANYA    60
DSVKGRFTIS RDTSRNTLYL QMNSLRTEDT AVYYCARGGG MDVWGQGTTV TVSS         114

SEQ ID NO: 325          moltype = AA  length = 118
FEATURE                 Location/Qualifiers
REGION                  1..118
                        note = chemically synthesized
source                  1..118
                        mol_type = protein
                        organism = synthetic construct
SEQUENCE: 325
QVQLVQSGAE VKKPGSSVKV SCKASGGTFN TYVLSWVRQA PGQGLEWMGE IIPILGAANY    60
AQNFQGRVTF TTDESTNTAY MDLSSLRSED TAVYYCARDR TSGGFDPWGQ GTLVTVSS    118

SEQ ID NO: 326          moltype = AA  length = 119
FEATURE                 Location/Qualifiers
REGION                  1..119
                        note = chemically synthesized
source                  1..119
                        mol_type = protein
                        organism = synthetic construct
SEQUENCE: 326
QVQLVQSGAE VEKPGASVKV SCKASGYIFT HYGISWVRQA PGQGLEWVGW ISPYNGYTDY    60
AQKLQGRVTL TTDTSTTTAY MELRNLRSDD TAMYYCSRGR GPYWSFDLWG RGTLVTVSS   119

SEQ ID NO: 327          moltype = AA  length = 106
FEATURE                 Location/Qualifiers
REGION                  1..106
                        note = chemically synthesized
source                  1..106
                        mol_type = protein
                        organism = synthetic construct
SEQUENCE: 327
DIQMTQSPST LSASVGDRVT ITCRASQSIS NWLAWYQQKP GKAPKLLIYK ASSLESGVPS    60
RFSGSGSGTE FTLTISSLQP DDFATYYCQQ YHSYSYTFGQ GTKEIK                 106

SEQ ID NO: 328          moltype = AA  length = 107
FEATURE                 Location/Qualifiers
REGION                  1..107
                        note = chemically synthesized
source                  1..107
                        mol_type = protein
                        organism = synthetic construct
SEQUENCE: 328
DIQMTQSPSS LSASVGDRVT ITCRASQGIR NDLGWYQQKP GKAPKRLIYT ASSLQSGVPS    60
RFSGSGSGTE FTLTISSLQP EDFATYYCLQ HNSYPLTFGG GTKVAIK                107

SEQ ID NO: 329          moltype = AA  length = 107
FEATURE                 Location/Qualifiers
REGION                  1..107
                        note = chemically synthesized
source                  1..107
                        mol_type = protein
                        organism = synthetic construct
SEQUENCE: 329
DIQMTQSPSS LSASVGDRVT ITCRTSQGIR NDLGWYQQKP GKAPKRLIYA ASSLQSGVPS    60
RFSGSGSGTE FTLTISSLQP EDFATYYCLQ HNNYPYTFGQ GTKLEIK                107

SEQ ID NO: 330          moltype = AA  length = 112
FEATURE                 Location/Qualifiers
REGION                  1..112
                        note = chemically synthesized
source                  1..112
                        mol_type = protein
                        organism = synthetic construct
SEQUENCE: 330
DIVMTQTPLS SPVTLGQPAS ISCRSSQTLV HGDGNTYLSW IQQRPGQPPR LLIYKVSNQF    60
SGVPDRFSGS GAGTDFTLKI SRVEAEDVGL YFCMQATHFP ITFGQGTRLE IK          112
```

```
SEQ ID NO: 331          moltype = AA  length = 112
FEATURE                 Location/Qualifiers
REGION                  1..112
                        note = chemically synthesized
source                  1..112
                        mol_type = protein
                        organism = synthetic construct
SEQUENCE: 331
DIVMTQTPLS SPVTLGQPAS ISCRSSPSLV HSDGNTYLSW LQQRPGQPPR LLIYKISNRF    60
SGVPDRFSGS GAGTDFTLKI SRVEAEDVGV YYCMQATHFP ITFGQGTRLE IR           112

SEQ ID NO: 332          moltype = AA  length = 108
FEATURE                 Location/Qualifiers
REGION                  1..108
                        note = chemically synthesized
source                  1..108
                        mol_type = protein
                        organism = synthetic construct
SEQUENCE: 332
DIQMTQSPSS LSASLGDRVT ITCRASQSIN SYLNWYQQKP GKAPKLLIYV ASSLQSGVPS    60
RFSGSGSGTE FTLTISNLQP EDFATYYCQQ SYSTPPITFG QGTRLEIK                108

SEQ ID NO: 333          moltype = AA  length = 108
FEATURE                 Location/Qualifiers
REGION                  1..108
                        note = chemically synthesized
source                  1..108
                        mol_type = protein
                        organism = synthetic construct
SEQUENCE: 333
DIQMTQSPSS LSASVGDRVT ITCRASQSIS SYLNWYQQKP GKAPKLLIYV ASSLQSGVPS    60
RFSGSGSGTD FTLTISSLQP EDFATYYCQQ SYSTPPITFG QGTRLEIK                108

SEQ ID NO: 334          moltype = AA  length = 108
FEATURE                 Location/Qualifiers
REGION                  1..108
                        note = chemically synthesized
source                  1..108
                        mol_type = protein
                        organism = synthetic construct
SEQUENCE: 334
DIQMTQSPSS LSASVGDRVT ITCRASQTIN IYLNWYQQKP GRAPRLLIYA ASSLQSGVPS    60
RFSGSGSGTD FTLTISSLQP EDFATYYCHQ SYSTPPITFG QGTRLEIK                108

SEQ ID NO: 335          moltype = AA  length = 108
FEATURE                 Location/Qualifiers
REGION                  1..108
                        note = chemically synthesized
source                  1..108
                        mol_type = protein
                        organism = synthetic construct
SEQUENCE: 335
DIQMTQSPSS LSASVGDRVT ITCRASQSMS SYLNWYQQKP GRAPKLLIFA ASSLQSGVPS    60
RFSGSGSGTD FTLTISSLQP EDFATYYCQQ SYSTPPITFG QGTRLEIK                108

SEQ ID NO: 336          moltype = AA  length = 108
FEATURE                 Location/Qualifiers
REGION                  1..108
                        note = chemically synthesized
source                  1..108
                        mol_type = protein
                        organism = synthetic construct
SEQUENCE: 336
EIVLTQSPGT LSLSPGERAT LSCRASQSFN FNYLAWYQQK PGQAPRLLIY GASSRATGIP    60
DRFSGSGSGT DFTLTINRLE PEDFGVFYCQ QYESAPWTFG QGTKVEIK                108

SEQ ID NO: 337          moltype = AA  length = 105
FEATURE                 Location/Qualifiers
REGION                  1..105
                        note = chemically synthesized
source                  1..105
                        mol_type = protein
                        organism = synthetic construct
SEQUENCE: 337
DIQMTQSPSS LSASVGDRVT ITCRASQSIS SYLNWYQQKP GKLLIYAASS LQSGVPSRFS    60
GGGSGTDFTL TISSLRPEDF ATYYCQQSYC TPPITFGQGT RLEIK                   105

SEQ ID NO: 338          moltype = AA  length = 108
```

```
FEATURE                 Location/Qualifiers
REGION                  1..108
                        note = chemically synthesized
source                  1..108
                        mol_type = protein
                        organism = synthetic construct
SEQUENCE: 338
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPPITFG QGTRLEIK                108

SEQ ID NO: 339          moltype = AA  length = 91
FEATURE                 Location/Qualifiers
REGION                  1..91
                        note = chemically synthesized
source                  1..91
                        mol_type = protein
                        organism = synthetic construct
SEQUENCE: 339
DRVTITCRAS QVISNYLAWY QQKPGKVPRL LIYAASTLQS GVPSRFSGSG SGTDFTLTIS    60
SLQPEDVATY YCQKYNSAPR TFGQGTKVEI K                                  91

SEQ ID NO: 340          moltype = AA  length = 107
FEATURE                 Location/Qualifiers
REGION                  1..107
                        note = chemically synthesized
source                  1..107
                        mol_type = protein
                        organism = synthetic construct
SEQUENCE: 340
DIQMTQSPSS LSASVGDRVT ITCRASQNIN NYLNWYQQKP GKAPKLLIYA ASSFQNAVPS    60
RFSGSGSGTD FTLTISSLQP EDFATYYCQQ SYNTPLTFGG GTKVEIK                 107

SEQ ID NO: 341          moltype = AA  length = 107
FEATURE                 Location/Qualifiers
REGION                  1..107
                        note = chemically synthesized
source                  1..107
                        mol_type = protein
                        organism = synthetic construct
SEQUENCE: 341
DIQMTQSPSS LSASVGDRVT ITCRASQGIR NDLGWYQQKP GKAPKRLIYA ASSLQSGVPS    60
RFSGSGSGTE FTLTISSLQP EDFATYYCLQ HNSYPYTFGQ GTKLEIK                 107

SEQ ID NO: 342          moltype = AA  length = 108
FEATURE                 Location/Qualifiers
REGION                  1..108
                        note = chemically synthesized
source                  1..108
                        mol_type = protein
                        organism = synthetic construct
SEQUENCE: 342
DIQMTQSPSS LSASVGDRVT ITCRASQSIS SYLNWYQQKP GKAPKLLIYA ASSLQSGVPS    60
RFSGSGSGTD FTLTISSLQP EDFATYYCQQ SYSTPPITFG QGTRLEIK                108

SEQ ID NO: 343          moltype = AA  length = 115
FEATURE                 Location/Qualifiers
REGION                  1..115
                        note = chemically synthesized
source                  1..115
                        mol_type = protein
                        organism = synthetic construct
SEQUENCE: 343
QSLEESGGRL VKPDETLTIT CTVSGIDLSS NGLTWVRQAP GEGLEWIGTI NKDASAYYAS    60
WAKGRLTISK PSSTKVDLKI TSPTTEDTAT YFCGRIAFKT GTSIWGPGTL VTVSS        115

SEQ ID NO: 344          moltype = AA  length = 112
FEATURE                 Location/Qualifiers
REGION                  1..112
                        note = chemically synthesized
source                  1..112
                        mol_type = protein
                        organism = synthetic construct
SEQUENCE: 344
AIVMTQTPSP VSAAVGGTVT INCQASESVY SNNYLSWFQQ KPGQPPKLLI YLASTLASGV    60
PSRFKGSGSG TQFTLTISGV QCDDAATYYC IGGKSSSTDG NAFGGGTEVV VR           112

SEQ ID NO: 345          moltype = AA  length = 121
FEATURE                 Location/Qualifiers
REGION                  1..121
```

```
                            note = chemically synthesized
source                      1..121
                            mol_type = protein
                            organism = synthetic construct
SEQUENCE: 345
QMQLVQSGAE VKKPGSSVKV SCKASGGTFS SYAISWVRQA PGQGLEWMGG IIPIFGTANY        60
AQKFQGRVTI TADESTSTAY MELSSLRSED TAVYYCARGN IVATITPLDY WGQGTLVTVS       120
S                                                                     121

SEQ ID NO: 346              moltype = AA  length = 110
FEATURE                     Location/Qualifiers
REGION                      1..110
                            note = chemically synthesized
source                      1..110
                            mol_type = protein
                            organism = synthetic construct
SEQUENCE: 346
QPVLTQPPSV SAAPGQKVTI SCSGSSSNIA NNYVSWYQQL PGTAPKLLIF ANNKRPSGIP        60
DRFSGSKSGT SAALDITGLQ TGDEADYYCG TWDSDLRAGV FGGGTKLTVL                  110

SEQ ID NO: 347              moltype = AA  length = 123
FEATURE                     Location/Qualifiers
REGION                      1..123
                            note = chemically synthesized
source                      1..123
                            mol_type = protein
                            organism = synthetic construct
SEQUENCE: 347
EVQLVQSGAE VKKPGSSVKV SCKASGGTFS SYAISWVRQA PGQGLEWMGG IIPIFGTANY        60
AQKFQGRVTI TADKSTSTAY MELSSLRSED TAVYYCAREG TIYDSSGYSF DYWGQGTLVT       120
VSS                                                                   123

SEQ ID NO: 348              moltype = AA  length = 118
FEATURE                     Location/Qualifiers
REGION                      1..118
                            note = chemically synthesized
source                      1..118
                            mol_type = protein
                            organism = synthetic construct
SEQUENCE: 348
QVQLVESGGG VVQPGRSLRL SCAASGFTFS SYAMHWVRQA PGKGLEWVAV ISFDGSNKYY        60
ADSVRGRFTI SRDNSKNTLY LQMNSLRTED TAVYYCARGW LDRDIDYWGQ GTLVTVSS        118

SEQ ID NO: 349              moltype = AA  length = 118
FEATURE                     Location/Qualifiers
REGION                      1..118
                            note = chemically synthesized
source                      1..118
                            mol_type = protein
                            organism = synthetic construct
SEQUENCE: 349
EVQLVESGGG VVQPGRSLRL SCAASGFTFS SYAMHWVRQA PGKGLEWVAV ISFDGSNKYY        60
ADSVRGRFTI SRDNSKNTLY LQMNSLRTED TAVYYCARGW LDRDIDYWGQ GTLVTVSS        118

SEQ ID NO: 350              moltype = AA  length = 118
FEATURE                     Location/Qualifiers
REGION                      1..118
                            note = chemically synthesized
source                      1..118
                            mol_type = protein
                            organism = synthetic construct
SEQUENCE: 350
QVQLVESGGG VVQPGRSLRL SCAASGFTFS SYAMHWVRQA PGKGLEWVAV ISFDGSNKYY        60
ADSVRGRFTI SRDNSKNTLY LQMNSLRTED TAVYYCARGW LDRDIDYWGQ GTLVTVSS        118

SEQ ID NO: 351              moltype = AA  length = 118
FEATURE                     Location/Qualifiers
REGION                      1..118
                            note = chemically synthesized
source                      1..118
                            mol_type = protein
                            organism = synthetic construct
SEQUENCE: 351
EVQLVESGGG VVQPGRSLRL SCAASGFTFS SYAMHWVRQA PGKGLEWVAV ISFDGSNKYY        60
ADSVRGRFTI SRDNSKNTLY LQMNSLRTED TAVYYCARGW LDRDIDYWGQ GTLVTVSS        118

SEQ ID NO: 352              moltype = AA  length = 118
FEATURE                     Location/Qualifiers
REGION                      1..118
```

```
                         note = chemically synthesized
source                   1..118
                         mol_type = protein
                         organism = synthetic construct
SEQUENCE: 352
EVQLVESGGG VVQPGRSLRL SCAASGFTFS SYAMHWVRQA PGKGLEWVAV ISFDGSNKYY   60
ADSVRGRFTI SRDNSKNTLY LQMNSLRTED TAVYYCARGW LDRDIDYWGQ GTLVTVSS   118

SEQ ID NO: 353           moltype = AA   length = 118
FEATURE                  Location/Qualifiers
REGION                   1..118
                         note = chemically synthesized
source                   1..118
                         mol_type = protein
                         organism = synthetic construct
SEQUENCE: 353
QVQLVESGGG VVQPGRSLRL SCAASGFTFS SYAMHWVRQA PGKGLEWVAV ISFDGSNKYY   60
ADSVRGRFTI SRDNSKNTLY LQMNSLRTED TAVYYCARGW LDRDIDYWGQ GTLVTVSS   118

SEQ ID NO: 354           moltype = AA   length = 120
FEATURE                  Location/Qualifiers
REGION                   1..120
                         note = chemically synthesized
source                   1..120
                         mol_type = protein
                         organism = synthetic construct
SEQUENCE: 354
QVQLVQSGAE VKKPGSSVKV SCKASGGTFS RYGVHWVRQA PGQGLEWMGR LIPIVSMTNY   60
AQKFQDRVSI TTDKSTGTAY MELRSLTSED TALYYCASVG QQLPWVFFAW GQGTLVTVSS  120

SEQ ID NO: 355           moltype = AA   length = 118
FEATURE                  Location/Qualifiers
REGION                   1..118
                         note = chemically synthesized
source                   1..118
                         mol_type = protein
                         organism = synthetic construct
SEQUENCE: 355
QMQLVQSGGG VVQPGRSLRL SCAASGFTFS SYAMHWVRQA PGKGLEWVAV ISFDGSNKYY   60
ADSVRGRFTI SRDNSKNTLY LQMNSLRTED TAVYYCARGW LDRDIDYWGQ GTLVTVSS   118

SEQ ID NO: 356           moltype = AA   length = 118
FEATURE                  Location/Qualifiers
REGION                   1..118
                         note = chemically synthesized
source                   1..118
                         mol_type = protein
                         organism = synthetic construct
SEQUENCE: 356
QVQLVQSGGG VVQPGRSLRL SCAASGFTFS SYAMHWVRQA PGKGLEWVAV ISFDGSNKYY   60
ADSVRGRFTI SRDNSKNTLY LQMNSLRTED TAVYYCARGW LDRDIDYWGQ GTLVTVSS   118

SEQ ID NO: 357           moltype = AA   length = 121
FEATURE                  Location/Qualifiers
REGION                   1..121
                         note = chemically synthesized
source                   1..121
                         mol_type = protein
                         organism = synthetic construct
SEQUENCE: 357
QMQLVQSGAE VKKPGSSVKV SCKASGGTFS SYAYSWVRQA PGQGLEWMGG IIPSFGTANY   60
AQKFQGRVTI TADESTSTAY MELSSLRSED TAVYYCARGP IVATITPLDY WGQGTLVTVS  120
S                                                                 121

SEQ ID NO: 358           moltype = AA   length = 121
FEATURE                  Location/Qualifiers
REGION                   1..121
                         note = chemically synthesized
source                   1..121
                         mol_type = protein
                         organism = synthetic construct
SEQUENCE: 358
QMQLVQSGAE VKKPGSSVKV SCKASGGTFS SYAYSWVRQA PGQGLEWMGG IIPIFGTANY   60
AQKFQGRVTI TADESTSTAY MELSSLRSED TAVYYCARGP IVATITPLDY WGQGTLVTVS  120
S                                                                 121

SEQ ID NO: 359           moltype = AA   length = 121
FEATURE                  Location/Qualifiers
REGION                   1..121
```

```
                       note = chemically synthesized
source                 1..121
                       mol_type = protein
                       organism = synthetic construct
SEQUENCE: 359
QMQLVQSGAE VKKPGSSVKV SCKASGGTFS SYAYSWVRQA PGQGLEWMGG IIPSFGTANY    60
AQKFQGRVTI TADESTSTAY MELSSLRSED TAVYYCARGP IVATITPLDY WGQGTLVTVS   120
S                                                                   121

SEQ ID NO: 360         moltype = AA  length = 121
FEATURE                Location/Qualifiers
REGION                 1..121
                       note = chemically synthesized
source                 1..121
                       mol_type = protein
                       organism = synthetic construct
SEQUENCE: 360
QMQLVQSGAE VKKPGSSVKV SCKASGGTFS SYAISWVRQA PGQGLEWMGG IIPAFGTANY    60
AQKFQGRVTI TADESTSTAY MELSSLRSED TAVYYCARGP IVATITPLDY WGQGTLVTVS   120
S                                                                   121

SEQ ID NO: 361         moltype = AA  length = 108
FEATURE                Location/Qualifiers
REGION                 1..108
                       note = chemically synthesized
source                 1..108
                       mol_type = protein
                       organism = synthetic construct
SEQUENCE: 361
SYELMQPPSV SVAPGKTATI ACGGENIGRK TVHWYQQKPG QAPVLVIYYD SDRPSGIPER    60
FSGSNSGNTA TLTISRVEAG DEADYYCQVW DSSSDHRIFG GGTKLTVL                108

SEQ ID NO: 362         moltype = AA  length = 107
FEATURE                Location/Qualifiers
REGION                 1..107
                       note = chemically synthesized
source                 1..107
                       mol_type = protein
                       organism = synthetic construct
SEQUENCE: 362
AIRMTQSPSS LSASVGDRVT ITCRASQSIS SYLNWYQQKP GKAPKLLIYT TSSLKSGVPS    60
RFSGSGSGTD FTLTISRLQP EDFATYYCQQ SYSSTWTFGR GTKVEIK                 107

SEQ ID NO: 363         moltype = AA  length = 110
FEATURE                Location/Qualifiers
REGION                 1..110
                       note = chemically synthesized
source                 1..110
                       mol_type = protein
                       organism = synthetic construct
SEQUENCE: 363
QSVLTQPPSV SAAPGQKVTI SCSGNNSNIA NNYVSWYQQL PGTAPKLLIY DNNYRPSGIP    60
DRFSGSKSGT SATLDITGLQ TGDEADYYCG VWDGSLTTGV FGGGTKLTVL              110

SEQ ID NO: 364         moltype = AA  length = 110
FEATURE                Location/Qualifiers
REGION                 1..110
                       note = chemically synthesized
source                 1..110
                       mol_type = protein
                       organism = synthetic construct
SEQUENCE: 364
LPVLTQPASV SGSPGQSITI SCTGTTSDIG GYDYVSWYQQ HPGKAPKLMI YDVSKRPSGV    60
SNRFSGSKSG NTASLTISGL QAEDEADYYC SSYTSSSTHV FGTGTKLTVL              110

SEQ ID NO: 365         moltype = AA  length = 111
FEATURE                Location/Qualifiers
REGION                 1..111
                       note = chemically synthesized
source                 1..111
                       mol_type = protein
                       organism = synthetic construct
SEQUENCE: 365
QSALTQPASV SGSPGQSITI SCTGTSSDVG GYNYVSWYQQ HPGKAPKLMI YDVSNRPSGV    60
SNRFSGSKSG NTASLTISGL QAEDEADYYC SSYRSSTLGP VFGGGTKLTV L            111

SEQ ID NO: 366         moltype = AA  length = 110
FEATURE                Location/Qualifiers
REGION                 1..110
```

```
                        note = chemically synthesized
source                  1..110
                        mol_type = protein
                        organism = synthetic construct
SEQUENCE: 366
QAGLTQPPSV SEAPRQRVTI SCSGSSSNIG NNAVNWYQQL PGKAPKLLIY YDDLLPSGVS    60
DRFSGSKSGT SASLAISGLQ SEDEADYYCA AWDDSLNGYV FGTGTKLTVL              110

SEQ ID NO: 367          moltype = AA  length = 110
FEATURE                 Location/Qualifiers
REGION                  1..110
                        note = chemically synthesized
source                  1..110
                        mol_type = protein
                        organism = synthetic construct
SEQUENCE: 367
QSALTQPRSV SGSPGQSVTI SCTGTSSDVG GYNYVSWYQQ HPGKAPKLMI YDVSKRPSGV    60
PDRFSGSKSG NTASLTISGL QAEDEADYYC SSYTSSTTHV FGTGTKVTVL              110

SEQ ID NO: 368          moltype = AA  length = 110
FEATURE                 Location/Qualifiers
REGION                  1..110
                        note = chemically synthesized
source                  1..110
                        mol_type = protein
                        organism = synthetic construct
SEQUENCE: 368
QSVVTQPPSV SAAPGQKVTI SCSGSSSNIG NNYVSWYQQL PGTAPKLLIY DNNKRPSGIP    60
DRFSGSKSGT SATLGITGLQ TGDEADYYCG TWDSSLSVWV FGGGTQLTVL              110

SEQ ID NO: 369          moltype = AA  length = 112
FEATURE                 Location/Qualifiers
REGION                  1..112
                        note = chemically synthesized
source                  1..112
                        mol_type = protein
                        organism = synthetic construct
SEQUENCE: 369
QSVLTQPASV SGSPGQSITI SCTGTSSDVG GYNYVSWYQQ HPGRAPRLMI YDVSNRPSGV    60
SNRFSGSKSG NTASLTISGL QAEDEGDYYC SSYTSGGTLG PVFGGGTKLT VL           112

SEQ ID NO: 370          moltype = AA  length = 110
FEATURE                 Location/Qualifiers
REGION                  1..110
                        note = chemically synthesized
source                  1..110
                        mol_type = protein
                        organism = synthetic construct
SEQUENCE: 370
QSVVTQPPSV SAAPGQKVTI SCSGSSSNIG NNYVSWYQQL PGTAPKLLIY DNNKRPSGIP    60
DRFSGSKSGT SATLGITGLQ TGDEADYYCG TWDSSLSAVV FGGGTKLTVL              110

SEQ ID NO: 371          moltype = AA  length = 110
FEATURE                 Location/Qualifiers
REGION                  1..110
                        note = chemically synthesized
source                  1..110
                        mol_type = protein
                        organism = synthetic construct
SEQUENCE: 371
QSVVTQPPSV SAAPGQKVTI SCSGSSSNIG NNYVSWYQQV PGTAPKLLIY DNNKRPSGIP    60
DRFSGSNSDT SATLGITGLQ TGDEADYYCG TWDSSLSAWV FGGGTKLTVL              110

SEQ ID NO: 372          moltype = AA  length = 112
FEATURE                 Location/Qualifiers
REGION                  1..112
                        note = chemically synthesized
source                  1..112
                        mol_type = protein
                        organism = synthetic construct
SEQUENCE: 372
QSVVTQPPSV SAAPGQKVTI SCSGSSSNIG NNYVSWYQQL PGTAPKLLIY DNNKRPSGIP    60
DRFSGSKSGT SATLGITGLQ TGDEADYYCG TWDSSLSAGS VVFGGGTKLT VL           112

SEQ ID NO: 373          moltype = AA  length = 108
FEATURE                 Location/Qualifiers
REGION                  1..108
                        note = chemically synthesized
source                  1..108
```

```
                        mol_type = protein
                        organism = synthetic construct
SEQUENCE: 373
SYELMQPPSV SVAPGKTATI ACGGENIGRK TVHWYQQKPG QAPVLVIYYD SDRPSGIPER    60
FSGSNSGNTA TLTISRVEAG DEADYYCLVW DSSSDHRIFG GGTKLTVL                108

SEQ ID NO: 374          moltype = AA  length = 108
FEATURE                 Location/Qualifiers
REGION                  1..108
                        note = chemically synthesized
source                  1..108
                        mol_type = protein
                        organism = synthetic construct
SEQUENCE: 374
SYELMQPPSV SVAPGKTATI ACGGENIGRK TVHWYQQKPG QAPVLVIYYD SDRPSGIPER    60
FSGSNSGNTA TLTISRVEAG DEADYYCQVW DSSSDHRIFG GGTKLTVL                108

SEQ ID NO: 375          moltype = AA  length = 108
FEATURE                 Location/Qualifiers
REGION                  1..108
                        note = chemically synthesized
source                  1..108
                        mol_type = protein
                        organism = synthetic construct
SEQUENCE: 375
SYELMQPPSV SVAPGKTATI ACGGENIGRK TVHWYQQKPG QAPVLVIYYD SDRPSGIPER    60
FSGSNSGNTA TLTISRVEAG DEADYYCQVW DSSSDHRIFG GGTKLTVL                108

SEQ ID NO: 376          moltype = AA  length = 108
FEATURE                 Location/Qualifiers
REGION                  1..108
                        note = chemically synthesized
source                  1..108
                        mol_type = protein
                        organism = synthetic construct
SEQUENCE: 376
SYELMQPPSV SVAPGKTATI ACGGENIGRK TVHWYQQKPG QAPVLVIYYD SDRPSGIPER    60
FSGSNSGNTA TLTISRVEAG DEADYYCQVW DSSSDHRIFG GGTKLTVL                108

SEQ ID NO: 377          moltype = AA  length = 122
FEATURE                 Location/Qualifiers
REGION                  1..122
                        note = chemically synthesized
source                  1..122
                        mol_type = protein
                        organism = synthetic construct
SEQUENCE: 377
QVQLVQSGSE VKKSGSSVKV SCKTSGGTFS ITNYAINWVR QAPGQGLEWM GGILPIFGAA    60
KYAQKFQDRV TITADESTNT AYLELSSLTS EDTAMYYCAR GKRWLQSDLQ YWGQGTLVTV   120
SS                                                                 122

SEQ ID NO: 378          moltype = AA  length = 110
FEATURE                 Location/Qualifiers
REGION                  1..110
                        note = chemically synthesized
source                  1..110
                        mol_type = protein
                        organism = synthetic construct
SEQUENCE: 378
QPVLTQPASV SGSPGQSITI SCTGSSSDVG SYDLVSWYQQ SPGKVPKLLI YEGVKRPSGV    60
SNRFSGSKSG NTASLTISGL QAEDEADYYC SSYAGTRNFV FGGGTQLTVL              110

SEQ ID NO: 379          moltype = AA  length = 121
FEATURE                 Location/Qualifiers
REGION                  1..121
                        note = chemically synthesized
source                  1..121
                        mol_type = protein
                        organism = synthetic construct
SEQUENCE: 379
EVQLLESGGG LVQPGGSLRL SCAASGFTFS SYAMSWVRQA PGKGLEWVSS IYSTGGATAY    60
ADSVKGRFTI SRDNSKNTLY LQMNSLRAED TAVYYCAKSS AGQSRPGFDY WGQGTLVTVS   120
S                                                                  121

SEQ ID NO: 380          moltype = AA  length = 121
FEATURE                 Location/Qualifiers
REGION                  1..121
                        note = chemically synthesized
source                  1..121
```

```
                        mol_type = protein
                        organism = synthetic construct
SEQUENCE: 380
EVQLLESGGG LVQPGGSLRL SCAASGFTFS SYAMSWVRQA PGKGLEWVSS IYSTGGATAY    60
ADSVKGRFTI SRDNSKNTLY LQMNSLRAED TAVYYCAKSS AGQSWPGFDY WGQGTLVTVS   120
S                                                                  121

SEQ ID NO: 381          moltype = AA   length = 121
FEATURE                 Location/Qualifiers
REGION                  1..121
                        note = chemically synthesized
source                  1..121
                        mol_type = protein
                        organism = synthetic construct
SEQUENCE: 381
EVQLLESGGG LVQPGGSLRL SCAASGFTFS SYAMSWVRQA PGKGLEWVSS IYSTGGATAY    60
ADSVKGRFTI SRDNSKNTLY LQMNSLRAED TAVYYCAKSS AGQSFPGFDY WGQGTLVTVS   120
S                                                                  121

SEQ ID NO: 382          moltype = AA   length = 116
FEATURE                 Location/Qualifiers
REGION                  1..116
                        note = chemically synthesized
source                  1..116
                        mol_type = protein
                        organism = synthetic construct
SEQUENCE: 382
EVQLLESGGG LVQPGGSLRL SCAASGFTFS SYAMSWVRQA PGKGLEWVSS IYSTGGATAY    60
ADSVKGRFTI SRDNSKNTLY LQMNSLRAED TAVYYCAKWS AAFDYWGQGT LVTVSS       116

SEQ ID NO: 383          moltype = AA   length = 116
FEATURE                 Location/Qualifiers
REGION                  1..116
                        note = chemically synthesized
source                  1..116
                        mol_type = protein
                        organism = synthetic construct
SEQUENCE: 383
EVQLLESGGG LVQPGGSLRL SCAASGFTFS SYAMSWVRQA PGKGLEWVSS IYSTGGATAY    60
ADSVKGRFTI SRDNSKNTLY LQMNSLRAED TAVYYCAKWS AGYDYWGQGT LVTVSS       116

SEQ ID NO: 384          moltype = AA   length = 116
FEATURE                 Location/Qualifiers
REGION                  1..116
                        note = chemically synthesized
source                  1..116
                        mol_type = protein
                        organism = synthetic construct
SEQUENCE: 384
EVQLLESGGG LVQPGGSLRL SCAASGFTFS SYAMSWVRQA PGKGLEWVSS IYSTGGATAY    60
ADSVKGRFTI SRDNSKNTLY LQMNSLRAED TAVYYCAKWS KGFDYWGQGT LVTVSS       116

SEQ ID NO: 385          moltype = AA   length = 113
FEATURE                 Location/Qualifiers
REGION                  1..113
                        note = chemically synthesized
source                  1..113
                        mol_type = protein
                        organism = synthetic construct
SEQUENCE: 385
EVQLLESGGG LVQPGGSLRL SCAASGFTFS SYAMSWVRQA PGKGLEWVSS IWKQGIVTVY    60
DSVKGRFTIS RDNSKNTLYL QMNSLRAEDT AVYYCAKSSA GFDYWGQGTL VTV          113

SEQ ID NO: 386          moltype = AA   length = 115
FEATURE                 Location/Qualifiers
REGION                  1..115
                        note = chemically synthesized
source                  1..115
                        mol_type = protein
                        organism = synthetic construct
SEQUENCE: 386
EVQLLESGGG LVQPGGSLRL SCAASGFTFS SYAMSWVRQA PGKGLEWVSS IWRNGIVTVY    60
DSVKGRFTIS RDNSKNTLYL QMNSLRAEDT AVYYCAKSSA GFDYWGQGTL VTVSS        115

SEQ ID NO: 387          moltype = AA   length = 115
FEATURE                 Location/Qualifiers
REGION                  1..115
                        note = chemically synthesized
source                  1..115
```

```
                           mol_type = protein
                           organism = synthetic construct
SEQUENCE: 387
EVQLLESGGG  LVQPGGSLRL  SCAASGFTFS  SYAMSWVRQA  PGKGLEWVSD  IWKQGMVTVY   60
DSVKGRFTIS  RDNSKNTLYL  QMNSLRAEDT  AVYYCAKSSA  GFDYWGQGTL  VTVSS        115

SEQ ID NO: 388             moltype = AA  length = 115
FEATURE                    Location/Qualifiers
REGION                     1..115
                           note = chemically synthesized
source                     1..115
                           mol_type = protein
                           organism = synthetic construct
SEQUENCE: 388
EVQLLESGGG  LVQPGGSLRL  SCAASGFTFS  SYAMSWVRQA  PGKGLEWVSS  IWRQGLATAY   60
DSVKGRFTIS  RDNSKNTLYL  QMNSLRAEDT  AVYYCAKSSA  GFDYWGQGTL  VTVSS        115

SEQ ID NO: 389             moltype = AA  length = 115
FEATURE                    Location/Qualifiers
REGION                     1..115
                           note = chemically synthesized
source                     1..115
                           mol_type = protein
                           organism = synthetic construct
SEQUENCE: 389
EVQLLESGGG  LVQPGGSLRL  SCAASGFTFS  SYAMSWVRQA  PGKGLEWVSE  IVATGILTSY   60
DSVKGRFTIS  RDNSKNTLYL  QMNSLRAEDT  AVYYCAKSSA  GFDYWGQGTL  VTVSS        115

SEQ ID NO: 390             moltype = AA  length = 115
FEATURE                    Location/Qualifiers
REGION                     1..115
                           note = chemically synthesized
source                     1..115
                           mol_type = protein
                           organism = synthetic construct
SEQUENCE: 390
EVQLLESGGG  LVQPGGSLRL  SCAASGFTFS  SYAMSWVRQA  PGKGLEWVSS  IGRQGLITVY   60
DSVKGRFTIS  RDNSKNTLYL  QMNSLRAEDT  AVYYCAKSSA  GFDYWGQGTL  VTVSS        115

SEQ ID NO: 391             moltype = AA  length = 115
FEATURE                    Location/Qualifiers
REGION                     1..115
                           note = chemically synthesized
source                     1..115
                           mol_type = protein
                           organism = synthetic construct
SEQUENCE: 391
EVQLLESGGG  LVQPGGSLRL  SCAASGFTFS  SYAMSWVRQA  PGKGLEWVSS  IWYQGLVTVY   60
DSVKGRFTIS  RDNSKNTLYL  QMNSLRAEDT  AVYYCAKSSA  GFDYWGQGTL  VTVSS        115

SEQ ID NO: 392             moltype = AA  length = 114
FEATURE                    Location/Qualifiers
REGION                     1..114
                           note = chemically synthesized
source                     1..114
                           mol_type = protein
                           organism = synthetic construct
SEQUENCE: 392
EVQLLESGGG  LVQPGGSLRL  SCAASGFTFS  SYAMSWVRQA  PGKGLEWVSD  IWKQGFATAD   60
SVKGRFTISR  DNSKNTLYLQ  MNSLRAEDTA  VYYCAKSSAG  FDYWGQGTLV  TVSS         114

SEQ ID NO: 393             moltype = AA  length = 115
FEATURE                    Location/Qualifiers
REGION                     1..115
                           note = chemically synthesized
source                     1..115
                           mol_type = protein
                           organism = synthetic construct
SEQUENCE: 393
EVQLLESGGG  LVQPGGSLRL  SCAASGFTFS  SYAMSWVRQA  PGKGLEWVSS  IWKQGIVTVY   60
DSVKGRFTIS  RDNSKNTLYL  QMNSLRAEDT  AVYYCAKSSA  GFDYWGQGTL  VTVSS        115

SEQ ID NO: 394             moltype = AA  length = 115
FEATURE                    Location/Qualifiers
REGION                     1..115
                           note = chemically synthesized
source                     1..115
                           mol_type = protein
                           organism = synthetic construct
```

```
SEQUENCE: 394
EVQLLESGGG LVQPGGSLRL SCAASGFTFS SYAMSWVRQA PGKGLEWVSS IWRQGLATAY     60
DSVKGRFTIS RDNSKNTLYL QMNSLRAEDT AVYYCAKSSA GFDYWGQGTL VTVSS         115

SEQ ID NO: 395          moltype = AA   length = 116
FEATURE                 Location/Qualifiers
REGION                  1..116
                        note = chemically synthesized
source                  1..116
                        mol_type = protein
                        organism = synthetic construct
SEQUENCE: 395
EVQLLESGGG LVQPGGSLRL SCAASGFTFS SYAMSWVRQA PGKGLEWVSS IWRNGIVTVY     60
ADSVKGRFTI SRDNSKNTLY LQMNSLRAED TAVYYCAKWS AAFDYWGQGT LVTVSS        116

SEQ ID NO: 396          moltype = AA   length = 116
FEATURE                 Location/Qualifiers
REGION                  1..116
                        note = chemically synthesized
source                  1..116
                        mol_type = protein
                        organism = synthetic construct
SEQUENCE: 396
EVQLLESGGG LVQPGGSLRL SCAASGFTFS SYAMSWVRQA PGKGLEWVSS IWRNGIVTVY     60
ADSVKGRFTI SRDNSKNTLY LQMNSLRAED TAVYYCAKWS AGYDYWGQGT LVTVSS        116

SEQ ID NO: 397          moltype = AA   length = 116
FEATURE                 Location/Qualifiers
REGION                  1..116
                        note = chemically synthesized
source                  1..116
                        mol_type = protein
                        organism = synthetic construct
SEQUENCE: 397
EVQLLESGGG LVQPGGSLRL SCAASGFTFS SYAMSWVRQA PGKGLEWVSS IWRNGIVTVY     60
ADSVKGRFTI SRDNSKNTLY LQMNSLRAED TAVYYCAKWS KGFDYWGQGT LVTVSS        116

SEQ ID NO: 398          moltype = AA   length = 120
FEATURE                 Location/Qualifiers
REGION                  1..120
                        note = chemically synthesized
source                  1..120
                        mol_type = protein
                        organism = synthetic construct
SEQUENCE: 398
EVQLLESGGG LVQPGGSLRL SCAASGFTFS SYAMETSWVR QAPGKGLEWV SSIWYQGLVT     60
VYADSVKGRF TISRDNSKNT LYLQMETNSL RAEDTAVYYC AKWSAAFDYW GQGTLVTVSS   120

SEQ ID NO: 399          moltype = AA   length = 116
FEATURE                 Location/Qualifiers
REGION                  1..116
                        note = chemically synthesized
source                  1..116
                        mol_type = protein
                        organism = synthetic construct
SEQUENCE: 399
EVQLLESGGG LVQPGGSLRL SCAASGFTFS SYAMSWVRQA PGKGLEWVSS IWYQGLVTVY     60
ADSVKGRFTI SRDNSKNTLY LQMNSLRAED TAVYYCAKWS AGYDYWGQGT LVTVSS        116

SEQ ID NO: 400          moltype = AA   length = 116
FEATURE                 Location/Qualifiers
REGION                  1..116
                        note = chemically synthesized
source                  1..116
                        mol_type = protein
                        organism = synthetic construct
SEQUENCE: 400
EVQLLESGGG LVQPGGSLRL SCAASGFTFS SYAMSWVRQA PGKGLEWVSS IWYQGLVTVY     60
ADSVKGRFTI SRDNSKNTLY LQMNSLRAED TAVYYCAKWS KGFDYWGQGT LVTVSS        116

SEQ ID NO: 401          moltype = AA   length = 108
FEATURE                 Location/Qualifiers
REGION                  1..108
                        note = chemically synthesized
source                  1..108
                        mol_type = protein
                        organism = synthetic construct
SEQUENCE: 401
DIQMTQSPSS LSASVGDRVT ITCRASQSIS SYLNWYQQKP GKAPKLLIYY ASTLQSGVPS     60
```

```
RFSGSGSGTD FTLTISSLQP EDFATYYCQQ DNGYPSTFGQ GTKVEIKR            108

SEQ ID NO: 402            moltype = AA   length = 108
FEATURE                   Location/Qualifiers
REGION                    1..108
                          note = chemically synthesized
source                    1..108
                          mol_type = protein
                          organism = synthetic construct
SEQUENCE: 402
DIQMTQSPSS LSASVGDRVT ITCRASQSIS SYLNWYQQKP GKAPKLLIYY ASTLQSGVPS   60
RFSGSGSGTD FTLTISSLQP EDFATYYCQQ DNGYPSTFGQ GTKVEIKR              108

SEQ ID NO: 403            moltype = AA   length = 108
FEATURE                   Location/Qualifiers
REGION                    1..108
                          note = chemically synthesized
source                    1..108
                          mol_type = protein
                          organism = synthetic construct
SEQUENCE: 403
DIQMTQSPSS LSASVGDRVT ITCRASQSIS SYLNWYQQKP GKAPKLLIYA ASSLQSGVPS   60
RFSGSGSGTD FTLTISSLQP EDFATYYCQQ DNGYPSTFGG GTKVEIKR              108

SEQ ID NO: 404            moltype = AA   length = 240
FEATURE                   Location/Qualifiers
REGION                    1..240
                          note = chemically synthesized
source                    1..240
                          mol_type = protein
                          organism = synthetic construct
SEQUENCE: 404
EVQLLESGGG LVQPGGSLRL SCAASGFTFS SYAMSWVRQA PGKGLEWVSD ITASGQRTTY   60
ADSVKGRFTI SRDNSKNTLY LQMNSLRAED TAVYYCARSK IAFDYWGQGT LVTVSSGGGG  120
SGGGGSGGGG STDIQMTQSP SSLSASVGDR VTITCRASQS ISSYLNWYQQ KPGKAPKLLI  180
YKASRLQSGV PSRFSGSGSG TDFTLTISSL QPEDFATYYC QQRALKPVTF GQGTKVEIKR  240

SEQ ID NO: 405            moltype = AA   length = 240
FEATURE                   Location/Qualifiers
REGION                    1..240
                          note = chemically synthesized
source                    1..240
                          mol_type = protein
                          organism = synthetic construct
SEQUENCE: 405
EVQLLESGGG LVQPGGSLRL SCAASGFTFS SYAMSWVRQA PGKGLEWVSS INKDGHYTSY   60
ADSVKGRFTI SRDNSKNTLY LQMNSLRAED TAVYYCAKNL DEFDYWGQGT LVTVSSGGGG  120
SGGGGSGGGG STDIQMTQSP SSLSASVGDR VTITCRASQS ISSYLNWYQQ KPGKAPKLLI  180
YAASSLQSGV PSRFSGSGSG TDFTLTISSL QPEDFATYYC QQSYSTPNTF GQGTKVEIKR  240

SEQ ID NO: 406            moltype = AA   length = 240
FEATURE                   Location/Qualifiers
REGION                    1..240
                          note = chemically synthesized
source                    1..240
                          mol_type = protein
                          organism = synthetic construct
SEQUENCE: 406
EVQLLESGGG LVQPGGSLRL SCAASGFTFS SYAMSWVRQA PGKGLEWVSS IMATGAGTLY   60
ADSVKGRFTI SRDNSKNTLY LQMNSLRAED TAVYYCAKDG AGFDYWGQGT LVTVSSGGGG  120
SGGGGSGGGG STDIQMTQSP SSLSASVGDR VTITCRASQS ISSYLNWYQQ KPGKAPKLLI  180
YSASQLQSGV PSRFSGSGSG TDFTLTISSL QPEDFATYYC QQANSRPSTF GQGTKVEIKR  240

SEQ ID NO: 407            moltype = AA   length = 240
FEATURE                   Location/Qualifiers
REGION                    1..240
                          note = chemically synthesized
source                    1..240
                          mol_type = protein
                          organism = synthetic construct
SEQUENCE: 407
EVQLLESGGG LVQPGGSLRL SCAASGFTFS SYAMSWVRQA PGKGLQWVST ITSSGAATYY   60
ADSVKGRFTI SRDNSKNTLY LQMNSLRAED TAVYYCAKNY TGFDYWGQGT LVTVSSGGGG  120
SGGGGSGGGG STDIQMTQSP SSLSASVGDR VTITCRASQS ISSYLNWYQQ KPGKAPKLLI  180
YNASSLQSGV PSRFSGSGSG TDFTLTISSL QPEDFATYYC QQYTYGPGTF GQGTKVEIKR  240

SEQ ID NO: 408            moltype = AA   length = 240
FEATURE                   Location/Qualifiers
REGION                    1..240
```

```
                        note = chemically synthesized
source                  1..240
                        mol_type = protein
                        organism = synthetic construct
SEQUENCE: 408
EVQLLESGGG LVQPGGSLRL SCAASGFTFS SYAMSWVRQA PGKGLEWVSS IYSTGGATAY      60
ADSVKGRFTI SRDNSKNTLY LQMNSLRAED TAVYYCAKSS AGFDYWGQGT LVTVSSGGGG     120
SGGGGSGGGG STDIQMTQSP SSLSASVGDR VTITCRASQS ISSYLNWYQQ KPGKAPKLLI     180
YYASTLQSGV PSRFSGSGSG TDFTLTISSL QPEDFATYYC QQDNGYPSTF GQGTKVEIKR     240

SEQ ID NO: 409          moltype = AA  length = 122
FEATURE                 Location/Qualifiers
REGION                  1..122
                        note = chemically synthesized
source                  1..122
                        mol_type = protein
                        organism = synthetic construct
SEQUENCE: 409
QLQLQESGGG LVQAGGSLRL SCAASGIMFY ISDMGWYRQA PGKQREFVAT ITSGGTTNYA      60
DSVEGRFSIS RDNAKNTVYL QMNSLEPEDT AVYYCTAHGP TYGSTWDDLW GQGTQVTVKP     120
GG                                                                    122

SEQ ID NO: 410          moltype = AA  length = 8
FEATURE                 Location/Qualifiers
REGION                  1..8
                        note = chemically synthesized
source                  1..8
                        mol_type = protein
                        organism = synthetic construct
SEQUENCE: 410
GIMFYISD                                                                8

SEQ ID NO: 411          moltype = AA  length = 10
FEATURE                 Location/Qualifiers
REGION                  1..10
                        note = chemically synthesized
source                  1..10
                        mol_type = protein
                        organism = synthetic construct
SEQUENCE: 411
TITSGGTTNY                                                             10

SEQ ID NO: 412          moltype = AA  length = 14
FEATURE                 Location/Qualifiers
REGION                  1..14
                        note = chemically synthesized
source                  1..14
                        mol_type = protein
                        organism = synthetic construct
SEQUENCE: 412
TAHGPTYGST WDDL                                                        14

SEQ ID NO: 413          moltype = AA  length = 113
FEATURE                 Location/Qualifiers
REGION                  1..113
                        note = chemically synthesized
source                  1..113
                        mol_type = protein
                        organism = synthetic construct
SEQUENCE: 413
QVQLQESGGG LVQAGGSLRL SCAASETFGV VFTLGWYRQT PGKQREFVAR VTGTDTVDYA      60
DSVKGRFTIS SDFARNTVYL QMNNLKPEDT AVYYCNTGAY WGQGTQVTVK PGG            113

SEQ ID NO: 414          moltype = AA  length = 7
FEATURE                 Location/Qualifiers
REGION                  1..7
                        note = chemically synthesized
source                  1..7
                        mol_type = protein
                        organism = synthetic construct
SEQUENCE: 414
TFGVVFT                                                                 7

SEQ ID NO: 415          moltype = AA  length = 7
FEATURE                 Location/Qualifiers
REGION                  1..7
                        note = chemically synthesized
source                  1..7
                        mol_type = protein
```

```
                        organism = synthetic construct
SEQUENCE: 415
VTGTDTV                                                                 7

SEQ ID NO: 416          moltype = AA  length = 5
FEATURE                 Location/Qualifiers
REGION                  1..5
                        note = chemically synthesized
source                  1..5
                        mol_type = protein
                        organism = synthetic construct
SEQUENCE: 416
NTGAY                                                                   5

SEQ ID NO: 417          moltype = AA  length = 119
FEATURE                 Location/Qualifiers
REGION                  1..119
                        note = chemically synthesized
source                  1..119
                        mol_type = protein
                        organism = synthetic construct
SEQUENCE: 417
QVQLVQSGGG LVQTGGSLRL SCAASGRTAS TYSMGWFRQA PGKERQFVAR IIWSTGSTYY        60
TNSVEGRFTI SRDIAKNTLY LQMNSLEPED TAVYYCTARE PTGYDYWGQG TQVTVKPGG        119

SEQ ID NO: 418          moltype = AA  length = 8
FEATURE                 Location/Qualifiers
REGION                  1..8
                        note = chemically synthesized
source                  1..8
                        mol_type = protein
                        organism = synthetic construct
SEQUENCE: 418
GRTASTYS                                                                8

SEQ ID NO: 419          moltype = AA  length = 7
FEATURE                 Location/Qualifiers
REGION                  1..7
                        note = chemically synthesized
source                  1..7
                        mol_type = protein
                        organism = synthetic construct
SEQUENCE: 419
IWSTGST                                                                 7

SEQ ID NO: 420          moltype = AA  length = 10
FEATURE                 Location/Qualifiers
REGION                  1..10
                        note = chemically synthesized
source                  1..10
                        mol_type = protein
                        organism = synthetic construct
SEQUENCE: 420
TAREPTGYDY                                                             10

SEQ ID NO: 421          moltype = AA  length = 122
FEATURE                 Location/Qualifiers
REGION                  1..122
                        note = chemically synthesized
source                  1..122
                        mol_type = protein
                        organism = synthetic construct
SEQUENCE: 421
QLQLQESGGG LVQAGGSLGL SCAASGSIFR FGARGWYRQA PGKQRELVAI ITSGGSTNYA        60
DSVQGRFTIS RDNAKNMVYL QMNGLKSGDT AVYYCAADRS DAVGVGWDYW GQGTQVTVKP       120
GG                                                                    122

SEQ ID NO: 422          moltype = AA  length = 8
FEATURE                 Location/Qualifiers
REGION                  1..8
                        note = chemically synthesized
source                  1..8
                        mol_type = protein
                        organism = synthetic construct
SEQUENCE: 422
GSIFRFGA                                                                8

SEQ ID NO: 423          moltype = AA  length = 7
FEATURE                 Location/Qualifiers
```

| | | |
|---|---|---|
| REGION | 1..7 | |
| | note = chemically synthesized | |
| source | 1..7 | |
| | mol_type = protein | |
| | organism = synthetic construct | |

SEQUENCE: 423
ITSGGST                                                              7

| | | |
|---|---|---|
| SEQ ID NO: 424 | moltype = AA   length = 14 | |
| FEATURE | Location/Qualifiers | |
| REGION | 1..14 | |
| | note = chemically synthesized | |
| source | 1..14 | |
| | mol_type = protein | |
| | organism = synthetic construct | |

SEQUENCE: 424
AADRSDAVGV GWDY                                                     14

| | | |
|---|---|---|
| SEQ ID NO: 425 | moltype = AA   length = 119 | |
| FEATURE | Location/Qualifiers | |
| REGION | 1..119 | |
| | note = chemically synthesized | |
| source | 1..119 | |
| | mol_type = protein | |
| | organism = synthetic construct | |

SEQUENCE: 425
QVQLQQSGGG LVQTGGSLRL SCAASGRTAS TYSMGWFRQA PGKERQFVAR IIWSTGSTYY     60
TNSVEGRFTI SRDIAKNTLY LQMNSLEPED TAVYYCTARD PTGYDYWGQG TQVTVKPGG    119

| | | |
|---|---|---|
| SEQ ID NO: 426 | moltype = AA   length = 8 | |
| FEATURE | Location/Qualifiers | |
| REGION | 1..8 | |
| | note = chemically synthesized | |
| source | 1..8 | |
| | mol_type = protein | |
| | organism = synthetic construct | |

SEQUENCE: 426
IIWSTGST                                                             8

| | | |
|---|---|---|
| SEQ ID NO: 427 | moltype = AA   length = 10 | |
| FEATURE | Location/Qualifiers | |
| REGION | 1..10 | |
| | note = chemically synthesized | |
| source | 1..10 | |
| | mol_type = protein | |
| | organism = synthetic construct | |

SEQUENCE: 427
TARDPTGYDY                                                          10

| | | |
|---|---|---|
| SEQ ID NO: 428 | moltype = AA   length = 121 | |
| FEATURE | Location/Qualifiers | |
| REGION | 1..121 | |
| | note = chemically synthesized | |
| source | 1..121 | |
| | mol_type = protein | |
| | organism = synthetic construct | |

SEQUENCE: 428
QLQLQESGGG LVQAGGSLRL SCAASGSIFS IDATAWYRQA PGKQRELVAI ITSSGSTNYP     60
DSVKGRFTIS RDNAKNTVYL QMNSLNPEDT ALYSCNAITR MGGSTYDFWG QGTQVTVKPG    120
G                                                                   121

| | | |
|---|---|---|
| SEQ ID NO: 429 | moltype = AA   length = 8 | |
| FEATURE | Location/Qualifiers | |
| REGION | 1..8 | |
| | note = chemically synthesized | |
| source | 1..8 | |
| | mol_type = protein | |
| | organism = synthetic construct | |

SEQUENCE: 429
GSIFSIDA                                                             8

| | | |
|---|---|---|
| SEQ ID NO: 430 | moltype = AA   length = 7 | |
| FEATURE | Location/Qualifiers | |
| REGION | 1..7 | |
| | note = chemically synthesized | |
| source | 1..7 | |
| | mol_type = protein | |
| | organism = synthetic construct | |

SEQUENCE: 430

```
ITSSGST                                                                      7

SEQ ID NO: 431          moltype = AA   length = 13
FEATURE                 Location/Qualifiers
REGION                  1..13
                        note = chemically synthesized
source                  1..13
                        mol_type = protein
                        organism = synthetic construct
SEQUENCE: 431
NAITRMGGST YDF                                                              13

SEQ ID NO: 432          moltype = AA   length = 117
FEATURE                 Location/Qualifiers
REGION                  1..117
                        note = chemically synthesized
source                  1..117
                        mol_type = protein
                        organism = synthetic construct
SEQUENCE: 432
QVQLVQSGGG LVQPGGSLRL SCAASGFTFS SYAMSWVRQA PGKGLEWVSA IPAGDGSTKY            60
ADSVKGRFTI SRDNAKNTVY LQMDSLKPED TAVYFCAKSR GWSTVDDMDY WGKGTQV             117

SEQ ID NO: 433          moltype = AA   length = 8
FEATURE                 Location/Qualifiers
REGION                  1..8
                        note = chemically synthesized
source                  1..8
                        mol_type = protein
                        organism = synthetic construct
SEQUENCE: 433
GFTFSSYA                                                                     8

SEQ ID NO: 434          moltype = AA   length = 8
FEATURE                 Location/Qualifiers
REGION                  1..8
                        note = chemically synthesized
source                  1..8
                        mol_type = protein
                        organism = synthetic construct
SEQUENCE: 434
IPAGDGST                                                                     8

SEQ ID NO: 435          moltype = AA   length = 14
FEATURE                 Location/Qualifiers
REGION                  1..14
                        note = chemically synthesized
source                  1..14
                        mol_type = protein
                        organism = synthetic construct
SEQUENCE: 435
AKSRGWSTVD DMDY                                                             14

SEQ ID NO: 436          moltype = AA   length = 117
FEATURE                 Location/Qualifiers
REGION                  1..117
                        note = chemically synthesized
source                  1..117
                        mol_type = protein
                        organism = synthetic construct
SEQUENCE: 436
QVQLVQSGGG LVQPGGSLRL SCVVSGFTFR SYAMSWVRQA PGKGLEWVST INSGESSTKY            60
ADSVKGRFTI SRDDAKNTLY LQMSDLKPED TAVYFCAKHR GWSTVDDINY WGKGTQV             117

SEQ ID NO: 437          moltype = AA   length = 8
FEATURE                 Location/Qualifiers
REGION                  1..8
                        note = chemically synthesized
source                  1..8
                        mol_type = protein
                        organism = synthetic construct
SEQUENCE: 437
GFTFRSYA                                                                     8

SEQ ID NO: 438          moltype = AA   length = 8
FEATURE                 Location/Qualifiers
REGION                  1..8
                        note = chemically synthesized
source                  1..8
```

```
                        mol_type = protein
                        organism = synthetic construct
SEQUENCE: 438
INSGESST                                                                    8

SEQ ID NO: 439          moltype = AA   length = 14
FEATURE                 Location/Qualifiers
REGION                  1..14
                        note = chemically synthesized
source                  1..14
                        mol_type = protein
                        organism = synthetic construct
SEQUENCE: 439
AKHRGWSTVD DINY                                                             14

SEQ ID NO: 440          moltype = AA   length = 119
FEATURE                 Location/Qualifiers
REGION                  1..119
                        note = chemically synthesized
source                  1..119
                        mol_type = protein
                        organism = synthetic construct
SEQUENCE: 440
QVQLVQSGGG LVQPGGSLRL SCAASGFTFD DHAMSWVRQA PGKGLEWVSA ISWNGHYTYY            60
AESMKGRFAI SRDNAKNTLY LQMNSLKSED TAVYYCVKGW RGSYTRDRPF ASWGQGTQV            119

SEQ ID NO: 441          moltype = AA   length = 8
FEATURE                 Location/Qualifiers
REGION                  1..8
                        note = chemically synthesized
source                  1..8
                        mol_type = protein
                        organism = synthetic construct
SEQUENCE: 441
GFTFDDHA                                                                    8

SEQ ID NO: 442          moltype = AA   length = 8
FEATURE                 Location/Qualifiers
REGION                  1..8
                        note = chemically synthesized
source                  1..8
                        mol_type = protein
                        organism = synthetic construct
SEQUENCE: 442
ISWNGHYT                                                                    8

SEQ ID NO: 443          moltype = AA   length = 16
FEATURE                 Location/Qualifiers
REGION                  1..16
                        note = chemically synthesized
source                  1..16
                        mol_type = protein
                        organism = synthetic construct
SEQUENCE: 443
VKGWRGSYTR DRPFAS                                                           16

SEQ ID NO: 444          moltype = AA   length = 118
FEATURE                 Location/Qualifiers
REGION                  1..118
                        note = chemically synthesized
source                  1..118
                        mol_type = protein
                        organism = synthetic construct
SEQUENCE: 444
EVQLVQSGGG LVQPGGSLRL SCAASGFTFS SYYMSWVRQA PGKGLEWVST ISTNTGGGST            60
YYAYADSVKG RFTISRDNAK NTLYLEMNSL KPEDTAQYYC VRTRWEGVYD YWGLGTQV             118

SEQ ID NO: 445          moltype = AA   length = 8
FEATURE                 Location/Qualifiers
REGION                  1..8
                        note = chemically synthesized
source                  1..8
                        mol_type = protein
                        organism = synthetic construct
SEQUENCE: 445
GFTFSSYY                                                                    8

SEQ ID NO: 446          moltype = AA   length = 10
FEATURE                 Location/Qualifiers
```

```
REGION              1..10
                    note = chemically synthesized
source              1..10
                    mol_type = protein
                    organism = synthetic construct
SEQUENCE: 446
ISTNTGGGST                                                              10

SEQ ID NO: 447      moltype = AA   length = 11
FEATURE             Location/Qualifiers
REGION              1..11
                    note = chemically synthesized
source              1..11
                    mol_type = protein
                    organism = synthetic construct
SEQUENCE: 447
VRTRWEGVYD Y                                                            11

SEQ ID NO: 448      moltype = AA   length = 482
FEATURE             Location/Qualifiers
REGION              1..482
                    note = chemically synthesized
source              1..482
                    mol_type = protein
                    organism = synthetic construct
SEQUENCE: 448
EVQLLESGGG EVQPGGSLRL SCAASGFSFS INAMGWYRQA PGKRREFVAA IESGRNTVYA        60
ESVKGRFTIS RDNAKNTVYL QMSSLRAEDT AVYYCGLLKG NRVVSPSVAY WGQGTLVTVK       120
PGGGGDKTHT CPPCPAPGGP SVFLFPPKPK DTLMISRTPE VTCVVVDVSH EDPEVKFNWY       180
VDGVEVHNAK TKPREEQYNS TYRVVSVLTV LHQDWLNGKE YKCKVSNKAL PAPIEKTISK       240
AKGQPREPQV YTLPPSRDEL TKNQVSLTCL VKGFYPSDIA VEWESNGQPE NNYKTTPPVL       300
DSDGSFFLYS KLTVDKSRWQ QGNVFSCSVM HEALHNHYTQ KSLSLSPGSG GGGSGGGGSE       360
VQLLESGGGE VQPGGSLRLS CAASGFSFSI NAMGWYRQAP GKRREFVAAI ESGRNTVYAE       420
SVKGRFTISR DNAKNTVYLQ MSSLRAEDTA VYYCGLLKGN RVVSPSVAYW GQGTLVTVKP       480
GG                                                                     482

SEQ ID NO: 449      moltype = AA   length = 466
FEATURE             Location/Qualifiers
REGION              1..466
                    note = chemically synthesized
source              1..466
                    mol_type = protein
                    organism = synthetic construct
SEQUENCE: 449
EVQLLESGGG EVQPGGSLRL SCAASGGIFA IKPISWYRQA PGKQREWVST TTSSGATNYA        60
ESVKGRFTIS RDNAKNTLYL QMSSLRAEDT AVYYCNVFEY WGQGTLVTVK PGGSGGSEVQ       120
LLESGGGEVQ PGGSLRLSCA ASGFSFSINA MGWYRQAPGK RREFVAAIES GRNTVYAESV       180
KGRFTISRDN AKNTVYLQMS SLRAEDTAVY YCGLLKGNRV VSPSVAYWGQ GTLVTVKPGG       240
GGDKTHTCPP CPAPGGPSVF LFPPKPKDTL MISRTPEVTC VVVDVSHEDP EVKFNWYVDG       300
VEVHNAKTKP REEQYNSTYR VVSVLTVLHQ DWLNGKEYKC KVSNKALPAP IEKTISKAKG       360
QPREPQVYTL PPSRDELTKN QVSLTCLVKG FYPSDIAVEW ESNGQPENNY KTTPPVLDSD       420
GSFFLYSKLT VDKSRWQQGN VFSCSVMHEA LHNHYTQKSL SLSPGK                     466

SEQ ID NO: 450      moltype = AA   length = 466
FEATURE             Location/Qualifiers
REGION              1..466
                    note = chemically synthesized
source              1..466
                    mol_type = protein
                    organism = synthetic construct
SEQUENCE: 450
EVQLLESGGG EVQPGGSLRL SCAASGGIFA IKPISWYRQA PGKQREWVST TTSSGATNYA        60
ESVKGRFTIS RDNAKNTLYL QMSSLRAEDT AVYYCNVFEY WGQGTLVTVK PGGSGGSEVQ       120
LLESGGGEVQ PGGSLRLSCA ASGFSFSINA MGWYRQAPGK RREFVAAIYS GRNTVYAESV       180
KGRFTISRDN AKNTVYLQMS SLRAEDTAVY YCGLLKGNRV VSPSVAYWGQ GTLVTVKPGG       240
GGDKTHTCPP CPAPGGPSVF LFPPKPKDTL MISRTPEVTC VVVDVSHEDP EVKFNWYVDG       300
VEVHNAKTKP REEQYNSTYR VVSVLTVLHQ DWLNGKEYKC KVSNKALPAP IEKTISKAKG       360
QPREPQVYTL PPSRDELTKN QVSLTCLVKG FYPSDIAVEW ESNGQPENNY KTTPPVLDSD       420
GSFFLYSKLT VDKSRWQQGN VFSCSVMHEA LHNHYTQKSL SLSPGK                     466

SEQ ID NO: 451      moltype = AA   length = 466
FEATURE             Location/Qualifiers
REGION              1..466
                    note = chemically synthesized
source              1..466
                    mol_type = protein
                    organism = synthetic construct
SEQUENCE: 451
EVQLLESGGG EVQPGGSLRL SCAASGGIFA IKPISWYRQA PGKQREWVST TTSSGATNYA        60
```

```
ESVKGRFTIS RDNAKNTLYL QMSSLRAEDT AVYYCNVFEY WGQGTLVTVK PGGSGGSEVQ   120
LLESGGGEVQ PGGSLRLSCA ASGFSFSINA MGWYRQAPGK RREFVAAIYS GSSTVYAESV   180
KGRFTISRDN AKNTVYLQMS SLRAEDTAVY YCGLLKGNRV VSPSVAYWGQ GTLVTVKPGG   240
GGDKTHTCPP CPAPGGPSVF LFPPKPKDTL MISRTPEVTC VVVDVSHEDP EVKFNWYVDG   300
VEVHNAKTKP REEQYNSTYR VVSVLTVLHQ DWLNGKEYKC KVSNKALPAP IEKTISKAKG   360
QPREPQVYTL PPSRDELTKN QVSLTCLVKG FYPSDIAVEW ESNGQPENNY KTTPPVLDSD   420
GSFFLYSKLT VDKSRWQQGN VFSCSVMHEA LHNHYTQKSL SLSPGK                 466

SEQ ID NO: 452         moltype = AA   length = 481
FEATURE                Location/Qualifiers
REGION                 1..481
                       note = chemically synthesized
source                 1..481
                       mol_type = protein
                       organism = synthetic construct
SEQUENCE: 452
EVQLLESGGG EVQPGGSLRL SCAASGGIFA IKPISWYRQA PGKQREWVST TTSSGATNYA    60
ESVKGRFTIS RDNAKNTLYL QMSSLRAEDT AVYYCNVFEY WGQGTLVTVK PGGSGGSEVQ   120
LLESGGGEVQ LLESGGGEVQ PGGSLRLSCA ASGWAFGNYG MAWFRQAPGK EREFVSRLAW   180
QGGSTDYVES VKGRFTISRD NAKNTLYLQM SSLRAEDTAV YYCARQRSYS RYDIRTPQTY   240
DYWGQGTLVT VKPGGGGDKT HTCPPCPAPG GPSVFLFPPK PKDTLMISRT PEVTCVVVDV   300
SHEDPEVKFN WYVDGVEVHN AKTKPREEQY NSTYRVVSVL TVLHQDWLNG KEYKCKVSNK   360
ALPAPIEKTI SKAKGQPREP QVYTLPPSRD ELTKNQVSLT CLVKGFYPSD IAVEWESNGQ   420
PENNYKTTPP VLDSDGSFFL YSKLTVDKSR WQQGNVFSCS VMHEALHNHY TQKSLSLSPG   480
K                                                                  481

SEQ ID NO: 453         moltype = AA   length = 481
FEATURE                Location/Qualifiers
REGION                 1..481
                       note = chemically synthesized
source                 1..481
                       mol_type = protein
                       organism = synthetic construct
SEQUENCE: 453
EVQLLESGGG EVQPGGSLRL SCAASGGIFA IKPISWYRQA PGKQREWVST TTSSGATNYA    60
ESVKGRFTIS RDNAKNTLYL QMSSLRAEDT AVYYCNVFEY WGQGTLVTVK PGGSGGSEVQ   120
LLESGGGEVQ LLESGGGEVQ PGGSLRLSCA ASGWAFGNYG MAWFRQAPGK EREFVSRLAW   180
GGGSTDYVES VKGRFTISRD NAKNTLYLQM SSLRAEDTAV YYCARQRSYS RYDIRTPQTY   240
DYWGQGTLVT VKPGGGGDKT HTCPPCPAPG GPSVFLFPPK PKDTLMISRT PEVTCVVVDV   300
SHEDPEVKFN WYVDGVEVHN AKTKPREEQY NSTYRVVSVL TVLHQDWLNG KEYKCKVSNK   360
ALPAPIEKTI SKAKGQPREP QVYTLPPSRD ELTKNQVSLT CLVKGFYPSD IAVEWESNGQ   420
PENNYKTTPP VLDSDGSFFL YSKLTVDKSR WQQGNVFSCS VMHEALHNHY TQKSLSLSPG   480
K                                                                  481

SEQ ID NO: 454         moltype = AA   length = 481
FEATURE                Location/Qualifiers
REGION                 1..481
                       note = chemically synthesized
source                 1..481
                       mol_type = protein
                       organism = synthetic construct
SEQUENCE: 454
EVQLLESGGG EVQPGGSLRL SCAASGGIFA IKPISWYRQA PGKQREWVST TTSSGATNYA    60
ESVKGRFTIS RDNAKNTLYL QMSSLRAEDT AVYYCNVFEY WGQGTLVTVK PGGSGGSEVQ   120
LLESGGGEVQ PGGSLRLSCA ASGWAFSNYG MAWFRQAPGK EREFVSRLAW               180
GGGSTDYVES VKGRFTISRD NAKNTLYLQM SSLRAEDTAV YYCARQRSYS RYDIRTPQTY   240
DYWGQGTLVT VKPGGGGDKT HTCPPCPAPG GPSVFLFPPK PKDTLMISRT PEVTCVVVDV   300
SHEDPEVKFN WYVDGVEVHN AKTKPREEQY NSTYRVVSVL TVLHQDWLNG KEYKCKVSNK   360
ALPAPIEKTI SKAKGQPREP QVYTLPPSRD ELTKNQVSLT CLVKGFYPSD IAVEWESNGQ   420
PENNYKTTPP VLDSDGSFFL YSKLTVDKSR WQQGNVFSCS VMHEALHNHY TQKSLSLSPG   480
K                                                                  481

SEQ ID NO: 455         moltype = AA   length = 481
FEATURE                Location/Qualifiers
REGION                 1..481
                       note = chemically synthesized
source                 1..481
                       mol_type = protein
                       organism = synthetic construct
SEQUENCE: 455
EVQLLESGGG EVQPGGSLRL SCAASGGIFA IKPISWYRQA PGKQREWVST TTSSGATNYA    60
ESVKGRFTIS RDNAKNTLYL QMSSLRAEDT AVYYCNVFEY WGQGTLVTVK PGGSGGSEVQ   120
LLESGGGEVQ PGGSLRLSCA ASGWAFGNYG MAWFRQAPGK EREFVSRLAW               180
SGGSTDYVES VKGRFTISRD NAKNTLYLQM SSLRAEDTAV YYCARQRSYS RYDIRTPQTY   240
DYWGQGTLVT VKPGGGGDKT HTCPPCPAPG GPSVFLFPPK PKDTLMISRT PEVTCVVVDV   300
SHEDPEVKFN WYVDGVEVHN AKTKPREEQY NSTYRVVSVL TVLHQDWLNG KEYKCKVSNK   360
ALPAPIEKTI SKAKGQPREP QVYTLPPSRD ELTKNQVSLT CLVKGFYPSD IAVEWESNGQ   420
PENNYKTTPP VLDSDGSFFL YSKLTVDKSR WQQGNVFSCS VMHEALHNHY TQKSLSLSPG   480
K                                                                  481
```

```
SEQ ID NO: 456          moltype = AA  length = 481
FEATURE                 Location/Qualifiers
REGION                  1..481
                        note = chemically synthesized
source                  1..481
                        mol_type = protein
                        organism = synthetic construct
SEQUENCE: 456
EVQLLESGGG EVQPGGSLRL SCAASGGIFA IKPISWYRQA PGKQREWVST TTSSGATNYA   60
ESVKGRFTIS RDNAKNTLYL QMSSLRAEDT AVYYCNVFEY WGQGTLVTVK PGGSGGSEVQ  120
LLESGGGEVQ LLESGGGEVQ PGGSLRLSCA ASGWAFSNYG MAWFRQAPGK EREFVSRLAW  180
SGGSTDYVES VKGRFTISRD NAKNTLYLQM SSLRAEDTAV YYCARQRSYS RYDIRTPQTY  240
DYWGQGTLVT VKPGGGDKT HTCPPCPAPG GPSVFLFPPK PKDTLMISRT PEVTCVVVDV  300
SHEDPEVKFN WYVDGVEVHN AKTKPREEQY NSTYRVVSVL TVLHQDWLNG KEYKCKVSNK  360
ALPAPIEKTI SKAKGQPREP QVYTLPPSRD ELTKNQVSLT CLVKGFYPSD IAVEWESNGQ  420
PENNYKTTPP VLDSDGSFFL YSKLTVDKSR WQQGNVFSCS VMHEALHNHY TQKSLSLSPG  480
K                                                                 481
```

What is claimed is:

1. An isolated polypeptide comprising at least one VHH domain that binds 41BB, wherein each VHH domain that binds 41BB comprises a CDR1, a CDR2, and a CDR3, respectively, comprising the amino acid sequences of SEQ ID NOs: 26, 27 and 28; or SEQ ID NOs: 26, 61, and 28; or SEQ ID NOs: 26, 63, and 28; or SEQ ID NOs: 26, 71, and 28; or SEQ ID NOs: 26, 73, and 28; or SEQ ID NOs: 26, 75, and 28; or SEQ ID NOs: 26, 77, and 28; or SEQ ID NOs: 26, 79, and 28; or SEQ ID NOs: 65, 61, and 28; or SEQ ID NOs: 67, 61, and 28; or SEQ ID NOs: 69, 61, and 28.

2. The isolated polypeptide of claim 1, wherein at least one VHH domain that binds 41BB is humanized.

3. The isolated polypeptide of claim 1, wherein at least one VHH domain that binds 41BB comprises an amino acid sequence that is at least 95% identical to an amino acid sequence selected from SEQ ID NOs: 25, 59, 60, 62, 64, 66, 68, 70, 72, 74, 76, 78, 80, 81, 82, and 83.

4. The isolated polypeptide of claim 1, wherein at least one VHH domain that binds 41BB comprises an amino acid sequence selected from SEQ ID NOs: 25, 59, 60, 62, 64, 66, 68, 70, 72, 74, 76, 78, 80, 81, 82, and 83.

5. The isolated polypeptide of claim 1, wherein at least one VHH domain that binds 41BB comprises the amino acid sequence of SEQ ID NO: 60.

6. The isolated polypeptide of claim 1, wherein at least one VHH domain that binds 41BB comprises a CDR1 comprising the amino acid sequence of SEQ ID NO: 26, a CDR2 comprising the amino acid sequence of SEQ ID NO: 61, and a CDR3 comprising the amino acid sequence of SEQ ID NO: 28.

7. The isolated polypeptide of claim 6, wherein the polypeptide comprises one VHH domain that binds 41BB.

8. The isolated polypeptide of claim 1, wherein the isolated polypeptide comprises an Fc region.

9. The isolated polypeptide of claim 8, wherein the Fc region comprises an amino acid sequence that is at least 97% identical to an amino acid sequence selected from SEQ ID NOs: 1-6.

10. The isolated polypeptide of claim 8, wherein the Fc region comprises an amino acid sequence selected from SEQ ID NOs: 1-6.

11. The isolated polypeptide of claim 8, which forms a homodimer under physiological conditions.

12. The isolated polypeptide of claim 1, wherein each VHH domain that binds 41BB comprises a CDR1 comprising the amino acid sequence of SEQ ID NO: 26, a CDR2 comprising the amino acid sequence of SEQ ID NO: 61, and a CDR3 comprising the amino acid sequence of SEQ ID NO: 28.

* * * * *